(12) United States Patent
Sawada et al.

(10) Patent No.: US 10,570,334 B2
(45) Date of Patent: Feb. 25, 2020

(54) LIQUID CRYSTAL COMPOUND, LIQUID CRYSTAL COMPOSITION, COMPOSITE MATERIAL WITH ENCAPSULATED LIQUID CRYSTAL, AND LIQUID CRYSTAL DISPLAY DEVICE USING SAME

(71) Applicants: JNC CORPORATION, Tokyo (JP); JNC PETROCHEMICAL CORPORATION, Tokyo (JP)

(72) Inventors: Michiko Sawada, Chiba (JP); Yasuyuki Sasada, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 4 days.

(21) Appl. No.: 15/557,798

(22) PCT Filed: Mar. 2, 2016

(86) PCT No.: PCT/JP2016/056434
§ 371 (c)(1),
(2) Date: Sep. 12, 2017

(87) PCT Pub. No.: WO2016/143634
PCT Pub. Date: Sep. 15, 2016

(65) Prior Publication Data
US 2018/0051210 A1  Feb. 22, 2018

(30) Foreign Application Priority Data
Mar. 12, 2015  (JP) .................. 2015-049604

(51) Int. Cl.
| | | |
|---|---|---|
| G02F 1/1333 | (2006.01) |
| C09K 19/30 | (2006.01) |
| C09K 19/20 | (2006.01) |
| C07C 331/28 | (2006.01) |
| C07C 43/225 | (2006.01) |
| C07C 319/06 | (2006.01) |
| C07C 255/55 | (2006.01) |
| C07C 313/16 | (2006.01) |
| C09K 19/58 | (2006.01) |
| C07C 69/593 | (2006.01) |
| C07C 49/175 | (2006.01) |
| C07D 319/06 | (2006.01) |

(Continued)

(52) U.S. Cl.
CPC .......... *C09K 19/3003* (2013.01); *C07C 13/28* (2013.01); *C07C 43/225* (2013.01); *C07C 43/23* (2013.01); *C07C 43/315* (2013.01); *C07C 47/198* (2013.01); *C07C 49/175* (2013.01); *C07C 49/782* (2013.01); *C07C 69/34* (2013.01); *C07C 69/593* (2013.01); *C07C 69/757* (2013.01); *C07C 69/76* (2013.01); *C07C 69/94* (2013.01); *C07C 255/55* (2013.01); *C07C 313/16* (2013.01); *C07C 319/06* (2013.01); *C07C 331/28* (2013.01); *C07C 381/00* (2013.01); *C07D 309/06* (2013.01); *C07D 319/06* (2013.01); *C09K 19/12* (2013.01); *C09K 19/20* (2013.01); *C09K 19/3066* (2013.01); *C09K 19/54* (2013.01); *C09K 19/586* (2013.01); *D01F 8/16* (2013.01); *G02F 1/13* (2013.01); *C07C 2601/14* (2017.05); *C07C 2602/44* (2017.05); *C09K 2019/0444* (2013.01); *C09K 2019/0448* (2013.01); *C09K 2019/0466* (2013.01); *C09K 2019/122* (2013.01); *C09K 2019/123* (2013.01); *C09K 2019/301* (2013.01); *C09K 2019/3004* (2013.01); *C09K 2019/3009* (2013.01); *C09K 2019/3016* (2013.01); *C09K 2019/3027* (2013.01); *C09K 2019/3422* (2013.01); *D01F 8/04* (2013.01)

(58) Field of Classification Search
USPC ...................................................... 252/299.6
See application file for complete search history.

(56) References Cited

U.S. PATENT DOCUMENTS

| | | | | |
|---|---|---|---|---|
| 9,914,876 B2 * | 3/2018 | Adlem | ............... | C09K 19/0258 |
| 10,087,370 B2 * | 10/2018 | Tuffin | .................... | C09K 19/42 |
| 2014/0303391 A1 | 10/2014 | Fenoli et al. | | |

FOREIGN PATENT DOCUMENTS

| | | |
|---|---|---|
| GB | 2356629 | 5/2001 |
| JP | H10-237004 | 9/1998 |

(Continued)

OTHER PUBLICATIONS

"International Search Report (Form PCT/ISA/210) of PCT/JP2016/056434", with English translation thereof, dated May 10, 2016, pp. 1-8.

(Continued)

*Primary Examiner* — Geraldina Visconti
(74) *Attorney, Agent, or Firm* — JCIPRNET

(57) ABSTRACT

Shown is a bimesogenic compound having high solubility in a liquid crystal compound, a liquid crystal composition, a chiral dopant, an additive including an antioxidant or an ultraviolet light absorber, and a polymerizable liquid crystal compound, each of which is used in other bimesogenic compounds or a liquid crystal display device, while maintaining desired physical properties.
A compound is represented by formula (1), a liquid crystal composition contains the compound, conjugate fibers with an encapsulated liquid crystal obtained from the liquid crystal composition, and a liquid crystal display device is obtained from the conjugate fibers with the encapsulated liquid crystal.

$$MG^1\text{-}Z^a\text{-}Sp\text{-}Z^b\text{-}MG^2 \qquad (1)$$

20 Claims, 3 Drawing Sheets

(51) Int. Cl.
  C07C 43/23    (2006.01)
  C07C 69/76    (2006.01)
  C07C 69/34    (2006.01)
  C07C 49/782   (2006.01)
  C07C 43/315   (2006.01)
  C07C 13/28    (2006.01)
  D01F 8/16     (2006.01)
  C07C 381/00   (2006.01)
  C07D 309/06   (2006.01)
  C07C 69/757   (2006.01)
  C07C 69/94    (2006.01)
  C07C 47/198   (2006.01)
  C09K 19/12    (2006.01)
  C09K 19/54    (2006.01)
  G02F 1/13     (2006.01)
  D01F 8/04     (2006.01)
  C09K 19/04    (2006.01)
  C09K 19/34    (2006.01)

(56) References Cited

FOREIGN PATENT DOCUMENTS

| | | |
|---|---|---|
| JP | 2014-524912 | 9/2014 |
| JP | 2014-218445 | 11/2014 |
| WO | 2014005670 | 1/2014 |
| WO | 2015029436 | 3/2015 |

OTHER PUBLICATIONS

Nieuwhof et al., "Highly ordered side-chain liquid-crystalline polymers from maleic anhydride and swallow-tailed 1-alkenes having two mesogens," Macromolecular Chemistry and Physics, Nov. 2000, pp. 2394-2400.

Narita et al., "Bottom-Up Synthesis of Liquid-Phase-Processable Graphene Nanoribbons with Near-Infrared Absorption," ACS Nano, Oct. 2014, pp. 11622-11630.

Wang et al., "Synthesis of Highly Substituted 3-Formylfurans by a Gold(I)-Catalyzed Oxidation/1,2-Alkynyl Migration/Cyclization Cascade," Angewandte Chemie International Edition, Feb. 2014, pp. 3715-3719.

Wyrick et al., "Effects of Molecular Modification on Hypocholesteremic Activity of 1,3-Bis(substituted phenoxy)-2-propanones and Related Derivatives," Journal of Medicinal Chemistry, Apr. 1978, pp. 386-390.

Keegstra et al., "Synthesis and electroluminescent properties of quaterphenyl and sexiphenyl containing copolymers," Macromolecular Chemistry and Physics, Aug. 1996, pp. 2511-2519.

Adlerova et al., "Synthetic Sympatholytics. III. Some 3-Aryl-2-Hydroxypropylamines and 4-Aryl-2Hydroxybutylamines", Collection Czechoslov. Chem. Commun, Feb. 1969, pp. 479-484.

Marcos et al., "Ferroelectric Dimeric Liquid Crystals with a Chiral Flexible Spacer", Chem. Mater, Mar. 1992, pp. 331-338.

Chandrasekhar, "Liquid Crystals", Second edition, Cambridge University, 1992, pp. 204-213.

Degennes et al., "The Physics of Liquid Crystals," Second edition, Oxford Science Publications, 1995, pp. 135-139.

Patel et al., "Flexoelectric Electro-optics of a Cholesteric Liquid Crystal", Physical Review Letters, Apr. 13, 1987, pp. 1538-1540.

Rudquist et al., "On the flexoelectric effect in nematics", Liquid Crystals, 1997, pp. 503-510.

Doles et al., "The effect of the molecular structure on flexoelectric coupling in the chiral nematic phase", J. Mater. Chem., Oct. 5, 2001, pp. 2709-2716.

* cited by examiner

LIQUID CRYSTAL COMPOUND, LIQUID CRYSTAL COMPOSITION, COMPOSITE MATERIAL WITH ENCAPSULATED LIQUID CRYSTAL, AND LIQUID CRYSTAL DISPLAY DEVICE USING SAME

CROSS-REFERENCE TO RELATED APPLICATION

This application is a 371 application of the international PCT application serial no. PCT/JP2016/056434, filed on Mar. 2, 2016, which claims the priority benefit of Japan application no. 2015-049604, filed on Mar. 12, 2015. The entirety of each of the abovementioned patent applications is hereby incorporated by reference herein and made a part of this specification.

TECHNICAL FIELD

The invention relates to a bimesogenic liquid crystal compound, a liquid crystal composition, a liquid crystal composite and a liquid crystal display device. More specifically, the invention relates to a bimesogenic liquid crystal compound, a liquid crystal composition containing the compound and having a nematic phase or a cholesteric, a composite material including the former liquid crystal composition, and a liquid crystal display device including the composition or the composite material, particularly a liquid crystal display device utilizing a flexo-electric effect.

BACKGROUND ART

A liquid crystal display device typified by a liquid crystal display panel, a liquid crystal display module or the like is a device that utilizes dielectric anisotropy, optical anisotropy or the like of a liquid crystal compound. As an operating mode of the liquid crystal display device, a variety of modes are known, such as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a multi-domain vertical alignment (MVA) mode and polymer sustained alignment (PSA) mode.

In addition to the displays described above, as a new display mode using a cholesteric liquid crystal having a comparatively short pitch, a proposal has been made on a display that utilizes "flexo-electric" effect. In the displays, the cholesteric liquid crystals are aligned in an arrangement of "helical structure in which helical axes are uniformly aligned in parallel to a substrate" (Uniformed Lying Helix; ULH), and ULH is also used as a name of the display mode. However, in the mode, specific problems to be solved include difficulty of obtaining uniform alignment, high driving voltage, an insufficient contrast ratio and having electrooptical hysteresis.

In a similar manner, as a display mode in place of IPS, a proposal has been made on a display mode including a cholesteric liquid crystal having a short pitch, namely a mode of "helical structure in which helical axes are uniformly aligned vertically to a substrate" (Uniformed Standing Helix: USH) because a superb black level can be exhibited in comparison with other display modes providing a wide viewing angle (for example, an IPS mode or VA mode).

In the USH mode or ULH mode, a proposal has been made on use of the bimesogenic liquid crystal material to allow an electrooptical response by the flexo-electric effect.

For example, GB 2356629 B (Patent literature No. 1) discloses a display device using a bimesogenic compound and utilizing a flexo-electric effect. In the display devices, the bimesogenic compound exhibits several advantages over an ordinary monomesogenic compound, and examples thereof include a higher flexo-electric coefficient, and a tilt angle per unit electric field is maximized to be larger by one digit in comparison with the conventional mesogenic compound. Designing of molecules of the bimesogenic compound can cause minimization of dielectric coupling that reduces loosening of a helix, and on the other hand, can cause maximization of the flexo-electric response to allow faster switching and a lower electric field.

JP H10-237004 A (Patent literature No. 2) discloses a bimesogenic compound having a 2,3-difluorophenylene group, including alkylenedioxy compounds as shown in compound (I).

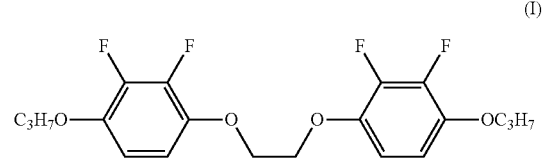
(I)

Moreover, Non-patent literature No. 5 discloses a bimesogenic compound having a cyanobiphenyl structure, including alkylenedioxy compounds as shown in compound (II).

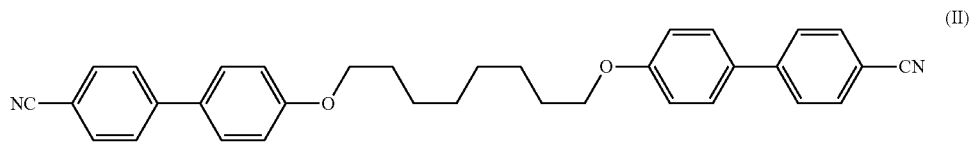 [SMILES: N#Cc1ccc(-c2ccc(OCCCCCCCCOc3ccc(-c4ccc(C#N)cc4)cc3)cc2)cc1]
(II)

CITATION LIST

Patent Literature

Patent literature No. 1: GB 2356629 B
Patent literature No. 2: JP H10-237004 A

Non-Patent Literature

Non-patent literature No. 1: Chandrasekhar, "Liquid Crystals," Second edition, Cambridge University Press (1992)

Non-patent literature No. 2: P. G. deGennes et al., "The Physics of Liquid Crystals," Second edition, Oxford Science Publications (1995)

Non-patent literature No. 3: R. B. Meyer and J. S. Patel, Phys. Rev. Lett. 58(15), 1538 (1987)

Non-patent literature No. 4: P. Rudquist et al., Liq. Cryst. 23(4), 503 (1997)

Non-patent literature No. 5: H. J. Coles et al., J. Mater. Chem. 11, 2709 (2001)

A disadvantage of bimesogenic compounds described above has included poor solubility in other liquid crystal compounds. For example, compound (II) described above has significantly low solubility in other liquid crystal compounds including the bimesogenic liquid crystal compound, and a liquid crystal composition. In consideration of a present situation in which no liquid crystal substance satisfying all of the characteristics described above by a single compound is currently found to use, in a liquid crystal display device, a liquid crystal composition in which twenty several kinds of liquid crystal compounds are mixed, desire has been expressed for a bimesogenic compound having high solubility in a liquid crystal compound, a liquid crystal composition, a chiral dopant, an additive including an antioxidant or an ultraviolet light absorber, and a polymerizable liquid crystal compound, each of which has been so far used in other bimesogenic compounds or a liquid crystal display device, while maintaining desired physical properties.

SUMMARY OF INVENTION

Technical Problem

The invention solves disadvantages of a prior technology as described above, and to provide a bimesogenic liquid crystal compound having high compatibility to any other liquid crystal compound, an additive and a polymerizable compound without adversely affecting values of various physical properties required when used in a liquid crystal display device, such as a value of dielectric anisotropy and a value of refractive index anisotropy, to provide a liquid crystal composition that develops excellent values of physical properties by incorporating the compound thereinto, to provide a liquid crystal composite material containing the liquid crystal composition, and to provide a liquid crystal display device using the liquid crystal composition or the liquid crystal composite material.

Solution to Problem

The present inventors have diligently continued to conduct study in order to solve the problem described above. As a result, the present inventors have found that the problem can be solved by a bimesogenic liquid crystal compound having a structure described below, and have completed the invention.

More specifically, the structure of the invention is as described below.

Item 1. A compound, represented by formula (1):

wherein, in formula (1), $MG^1$ and $MG^2$ are each independently a mesogenic group;

$Z^a$ and $Z^b$ are independently a single bond or alkylene having 1 to 4 carbons, and in the $Z^a$ and the $Z^b$, at least one piece of —$CH_2$— may be replaced by —O—, —S—, —CO— or —$SiH_2$—, at least one piece of —$(CH_2)_2$— may be replaced by —CH=CH— or —C≡C—, and at least one piece of hydrogen may be replaced by fluorine;

Sp has an achiral structure represented by formula (sp-1):

wherein, in formula (sp-1), α is each independently straight-chain alkylene having 1 to 20 carbons, and in the α, at least one piece of —$CH_2$— may be replaced by —O—, —S—, —CO— or —$SiH_2$—, at least one piece of —$(CH_2)_2$— may be replaced by —CH=CH— or —C≡C—, and at least one piece of hydrogen may be replaced by fluorine;

X is represented by formula (I), formula (II) or formula (III):

wherein, in formula (I), Ra is a hydroxyl group or alkyl having 1 to 10 carbons, and in the Ra, at least one piece of —$CH_2$— may be replaced by —O—, —S—, —CO— or —$SiH_2$—, at least one piece of —$(CH_2)_2$— may be replaced by —CH=CH— or —C≡C—, and at least one piece of hydrogen may be replaced by fluorine; and in formula (II), Rb and Rc are each independently fluorine, chlorine or alkyl having 1 to 10 carbons, and in the Rb and the Rc, at least one piece of —$CH_2$— may be replaced by —O—, —S—, —CO— or —$SiH_2$—, at least one piece of —$(CH_2)_2$— may be replaced by —CH=CH— or —C≡C—, and at least one piece of hydrogen may be replaced by fluorine; and in formula (III), Q is an oxygen atom, a sulfur atom or alkylidene having 1 to 10 carbons, and in the Q, at least one piece of —$CH_2$— may be replaced by —O—, —S—, —CO— or —$SiH_2$—, at least one piece of —$(CH_2)_2$— may be replaced by —CH=CH— or —C≡C—, and at least one piece of hydrogen may be replaced by fluorine.

Item 2. The compound according to item 1, wherein, in formula (1), $MG^1$ and $MG^2$ are represented by formula (IV):

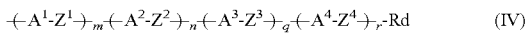

wherein, in formula (IV), Rd is independently —CN, —NCS, —C≡C—CN, —$SF_5$, fluorine, chlorine or straight-chain alkyl having 1 to 20 carbons, and in the Rd, at least one piece of —$CH_2$— may be replaced by —O—, —S—, —CO— or —$SiH_2$—, and at least one piece of —$(CH_2)_2$— may be replaced by —CH=CH— or —C≡C—; $A^1$, $A^2$, $A^3$ and $A^4$ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and in the rings, one piece of —$CH_2$— may be replaced by —O—, —S—, —CO— or —$SiH_2$—, and at least one piece of —$(CH_2)_2$— may be replaced by —CH=CH— or —CH=N—, and in the rings, at least one piece of hydrogen may be replaced by fluorine, chlorine, —$CF_3$, —$CHF_2$, —$CH_2F$, —$OCF_3$, —$OCHF_2$ or —$OCH_2F$;

$Z^1$, $Z^2$, $Z^3$ and $Z^4$ are independently a single bond or alkylene having 1 to 4 carbons, and in the $Z^1$, the $Z^2$, the $Z^3$ and the $Z^4$, at least one piece of —$CH_2$— may be replaced by —O—, —S—, —CO— or —SiH$_2$—, at least one piece of —(CH$_2$)$_2$— may be replaced by —CH═CH— or —C≡C—, and at least one piece of hydrogen may be replaced by fluorine; and m, n, q and r are independently 0 or 1, and a sum of m, n, q and r is 2, 3 or 4.

Item 3. The compound according to item 2, wherein, in formula (IV), Rd is fluorine, chlorine, straight-chain alkyl having 1 to 10 carbons, straight-chain alkenyl having 2 to 10 carbons, straight-chain alkoxy having 1 to 9 carbons, straight-chain alkoxyalkyl having 2 to 9 carbons, straight-chain alkenyloxy having 3 to 9 carbons, straight-chain polyfluoroalkyl having 1 to 10 carbons, straight-chain polyfluoroalkoxy having 1 to 9 carbons or straight-chain polyfluoroalkenyl having 2 to 10 carbons;

A$^1$, A$^2$, A$^3$ and A$^4$ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and in the rings, at least one piece of hydrogen may be replaced by fluorine, chlorine, —CF$_3$ or —CHF$_2$; and Z$^1$, Z$^2$ and Z$^4$ are independently a single bond, —(CH$_2$)$_2$—, —COO—, —OCO—, —CH$_2$O—, —OCH$_2$—, —CF$_2$O—, —OCF$_2$—, —CH═CH—, —CF═CF—, —C≡C—, —CH$_2$CO—, —COCH$_2$—, —CH$_2$SiH$_2$—, —SiH$_2$CH$_2$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O—, —O(CH$_2$)$_3$— or —(CH$_2$)$_4$—.

Item 4. The compound according to any one of items 1 to 3, wherein, in formula (1), Z$^a$ and Z$^b$ are independently a single bond, —COO—, —OCO—, —CH$_2$O—, —OCH$_2$—, —CF$_2$O—, —OCF$_2$—, —CH═CH—, —CF═CF—, —C≡C—, —CH$_2$CO—, —COCH$_2$—, —CH$_2$SiH$_2$— or —SiH$_2$CH$_2$—; and in formula (sp-1), α is straight-chain alkylene having 1 to 10 carbons, and in the α, at least one piece of —(CH$_2$)$_2$ may be replaced by —CH═CH— or —C≡C—, and at least one piece of hydrogen may be replaced by fluorine; and in formula (I), Ra is a hydroxyl group or alkyl having 1 to 5 carbons, alkenyl having 2 to 5 carbons, alkoxy having 1 to 4 carbons, alkoxyalkyl having 2 to 4 carbons, alkenyloxy having 3 to 4 carbons, polyfluoroalkyl having 1 to 5 carbons, polyfluoroalkoxy having 1 to 4 carbons or polyfluoroalkenyl having 2 to 5 carbons;

in formula (II), Rb and Rc are each independently fluorine, alkyl having 1 to 5 carbons, alkenyl having 2 to 5 carbons, alkoxy having 1 to 4 carbons, alkoxyalkyl having 2 to 4 carbons, alkenyloxy having 3 to 4 carbons, polyfluoroalkyl having 1 to 5 carbons, polyfluoroalkoxy having 1 to 4 carbons or polyfluoroalkenyl having 2 to 5 carbons; and in formula (III), Q is an oxygen atom, alkylidene having 1 to 5 carbons.

Item 5. The compound according to item 4, wherein, in formula (1), Z$^a$ and Z$^b$ are independently a single bond, —COO—, —OCO—, —CH$_2$O—, —OCH$_2$—, —CF$_2$O—, —OCF$_2$—, —CH═CH—, —CF═CF— or —C≡C—; and wherein, in formula (sp-1), α is straight-chain alkylene having 1 to 10 carbons; and in formula (I), Ra is alkyl having 1 to 5 carbons, alkenyl having 2 to 5 carbons or polyfluoroalkyl having 1 to 5 carbons; and in formula (II), Rb and Re are each independently fluorine, alkyl having 1 to 5 carbons, alkenyl having 2 to 5 carbons or polyfluoroalkyl having 1 to 5 carbons; and in formula (III), Q is an oxygen atom or alkylidene having 1 to 3 carbons.

Item 6. The compound according to any one of items 1 to 5, wherein, in formula (1), MG$^1$ and MG$^2$ are represented by formula (IV-1):

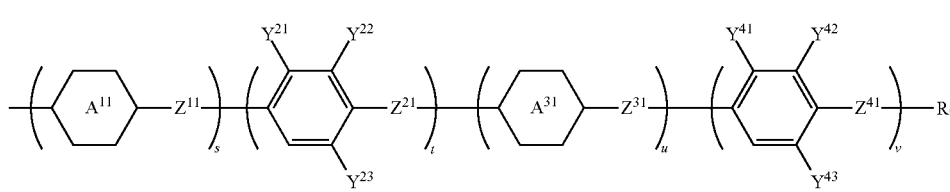

(IV-1)

wherein, Rd is independently —CN, —NCS, —C≡C—CN, —SF$_5$, fluorine, chlorine, straight-chain alkyl having 1 to 6 carbons, straight-chain alkenyl having 2 to 6 carbons, straight-chain alkoxy having 1 to 5 carbons, straight-chain polyfluoroalkyl having 1 to 6 carbons, straight-chain polyfluoroalkoxy having 1 to 5 carbons or straight-chain polyfluoroalkenyl having 2 to 6 carbons;

A$^{11}$ and A$^{31}$ are 1,4-cyclohexylene or 1,4-phenylene;

Y$^{21}$, Y$^{22}$, Y$^{23}$, Y$^{41}$, Y$^{42}$ and Y$^{43}$ are independently hydrogen, fluorine, —CF$_3$ or —CF$_2$H;

Z$^{11}$, Z$^{21}$, Z$^{31}$ and Z$^{41}$ are independently a single bond, —(CH$_2$)$_2$—, —CH$_2$O—, —OCH$_2$—, —CF$_2$O—, —OCF$_2$—, —CH═CH—, —CF═CF— or —C≡C—; and s, t, u and v are independently 0, 1 or 2, and a sum of s, t and u is 2, 3 or 4, in which t is 1 without exception, and when any one of s, t, u and v is 2, a plurality of ring structures may be an identical group or a different group, and a plurality of Z$^{11}$, Z$^{21}$, Z$^{31}$ and Z$^{41}$ may be an identical group or a different group.

Item 7. The compound according to any one of items 1 to 6, wherein, in formula (1), MG$^1$ and MG$^2$ are represented by formulas (IV-1-1-1) to (IV-1-1-55):

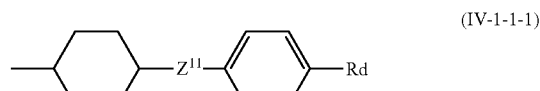

(IV-1-1-1)

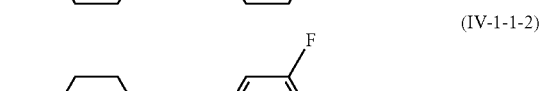

(IV-1-1-2)

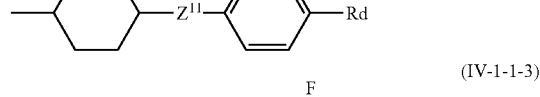

(IV-1-1-3)

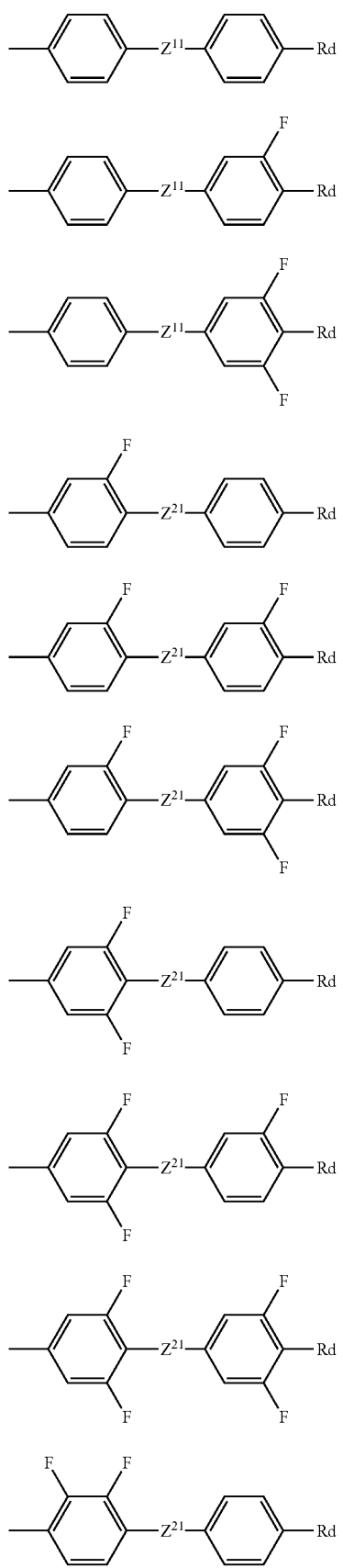
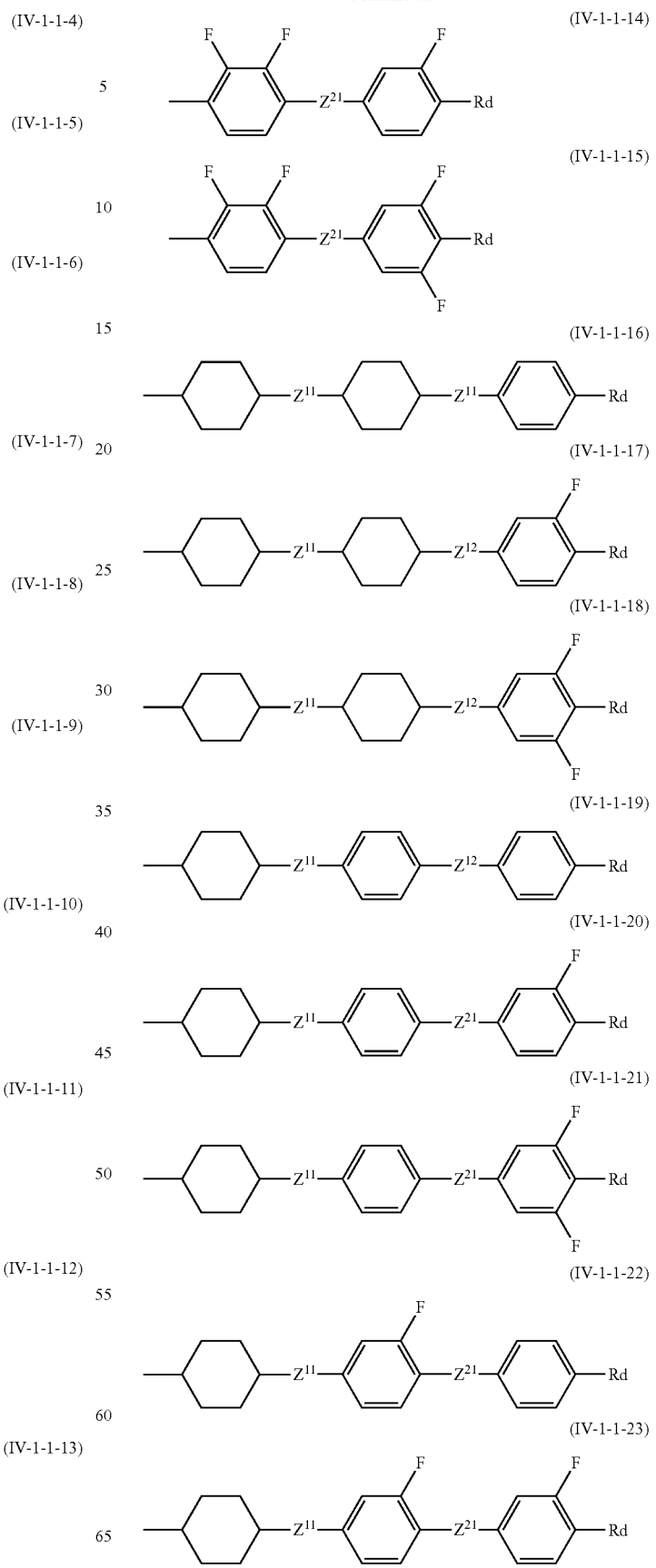

(IV-1-1-24)
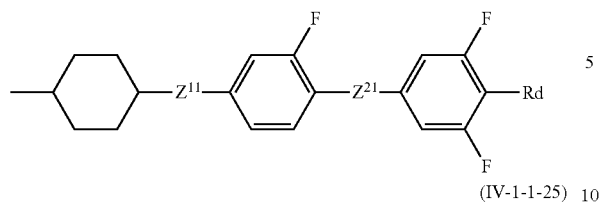
(IV-1-1-25)
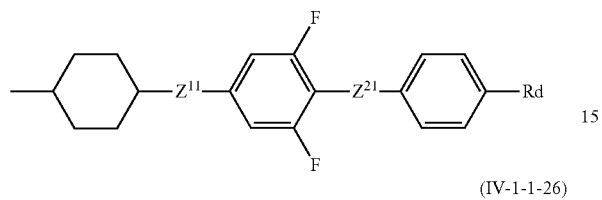
(IV-1-1-26)

(IV-1-1-27)

(IV-1-1-28)
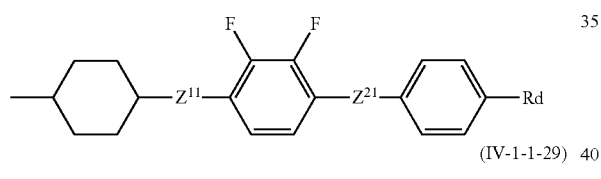
(IV-1-1-29)
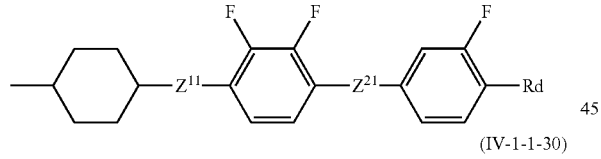
(IV-1-1-30)
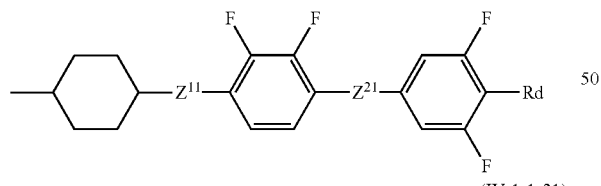
(IV-1-1-31)
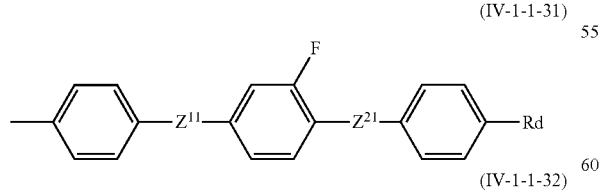
(IV-1-1-32)
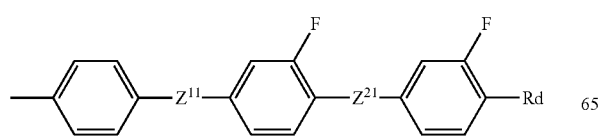
(IV-1-1-33)
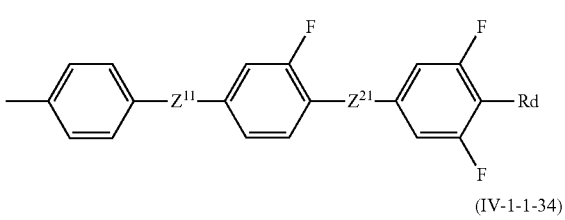
(IV-1-1-34)
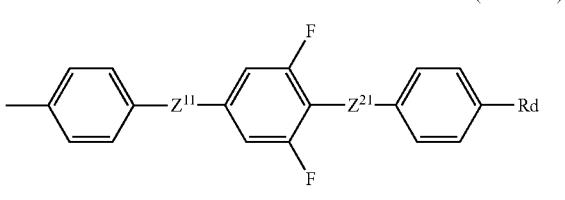
(IV-1-1-35)
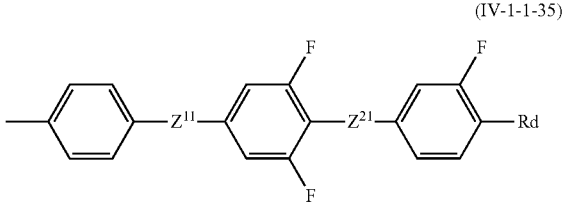
(IV-1-1-36)
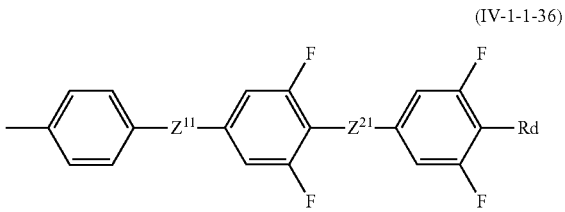
(IV-1-1-37)
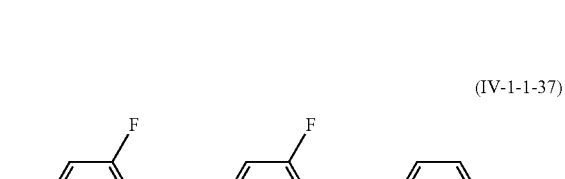
(IV-1-1-38)
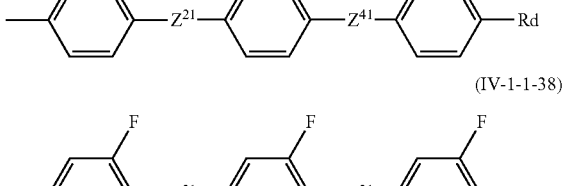
(IV-1-1-39)
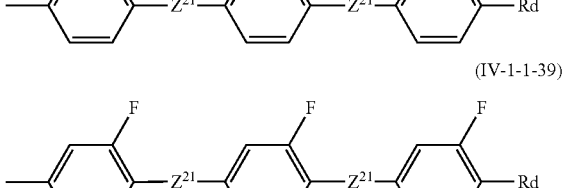
(IV-1-1-40)
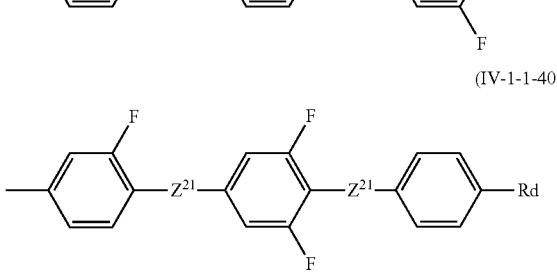

(IV-1-1-41)
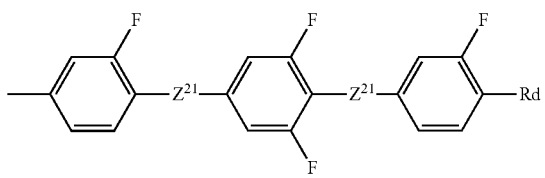

(IV-1-1-42)
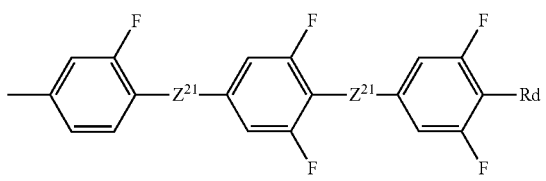

(IV-1-1-43)
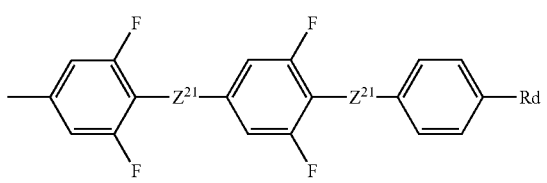

(IV-1-1-44)
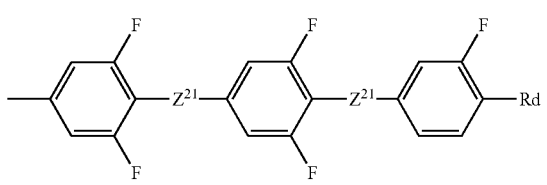

(IV-1-1-45)
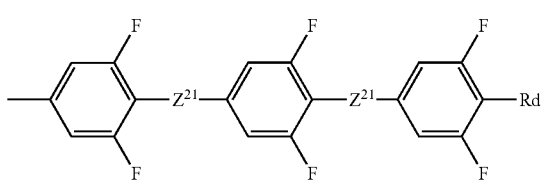

(IV-1-1-46)
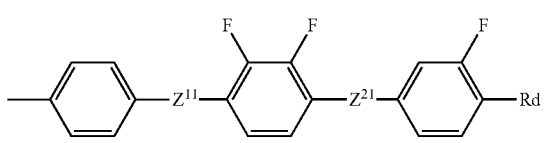

(IV-1-1-47)
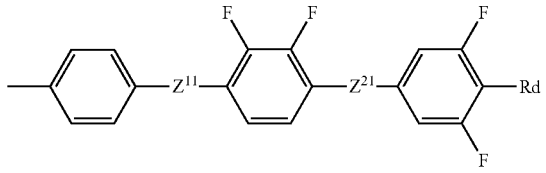

(IV-1-1-48)
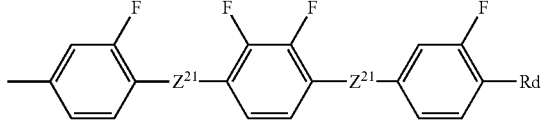

(IV-1-1-49)
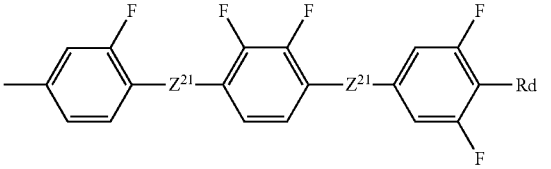

(IV-1-1-50)
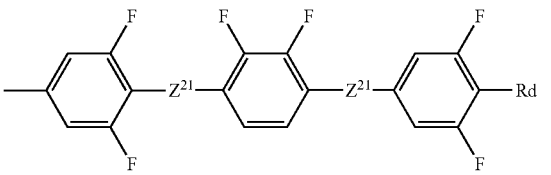

(IV-1-1-51)
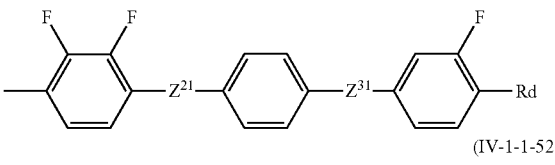

(IV-1-1-52)
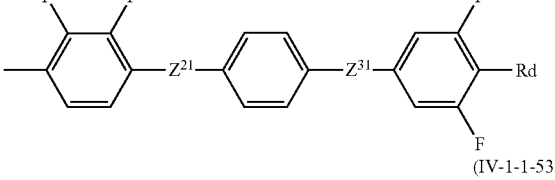

(IV-1-1-53)
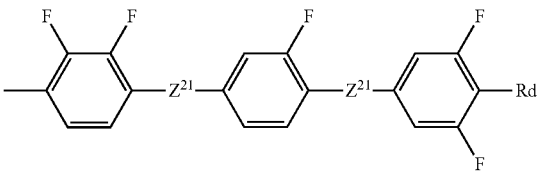

(IV-1-1-54)
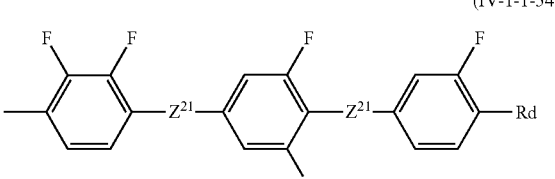

(IV-1-1-55)
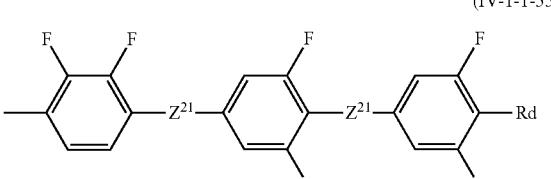

wherein, in formula (IV-1-1-1) to formula (IV-1-1-55), Rd is independently —CN, —NCS, —C≡C—CN, —SF$_5$, fluorine, —CF$_3$, —CF$_2$H, —OCF$_3$, or —C$_2$F$_5$; and Z$^{11}$, Z$^{21}$ and Z$^{31}$ are independently a single bond, —(CH$_2$)$_2$—, —CF$_2$O—, —CH=CH—, —CF=CF— or —C≡C—, and a plurality of Z$^{11}$, Z$^{21}$ or Z$^{31}$ may be an identical group or a different group.

Item 8. The compound according to any one of items 1 to 6, wherein, in formula (1), MG$^1$ and MG$^2$ are represented by formulas (IV-1-2-1) to (IV-1-2-30):

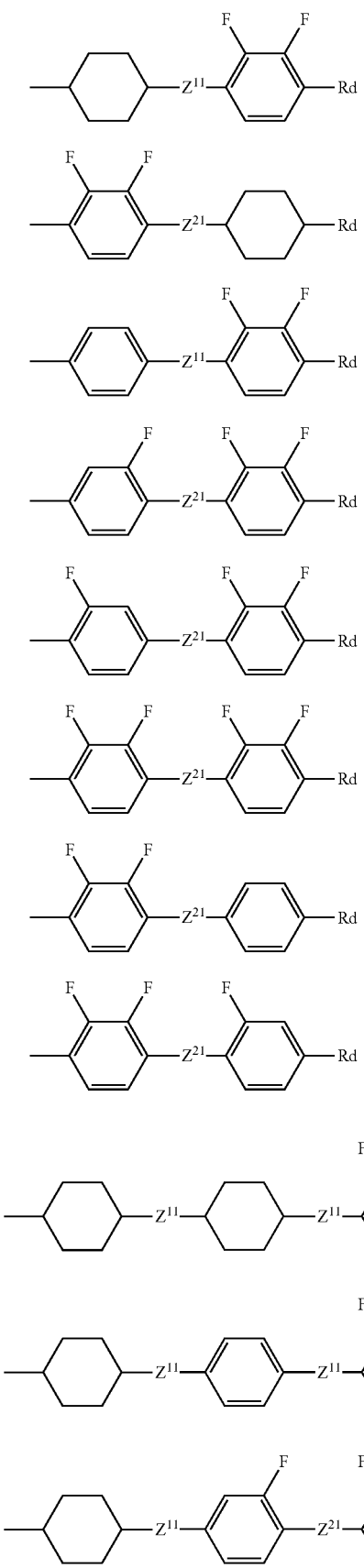
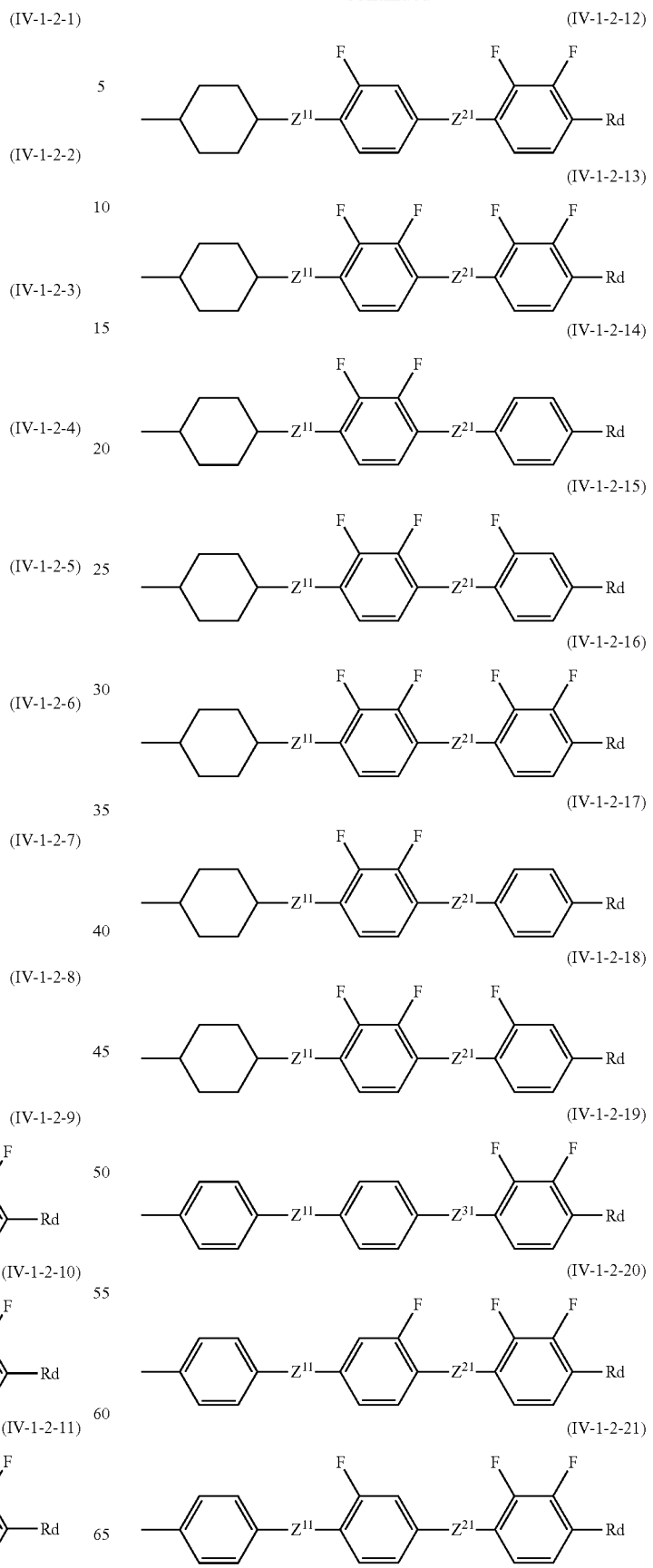

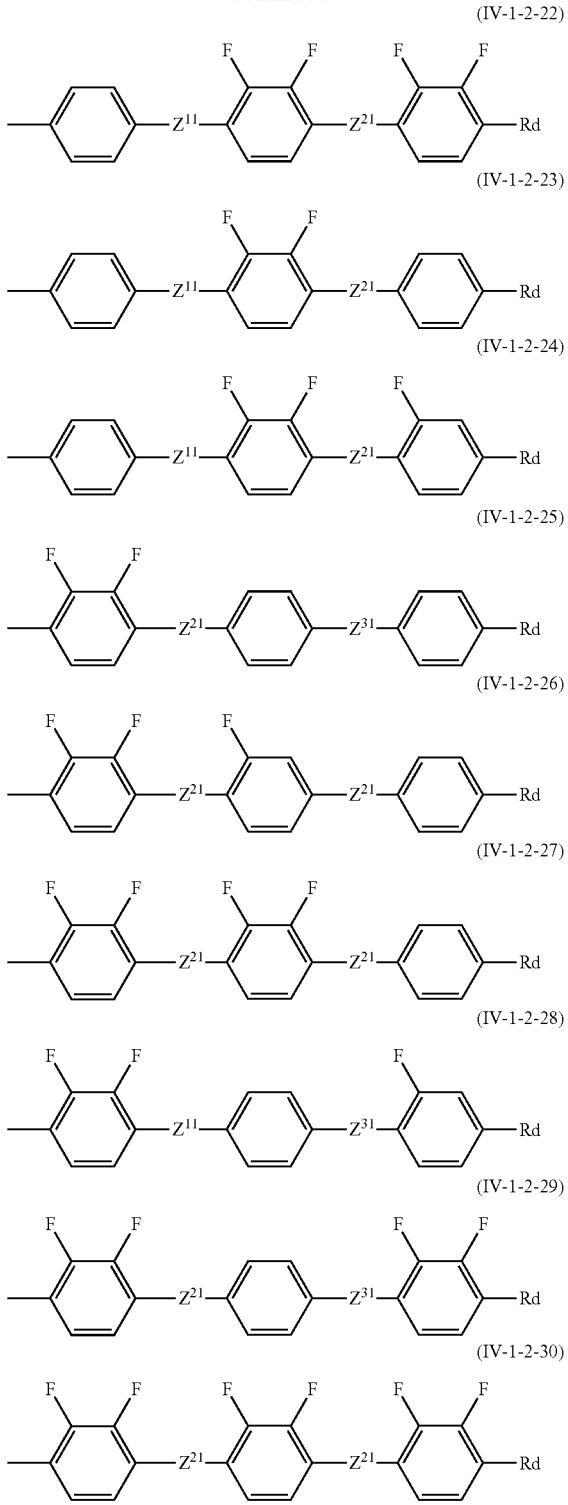

wherein, in formulas (IV-1-2-1) to (IV-1-2-30), Rd is independently straight-chain alkyl having 1 to 6 carbons, straight-chain alkenyl having 2 to 6 carbons or straight-chain alkoxy having 1 to 6 carbons; and $Z^{11}$, $Z^{21}$ and $Z^{31}$ are independently a single bond, —(CH$_2$)$_2$—, —CH$_2$O—, —OCH$_2$—, —CF$_2$O—, —OCF$_2$—, —CH=CH—, —CF=CF— or —C≡C—, and a plurality of $Z^{11}$, $Z^{21}$ and $Z^{31}$ may be an identical group or a different group.

Item 9. A liquid crystal composition, containing the compound according to any one of items 1 to 8.

Item 10. A liquid crystal composition, containing at least two kinds of the compounds according to any one of items 1 to 8.

Item 11. The liquid crystal composition according to item 10, further containing a compound represented by formula (cp-1):

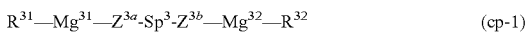

wherein, $R^{31}$ and $R^{32}$ are each independently fluorine, chlorine, —CN, —NCS, —SF$_5$ or alkyl having 1 to 20 carbons, and in the alkyl, at least one piece of —CH$_2$— may be replaced by —O—, —S—, —CO— or —SiH$_2$—, and at least one piece of —(CH$_2$)$_2$— may be replaced by —CH=CH— or —C≡C—; MG$^{31}$ and MG$^{32}$ are each independently a mesogenic group; $Z^{3a}$, $Z^{3b}$ are each independently —O—, —S—, —CO—, —COO—, —OCO—, —O—CO—O—, —CO—NH—, —NH—CO—, —CH$_2$CH$_2$—, —OCH$_2$—, —CH$_2$O—, —SCH$_2$—, —CH$_2$S—, —CH=CH—, —CH=CHCOO—, —OCO—CH=CH—, —C≡C— or a single bond; and Sp$^3$ is a straight-chain spacer group containing 4 to 40 carbons, and at least one piece of a —CH$_2$ group may be replaced by —O—, —S—, —NH—, —N(CH$_3$)—, —OCO—, —S—CO—, —O—COO—, —CO—S—, —CO—O—, —CH=CH— or —C≡C—.

Item 12. The liquid crystal composition according to any one of items 9 to 11, further containing at least one selected from an optically active compound and a polymerizable compound.

Item 13. The liquid crystal composition according to any one of items 9 to 12, further containing at least one selected from an antioxidant and an ultraviolet light absorber.

Item 14. Sheath-core conjugate fibers with an encapsulated liquid crystal, wherein the liquid crystal composition according to any one of items 9 to 13 is applied as a core component.

Item 15. A fiber aggregate containing a liquid crystal, formed by uniaxially arranging the conjugate fibers with the encapsulated liquid crystal according to item 14.

Item 16. A fiber composite containing a liquid crystal, composed of the conjugate fibers with the encapsulated liquid crystal according to item 14 or the fiber aggregate containing the liquid crystal according to item 15, and a binder.

Item 17. A liquid crystal display device, including the liquid crystal composition according to any one of items 9 to 13, the conjugate fibers with an encapsulated liquid crystal according to item 14, the fiber aggregate containing the liquid crystal according to item 15 or the fiber composite containing the liquid crystal according to item 16.

Item 18. The liquid crystal display device according to item 17, wherein the device is a flexo-electric apparatus.

Advantageous Effects of Invention

The invention can provide a bimesogenic liquid crystal compound that develops suitable values of physical properties, and exhibits high solubility in a liquid crystal compound, a liquid crystal composition and other bimesogenic compounds, a liquid crystal composition that allows a high speed response or low voltage driving in various display modes by containing the compound, a conjugate fiber aggregate and a composite each containing the liquid crystal composition, and a liquid crystal display device using the liquid crystal composition, the conjugate fiber aggregate and the composite.

DESCRIPTION OF EMBODIMENTS

Figure 1:
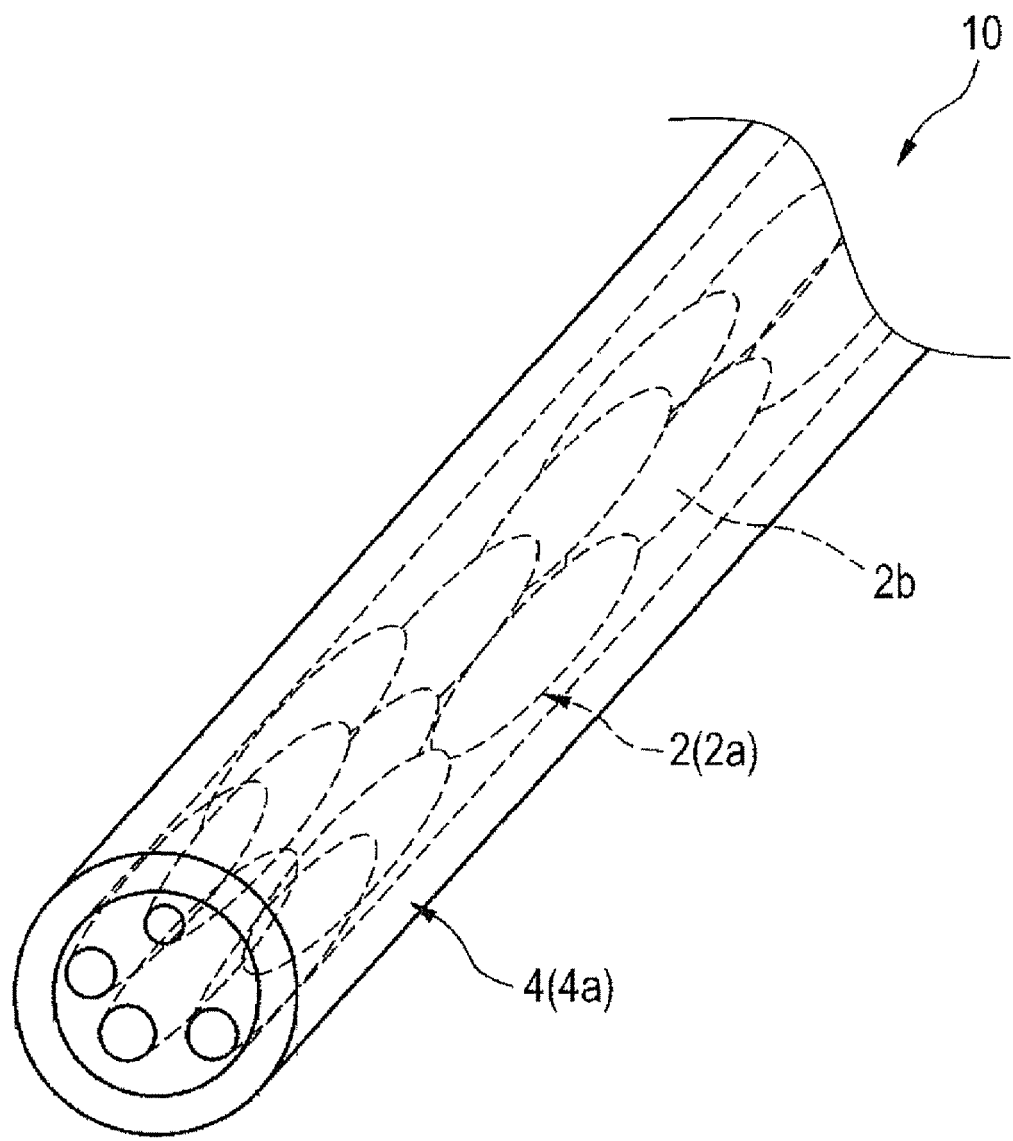
FIG. 1 shows a perspective view of conjugate fibers 10 with an encapsulated liquid crystal to be used in the invention.

Hereinafter, a bimesogenic compound, a liquid crystal composition containing the compound, and a liquid crystal display device composed of the composition, a conjugate fiber aggregate or a composite each containing the composition according to the invention will be described.

Usage of terms herein is as described below. "Liquid crystal compound" is a generic term for a compound having a liquid crystal phase such as a nematic phase and a smectic phase, and a compound having no liquid crystal phase but being useful as a component of a liquid crystal composition. "Liquid crystal conjugate fibers" are conjugate fibers in which a liquid crystal composition is encapsulated, and are sheath-core conjugate fibers in which the liquid crystal composition is applied as a core component. "The conjugate fibers with an encapsulated liquid crystal" is a conjugate fiber aggregate formed of uniaxially arranging conjugate fibers with an encapsulated liquid crystal composition. "Fiber aggregate containing a liquid crystal" is a composite in which a binder is filled among the liquid crystal conjugate fibers. "Liquid crystal display device" is a generic term for a liquid crystal display panel, a liquid crystal film and a liquid crystal display module. "Liquid crystal display device" may be occasionally abbreviated as "device."

A maximum temperature of the nematic phase is a phase transition temperature between the nematic phase and an isotropic phase, and may be simply occasionally abbreviated as "maximum temperature." A minimum temperature of the nematic phase is a phase transition temperature between the nematic phase and a crystal phase, and may be simply occasionally abbreviated as "minimum temperature."

A compound represented by formula (1) (1 represents a formula number) may be occasionally abbreviated as compound (1). In the description of each formula, a symbol such as $B^1$ and $E^1$ corresponds to ring $B^1$, ring $E^1$ or the like, respectively.

An expression "A and/or B" means that "A and B" or "A or B" can be arbitrarily selected. For example, an expression "when Ra and/or Rb is alkenyl" generically represents "when Ra is alkenyl," "when Rb is alkenyl," and "when Ra and Rb are alkenyl."

In the description of each formula, an expression "at least one of" in a context "at least one of (space) may be replaced by (space)" indicates that not only a position but also the number is arbitrary. For example, an expression "at least one piece of 'A' may be replaced by 'B', 'C' or 'D'" includes a case where arbitrary A is replaced by B, a case where arbitrary A is replaced by C, and a case where arbitrary A is replaced by D, and also a case where a plurality of pieces of A are replaced by at least two pieces of B, C and D.

For example, in a case where "in alkyl, at least one piece of —CH$_2$— may be replaced by —O—, and at least one piece of —CH$_2$CH$_2$— may be replaced by —CH=CH—," the alkyl includes alkoxy, alkoxyalkyl, alkenyl, alkoxyalkenyl, alkenyloxyalkyl, in addition to non-substituted alkyl.

To show the meaning of a phrase "in alkyl, at least one piece of —CH$_2$— may be replaced by —O—, —S—, —CO— or —SiH$_2$—, and at least one piece of —(CH$_2$)$_2$— may be replaced by —CH=CH— or —C≡C—" in C$_4$H$_9$—, specific examples include C$_3$H$_7$O—, CH$_3$—O—(CH$_2$)$_2$—, CH$_3$—O—CH$_2$—O—, H$_2$C=CH—(CH$_2$)$_2$—, CH$_3$—CH=CH—CH$_2$— and CH$_2$=CH—CH$_2$—O—.

In addition, in the invention, a case where two pieces of consecutive —CH$_2$— are replaced by —O— to form a group such as —O—O— is not preferred, in consideration of stability of a compound (for example, CH$_3$—O—CH$_2$—O— having non-adjacent oxygen is preferred to CH$_3$—O—O—CH$_2$— having an adjacent oxygen). Moreover, —CH$_2$— at a terminal in alkyl may be replaced by —O—.

In the description of each formula, "fluoroalkyl" is a group in which at least one piece of hydrogen in alkyl is replaced by fluorine, and "polyfluoroalkyl" is a group in which at least two pieces of hydrogen in alkyl are replaced by fluorine. A same rule applies also to (poly) fluoroalkoxy and (poly) fluoroalkenyl.

Bimesogenic Compound

The bimesogenic compound of the invention is represented by formula (1).

$$MG^1\text{-}Z^a\text{-}Sp\text{-}Z^b\text{-}MG^2 \qquad (1)$$

In formula (1), MG$^1$ and MG$^2$ are each independently a mesogenic group;

Z$^a$ and Z$^b$ are independently a single bond or alkylene having 1 to 4 carbons, in the Z$^a$ and the Z$^b$, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine;

Sp has an achiral structure represented by formula (sp-1):

$$\text{-}\alpha\text{-}X\text{-}\alpha\text{-} \qquad (sp\text{-}1)$$

in which, in formula (sp-1), α is straight-chain alkylene having 1 to 20 carbons, and in the α, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine;

X is represented by formula (I), formula (II) and formula (III):

(I)

(II)

(III)

in which, in formula (I), Ra is a hydroxyl group or alkyl having 1 to 10 carbons, and in the Ra, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine;

in formula (II), Rb and Rc are each independently fluorine, chlorine or alkyl having 1 to 10 carbons, and in the Rb and the Rc, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine; and in formula (III), Q is an oxygen atom, a sulfur atom or alkylidene having 1 to 10 carbons, and in the Q, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine.

Preferred MG$^1$ and MG$^2$ have a ring structure, and are an organic moiety composed of a bicyclic ring, a tricyclic ring, a tetracyclic ring, a pentacyclic ring or a hexacyclic ring. In addition, a fused ring such as a naphthalene ring is counted as a monocyclic ring. The ring structures may be directly bonded or may be bonded through a connecting group.

$Z^a$ and $Z^b$ are independently a single bond or alkylene having 1 to 4 carbons, and in the $Z^a$ and the $Z^b$, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine.

Preferred $Z^a$ and $Z^b$ are a single bond, —(CH$_2$)$_2$—, —COO—, —OCO—, —CH$_2$O—, —OCH$_2$—, —CF$_2$O—, —OCF$_2$—, —CH=CH—, —CF=CF—, —C≡C—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O—, —O(CH$_2$)$_3$— or —(CH$_2$)$_4$—. With regard to a configuration of a double bond such as —CH=CH— in a bonding group, trans is preferred to cis.

In formula (sp-1), α is straight-chain alkylene having 1 to 20 carbons, and in the α, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine.

Preferred α is alkylene having 1 to 10 carbons and polyfluoroalkylene having 1 to 9 carbons in which at least one piece of —CH$_2$— is both replaced by a fluorine atom. The number of carbons in alkylene is preferably 2 to 10, and further preferably 2 to 8.

In formula (I), Ra is a hydroxyl group or alkyl having 1 to 10 carbons, and in the Ra, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine.

Preferred Ra is a hydroxyl group, alkyl having 1 to 10 carbons, alkenyl, alkoxy, alkoxyalkyl, alkenyloxy, polyfluoroalkyl, polyfluoroalkoxy or polyfluoroalkenyl. The groups described above may have a straight chain or a cyclic structure. The straight chain is preferred to a branched chain. Further preferred Ra is a hydroxyl group, hydroxy-terminated alkyl having 1 to 10 carbons, alkyl, alkenyl having 2 to 10 carbons, alkoxy having 1 to 9 carbons, alkoxyalkyl or alkenyloxy. Most preferred Ra is a hydroxyl group, hydroxy-terminated alkyl having 1 to 3 carbons, alkyl or alkenyl having 2 to 6 carbons.

A preferred configuration of —CH=CH— in the alkenyl depends on a position of a double bond. A trans configuration is preferred in the alkenyl such as 1-propenyl, 1-butenyl, 1-pentenyl, 1-hexenyl, 3-pentenyl and 3-hexenyl. A cis configuration is preferred in the alkenyl such as 2-butenyl, 2-pentenyl and 2-hexenyl.

Ra is specifically a hydroxyl group, hydroxymethyl, 2-hydroxyethyl, 3-hydroxypropyl, 4-hydroxybutyl, 5-hydroxypentyl, 6-hydroxyhexyl, 7-hydroxyheptyl, 8-hydroxyoctyl, methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —CH$_2$F, —CHF$_2$, —CF$_3$, —(CH$_2$)$_2$F, —CF$_2$CH$_2$F, —CF$_2$CHF$_2$, —CH$_2$CF$_3$, —CF$_2$CF$_3$, —(CH$_2$)$_3$F, —(CF$_2$)$_2$CF$_3$, —CF$_2$CHFCF$_3$, —CHFCF$_2$CF$_3$, —OCHF$_2$, —OCH$_2$F, —OCF$_2$CF$_3$, —OCF$_2$CHF$_2$, —OCF$_2$CH$_2$F, —OCF$_2$CF$_2$CF$_3$, —OCF$_2$CHFCF$_3$, —OCHFCF$_2$CF$_3$, —CH=CHF, —CH=CF$_2$, —CF=CHF, —CH=CHCH$_2$F, —CH=CHCF$_3$ or —(CH$_2$)$_2$CH=CF$_2$.

Further preferred Ra is hydroxyl, hydroxymethyl, 2-hydroxyethyl, 3-hydroxypropyl, 4-hydroxybutyl, 5-hydroxypentyl, 6-hydroxyhexyl, 7-hydroxyheptyl, 8-hydroxyoctyl, methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —CH$_2$F, —CHF$_2$, —CF$_3$, —(CH$_2$)$_2$F, —CF$_2$CH$_2$F, —CF$_2$CHF$_2$, —CH$_2$CF$_3$, —CF$_2$CF$_3$, —(CH$_2$)$_3$F, —(CF$_2$)$_2$CF$_3$, —CF$_2$CHFCF$_3$ or —CHFCF$_2$CF$_3$. Most preferred Ra is hydroxyl, hydroxymethyl, 2-hydroxyethyl, 3-hydroxypropyl, 4-hydroxybutyl, 5-hydroxypentyl, 6-hydroxyhexyl, methyl, ethyl, propyl, butyl, pentyl, hexyl, heptyl, octyl, methoxy, ethoxy, propoxy, butoxy, pentyloxy one, hexyloxy, heptyloxy, vinyl, 1-propenyl, 2-propenyl, 1-butenyl, 2-butenyl, 3-butenyl, 1-pentenyl, 2-pentenyl, 3-pentenyl, 4-pentenyl, —CH$_2$F, —CHF$_2$, —CF$_3$, —(CH$_2$)$_2$F, —CF$_2$CH$_2$F, —CF$_2$CHF$_2$, —CH$_2$CF$_3$ or —CF$_2$CF$_3$.

In formula (II), Rb and Rc are each independently fluorine, chlorine or alkyl having 1 to 10 carbons, and in the Rb and the Rc, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine.

Preferred Rb and Rc are each independently fluorine, chlorine, alkyl having 1 to 10 carbons, alkenyl, alkoxy, alkoxyalkyl, alkenyloxy, polyfluoroalkyl, polyfluoroalkoxy or polyfluoroalkenyl. The groups described above may be of a straight chain, a branch chain or a fused cyclic structure, but the straight chain is preferred to the branched chain. Moreover, further preferred Rb and Rc in which Rb and Rc may be connected to each other are hydroxy-terminated alkyl or alkyl each having 1 to 10 carbons, alkenyl having 2 to 10 carbons, alkoxy, alkoxyalkyl or alkenyloxy each having 1 to 9 carbons. Most preferred Rb and Rc are hydroxy-terminated alkyl or alkyl each having 1 to 3 carbons or alkenyl having 2 to 6 carbons.

A preferred configuration of —CH=CH— in the alkenyl depends on a position of a double bond. A trans configuration is preferred in the alkenyl such as 1-propenyl, 1-butenyl, 1-pentenyl, 1-hexenyl, 3-pentenyl and 3-hexenyl. A cis configuration is preferred in the alkenyl such as 2-butenyl, 2-pentenyl and 2-hexenyl.

Specific Rb and Rc are each independently fluorine, chlorine, hydroxymethyl, 2-hydroxyethyl, 3-hydroxypropyl, 4-hydroxybutyl, 5-hydroxypentyl, 6-hydroxyhexyl, 7-hydroxyheptyl, 8-hydroxyoctyl, methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —CH$_2$F, —CHF$_2$, —CF$_3$, —(CH$_2$)$_2$F, —CF$_2$CH$_2$F, —CF$_2$CHF$_2$, —CH$_2$CF$_3$, —CF$_2$CF$_3$, —(CH$_2$)$_3$F, —(CF$_2$)$_2$CF$_3$, —CF$_2$CHFCF$_3$, —CHFCF$_2$CF$_3$, —OCF$_3$, —OCHF$_2$, —OCH$_2$F, —OCF$_2$CF$_3$, —OCF$_2$CHF$_2$, —OCF$_2$CH$_2$F, —OCF$_2$CF$_2$CF$_3$, —OCF$_2$CHFCF$_3$, —OCHFCF$_2$CF$_3$, —CH=CHF, —CH=CF$_2$, —CF=CHF, —CH=CHCH$_2$F, —CH=CHCF$_3$ or —(CH$_2$)$_2$CH=CF$_2$.

Further preferred Rb and Rc are each independently fluorine, hydroxymethyl, 2-hydroxyethyl, 3-hydroxypropyl, 4-hydroxybutyl, 5-hydroxypentyl, 6-hydroxyhexyl, 7-hydroxyheptyl, 8-hydroxyoctyl, methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —CH$_2$F, —CHF$_2$, —CF$_3$, —(CH$_2$)$_2$F, —CF$_2$CH$_2$F, —CF$_2$CHF$_2$, —CH$_2$CF$_3$, —CF$_2$CF$_3$, —(CH$_2$)$_3$F, —(CF$_2$)$_2$CF$_3$, —CF$_2$CHFCF$_3$ or —CHFCF$_2$CF$_3$. Most preferred Rb and Rc are fluorine, hydroxymethyl, 2-hydroxyethyl, 3-hydroxypropyl, 4-hydroxybutyl, 5-hydroxypentyl, 6-hydroxyhexyl, methyl, ethyl, propyl, butyl, pentyl, hexyl, heptyl, octyl, methoxy, ethoxy, propoxy, butoxy, pentyloxy, hexyloxy, heptyloxy, vinyl, 1-propenyl, 2-propenyl, 1-butenyl, 2-butenyl, 3-butenyl, 1-pentenyl, 2-pentenyl, 3-pentenyl, 4-pentenyl, —CH$_2$F, —CHF$_2$, —CF$_3$, —(CH$_2$)$_2$F, —CF$_2$CH$_2$F, —CF$_2$CHF$_2$, —CH$_2$CF$_3$ or —CF$_2$CF$_3$.

In formula (III), Q is an oxygen atom, a sulfur atom or alkylidene having 1 to 10 carbons, and in the Q, at least one piece of —CH$_2$— may be replaced by —O—, —S—, —CO— or —SiH$_2$—, at least one piece of —(CH$_2$)$_2$— may be replaced by —CH=CH— or —C≡C—, and at least one piece of hydrogen may be replaced by fluorine.

Preferred Q is an oxygen atom, alkylidene having 1 to 10 carbons, alkoxyalkylidene having 2 to 10 carbons, alkenylalkylidene having 1 to 3 carbons, polyfluoroalkylidene having 1 to 10 carbons and polyfluoroalkenylalkylidene having 3 to 10 carbons. In the groups, a straight chain is preferred to a branched chain. Further preferred Q is an oxygen atom, hydroxy-terminated alkylidene having 1 to 10 carbons, alkylidene or alkenylalkylidene each having 2 to 10 carbons, polyfluoroalkylidenethe and polyfluoroalkenylalkylidene each having 1 to 9 carbons. Most preferred Q is an oxygen atom, hydroxy-terminated alkylidene having 1 to 3 carbons, alkylidene or polyfluoroalkylidene each having 1 to 3 carbons.

Specific Q is an oxygen atom, 2-hydroxyethylidene, 3-hydroxypropylidene, 4-hydroxybutylidene, 5-hydroxypentylidene, 6-hydroxyhexylidene, 7-hydroxyheptylidene, 8-hydroxyoctylidene, methylidene, ethylidene, propylidene, butylidene, pentylidene, hexylidene, heptylidene, octylidene, 2-propenylidene, 2-butenylidene, 3-butenylidene, 2-pentenylidene, 3-pentenylidene, 4-pentenylidene, =CHF, =CF$_2$, =CHCH$_2$F, =CHCHF$_2$, =CHCF$_2$, =CFCF$_3$, =CHCH$_2$CH$_2$F, =CHCH$_2$CHF$_2$, =CHCH$_2$CF$_3$, =CHCHFCF$_3$, =CHCF$_2$CF$_3$, =CFCF$_2$CF$_3$, =CHCH$_2$CH$_2$CH$_2$F, =CHCH$_2$CH$_2$CHF$_2$, =CHCH$_2$CH$_2$CF$_3$, =CHCH$_2$CHFCF$_3$, =CHCH$_2$CF$_2$CF$_3$, =CHCHFCF$_2$CF$_3$, =CHCF$_2$CF$_2$CF$_3$, =CFCF$_2$CF$_2$CF$_3$, =CHCH=CHF, =CHCH=CF$_2$, =CFCF=CF$_2$, =CHCH=CHCH$_2$F, =CHCH=CHCHF$_2$, =CHCH=CHCF$_3$, =CHCH=CFCF$_3$, =CHCF=CFCF$_3$, =CFCF=CFCF$_3$, =CHCH$_2$CH=CHF, =CHCH$_2$CH=CF$_2$, =CHCH$_2$CF=CF$_2$, =CHCHFCF=CF$_2$, =CHCF$_2$CF=CF$_2$, =CFCF$_2$CF=CF$_2$, =CHCH=CHCH$_2$F, =CHCH=CHCH$_2$F, =CHCH=CHCH$_2$CHF$_2$, =CHCH=CHCH$_2$CF$_3$, =CHCH=CHCHFCF$_3$, =CHCH=CHCF$_2$CF$_3$, =CHCH=CFCF$_2$CF$_3$, =CFCF=CFCF$_2$CF$_3$, =CHCH$_2$CH=CHCH$_2$F, =CHCH$_2$CH=CHCHF$_2$, =CHCH$_2$CH=CHCF$_3$, =CHCH$_2$CH=CFCF$_3$, =CHCH$_2$CF=CFCF$_3$, =CHCHFCF=CFCF$_3$, =CHCF$_2$CF=CFCF$_3$, =CFCF$_2$CF=CFCF$_3$, =CHCH$_2$CH$_2$CH=CHF, =CHCH$_2$CH$_2$CH=CF$_2$, =CHCH$_2$CH$_2$CF=CF$_2$, =CHCH$_2$CHFCF=CF$_2$, =CHCH$_2$CF$_2$CF=CF$_2$, =CHCHFCF$_2$CF=CF$_2$, =CHCF$_2$CF$_2$CF=CF$_2$ or =CFCF$_2$CF$_2$CF=CF$_2$.

Further preferred Q is an oxygen atom, 2-hydroxyethylidene, 3-hydroxypropylidene, 4-hydroxybutylidene, 5-hydroxypentylidene, methylidene, ethylidene, propylidene, butylidene, pentylidene, 2-propenylidene, 2-butenylidene, 3-butenylidene, 2-pentenylidene, 3-pentenylidene, 4-pentenylidene, =CHF, =CF$_2$, =CHCH$_2$F, =CHCHF$_2$, =CHCF$_2$, =CFCF$_3$, =CHCH$_2$CH$_2$F, =CHCH$_2$CHF$_2$, =CHCH$_2$CF$_3$, =CHCHFCF$_3$, =CHCF$_2$CF$_3$, =CFCF$_2$CF$_3$, =CHCH$_2$CH=CHF, =CHCH$_2$CH=CF$_2$, =CHCH$_2$CF=CF$_2$, =CHCHFCF=CF$_2$, =CHCF$_2$CF=CF$_2$, =CFCF$_2$CF=CF$_2$, =CHCH$_2$CH=CHCH$_2$F, =CHCH$_2$CH=CHCHF$_2$, =CHCH$_2$CH=CHCF$_3$, =CHCH$_2$CH=CFCF$_3$, =CHCH$_2$CF=CFCF$_3$, =CHCHFCF=CFCF$_3$, =CHCF$_2$CF=CFCF$_3$, =CFCF$_2$CF=CFCF$_3$, =CHCH$_2$CH$_2$CH=CHF, =CHCH$_2$CH$_2$CH=CF$_2$, =CHCH$_2$CH$_2$CF=CF$_2$, =CHCH$_2$CHFCF=CF$_2$, =CHCH$_2$CF$_2$CF=CF$_2$, =CHCHFCF$_2$CF=CF$_2$, =CHCF$_2$CF$_2$CF=CF$_2$ or =CFCF$_2$CF$_2$CF=CF$_2$. Most preferred Q is an oxygen atom, 2-hydroxyethylidene, 3-hydroxypropylidene, methylidene, ethylidene, propylidene, 3-butenylidene, 4-pentenylidene, =CHF, =CF$_2$, =CHCF$_2$, =CFCF$_3$, =CHCH$_2$CF$_3$, =CHCF$_2$CF$_3$, =CFCF$_2$CF$_3$, =CHCH$_2$CH=CF$_2$, =CHCF$_2$CF=CF$_2$, =CFCF$_2$CF=CF$_2$, =CHCH$_2$CH=CHCF$_3$, =CHCH$_2$CF=CFCF$_3$, =CHCF$_2$CF=CFCF$_3$, =CFCF$_2$CF=CFCF$_3$, =CHCH$_2$CH$_2$CH=CF$_2$, =CHCH$_2$CF$_2$CF=CF$_2$, =CHCF$_2$CF$_2$CF=CF$_2$ or =CFCF$_2$CF$_2$CF=CF$_2$.

In formula (1), MG$^1$ and MG$^2$ are represented by formula (IV).

$$-(A^1\text{-}Z^1)_m-(A^2\text{-}Z^2)_n-(A^3\text{-}Z^3)_q-(A^4\text{-}Z^4)_r\text{-Rd} \qquad \text{(IV)}$$

In formula (IV), Rd is independently —CN, —NCS, —C≡C—CN, —SF$_5$, fluorine, chlorine or straight-chain alkyl having 1 to 20 carbons, and in the Rd, at least one piece of —CH$_2$— may be replaced by —O—, —S—, —CO— or —SiH$_2$—, and at least one piece of —(CH$_2$)$_2$— may be replaced by —CH=CH— or —C≡C—.

Preferred Rd is —CN, —NCS, —C≡C—CN, —SF$_5$, fluorine, and straight-chain alkyl, alkenyl, alkoxy, alkoxyalkyl, alkenyloxy, polyfluoroalkyl, polyfluoroalkoxy and polyfluoroalkenyl each having 2 to 10 carbons. Further preferred Rd is —CN, —NCS, —C≡C—CN, —SF₅, fluorine, and straight-chain alkyl, alkoxy, alkenyl, polyfluoroalkyl, polyfluoroalkoxy and polyfluoroalkenyl each having 1 to 6 carbons.

A preferred configuration of —CH=CH— in the alkenyl depends on a position of a double bond. A trans configuration is preferred in the alkenyl such as 1-propenyl, 1-butenyl, 1-pentenyl, 1-hexenyl, 3-pentenyl and 3-hexenyl. A cis configuration is preferred in the alkenyl such as 2-butenyl, 2-pentenyl and 2-hexenyl.

Specific Rd is —CN, —NCS, —C≡C—CN, —SF₅, fluorine, methyl, ethyl, propyl, butyl, pentyl, hexyl, heptyl, octyl, methoxy, ethoxy, propoxy, butoxy, pentyloxy, hexyloxy, heptyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —CH₂F, —CHF₂, —CF₃, —(CH₂)₂F, —CF₂CH₂F, —CF₂CHF₂, —CH₂CF₃, —CF₂CF₃, —(CH₂)₃F, —(CF₂)₂CF₃, —CF₂CHFCF₃, —CHFCF₂CF₃, —OCF₃, —OCHF₂, —OCH₂F, —OCF₂CF₃, —OCF₂CHF₂, —OCF₂CF₂F, —OCF₂CF₂CF₃, —OCF₂CHFCF₃, —OCHFCF₂CF₃, —CH=CHF, —CH=CF₂, —CF=CHF, —CH=CHCH₂F, —CH=CHCF₃, —(CH₂)₂CH=CF₂ or —C≡C—CF₃.

Further preferred Rd is —CN, —NCS, —C≡C—CN, —SF₅, fluorine, methyl, ethyl, propyl, butyl, pentyl, hexyl, methoxy, ethoxy, propoxy, butoxy, pentyloxy, hexyloxy, methoxymethyl, methoxyethyl, methoxypropyl, ethoxymethyl, ethoxyethyl, ethoxypropyl, propoxymethyl, butoxymethyl, pentoxymethyl, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —CHF₂, —CF₃, —CF₂CH₂F, —CF₂CHF₂, —CH₂CF₃, —CF₂CF₃, —(CH₂)₃F, —(CF₂)₂CF₃, —CF₂CHFCF₃, —OCF₃, —OCHF₂, —OCH₂F, —OCF₂CF₃, —OCF₂CHF₂, —OCF₂CF₂CF₃, —OCF₂CHFCF₃, —CH=CF₂, —CF=CHF, —CH=CHCF₃, —(CH₂)₂CH=CF₂ or —C≡C—CF₃. Most preferred Rd is —SF₅, fluorine, methyl, ethyl, propyl, butyl, pentyl, methoxy, ethoxy, propoxy, butoxy, pentyloxy, vinyl, 1-propenyl, 2-propenyl, 1-butenyl, 2-butenyl, 3-butenyl, 1-pentenyl, 2-pentenyl, 3-pentenyl, 4-pentenyl, 2-propenyloxy, 2-butenyloxy, 2-pentenyloxy, —CHF₂, —CF₃, —CF₂CF₃, —OCF₃, —OCHF₂, —OCF₂CF₃, —CH=CF₂, —CH=CHCF₃ or —C≡C—CF₃.

Rd is a straight-chain group (example: straight-chain alkyl and a substitution product described above), and therefore compound (1) has a wide temperature range of the liquid crystal phase and small viscosity.

When Rd is alkenyl, a preferred configuration depends on a position of a double bond. When compound (1) is an alkenyl compound having a preferred configuration, the compound has high maximum temperature or the wide temperature range of the liquid crystal phase. A detailed description is found in Mol. Cryst. Liq. Cryst., 1985, 131, 109 and Mol. Cryst. Liq. Cryst., 1985, 131, 327.

A preferred configuration of —CH=CH— in the alkenyl depends on a position of a double bond. A trans configuration is preferred in the alkenyl such as 1-propenyl, 1-butenyl, 1-pentenyl, 1-hexenyl, 3-pentenyl and 3-hexenyl. A cis configuration is preferred in the alkenyl such as 2-butenyl, 2-pentenyl and 2-hexenyl.

A¹, A², A³ and A⁴ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and in the rings, one piece of —CH₂— may be replaced by —O—, —S—, —CO— or —SiH₂—, and in the ring, at least one piece of —(CH₂)₂— may be replaced by —CH=CH— or —CH=N—, and in the rings, at least one piece of hydrogen may be replaced by fluorine, chlorine, —CF₃, —CHF₂, —CH₂F, —OCF₃, —OCHF₂ or —OCH₂F.

Preferred examples of the group under an expression "in the rings, at least one piece of —CH₂— may be replaced by —O—, —S—, —CO— or —SiH₂—, and at least one piece of —(CH₂)₂— may be replaced by —CH=CH— or —CH=N—" include a divalent group represented by formulas (16-1) to (16-50) described below. Further preferred examples include a divalent group represented by formulas (16-1) to (16-4), formula (16-15), formula (16-23), formulas (16-27) to (26-29), formula (16-36), formula (16-39) and formula (16-45).

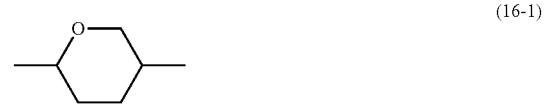

(16-1)

(16-2)

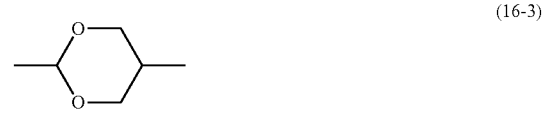

(16-3)

(16-4)

(16-5)

(16-6)

(16-7)

(16-8)

(16-9)

(16-10)

-continued (16-11) through (16-32): chemical structure diagrams (16-33) 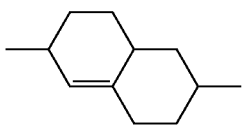

(16-34) 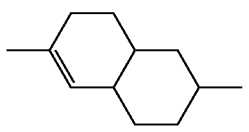

(16-35) 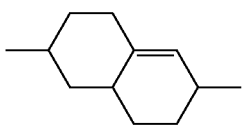

(16-36) 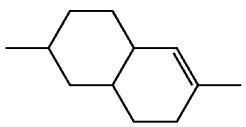

(16-37) 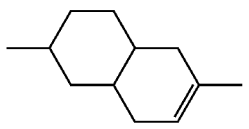

(16-38) 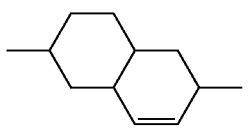

(16-39) 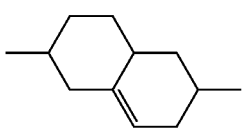

(16-40) 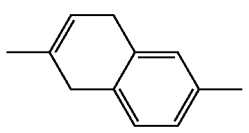

(16-41) 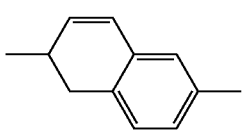

(16-42) 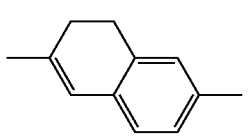

(16-43) 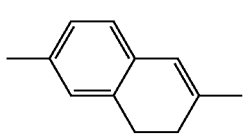

(16-44) 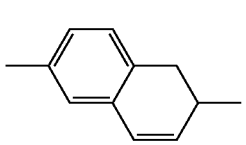

(16-45) 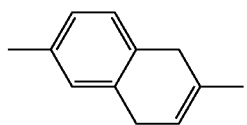

(16-46) 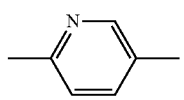

(16-47) 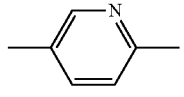

(16-48) 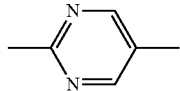

(16-49) 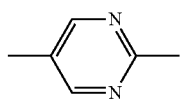

(16-50) 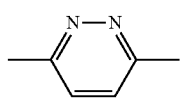

Preferred examples of the group under an expression "and in the rings, at least one piece of hydrogen may be replaced by fluorine, chlorine, —CF$_3$, —CHF$_2$, —CH$_2$F, —OCF$_3$, —OCHF$_2$ or —OCH$_2$F" include a divalent group represented by formulas (17-1) to (17-71) described below. Further preferred examples include a divalent group represented by formulas (17-1) to (17-4), formula (17-6), formulas (17-10) to (17-15) and formulas (17-54) to (17-59).

(17-1) 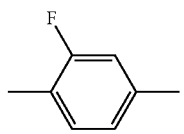

(17-2) 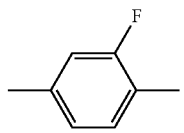

(17-3) 

(17-4) 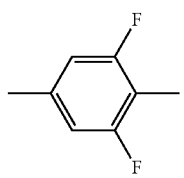

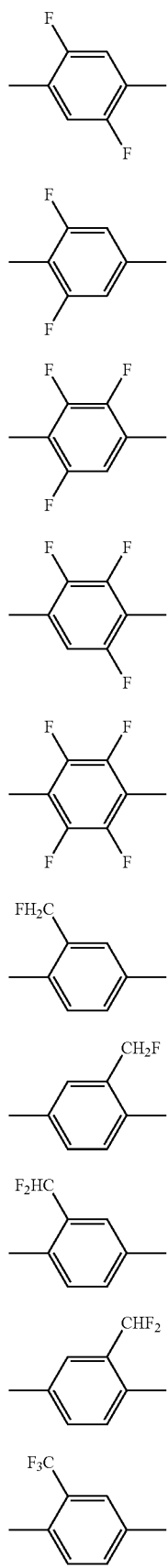
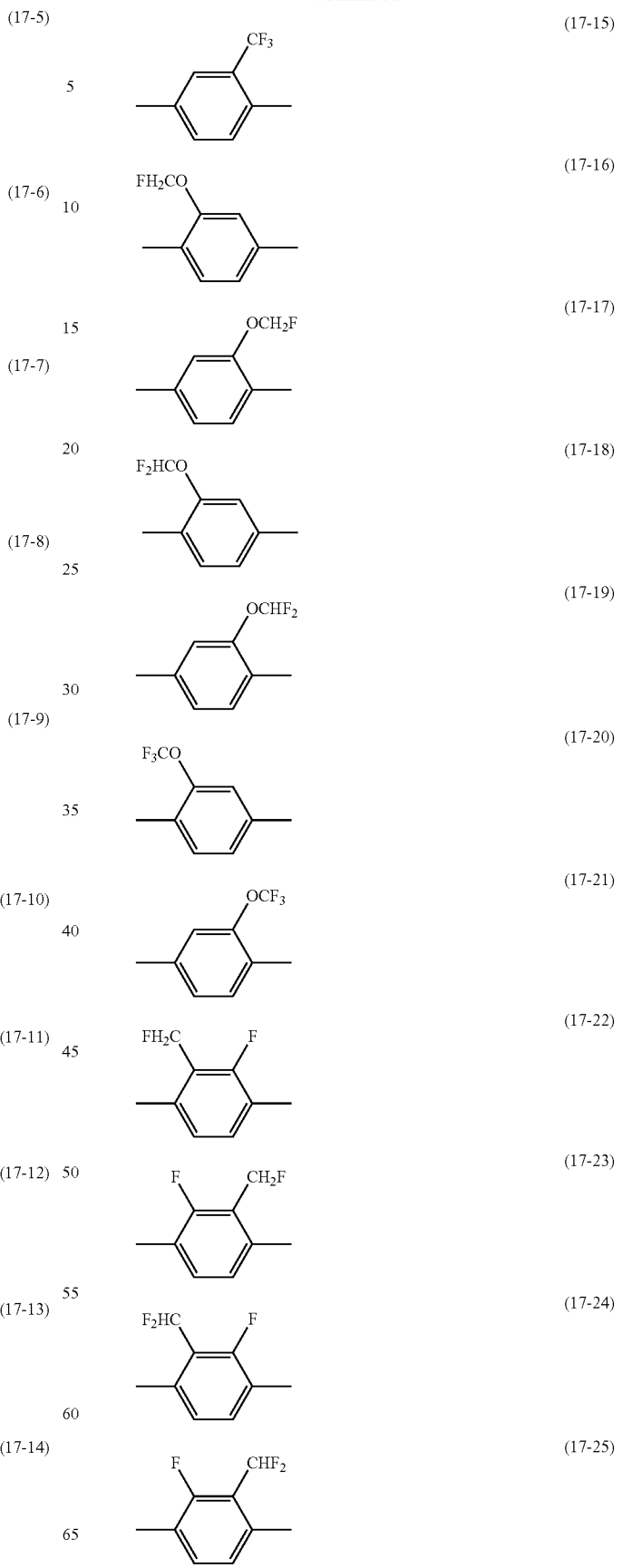

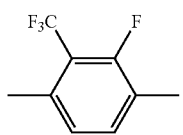 (17-26)
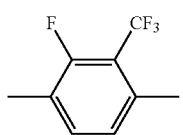 (17-27)
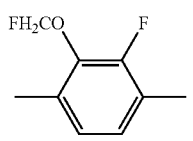 (17-28)
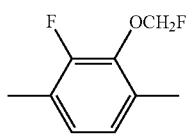 (17-29)
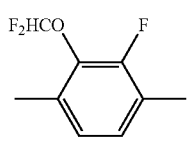 (17-30)
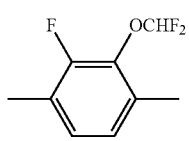 (17-31)
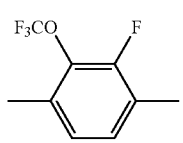 (17-32)
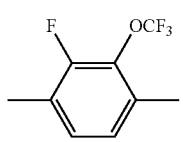 (17-33)
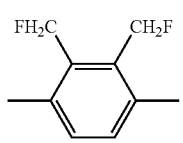 (17-34)
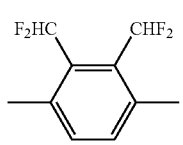 (17-35)
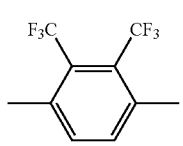 (17-36)
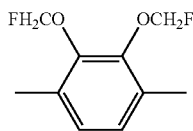 (17-37)
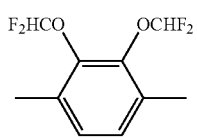 (17-38)
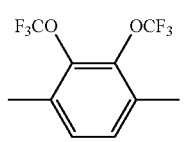 (17-39)
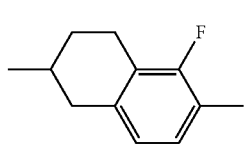 (17-40)
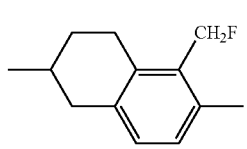 (17-41)
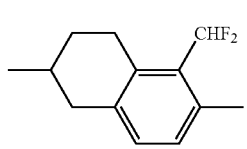 (17-42)
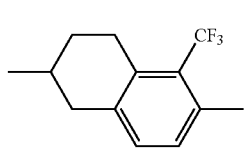 (17-43)
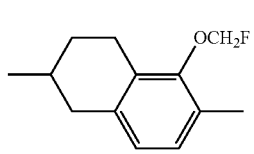 (17-44)
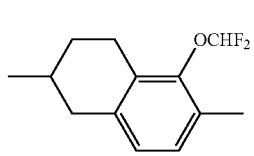 (17-45)
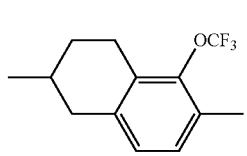 (17-46)
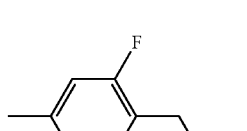 (17-47)
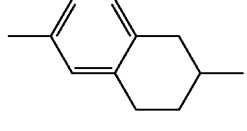

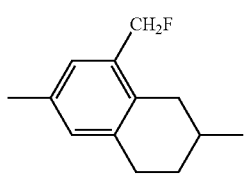 (17-48)
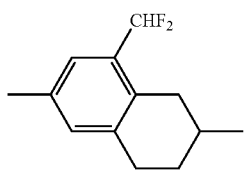 (17-49)
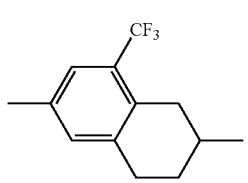 (17-50)
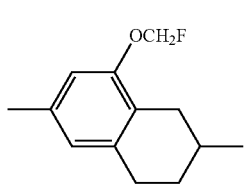 (17-51)
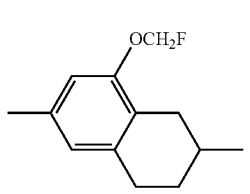 (17-52)
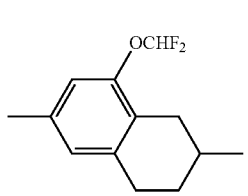 (17-53)
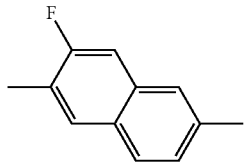 (17-54)
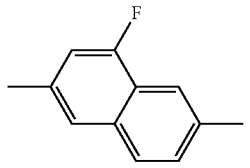 (17-55)
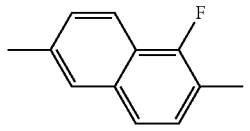 (17-56)
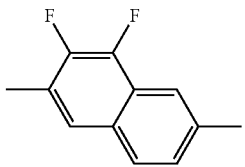 (17-57)
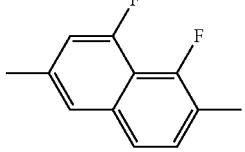 (17-58)
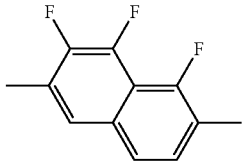 (17-59)
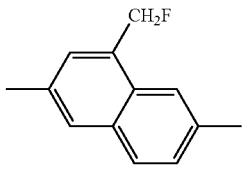 (17-60)
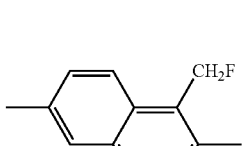 (17-61)
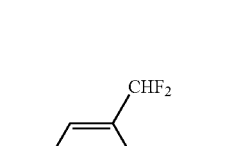 (17-62)
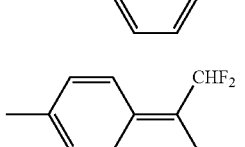 (17-63)
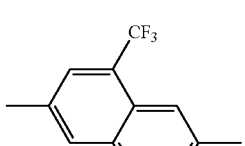 (17-64)
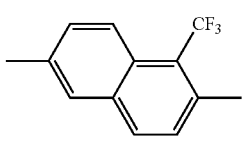 (17-65)

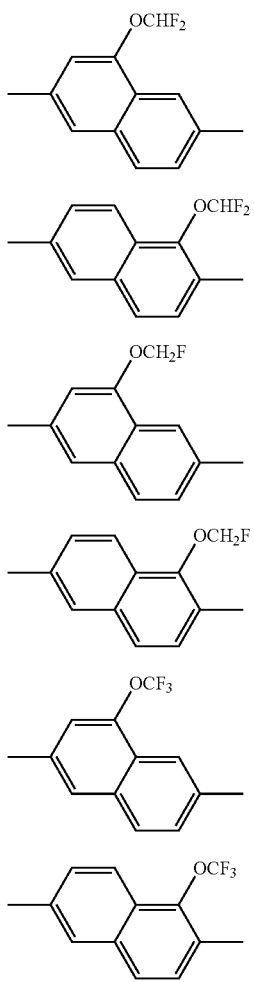

(17-66)

(17-67)

(17-68)

(17-69)

(17-70)

(17-71)

Preferred $A^1$, $A^2$, $A^3$ and $A^4$ are 1,4-cyclohexylene, 1,4-cyclohexenylene, 1,3-dioxane-2,5-diyl, 1,4-phenylene, 2-fluoro-1,4-phenylene, 2,3-difluoro-1,4-phenylene, 2,5-difluoro-1,4-phenylene, 2,6-difluoro-1,4-phenylene, 2,3,5-trifluoro-1,4-phenylene, pyridine-2,5-diyl, 3-fluoro pyridine-2,5-diyl, pyrimidine-2,5-diyl, pyridazine-2,5-diyl, decahydronaphthalene-2,6-diyl, 1,2,3,4-tetrahydronaphthalene-2,6-diyl and naphthalene-2,6-diyl. In a configuration of 1,4-cyclohexylene and 1,3-dioxane-2,5-diyl, trans is preferred to cis. Further preferred $A^1$, $A^2$, $A^3$ and $A^4$ are 1,4-cyclohexylene, 1,4-phenylene, cyclohexene-1,4-diyl, 2-fluoro-1,4-phenylene, 3-fluoro-1,4-phenylene, 2,3-difluoro-1,4-phenylene, 3,5-difluoro-1,4-phenylene, decahydronaphthalene-2,6-diyl, naphthalene-2,6-diyl, 3,4-difluoronaphthalene-2,6-diyl, 3,4,5-trifluoronaphthalene-2,6-diyl, 1,3-difluoronaphthalene-2,6-diyl or 1,3,8-trifluoronaphthalene-2,6-diyl. Most preferred $A^1$, $A^2$, $A^3$ and $A^4$ are 1,4-cyclohexylene, 1,4-phenylene, 2-fluoro-1,4-phenylene, 3-fluoro-1,4-phenylene, 2,3-difluoro-1,4-phenylene, 3,5-difluoro-1,4-phenylene, 3,4,5-trifluoronaphthalene-2,6-diyl and 1,3,8-trifluoronaphthalene-2,6-diyl.

If the number of aromatic rings is large in $A^1$ to $A^4$, a value of optical anisotropy of compound (1) tends to be large. If the number of alicyclic rings is large in $A^1$ to $A^4$, the value of optical anisotropy of compound (1) tends to be small. When $A^1$ to $A^5$ are 1,4-cyclohexylene, cyclohexene-1,4-diyl or 1,3-dioxane-2,5-diyl, the value of optical anisotropy of compound (1) is small. When $A^1$ to $A^5$ are 1,4-phenylene in which at least one piece of hydrogen may be replaced by halogen, the value of optical anisotropy of compound (1) is large.

When at least two of $A^1$ to $A^4$ are 1,4-cyclohexylene, a maximum temperature of compound (1) is high, a value of optical anisotropy thereof is small, and viscosity thereof is small. When at least one of $A^1$ to $A^5$ is 1,4-phenylene, the value of optical anisotropy thereof is comparatively large and an orientational order parameter thereof is large.

When $A^1$ to $A^4$ are 1,4-phenylene in which at least one piece of hydrogen is replaced by halogen or 1,3-dioxane-2,5-diyl, an absolute value of dielectric anisotropy thereof is large. When $A^1$ to $A^4$ are 3,5-difluoro-1,4-phenylene, 1,3,8-trifluoronaphthalene-2,6-diyl or 1,3-dioxane-2,5-diyl, a value of dielectric anisotropy thereof is positively further large. When $A^1$ to $A^5$ are 2,3-difluoro-1,4-phenylene, the value of dielectric anisotropy thereof is negatively large. When $A^1$ to $A^5$ are 3,4,5-trifluoronaphthalene-2,6-diyl, 2-(trifluoromethyl)-3-fluoro-1,4-phenylene, 2-(difluoromethyl)-3-fluoro-1,4-phenylene or 2-fluoro-3-(difluoromethyl)-1,4-phenylene, the value of negative dielectric anisotropy thereof is negatively further large.

When $A^1$ to $A^4$ are cyclohexene-1,4-diyl, a melting point of compound (1) is low. When compound (1) has both cyclohexene-1,4-diyl and 1,4-phenylene, the value of optical anisotropy thereof is large.

$Z^1$, $Z^2$, $Z^3$ and $Z^4$ are independently a single bond or alkylene having 1 to 4 carbons, and in the $Z^1$, the $Z^2$, the $Z^3$ and the $Z^4$, at least one piece of —$CH_2$— may be replaced by —O—, —S—, —CO— or —$SiH_2$—, at least one piece of —$(CH_2)_2$— may be replaced by —CH=CH— or —C≡C—, and at least one piece of hydrogen may be replaced by fluorine.

Preferred $Z^1$, $Z^2$, $Z^3$ and $Z^4$ are a single bond, —$(CH_2)_2$—, —COO—, —OCO—, —$CH_2$O—, —$OCH_2$—, —$CF_2$O—, —$OCF_2$—, —CH=CH—, —CF=CF—, —C≡C—, —$(CH_2)_2$COO—, —OCO$(CH_2)_2$—, —$(CH_2)_2CF_2$O—, —$OCF_2$ $(CH_2)_2$—, —$(CH_2)_3$O—, —O$(CH_2)_3$—, —CF=CF$CF_2$O—, —$OCF_2$CF=CF—, —C≡C$CF_2$O—, —$OCF_2$C≡C— or —$(CH_2)_4$—. With regard to a configuration of a double bond of a bonding group such as —CH=CH—, trans is preferred to cis.

Further preferred $Z^1$, $Z^2$, $Z^3$ and $Z^4$ are a single bond, —$(CH_2)_2$—, —$CH_2$O—, —$OCH_2$—, —$CF_2$O—, —$OCF_2$— or —CH=CH—. Most preferred $Z^1$, $Z^2$, $Z^3$ and $Z^4$ are a single bond, —$CH_2$O—, —$OCH_2$—, —$CF_2$O—, —$OCF_2$— or —CH=CH—.

When the bonding group described above is a single bond, —$(CH_2)_2$—, —$(CH_2)_4$—, —$CH_2$O—, —$OCH_2$—, —$CF_2$O—, —$OCF_2$—, —CH=CH—, —CF=CF$CF_2$O—, —$OCF_2$CF=CF— or —CF=CF—, the viscosity of compound (1) is small. When the bonding group described above is a single bond, —$(CH_2)_2$—, —CH=CH— or —CF=CF—, the viscosity of compound (1) is further small. When the bonding group described above is —CH=CH—, the temperature range of the liquid crystal phase of compound (1) is wide, and an elastic constant ratio: ($K_{33}/K_{11}$) ($K_{33}$: bend elastic constant, $K_{11}$: splay elastic constant) is large. When the bonding group described above is —C≡C—, the value of optical anisotropy of compound (1) is large.

For example, in order to obtain a liquid crystal compound having a large positive value of dielectric anisotropy, further preferred $Z^1$, $Z^2$, $Z^3$ and $Z^4$ are each independently a single bond, —$(CH_2)_2$—, —$CF_2$O—, —$OCF_2$—, —CH=CH—, —CF=CF— or —C≡C—; still further preferably a single bond, —(CH$_2$)$_2$—, —CF$_2$O—, —OCF$_2$— or —CH=CH—; and particularly preferably a single bond, —CF$_2$O—, —OCF2- or —CH=CH—.

For example, in order to obtain a liquid crystal compound having a large negative value of dielectric anisotropy, further preferred $Z^1$, $Z^2$, $Z^4$ and $Z^5$ are each independently a single bond, —(CH$_2$)$_2$—, —CH$_2$O—, —OCH$_2$—, —CF$_2$O—, —OCF$_2$—, —CH=CH—, —CF=CF— or —C≡C—; and still further preferably a single bond, —(CH$_2$)$_2$—, —CH$_2$O—, —OCH$_2$— or —CH=CH—.

Then, m, n, q and r are independently 0 or 1, and a sum of m, n, q and r is 2, 3 or 4.

When m, n, q or r is 2, two pieces of -A$^i$-Z$^i$-(i is 1, 2, 3 or 4.) may be identical or different. When MG$^1$ or MG$^2$ in formula (1) has a bicyclic ring or a tricyclic ring, the viscosity is small. When MG$^1$ or MG$^2$ in formula (1) has a tricyclic ring or a tetracyclic ring, the maximum temperature is high.

In formula (IV), Rd is fluorine, chlorine, alkyl having 1 to 10 carbons, straight-chain alkenyl having 2 to 10 carbons, straight-chain alkoxy having 1 to 9 carbons, straight-chain alkoxyalkyl having 2 to 9 carbons, straight-chain alkenyloxy having 3 to 9 carbons, straight-chain polyfluoroalkyl having 1 to 10 carbons, straight-chain polyfluoroalkoxy having 1 to 9 carbons or straight-chain polyfluoroalkenyl having 2 to 10 carbons;

$A^1$, $A^2$, $A^3$ and $A^4$ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and at least one piece of hydrogen may be replaced by fluorine, chlorine, —CF$_3$ or —CHF$_2$; and $Z^1$, $Z^2$ and $Z^4$ are independently a single bond, —(CH$_2$)$_2$—, —COO—, —OCO—, —CH$_2$O—, —OCH$_2$—, —CF$_2$O—, —OCF$_2$—, —CH=CH—, —CF=CF—, —C≡C—, —CH$_2$CO—, —COCH$_2$—, —CH$_2$SiH$_2$—, —SiH$_2$CH$_2$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O—, —O(CH$_2$)$_3$— or —(CH$_2$)$_4$—.

In formula (1), $Z^a$ and $Z^b$ are independently a single bond, —COO—, —OCO—, —CH$_2$O—, —OCH$_2$—, —CF$_2$O—, —OCF$_2$—, —CH=CH—, —CF=CF—, —C≡C—, —CH$_2$CO—, —COCH$_2$—, —CH$_2$SiH$_2$— or —SiH$_2$CH$_2$—;

in formula (2), α is straight-chain alkylene having 1 to 10 carbons, and in the α, at least one piece of —(CH$_2$)$_2$— may be replaced by —CH=CH— or —C≡C—, and at least one piece of hydrogen may be replaced by fluorine;

in formula (I), Ra is a hydroxyl group or alkyl having 1 to 5 carbons, alkenyl having 2 to 5 carbons, alkoxy having 1 to 4 carbons, alkoxyalkyl having 2 to 4 carbons, alkenyloxy having 3 to 4 carbons, polyfluoroalkyl having 1 to 5 carbons, polyfluoroalkoxy having 1 to 4 carbons or polyfluoroalkenyl having 2 to 5 carbons;

in formula (II), Rb and Rc are each independently fluorine, alkyl having 1 to 5 carbons, alkenyl having 2 to 5 carbons, alkoxy having 1 to 4 carbons, alkoxyalkyl having 2 to 4 carbons, alkenyloxy having 3 to 4 carbons, polyfluoroalkyl having 1 to 5 carbons, polyfluoroalkoxy having 1 to 4 carbons or polyfluoroalkenyl having 2 to 5 carbons; and in formula (III), Q is an oxygen atom or alkylidene having 1 to 5 carbons.

In formula (1), $Z^a$ and $Z^b$ are independently a single bond, —COO—, —OCO—, —CH$_2$O—, —OCH$_2$—, —CF$_2$O—, —OCF$_2$—, —CH=CH—, —CF=CF— or —C≡C—;

in formula (sp-1), a is straight-chain alkylene having 1 to 10 carbons;

in formula (I), Ra is alkyl having 1 to 5 carbons, alkenyl having 2 to 5 carbons or polyfluoroalkyl having 1 to 5 carbons;

in formula (II), Rb and Rc are each independently fluorine, alkyl having 1 to 5 carbons, alkenyl having 2 to 5 carbons or polyfluoroalkyl having 1 to 5 carbons; and in formula (III), Q is an oxygen atom or alkylidene having 1 to 3 carbons.

In formula (1), preferred MG$^1$ and MG$^2$ are represented by formula (IV-1).

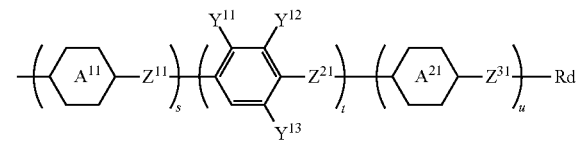

(IV-1)

In which, Rd is independently —CN, —NCS, —SF$_5$, fluorine, chlorine, straight-chain alkyl having 1 to 6 carbons, straight-chain alkenyl having 2 to 6 carbons, straight-chain alkoxy having 1 to 5 carbons, straight-chain polyfluoroalkyl having 1 to 6 carbons, straight-chain polyfluoroalkoxy having 1 to 5 carbons or straight-chain polyfluoroalkenyl having 2 to 6 carbons;

$A^{11}$ and $A^{12}$ are 1,4-cyclohexylene or 1,4-phenylene;

$Y^{11}$, $Y^{12}$ and $Y^{13}$ are independently hydrogen, fluorine, —CF$_3$ or —CF$_2$H;

$Z^1$, $Z^2$ and $Z^4$ are independently a single bond, —(CH$_2$)$_2$—, —CH$_2$O—, —OCH$_2$—, —CF$_2$O—, —OCF$_2$—, —CH=CH—, —CF=CF— or —C≡C—; and s, t and u are independently 0, 1 or 2, and a sum of s, t and u is 2, 3 and 4, in which t is 1 without exception.

Each formula described above corresponds to a case where, in formula (IV), $A^1$ to $A^4$ are 1,4-cyclohexylene, 1,4-phenylene or a group represented by formula (Ph), respectively.

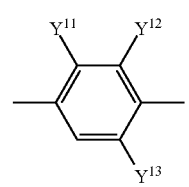

(Ph)

When s, t or u is 2, two pieces of -A$^{i1}$-Z$^{i1}$— or -Ph-Z$^{i1}$-(i is 1, 2 or 3.) may be identical or different.

In order to obtain a bimesogenic liquid crystal compound having a large positive value of dielectric anisotropy, Rd is fluorine, straight-chain alkyl having 1 to 7 carbons, straight-chain alkenyl having 2 to 7 carbons, —CN, —NCS, —SF$_5$, —CF$_3$, —C$_2$F$_5$ or —OCF$_3$; $Z^1$, $Z^2$, $Z^3$ and $Z^4$ are each independently a single bond, —(CH$_2$)$_2$—, —CF$_2$O—, —OCF$_2$— or —CH=CH—; and $Y^{12}$ or $Y^{13}$ is preferably fluorine. Moreover, in the bimesogenic liquid crystal compound having the large positive value of dielectric anisotropy, $Y^{11}$ or $Y^{12}$ is preferably fluorine in order to obtain a compound containing a large perpendicular component of dielectric anisotropy.

In order to obtain a liquid crystal compound having a further larger positive value of dielectric anisotropy, both $Y^{12}$ and $Y^{13}$ are preferably fluorine in the group represented by formula (Ph).

In order to obtain a bimesogenic liquid crystal compound having a large negative value of dielectric anisotropy, Rd is straight-chain alkyl having 1 to 7 carbons, straight-chain alkenyl having 2 to 7 carbons or straight-chain alkoxy having 1 to 6 carbons; $Z^1$, $Z^2$, $Z^4$ and $Z^5$ are each independently a single bond, —$(CH_2)_2$—, —$CH_2O$—, —$OCH_2$— or —CH=CH—; and in a group represented by formula (Ph), $Y^{11}$ and $Y^{12}$ are each independently preferably hydrogen, fluorine, —$CF_3$ or —$CF_2H$.

In order to obtain a liquid crystal compound having a large negative value of dielectric anisotropy, in the group represented by formula (Ph), $Y^{11}$ and $Y^{13}$ are independently further preferably fluorine or —$CF_3$.

Synthesis of Bimesogenic Compound

Bimesogenic compound (1) of the invention can be prepared by suitably combining techniques in synthetic organic chemistry. Methods for introducing an objective terminal group, ring and bonding group into a starting material are described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course" (Shin Jikken Kagaku Koza in Japanese) (Maruzen Co., Ltd.).

With regard to one example of a method for forming bonding groups $Z^1$, $Z^2$ or $Z^3$ in formula (IV), a scheme is first shown, and each scheme will be next described in sections (I) to (XI). Other bonding groups can also be easily formed according to the method of synthetic organic chemistry.

In the scheme, $MSG^1$ or $MSG^2$ is a monovalent organic group having at least one ring. Organic groups represented by a plurality of $MSG^1$ or $MSG^2$ may be identical or different. Compounds (1A) to (1K) correspond to compound (1).

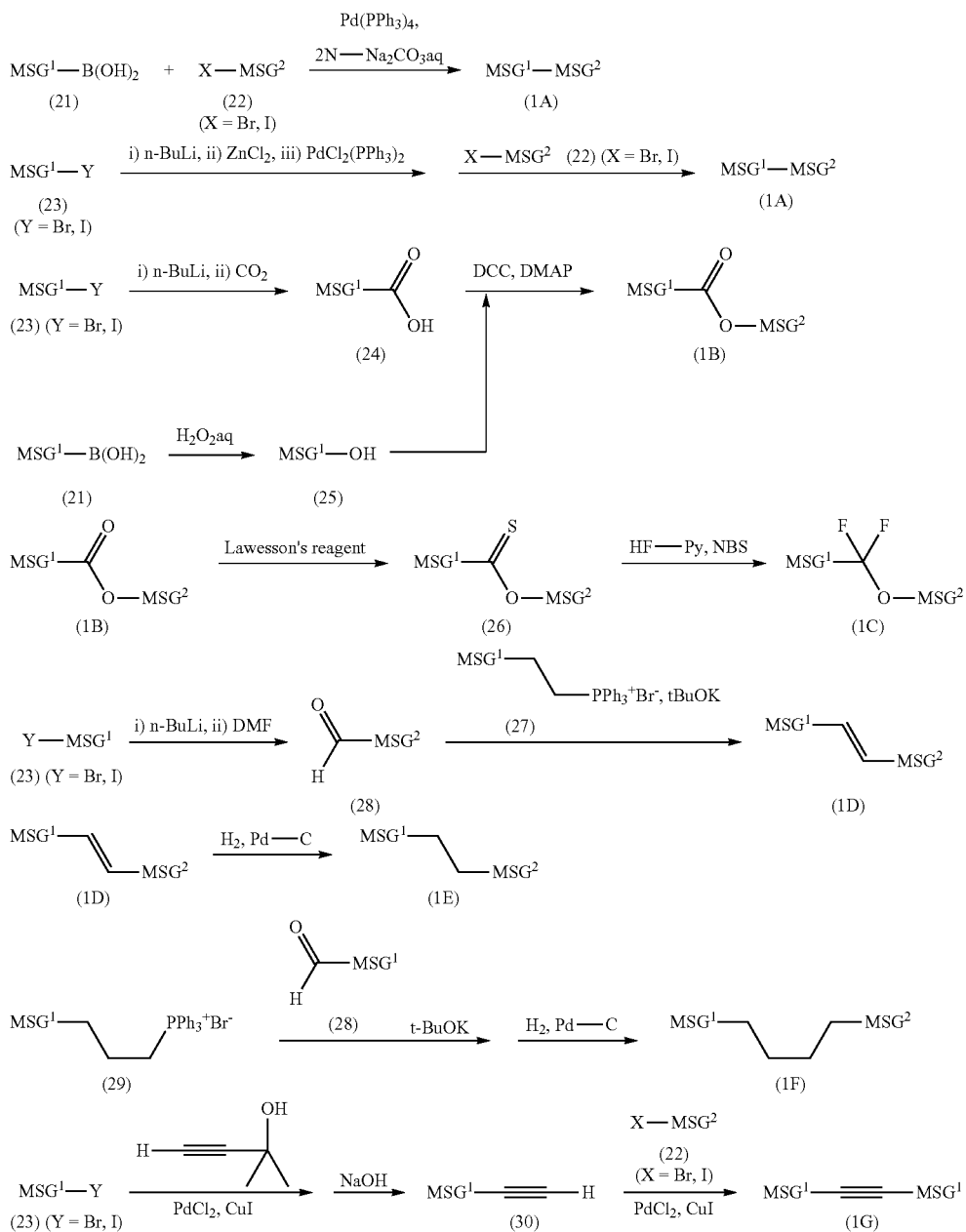

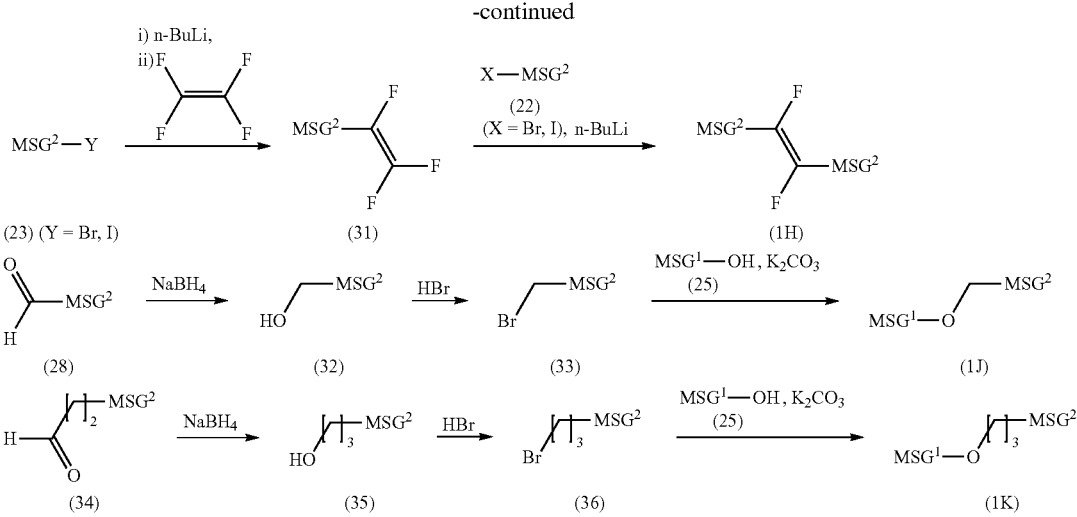

(I) Formation of a Single Bond

Compound (1A) is prepared by allowing aryl boronic acid (21) to react with compound (22) prepared according to a publicly known method, in the presence of an aqueous solution of carbonate and a catalyst such as tetrakis(triphenylphosphine)palladium.

Moreover, compound (1A) can also be prepared by allowing compound (23) prepared according to a publicly known method to react with n-butyllithium and subsequently with zinc chloride, and further with compound (22) in the presence of a catalyst such as dichlorobis(triphenylphosphine)palladium.

(II) Formation of —COO— and —OCO—

Carboxylic acid (24) is obtained by allowing compound (23) to react with n-butyllithium and subsequently with carbon dioxide. Compound (1B) having —COO— is prepared by dehydration of phenol (25) prepared according to a publicly known method and carboxylic acid (24) in the presence of 1,3-dicyclohexylcarbodiimide (DCC) and 4-dimethylaminopyridine (DMAP). A compound having —OCO— can also be prepared by the method.

(III) Formation of —CF$_2$O— and —OCF$_2$—

Compound (26) is obtained by treating compound (1B) with a thiation reagent such as Lawesson's reagent. Compound (1C) having —CF$_2$O— is prepared by fluorinating compound (26) with a hydrogen fluoride-pyridine complex and N-bromosuccinimide (NBS). Refer to M. Kuroboshi et al., Chem. Lett., 1992, 827. Compound (1C) can also be prepared by fluorinating compound (26) with (diethylamino)sulfur trifluoride (DAST). Refer to W. H. Bunnelle et al., J. Org. Chem. 1990, 55, 768. A compound having —OCF$_2$— can also be prepared by the method. The bonding groups described above can also be formed according to a method described in Peer. Kirsch et al., Angew. Chem. Int. Ed. 2001, 40, 1480.

(IV) Formation of —CH═CH—

Aldehyde (28) is obtained by treating compound (23) with n-butyllithium and then allowing the treated compound to react with formamide such as N,N-dimethylformamide (DMF). Compound (1D) is prepared by allowing phosphorus ylide generated by treating phosphonium salt (27) prepared according to a publicly known method with a base such as potassium tert-butoxide to react with aldehyde (28). A cis isomer may be formed depending on reaction conditions, and therefore the cis isomer is isomerized into a trans isomer according to a publicly known method when necessary.

(V) Formation of —(CH$_2$)$_2$—

Compound (1E) is prepared by hydrogenating compound (1D) in the presence of a catalyst such as palladium on carbon.

(VI) Formation of —(CH$_2$)$_4$—

A compound having —(CH$_2$)$_2$—CH═CH— is obtained by using phosphonium salt (29) in place of phosphonium salt (27) according to the method in section (IV). Compound (1F) is prepared by performing catalytic hydrogenation of the compound obtained.

(VII) Formation of —C≡C—

Compound (30) is obtained by allowing compound (23) to react with 2-methyl-3-butyn-2-ol in the presence of a catalyst including dichloropalladium and copper halide, and then performing deprotection under basic conditions. Compound (1G) is prepared by allowing compound (30) to react with compound (22) in the presence of the catalyst including dichloropalladium and copper halide.

(VIII) Formation of —CF═CF—.

Compound (31) is obtained by treating compound (23) with n-butyllithium, and then allowing the treated compound to react with tetrafluoroethylene. Compound (1H) is prepared by treating compound (22) with n-butyllithium, and then allowing the treated compound to react with compound (31).

(IX) Formation of —CH$_2$O— or —OCH$_2$—

Compound (32) is obtained by reducing compound (28) with a reducing agent such as sodium borohydride. Compound (33) is obtained by brominating compound (32) with hydrobromic acid or the like. Compound (1J) is prepared by allowing compound (33) to react with compound (25) in the presence of a material such as potassium carbonate.

(X) Formation of —(CH$_2$)$_3$O— or —O(CH$_2$)$_3$—

Compound (1K) is prepared by using compound (34) in place of compound (28) according to the method in section (IX).

(XI) Formation of —(CF$_2$)$_2$—

A compound having —(CF$_2$)$_2$— is obtained by fluorinating diketone (—COCO—) with sulfur tetrafluoride, in the presence of a hydrogen fluoride catalyst, according to a method described in J. Am. Chem. Soc., 2001, 123, 5414.

One example of a method for preparing compound (1) having a difluoroethyleneoxy group is shown in a scheme described below. However, the method for preparing compound (1) of the invention is not limited by the scheme described below.

Next, a synthesis method regarding to rings $A^1$ to $A^3$ will be described. A starting material is commercially available or a synthesis method is well known with regard to a ring such as 1,4-cyclohexylene, 1,3-dioxane-2,5-diyl, 1,4-phenylene, 2-fluoro-1,4-phenylene, 2,3-difluoro-1,4-phenylene, pyridine-2,5-diyl and pyrimidine-2,5-diyl. Thus, a synthesis method regarding to compounds (38), (41) and (45) shown below will be described.

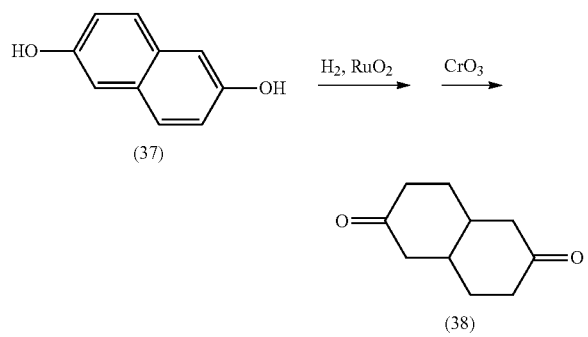

Decahydronaphthalene-2,6-dione (38) is a starting material for a compound having decahydronaphthalene-2,6-diyl. Compound (38) is prepared by performing catalytic hydrogenation with diol (37) in the presence of ruthenium oxide according to a method described in JP 2000-239564A, and subsequently oxidizing the resulting material with chromium oxide.

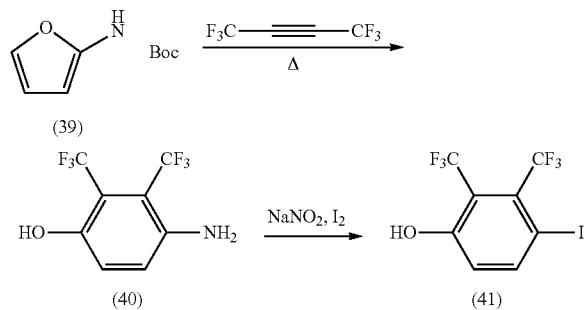

A structural unit of 2,3-(bistrifluoromethyl)phenylene is prepared according to a method described in Org. Lett., 2000, 2 (21), 3345. Aniline (40) is prepared by performing a Diels-Alder reaction between furan (39) and 1,1,1,4,4,4-hexafluoro-2-butyne at a high temperature. Iodide (41) is obtained by performing a Sandmeyer reaction to the compound obtained according to a method described in Org. Synth. Coll., Vol. 2, 1943, 355. The compound obtained is converted to compound (1) by a technique of general synthetic organic chemistry.

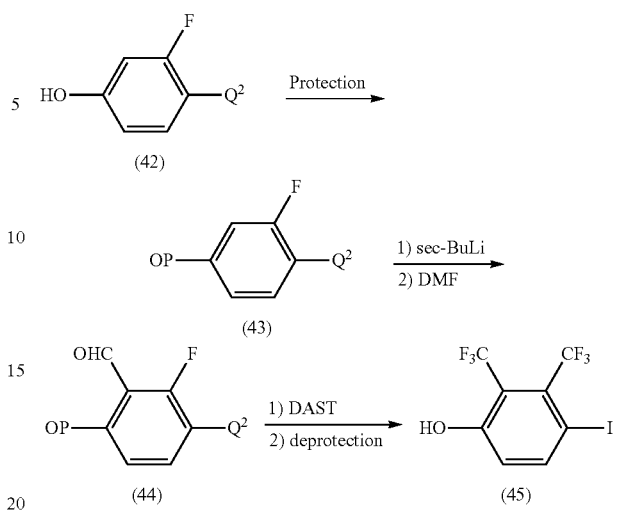

A structural unit of 2-difluoromethyl-3-fluorophenylene is prepared according a method described below. Compound (43) is obtained by protecting a hydroxyl group of compound (42) using a suitable protective group. P means a protective group. Aldehyde (44) is obtained by allowing compound (43) to act with sec-butyl lithium and subsequently allowing the obtained material to react with N,N-dimethylformamide (DMF). Phenol (45) is obtained by fluorinating the obtained compound with diethylamino sulfur trifluoride (DAST), and subsequently deprotecting the resulting material. The compound obtained is converted to compound (1) by a technique of common synthetic organic chemistry.

Next, a synthesis method regarding to Sp will be described by taking an example when $Z^1$ and $Z^2$ are —O— in formula (1), and X is a compound represented by formula (I) in formula (sp-1). First, alcohol compound (47) is obtained by acting, on magnesium, compound (46) being olefin-terminated halide corresponding to the number of carbons of a into a Grignard reagent, and subsequently acting methyl formate on the resulting material. Further, carbonyl compound (48) is obtained by acting an oxidizing agent such as Dess-Martin periodinane (DMP) on the resulting material. Diol compound (50) is obtained by acting ethylene glycol on the resulting material in the presence of an acid catalyst such as p-toluenesulfonic acid into acetal compound (49), and then acting a borane derivative such as a borane dimethylsulfide complex on the resulting material, and then acting hydrogen peroxide on the resulting material under basic conditions. Compound (51) is obtained by stepwise acting $MG^1$ and $MG^2$ each having a hydroxyl group corresponding thereto on the resulting material using triphenyl phosphine and diethyl azodicarboxylate (DEAD). Compound (1-I) is obtained by acting a Grignard reagent corresponding thereto on the resulting material into alcohol compound (52), and acting triethyl silane on the resulting material in the presence of Lewis acid such as a boron trifluoride-diethyl ether complex.

If compound (50) is used as a starting material and a publicly-known technique of synthetic organic chemistry is applied thereto, compound (1) in which X shown in formula (sp-1) has a structure shown in formula (ii) or formula (iii) can be obtained.

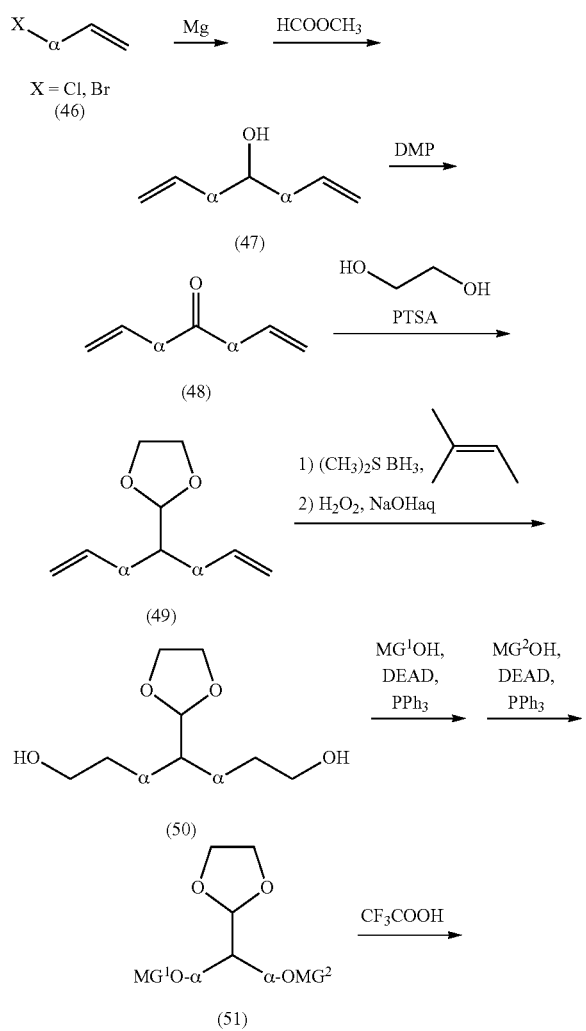

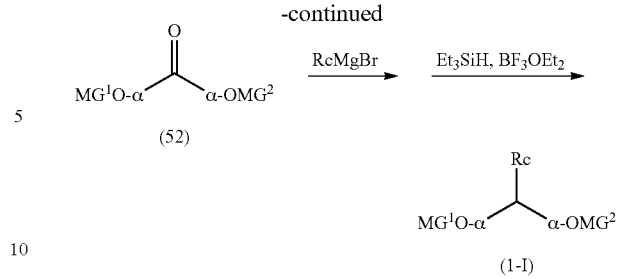

Liquid Crystal Composition

A liquid crystal composition of the invention contains bimesogenic compound (1) described above as component A. The liquid crystal composition of the invention may contain only one kind of bimesogenic compound (1), and may also contain two or more kinds of bimesogenic compounds (1). Moreover, in addition to bimesogenic compound (1), a bimesogen represented by formula (cp-1) may be contained therein.

Specific preferred examples of compound (cp-1) include compounds (cp-1-1) to (cp-1-12). $R^{31}$ and $R^{32}$ are each independently fluorine, chlorine, —CN, —NCS, —SF$_5$ or alkyl having 1 to 10 carbons, and in the alkyl, at least one piece of —CH$_2$— may be replaced by —O—, and at least one piece of —(CH$_2$)$_2$— may be replaced by —CH=CH— or —C≡C—; $Z^{31}$, $Z^{32}$ and $Z^4$ are independently a single bond, —(CH$_2$)$_2$—, —COO—, —OCO—, —CH$_2$O—, —OCH$_2$—, —CF$_2$O—, —OCF$_2$—, —CH=CH—, —CF=CF—, —C≡C—, —CH$_2$CO—, —COCH$_2$—, —CH$_2$SiH$_2$—, —SiH$_2$CH$_2$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O—, —O(CH$_2$)$_3$— or —(CH$_2$)$_4$—; r is 4 to 20; $Z^{3a}$ and $Z^{3b}$ are independently —O—, —S—, —OCO—, —S—CO—, —O—COO—, —CO—S—, —CO—O—, —CH=CH— or —C≡C—; and L is F, Cl or alkyl having 1 to 2 carbons which may be fluorinated, and r is independently 0, 1 or 2 every time when r appears.

(cp-1-1)

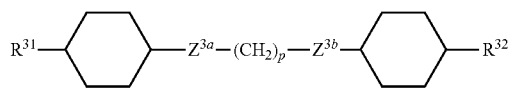

(cp-1-2)

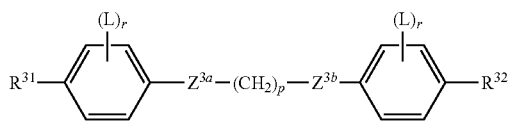

(cp-1-3)

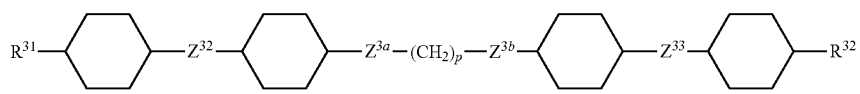

(cp-1-4)

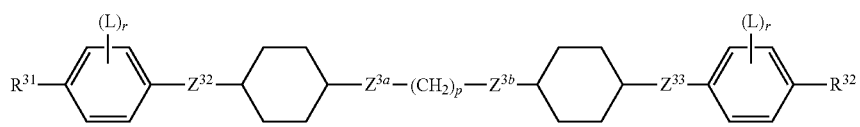

(cp-1-5)

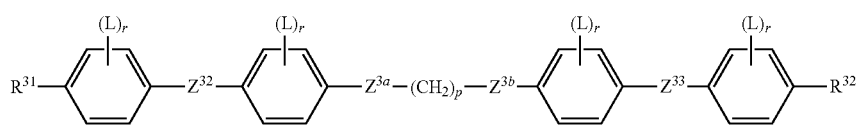

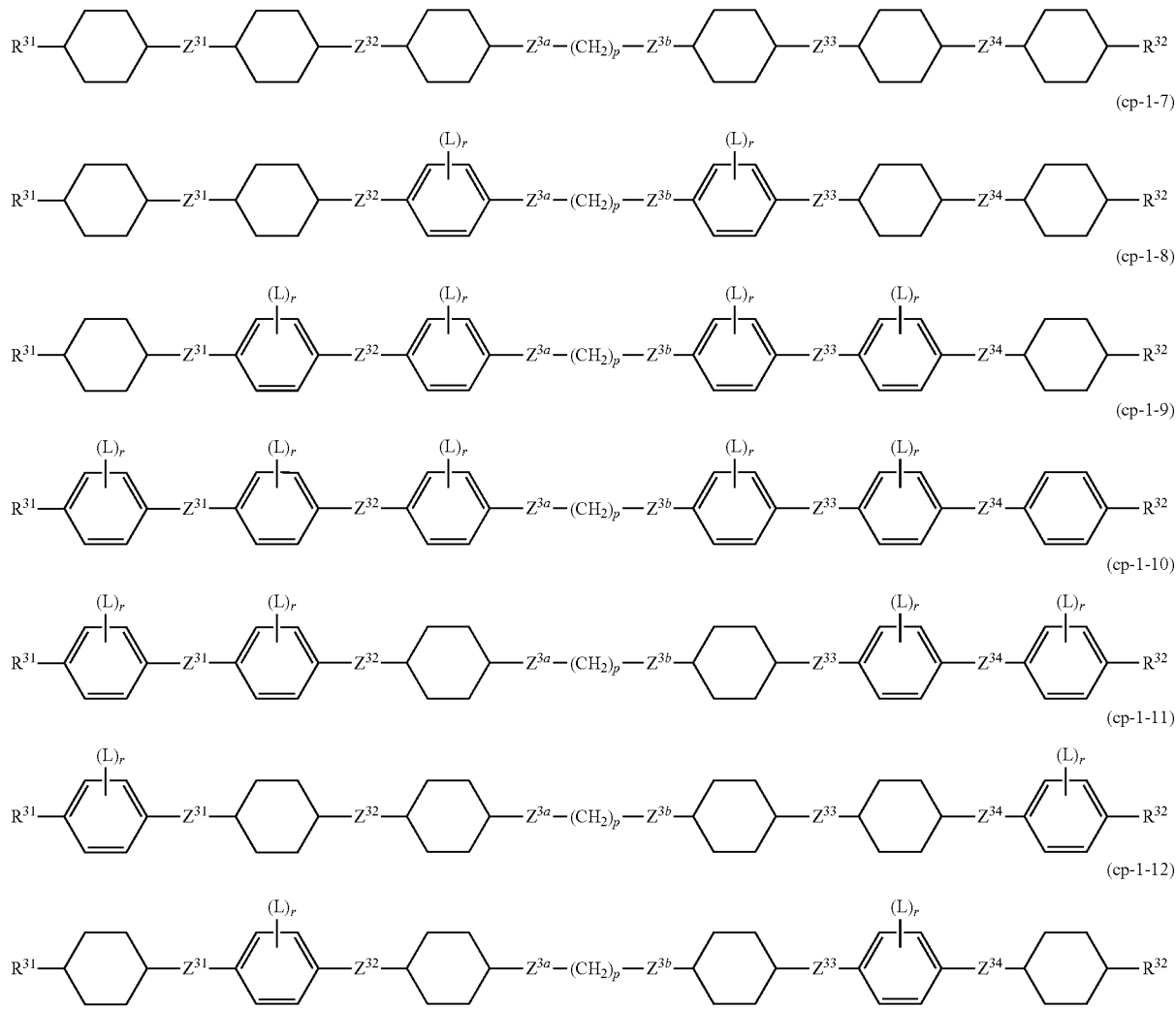

In order to develop characteristics such as threshold voltage, the temperature range of the liquid crystal phase, the optical anisotropy, the dielectric anisotropy and the viscosity in an excellent manner, the liquid crystal composition of the invention contains component A in a proportion of preferably 0.1 to 99% by weight, further preferably 1 to 99% by weight, and still further preferably 2 to 98% by weight, based on the total mass of the liquid crystal composition.

The liquid crystal composition of the invention may be a composition containing only component A, but in order to develop various characteristics, may further contain at least one kind of component selected from component B, component C, component D, component E and component F as described below.

Component B is at least one kind of compound selected from compounds represented by formulas (2) to (4) as described later; component C is a compound represented by formula (5) as described later; component D is at least one kind of compound selected from compounds represented by formulas (6) to (11) as described later; and component E is at least one kind of compound selected from compounds represented by formulas (12) to (14) as described later.

In addition, at least one kind of compound selected from the compounds represented by formula (2) to (4) means at least one kind of compound selected from the compounds represented by formula (2), by formula (3) and formula (4). A same rule applies also to other examples.

The liquid crystal composition of the invention may further contain at least one kind selected from an optically active compound and a polymerizable compound, and may further contain at least one kind selected from an antioxidant and an ultraviolet light absorber. Specific examples of the antioxidant include a phenolic antioxidant. Specific examples of the ultraviolet light absorber include a hindered amine-based light stabilizer.

Each component that composes the liquid crystal composition of the invention has no significant difference in chemical and physical characteristics, even if the component is an analog composed of an isotopic element of each element.

Component B (Compounds (2) to (4))

The liquid crystal composition of the invention may contain at least one compound selected from the compounds represented by formulas (2) to (4).

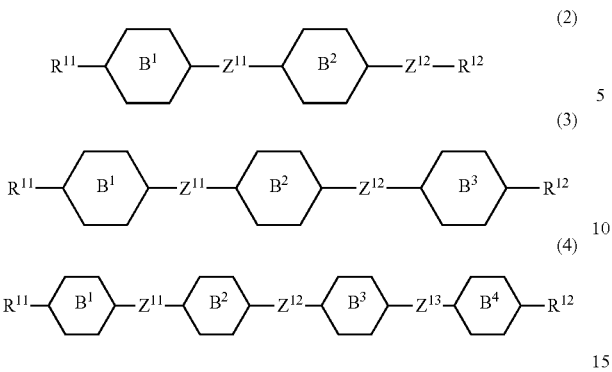

(2)

(3)

(4)

In formula (2) to formula (4), $R^{11}$ and $R^{12}$ are each independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

ring $B^1$, ring $B^2$, ring $B^3$ and ring $B^4$ are each independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are each independently a single bond, —CH$_2$CH$_2$—, —CH=CH—, —C≡C— or —COO—.

In compounds (2) to (4), two terminal groups are alkyl or the like, and the dielectric anisotropy is small. Specific preferred examples of the compounds include compounds (2-1) to (2-11), compounds (3-1) to (3-19) and compounds (4-1) to (4-7). In the compounds, $R^{11}$ and $R^{12}$ are independently alkyl having 1 to 10 carbons or alkenyl having 2 to 10 carbons, and in the alkyl or the alkenyl, at least one piece of —CH$_2$— may be replaced by —O—, and at least one piece of hydrogen may be replaced by fluorine.

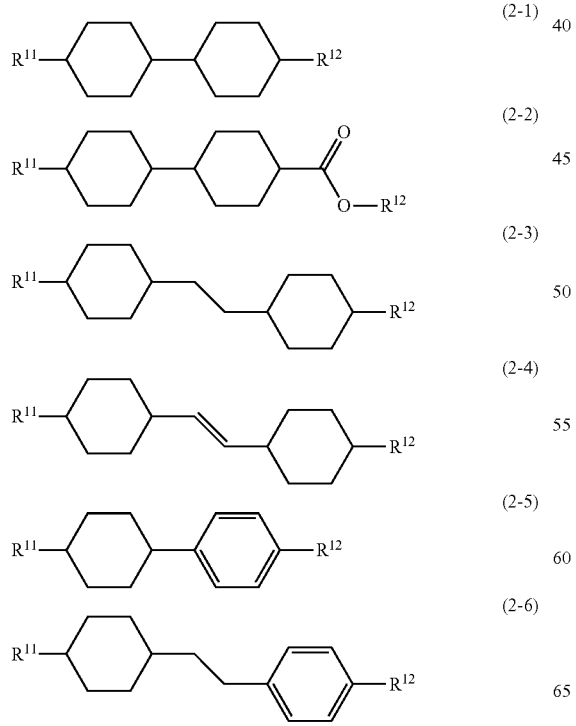

(3-8)
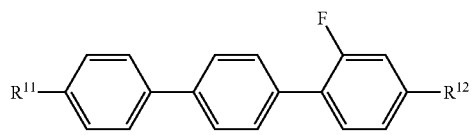

(3-9)
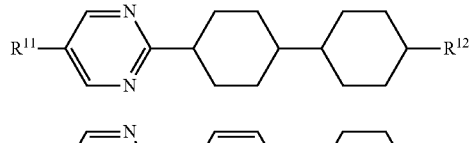

(3-10)
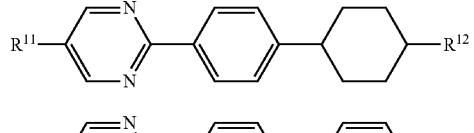

(3-11)

(3-12)
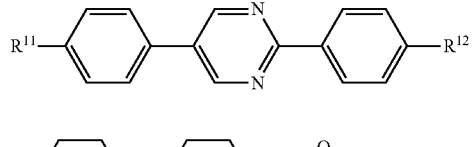

(3-13)
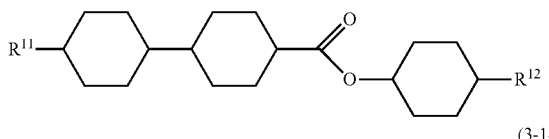

(3-14)
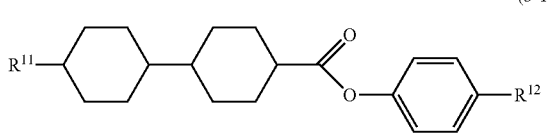

(3-15)
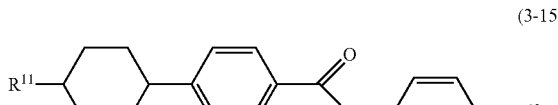

(3-16)
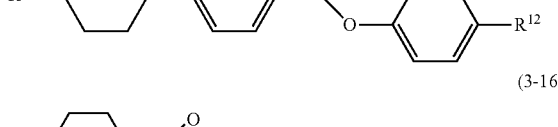

(3-17)
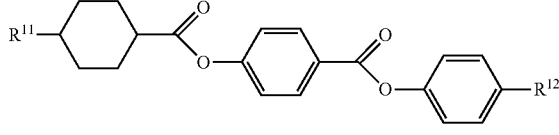

(3-18)
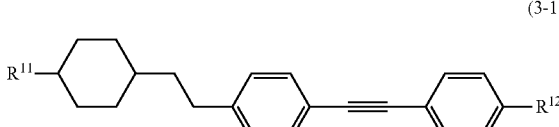

(3-19)
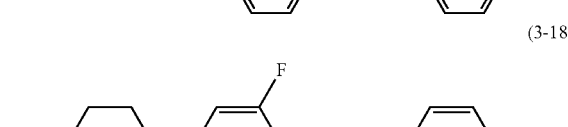

(4-1)
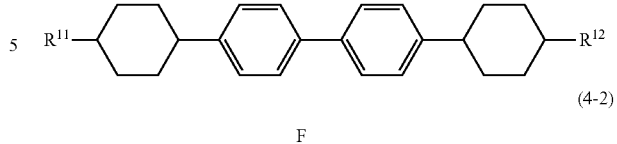

(4-2)
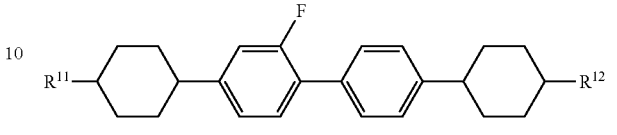

(4-3)

(4-4)
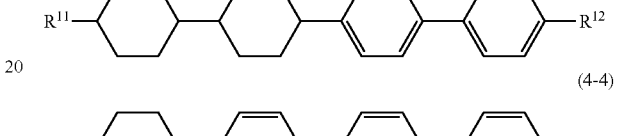

(4-5)
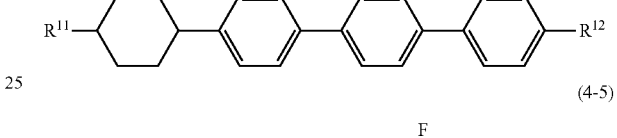

(4-6)
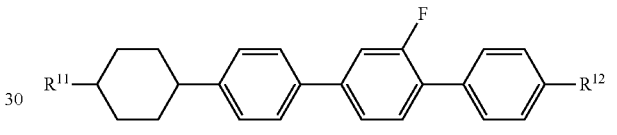

(4-7)
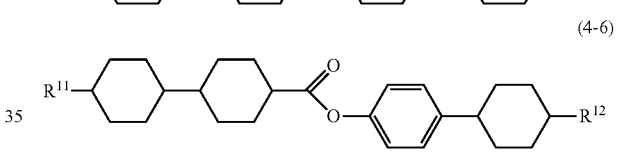

Compound (2) is mainly effective in decreasing the viscosity or adjusting the optical anisotropy. Compounds (3) and (4) are effective in extending the temperature range of the nematic phase by increasing the maximum temperature, or in adjusting the optical anisotropy.

Compounds (2) to (4) being component B have small dielectric anisotropy. As a content of compounds (2) to (4) each increases, the viscosity of the composition decreases, but the dielectric anisotropy thereof decreases. Thus, as long as a desired value of a threshold voltage of the device is met, the content is preferably as large as possible. Accordingly, when the composition for an IPS, VA or the like mode is prepared, the content of compounds (2) to (4) is preferably 30% by weight or more, and further preferably 40% by weight or more, based on the weight of the liquid crystal composition.

Component C (Compounds (5) to (7))

The liquid crystal composition of the invention may contain at least one kind of compound (component C) selected from the compounds represented by formulas (5) to (7).

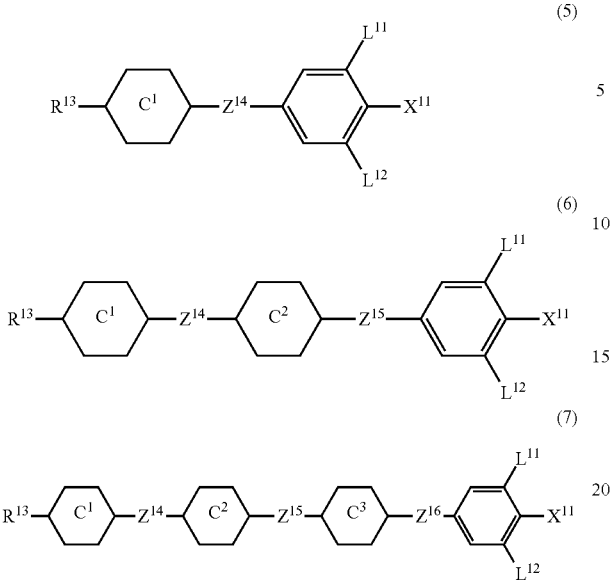

In formula (5) to formula (7), $R^{13}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are each independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are each independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are each independently hydrogen or fluorine.

Compounds (5) to (7) have halogen or a fluorine-containing group at a right terminal. Specific preferred examples of the compounds include compounds (5-1) to (5-16), compounds (6-1) to (6-113) and compounds (7-1) to (7-57). In the compounds, $R^{13}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine; and $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$.

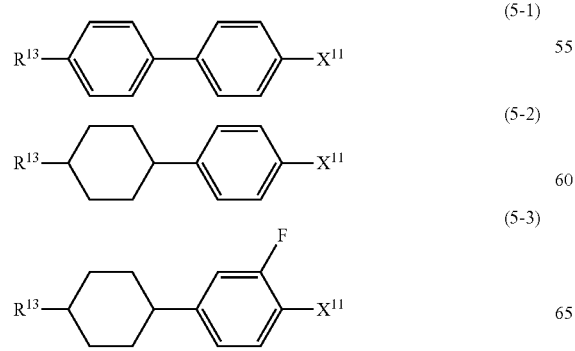

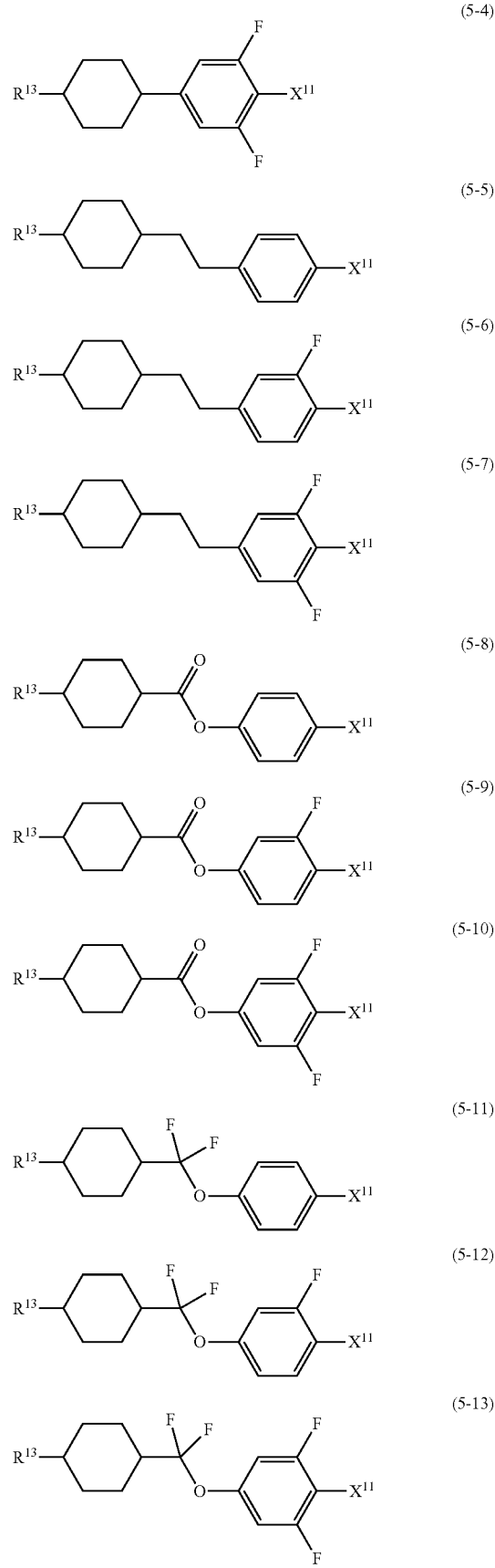

(5-14) 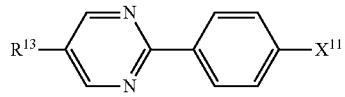
(5-15) 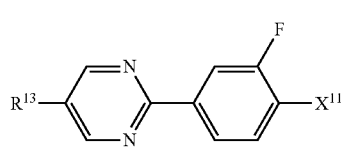
(5-16) 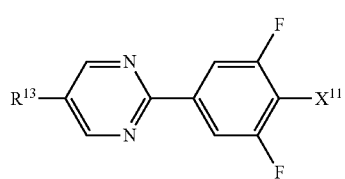
(6-1) 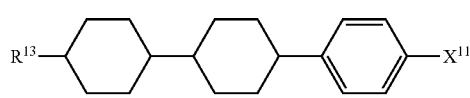
(6-2) 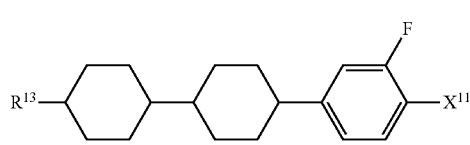
(6-3) 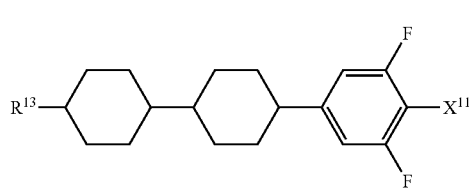
(6-4) 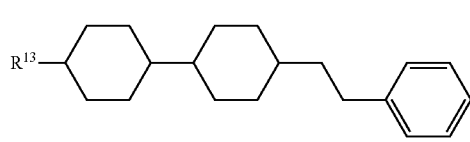
(6-5) 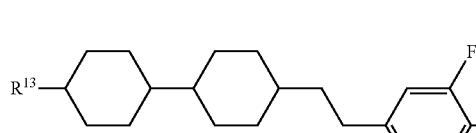
(6-6) 
(6-7) 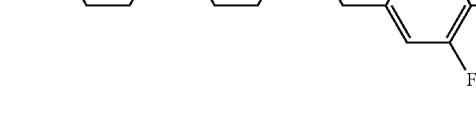
(6-8) 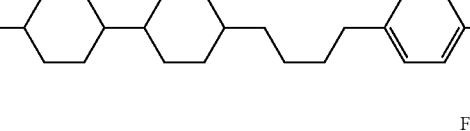
(6-9) 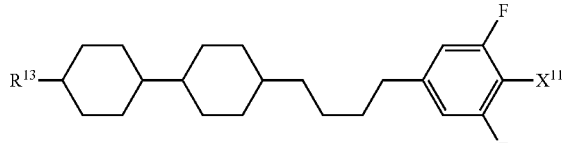
(6-10) 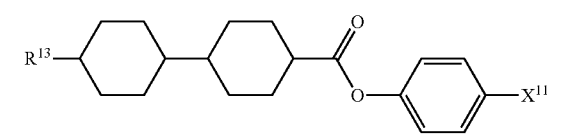
(6-11) 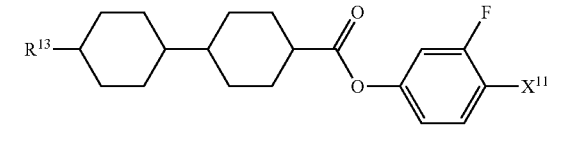
(6-12) 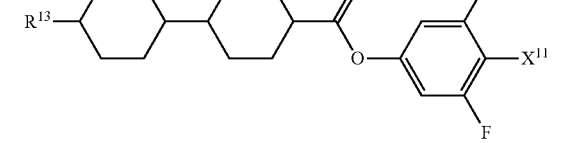
(6-13) 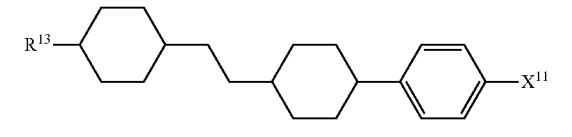
(6-14) 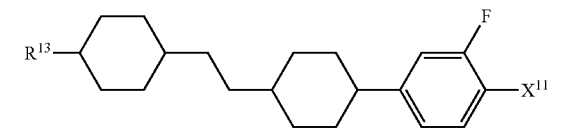
(6-15) 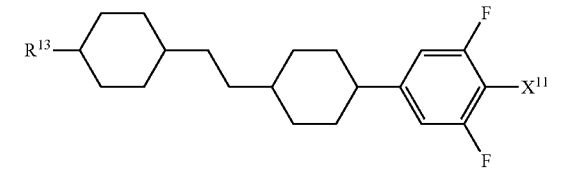
(6-16) 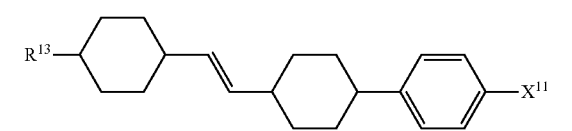
(6-17) 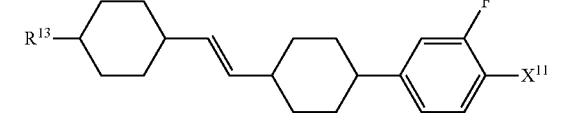

(6-18)
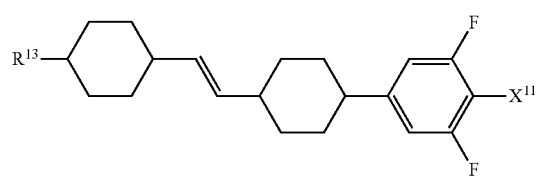
(6-19)
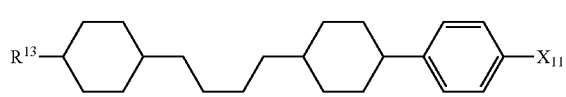
(6-20)
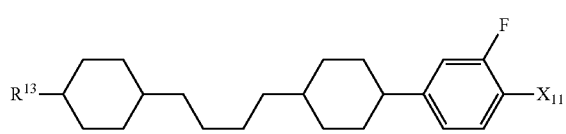
(6-21)
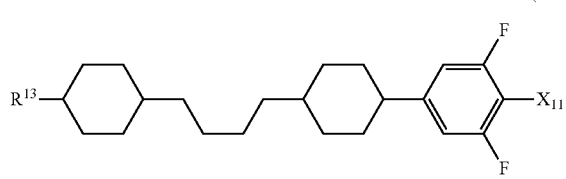
(6-22)
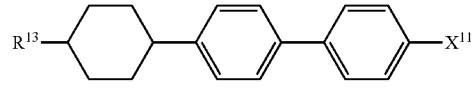
(6-23)
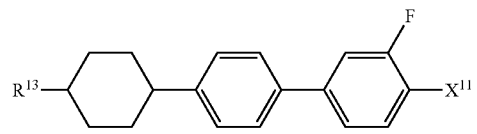
(6-24)
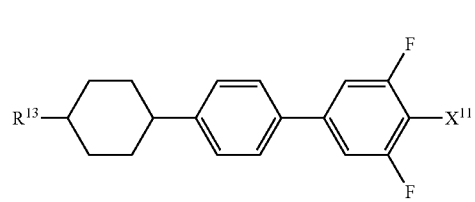
(6-25)
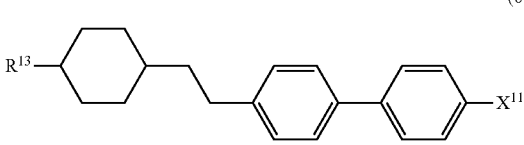
(6-26)
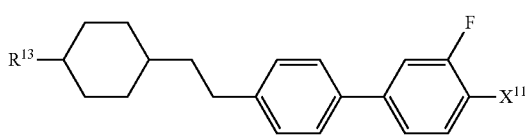
(6-27)
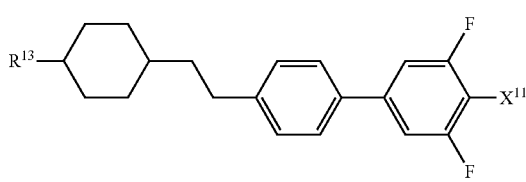
(6-28)
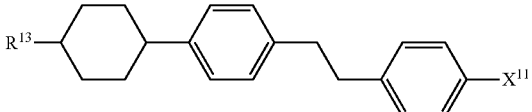
(6-29)
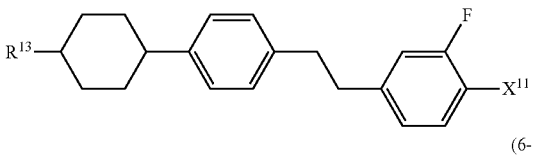
(6-30)
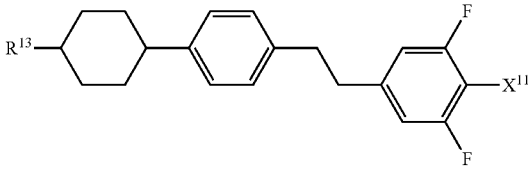
(6-31)
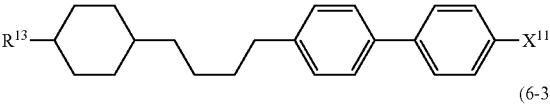
(6-32)
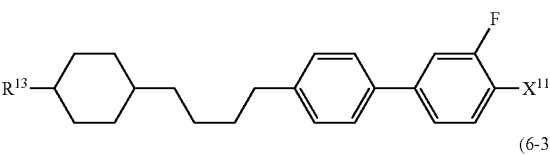
(6-33)
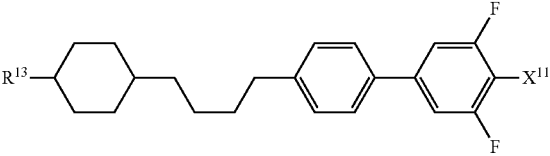
(6-34)
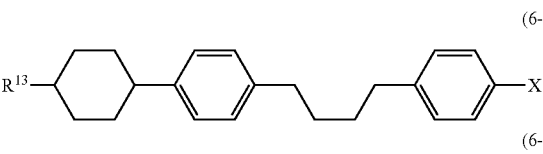
(6-35)
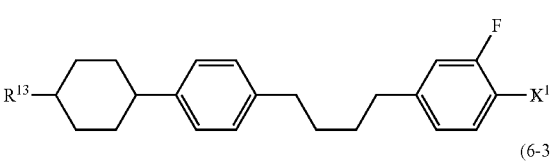
(6-36)
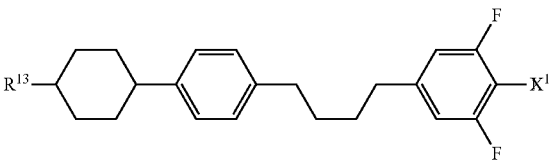

(6-37) 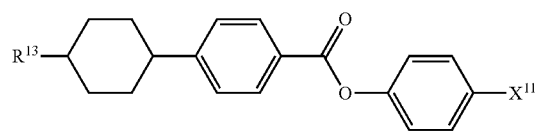
(6-38) 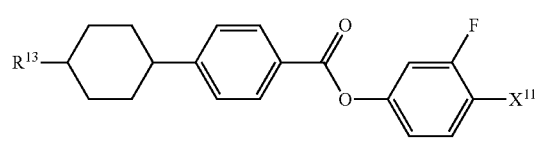
(6-39) 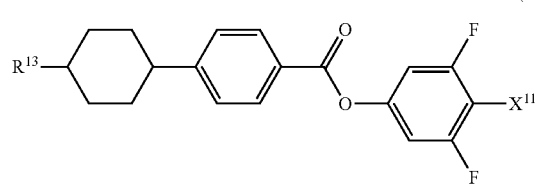
(6-40) 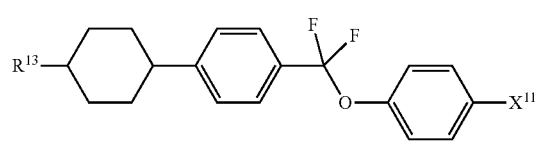
(6-41) 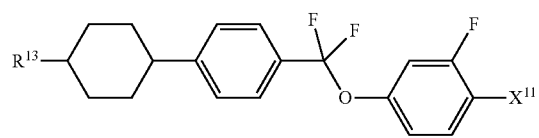
(6-42) 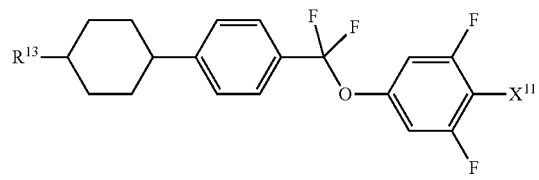
(6-43) 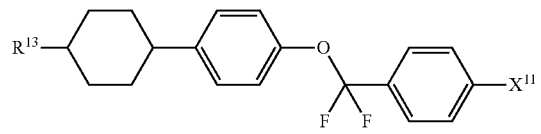
(6-44) 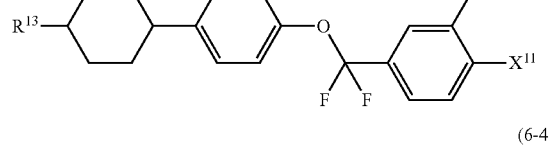
(6-45) 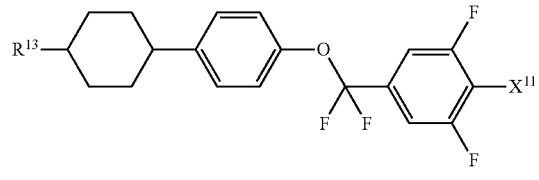
(6-46) 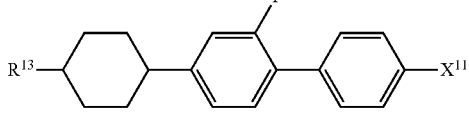
(6-47) 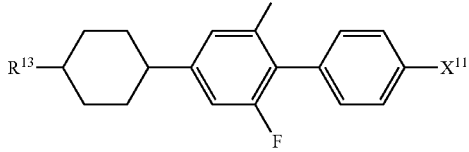
(6-48) 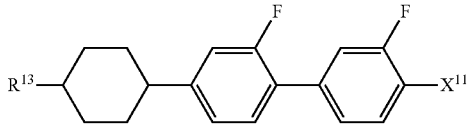
(6-49) 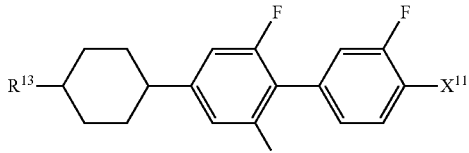
(6-50) 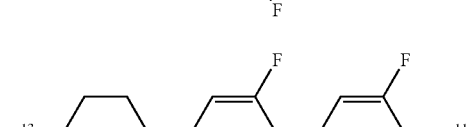
(6-51) 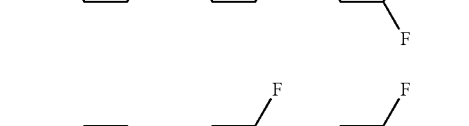
(6-52) 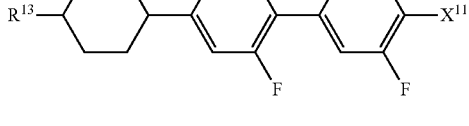
(6-53) 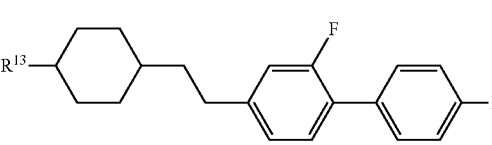
(6-54) 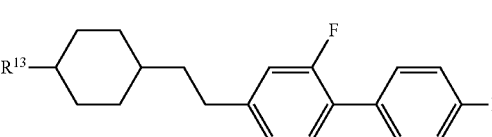

(6-55) 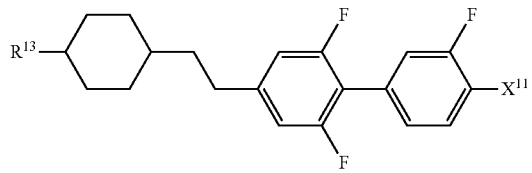
(6-56) 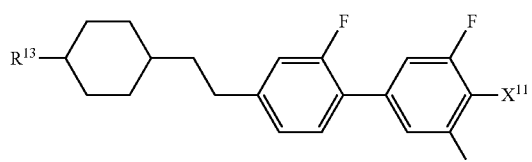
(6-57) 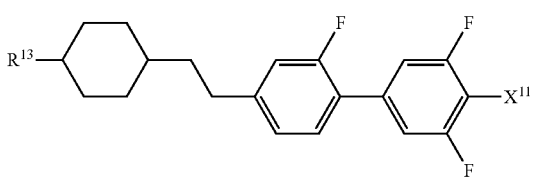
(6-58) 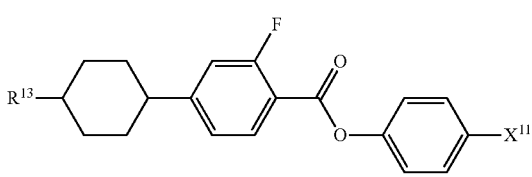
(6-59) 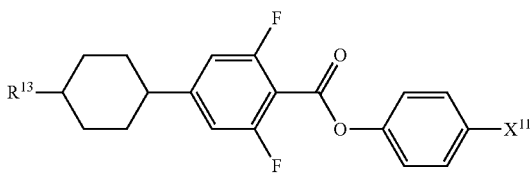
(6-60) 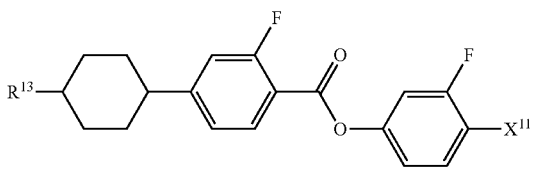
(6-61) 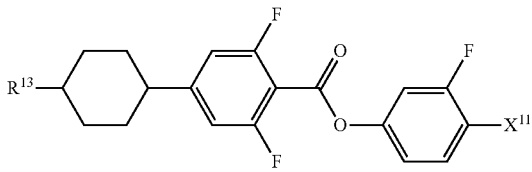
(6-62) 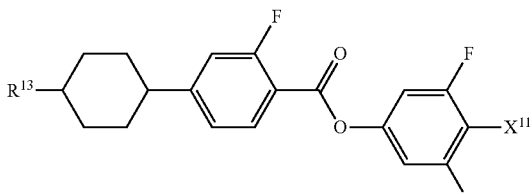
(6-63) 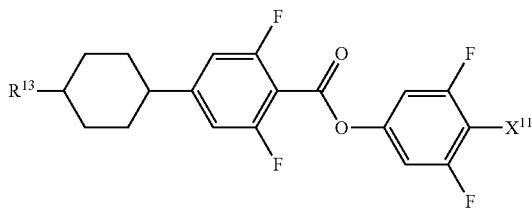
(6-64) 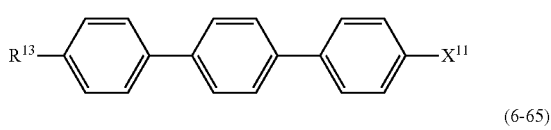
(6-65) 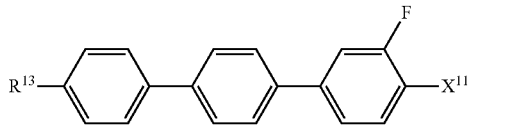
(6-66) 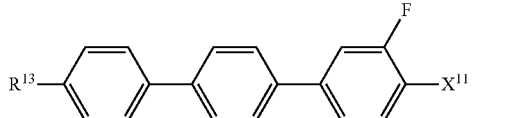
(6-67) 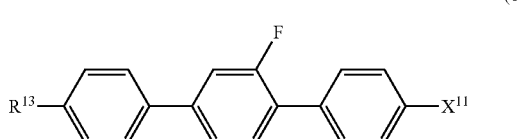
(6-68) 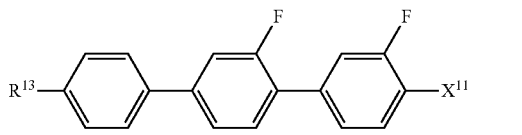
(6-69) 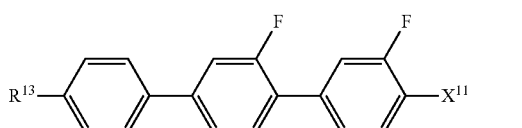
(6-70) 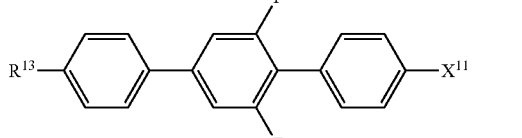
(6-71) 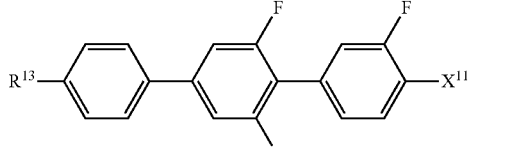

(6-72)
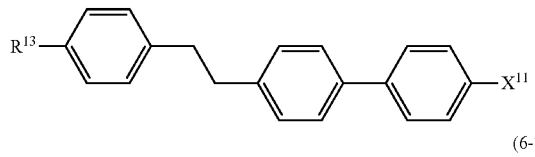
(6-73)
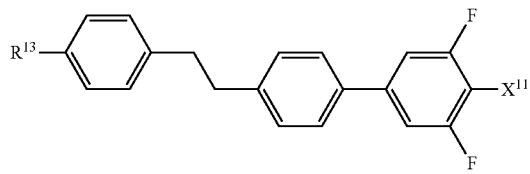
(6-74)
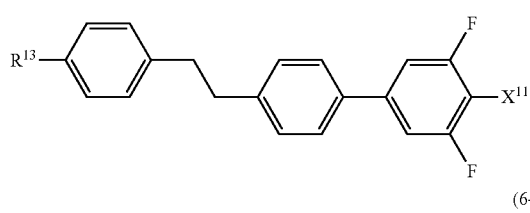
(6-75)
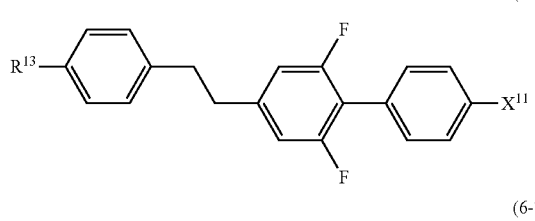
(6-76)
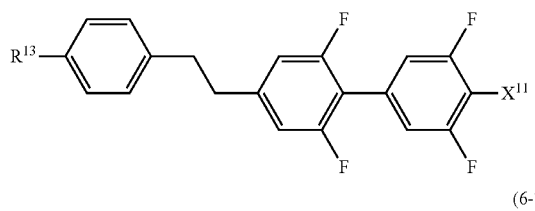
(6-77)
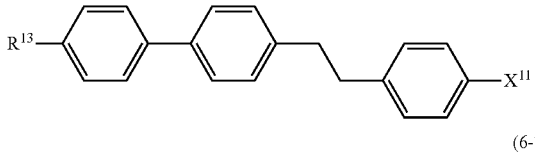
(6-78)
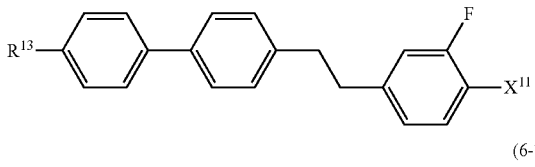
(6-79)
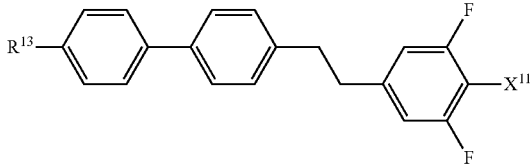
(6-80)
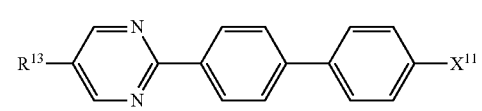
(6-81)
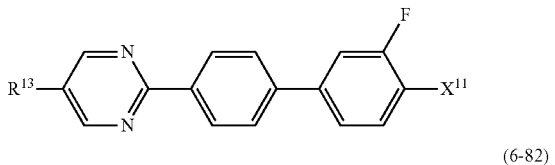
(6-82)
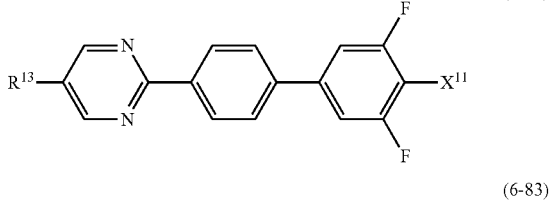
(6-83)
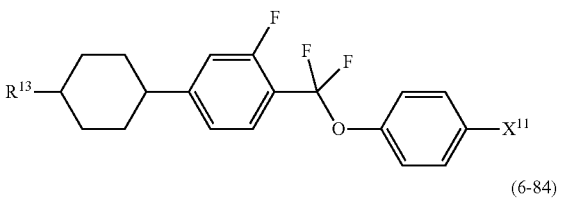
(6-84)
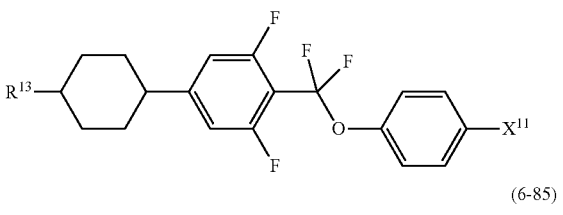
(6-85)
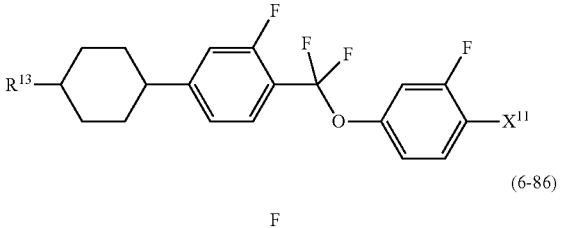
(6-86)
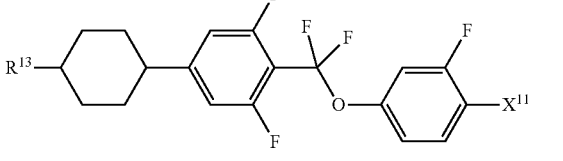
(6-87)
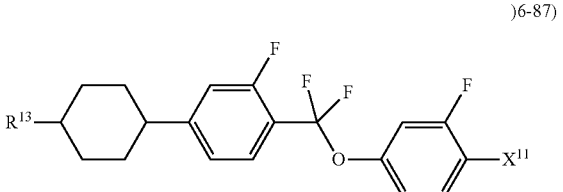
(6-88)
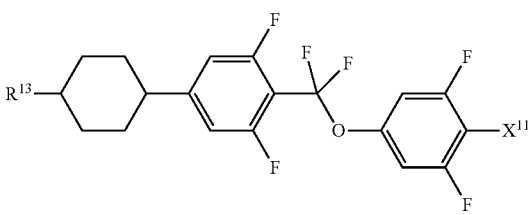

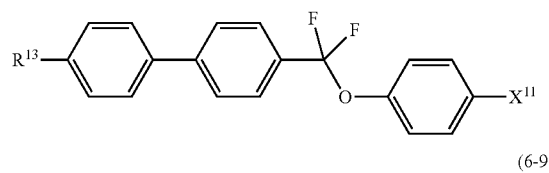
(6-89)
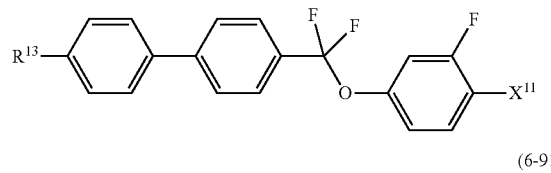
(6-90)
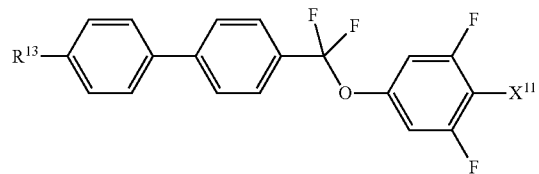
(6-91)
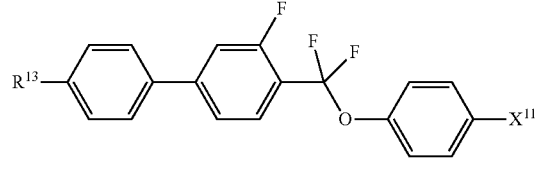
(6-92)
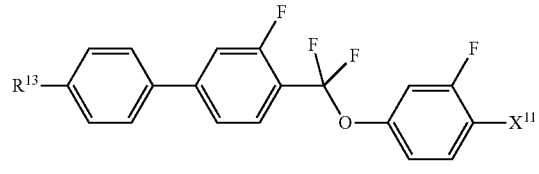
(6-93)
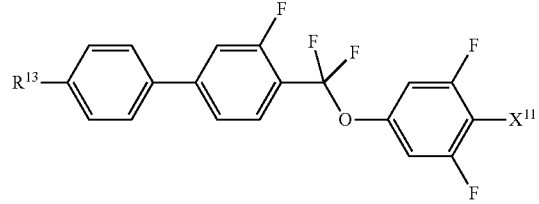
(6-94)
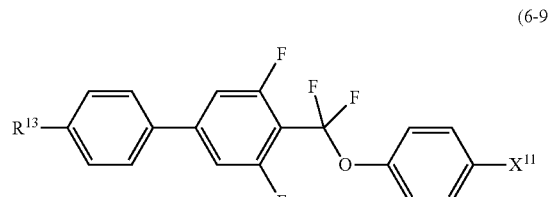
(6-95)
(6-96)
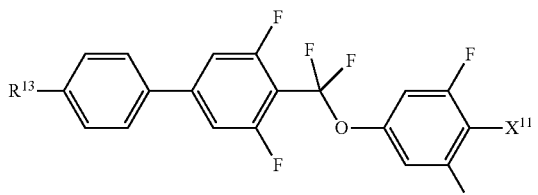
(6-97)
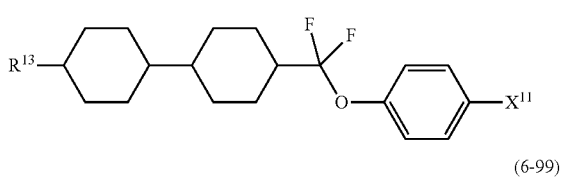
(6-98)
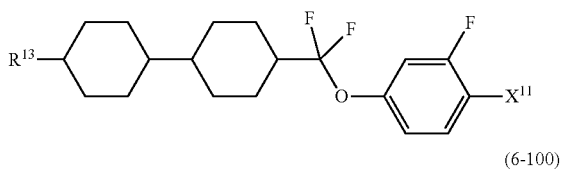
(6-99)
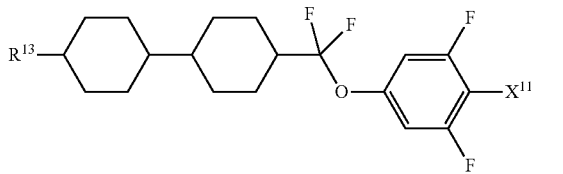
(6-100)
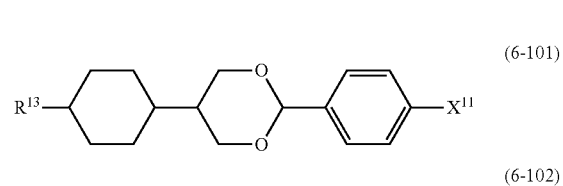
(6-101)
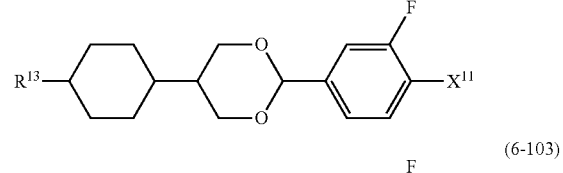
(6-102)
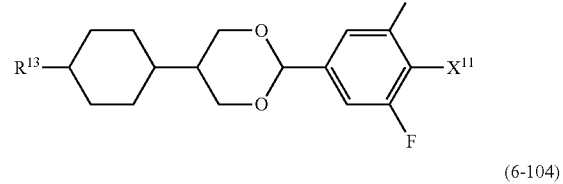
(6-103)
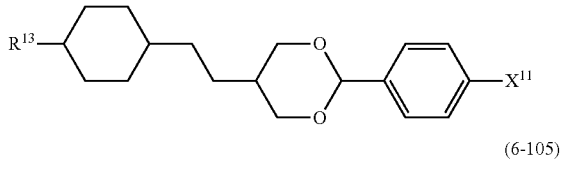
(6-104)
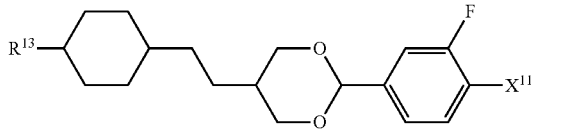
(6-105)

(6-106)
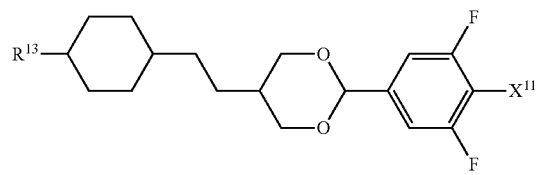
(6-107)
(6-108)
(6-109)
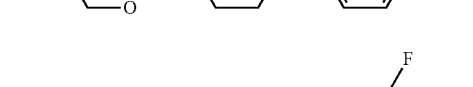
(6-110)
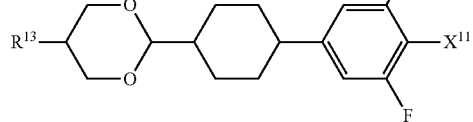
(6-111)
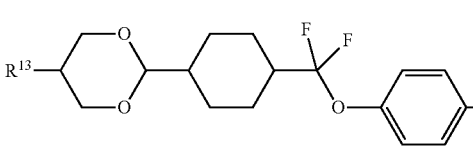
(6-112)
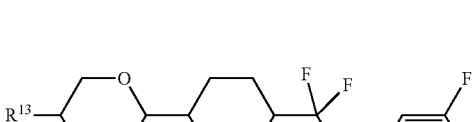
(6-113)
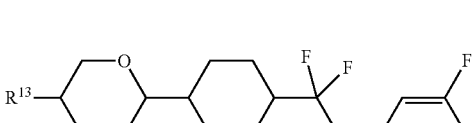
(7-1)
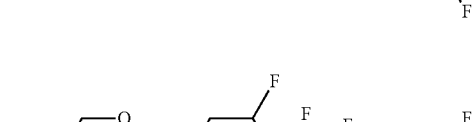
(7-2)
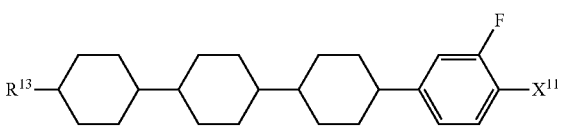
(7-3)
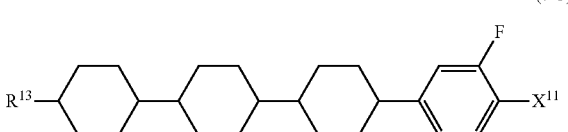
(7-4)
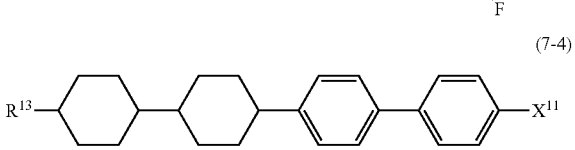
(7-5)
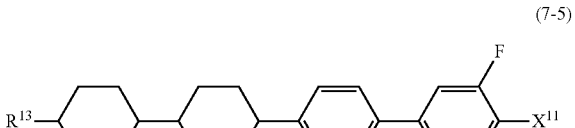
(7-6)
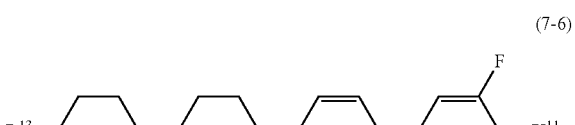
(7-7)
(7-8)
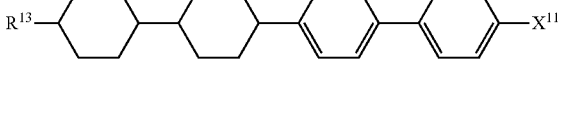
(7-9)
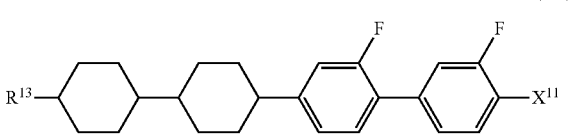
(7-10)

(7-11) through (7-29): chemical structure formulas

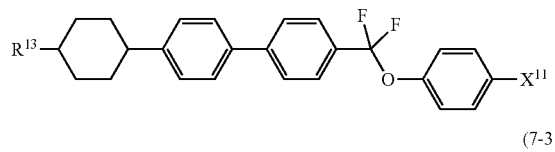
(7-30)
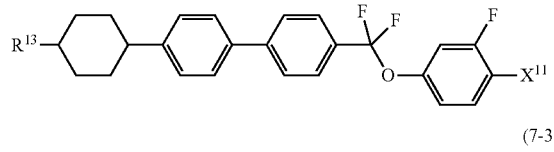
(7-31)
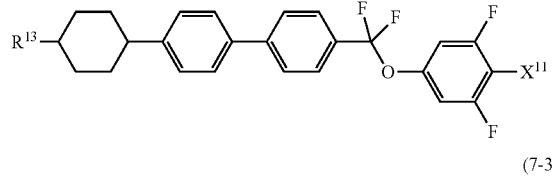
(7-32)
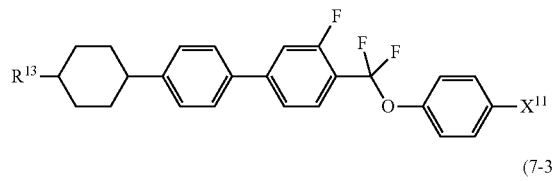
(7-33)
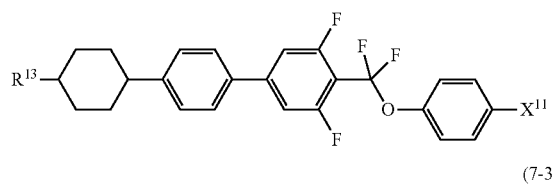
(7-34)
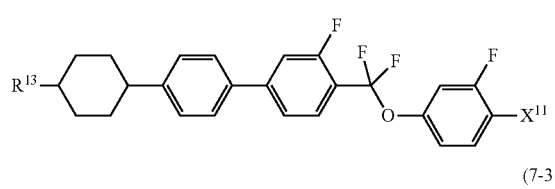
(7-35)
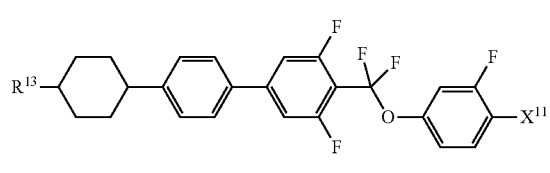
(7-36)
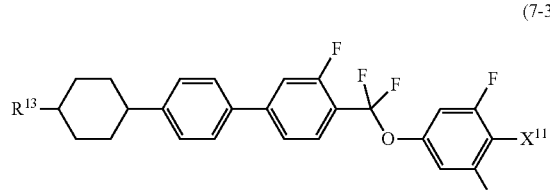
(7-37)
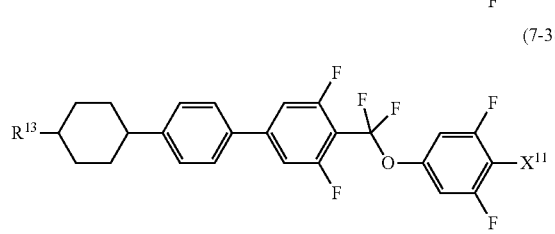
(7-38)
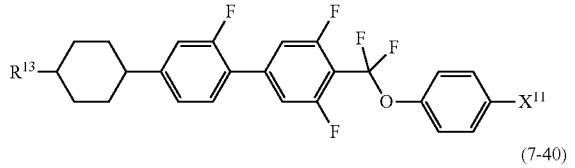
(7-39)
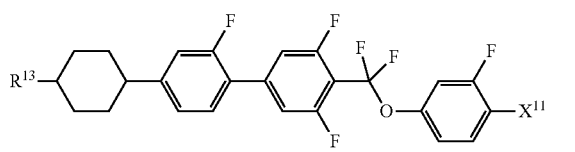
(7-40)
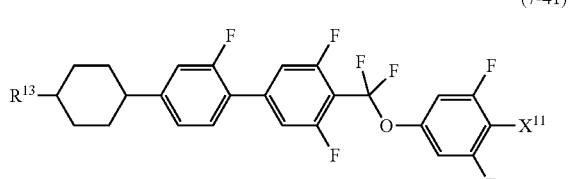
(7-41)
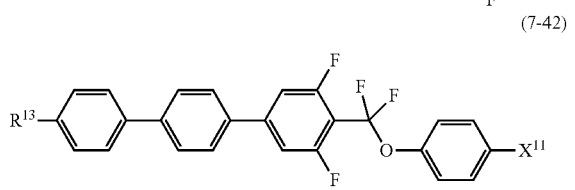
(7-42)
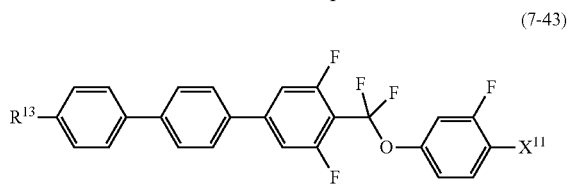
(7-43)
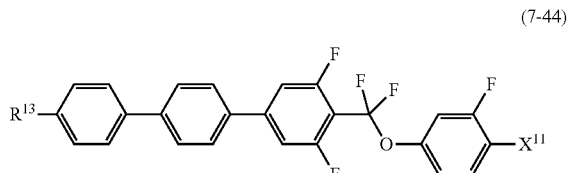
(7-44)
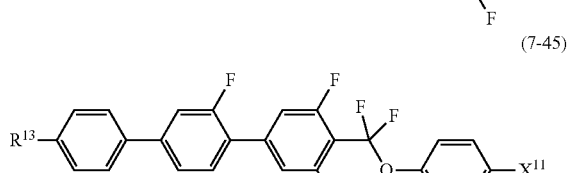
(7-45)
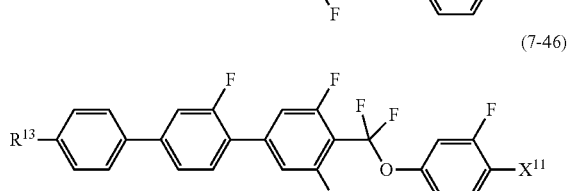
(7-46)
(7-47)

(7-48)
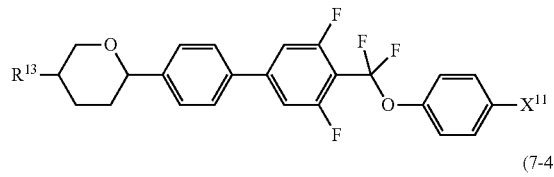

(7-49)
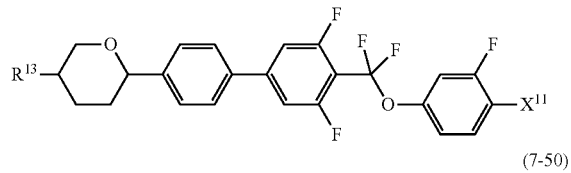

(7-50)
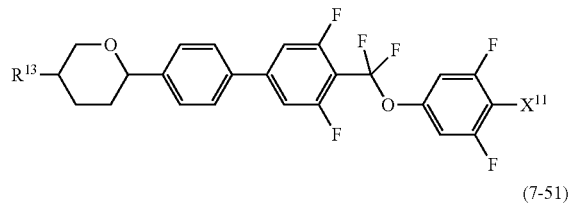

(7-51)
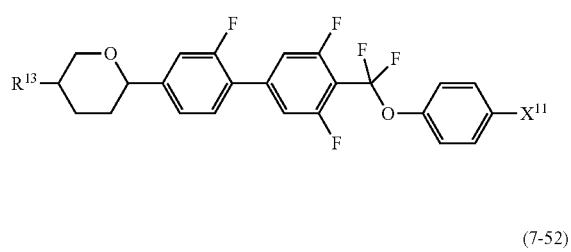

(7-52)
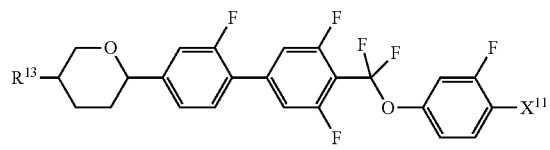

(7-53)
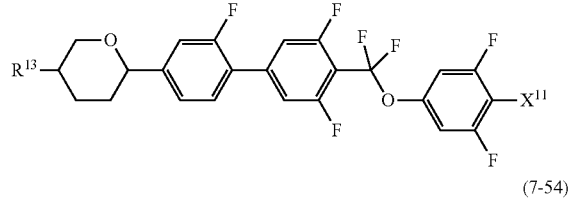

(7-54)
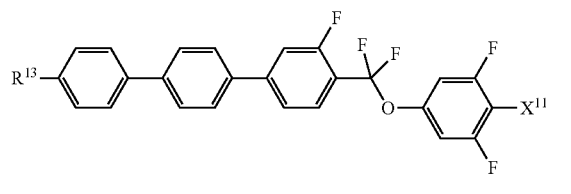

(7-55)
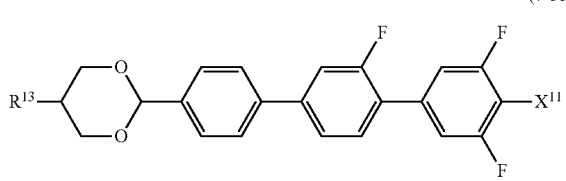

(7-56)
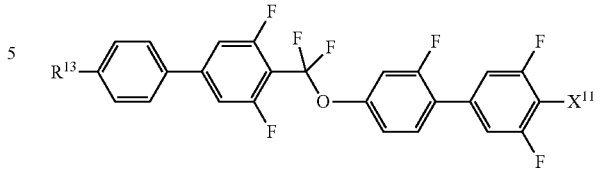

(7-57)
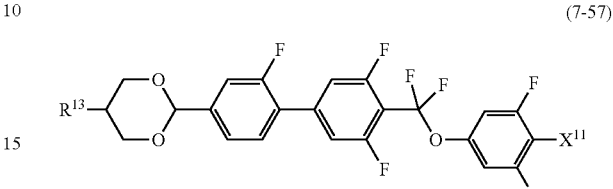

Compounds (5) to (7) being component C have positive dielectric anisotropy, and superb stability to heat, light or the like, and therefore are used when the composition for an IPS, FFS, OCB or the like mode is prepared. A content of components (5) to (7) each is suitably in the range of 1% by weight to 99% by weight, preferably in the range of 10% by weight to 97% by weight, and further preferably in the range of 40% by weight to 95% by weight, based on the weight of the liquid crystal composition. When the compounds are added to the composition having negative dielectric anisotropy, a content of the compounds is preferably 30% by weight or less based on the weight of the liquid crystal composition. An elastic constant of the composition can be adjusted, and a voltage-transmittance curve of the device can be adjusted by adding compounds (5) to (7) thereto.

Component D (Compound (8))

The liquid crystal composition of the invention may contain at least one kind of compound (component D) selected from the compounds represented by formula (8).

(8)
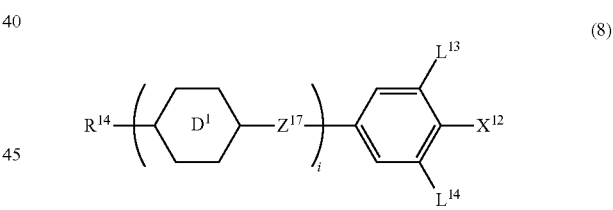

In formula (8), $R^{14}$ is alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

$X^{12}$ is —C≡N or —C≡C—C≡N;

ring $D^1$ is each independently 1,4-cyclohexylene, 1,4-phenylene in which at least one piece of hydrogen may be replaced by fluorine, tetrahydropyran-2,5-diyl, 1,3-dioxane-2,5-diyl or pyrimidine-2,5-diyl;

$Z^{17}$ is each independently a single bond, —CH$_2$CH$_2$—, —C≡C—, —COO—, —CF$_2$O—, —OCF$_2$— or —CH$_2$O—;

$L^{13}$ and $L^{14}$ are each independently hydrogen or fluorine; and i is 1, 2, 3 or 4.

In compound (8), a right-terminal group is —C≡N or —C≡C—C≡N. Specific preferred examples of the compound include compounds (8-1) to (8-64). In the compounds, $R^{14}$ is alkyl having 1 to 10 carbons or alkenyl having 2 to 10 carbons, and in the alkyl and the alkenyl, at least one piece of —$CH_2$— may be replaced by —O—, and at least one piece of hydrogen may be replaced by fluorine; and $X^{12}$ is —C≡N or —C≡C—C≡N.
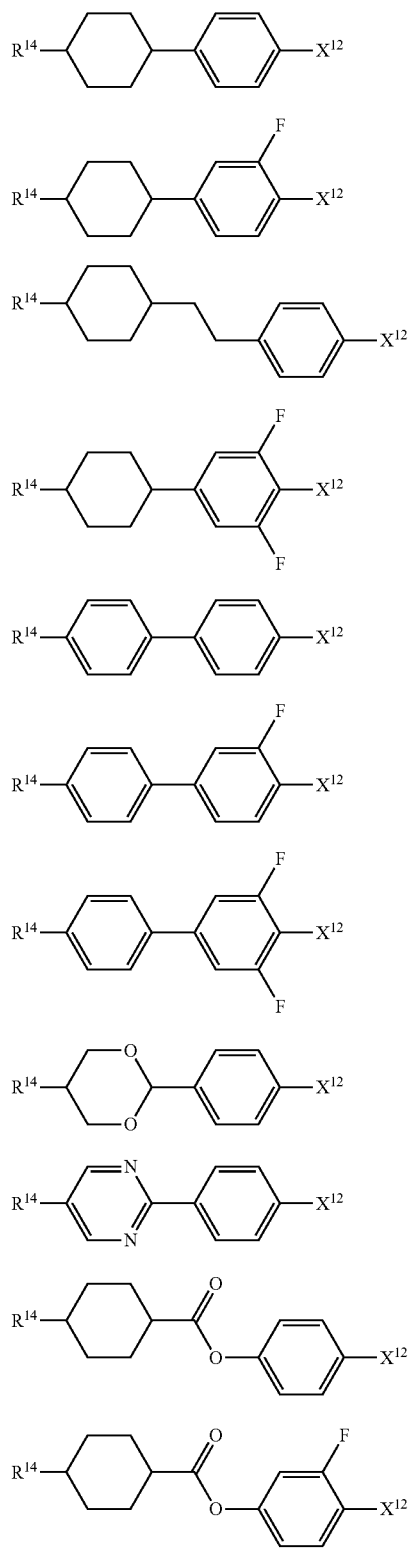
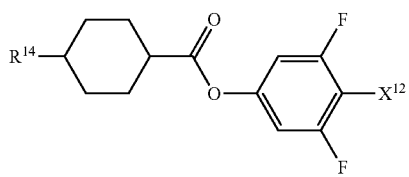
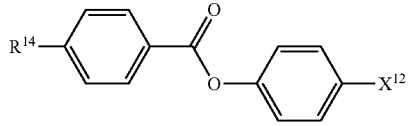
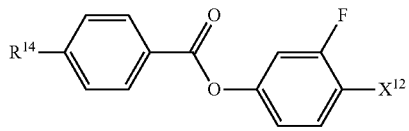
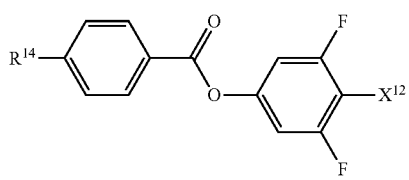
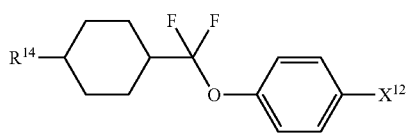
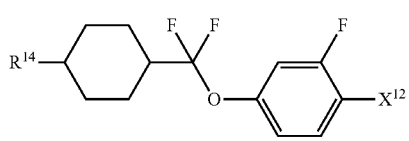
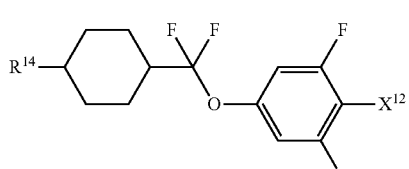
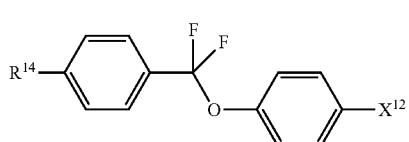
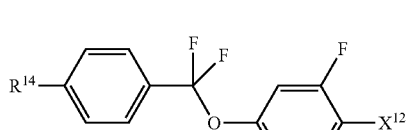
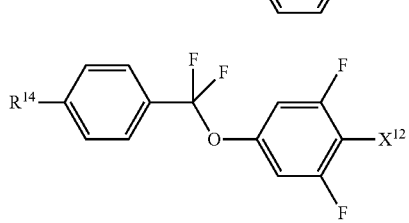

(8-22) 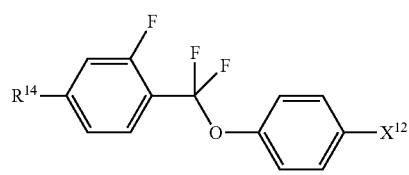
(8-23) 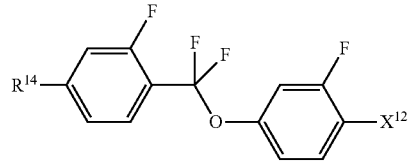
(8-24) 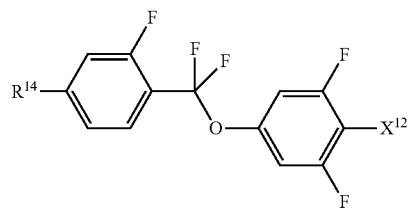
(8-25) 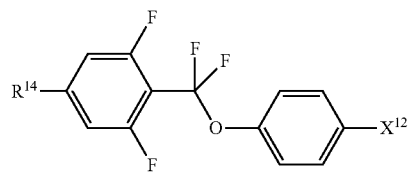
(8-26) 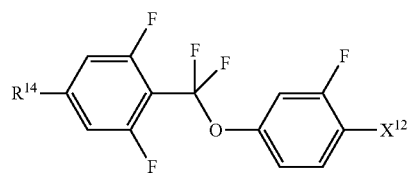
(8-27) 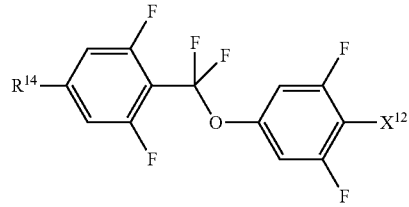
(8-28) 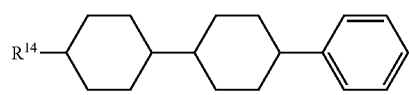
(8-29) 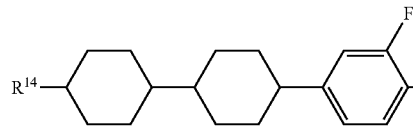
(8-30) 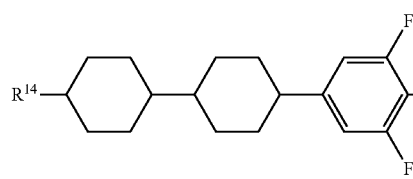
(8-31) 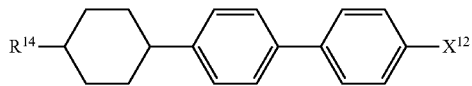
(8-32) 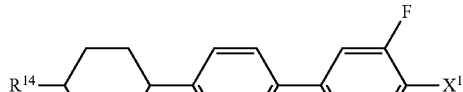
(8-33) 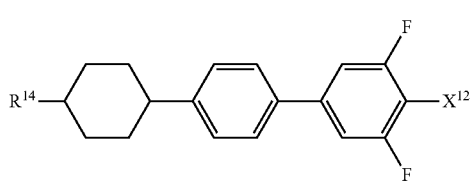
(8-34) 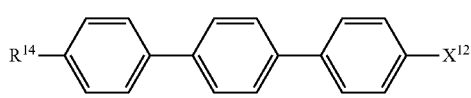
(8-35) 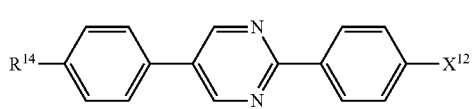
(8-36) 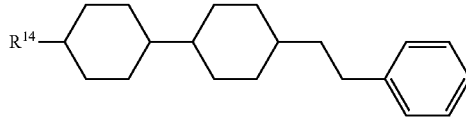
(8-37) 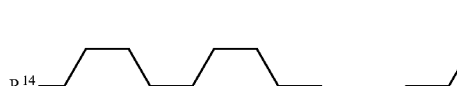
(8-38) 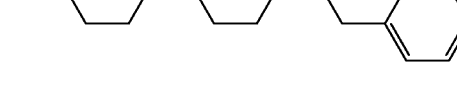
(8-39) 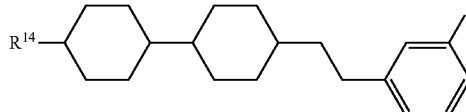
(8-40) 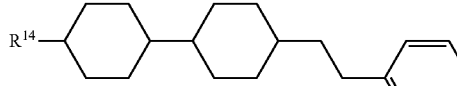
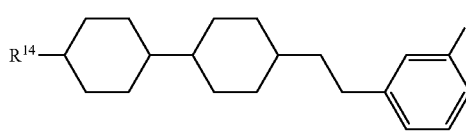

-continued
(8-41)
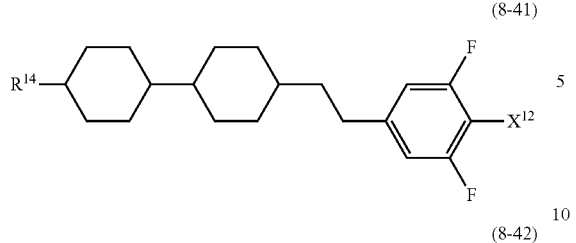
(8-42)
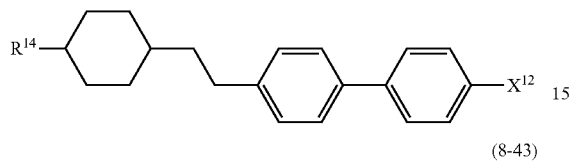
(8-43)
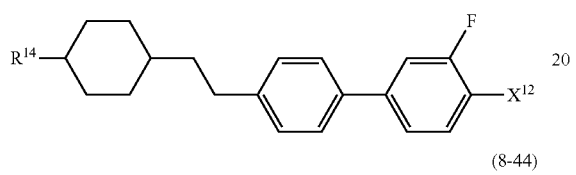
(8-44)
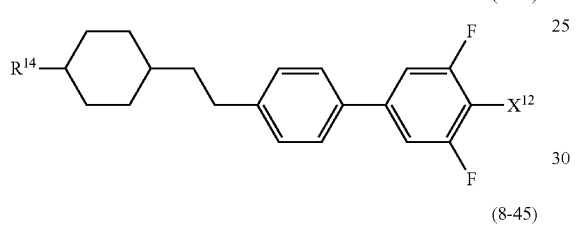
(8-45)
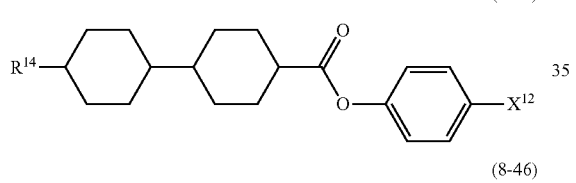
(8-46)
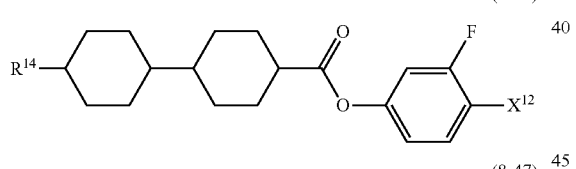
(8-47)
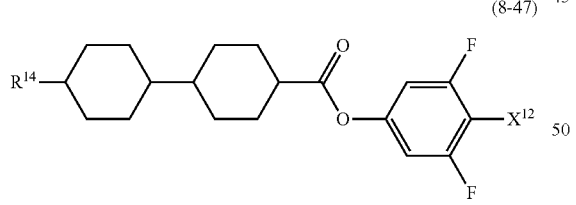
(8-48)
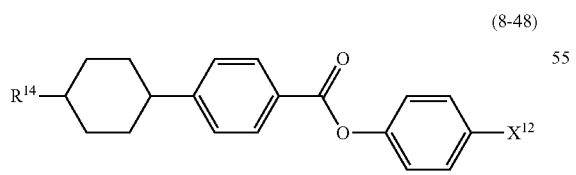
(8-49)
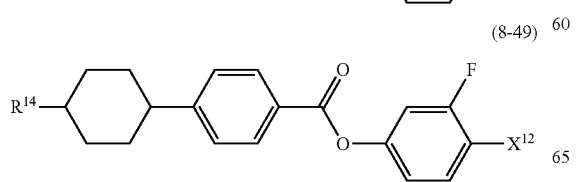
-continued
(8-50)
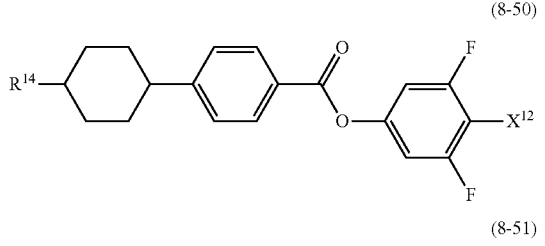
(8-51)
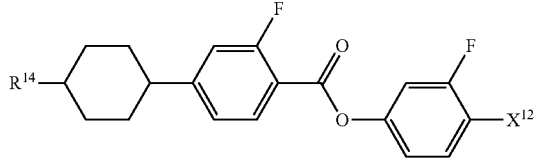
(8-52)
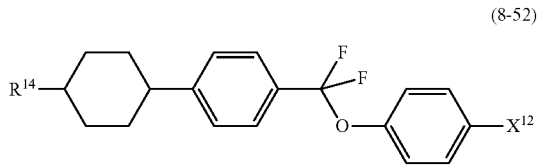
(8-53)
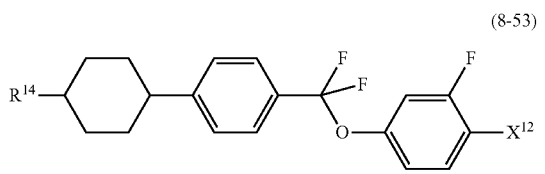
(8-54)
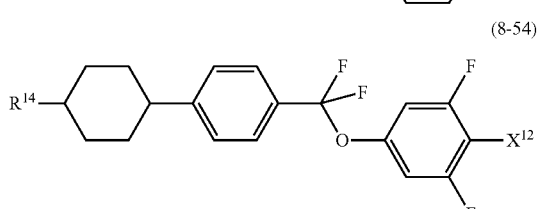
(8-55)
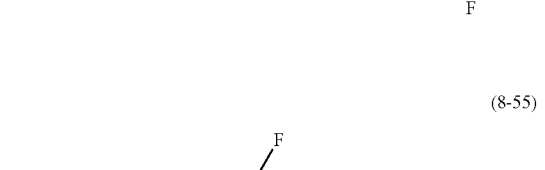
(8-56)
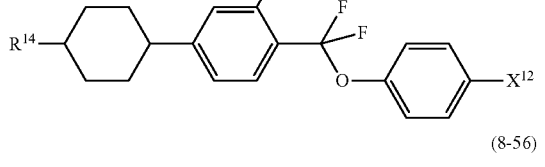
(8-57)
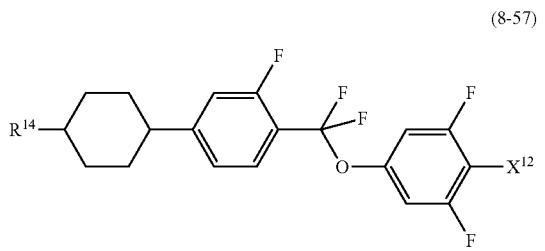

(8-58)
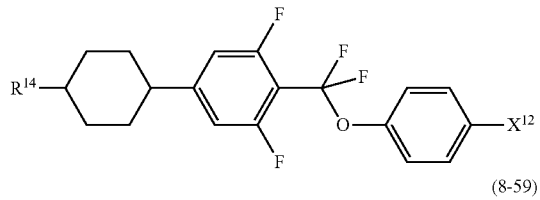

(8-59)
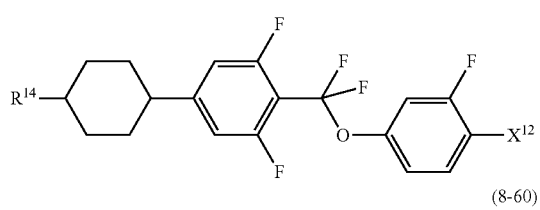

(8-60)

(8-61)
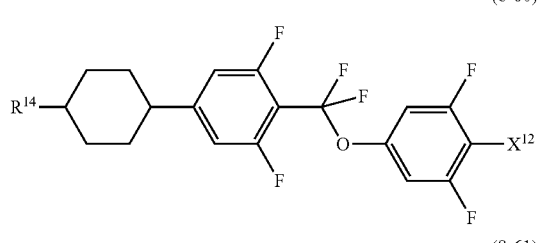

(8-62)
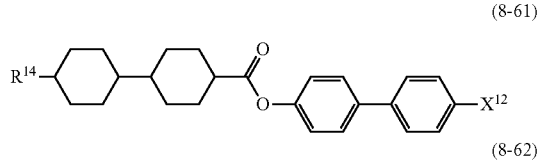

(8-63)
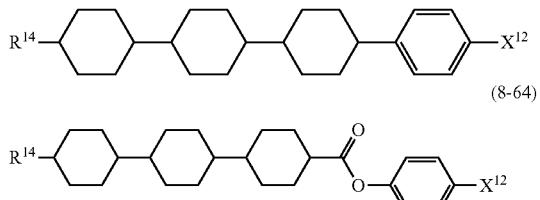

(8-64)
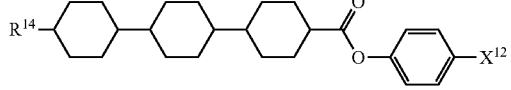

Compound (8) has positive dielectric anisotropy, and a value thereof is large, and therefore is mainly used when the composition for a TN, STN or the like mode is prepared. The dielectric anisotropy of the composition can be increased by adding compound (8) thereto. Compound (8) is effective in extending the temperature range of the liquid crystal phase, adjusting the viscosity or adjusting the optical anisotropy. The compound is also useful for adjustment of the voltage-transmittance curve of the device.

When the composition for the TN, STN or the like mode is prepared, a content of compound (8) is suitably in the range of 1% by weight to 99% by weight, and preferably 10% by weight to 97% by weight, and further preferably 40% by weight to 95% by weight, based on the weight of the liquid crystal composition. When compound (8) is added to the composition having negative dielectric anisotropy, a content of the compound is preferably 30% by weight or less based on the weight of the liquid crystal composition. The elastic constant of the composition can be adjusted and the voltage-transmittance curve of the device can be adjusted by adding compound (8) thereto.

Component E (Compounds (9) to (15))

The liquid crystal composition of the invention may contain at least one compound (component E) selected from the compounds represented by formulas (9) to (15).

(9)
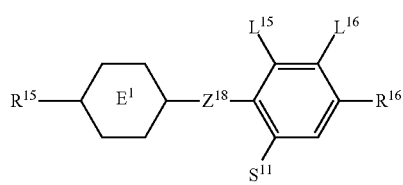

(10)
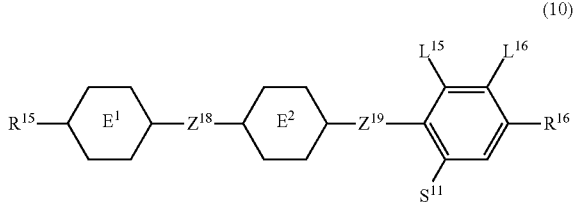

(11)
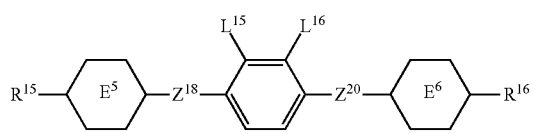

(12)
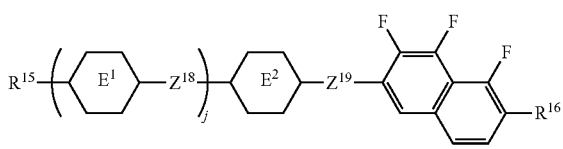

(13)
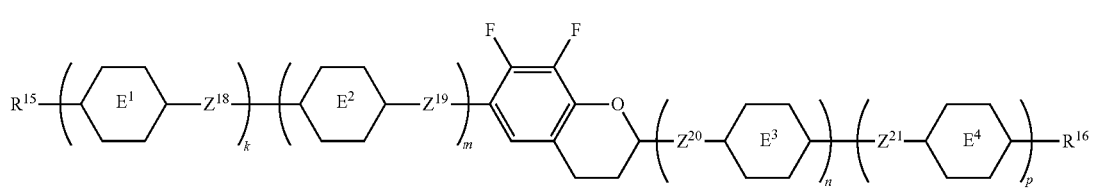

(14)
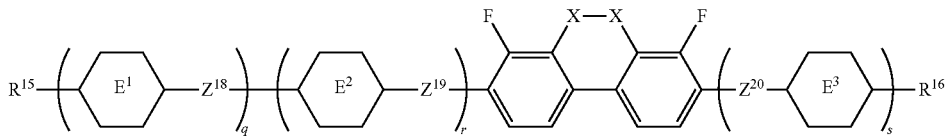

(15)
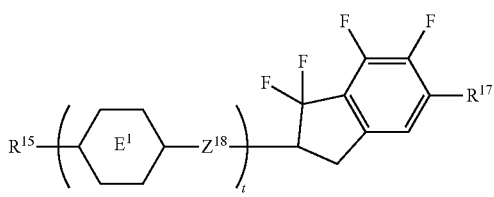

In formula (9) to formula (15), $R^{15}$ and $R^{16}$ are each independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine;

$R^{17}$ is hydrogen, fluorine, alkyl having 1 to 10, carbons or alkenyl having 2 to 10 carbons, and in the alkyl and the alkenyl, at least one piece of —CH$_2$— may be replaced by —O—, and at least one piece of hydrogen may be replaced by fluorine;

ring $E^1$, ring $E^2$, ring $E^3$ and ring $E^4$ are each independently 1,4-cyclohexylene, 1,4-cyclohexenylene, 1,4-phenylene in which at least one piece of hydrogen may be replaced by fluorine, tetrahydropyran-2,5-diyl or decahydronaphthalene-2,6-diyl;

ring $E^5$ and ring $E^6$ are each independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are each independently a single bond, —CH$_2$CH$_2$—, —COO—, —CH$_2$O—, —OCF$_2$— or —OCF$_2$CH$_2$CH$_2$—;

$L^{15}$ and $L^{16}$ are each independently fluorine or chlorine;

$S^{11}$ is hydrogen or methyl;

X is —CHF— or —CF$_2$—; and j, k, m, n, p, q, r and s are each independently 0 or 1, a sum of k, m, n and p is 1 or 2, a sum of q, r and s is 0, 1, 2 or 3, and t is 1, 2 or 3.

Compounds (9) to (15) have phenylene in which atoms in lateral positions thereof are replaced by two pieces of halogen, as in 2,3-difluoro-1,4-phenylene. Specific preferred examples of the compounds include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compounds, $R^{15}$ and $R^{16}$ are independently alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine; $R^{17}$ is hydrogen, fluorine, alkyl having 1 to 10 carbons or alkenyl having 2 to 10 carbons, and in the alkyl and the alkenyl, at least one piece of —CH$_2$— may be replaced by —O—, and at least one piece of hydrogen may be replaced by fluorine.

(9-1)
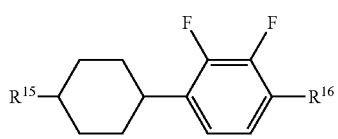

(9-2)
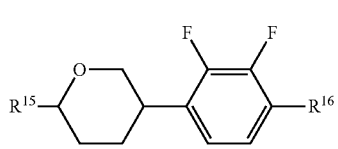

(9-3)
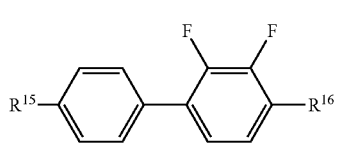

(9-4)
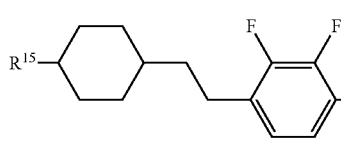

(9-5)
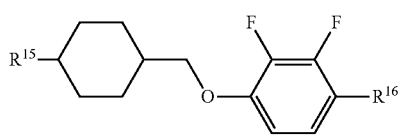

(9-6)
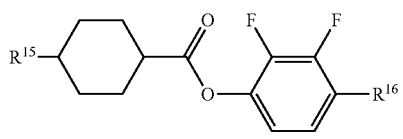

(9-7)
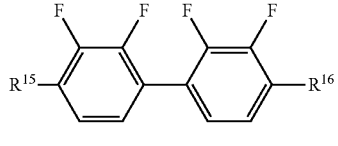

(9-8)
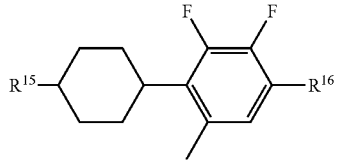

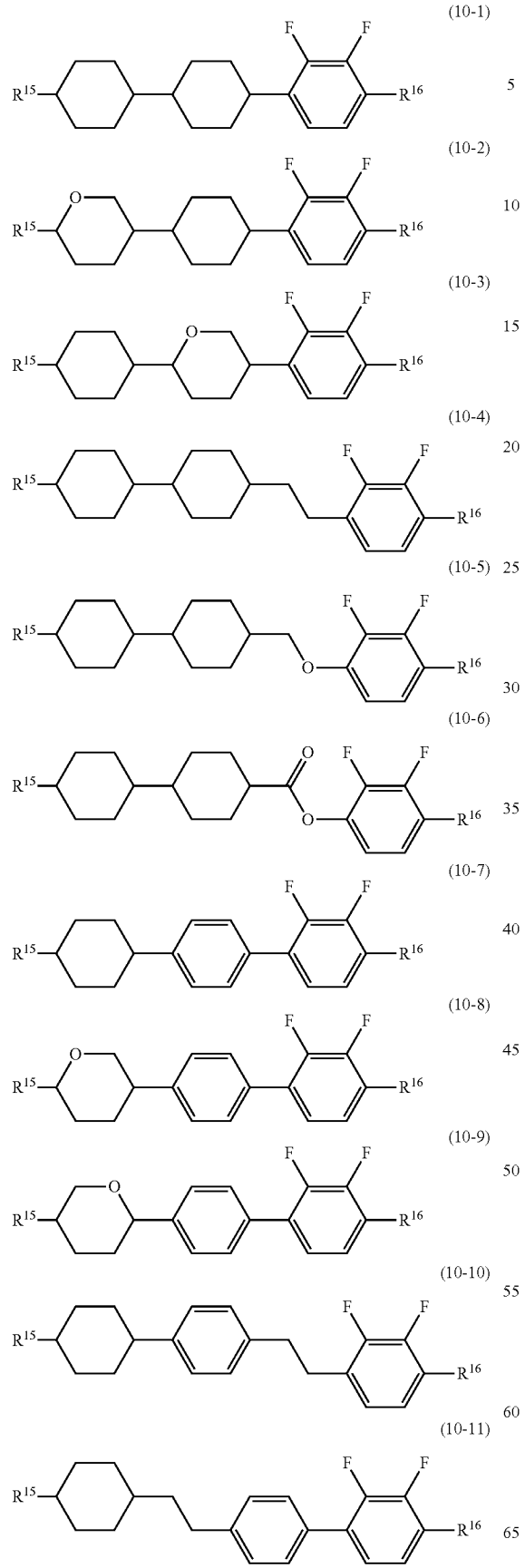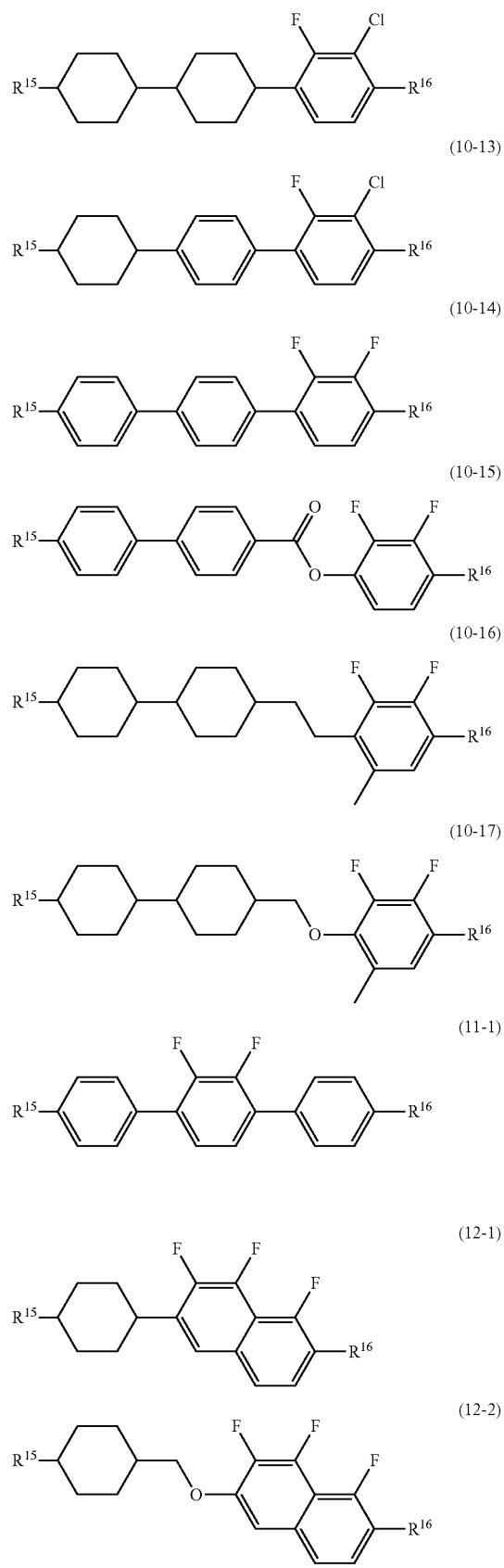

(12-3)
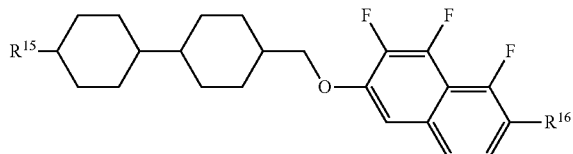
(13-1)
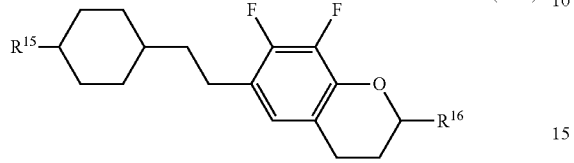
(13-2)
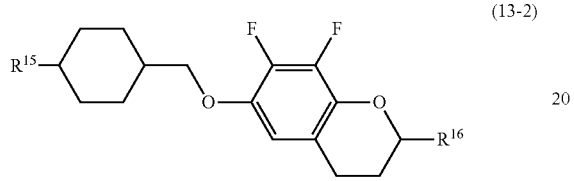
(13-3)
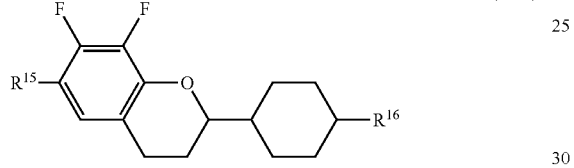
(13-4)
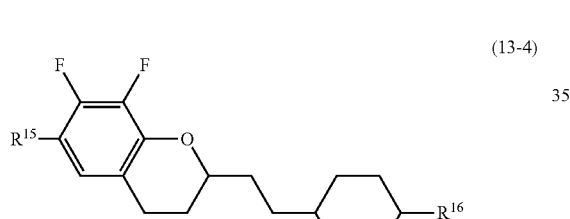
(13-5)
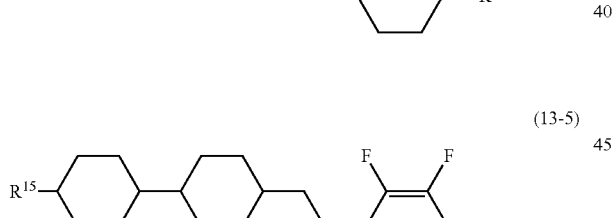
(13-6)
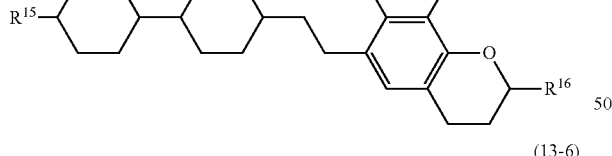
(13-7)
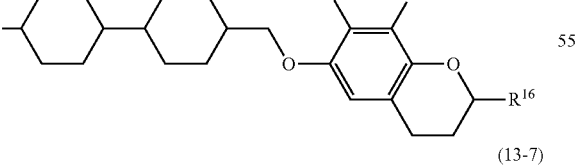
(13-8)
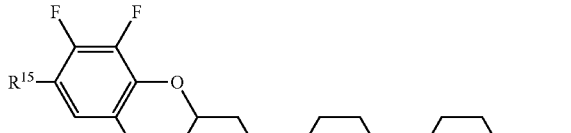
(13-9)
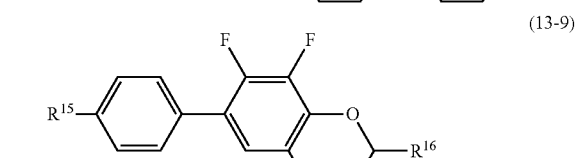
(13-10)
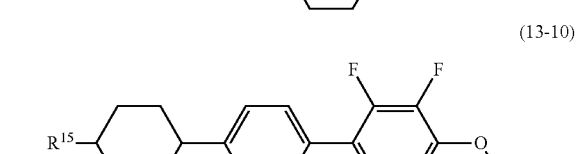
(13-11)
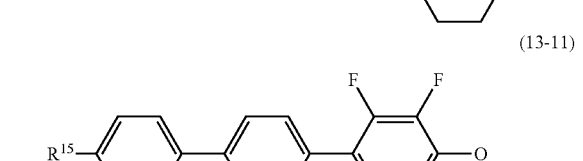
(14-1)
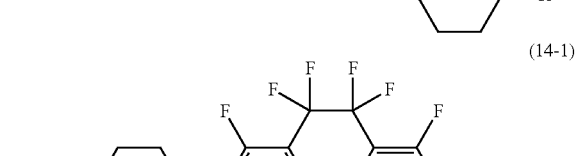
(14-2)
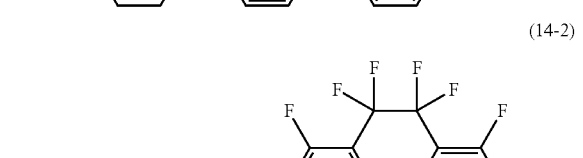
(14-3)
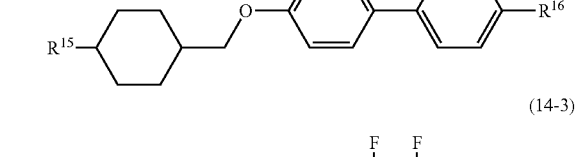
(15-1)
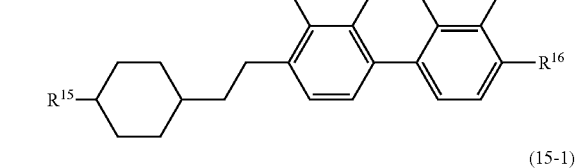

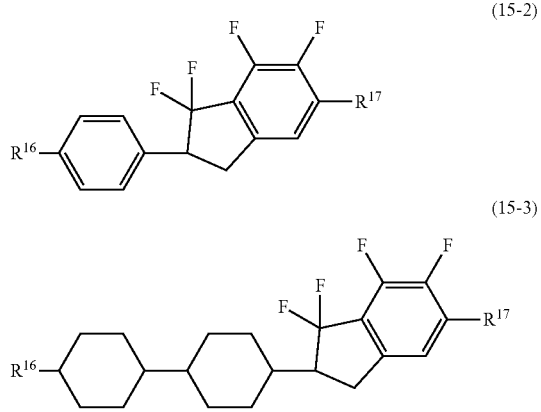

(15-2)

(15-3)

Compounds (9) to (15) being component (E) has large negative dielectric anisotropy. The compounds are used when the composition for an IPS, VA, PSA or the like mode is prepared. As a content of the compounds is increased, the dielectric anisotropy of the composition negatively increases, but the viscosity increases. Thus, as long as the desired value of the threshold voltage of the device is met, the content is preferably as small as possible. Accordingly, when taking into account the dielectric anisotropy being at a degree of −5, the content is preferably 40% by weight or more in order to allow sufficient voltage driving.

Among the compounds described above, compound (9) is a bicyclic compound, and therefore is mainly effective in decreasing the viscosity, adjusting the optical anisotropy or increasing the dielectric anisotropy. Compounds (10) and (11) are a tricyclic compound, and therefore are effective in increasing the maximum temperature, increasing the optical anisotropy or increasing the dielectric anisotropy. Compounds (12) to (15) are effective in increasing the dielectric anisotropy.

When the composition for the IPS, VA, PSA or the like mode is prepared, a content of compounds (9) to (15) each is preferably 40% by weight or more, and further preferably in the range of 50% by weight to 95% by weight, based on the weight of the liquid crystal composition. When compounds (9) to (15) are added to the composition having positive dielectric anisotropy, a content of the compounds each is preferably 30% by weight or less based on the weight of the liquid crystal composition. The elastic constant of the composition can be adjusted, and the voltage-transmittance curve of the device can be adjusted by adding the compounds thereto.

The liquid crystal composition is prepared according to a method in which required components are dissolved therein at a temperature higher than room temperature, or the like. According to an application, an additive may be added to the composition. Examples of the additive include an optically active compound, an antioxidant, an ultraviolet light absorber, a light stabilizer, a heat stabilizer, an antifoaming agent, a polymerizable compound, a polymerization initiator and a polymerization inhibitor. Such additives are well known to those skilled in the art, and described in literature.

Optically Active Compound

The optically active compound is effective in inducing a helical structure in liquid crystal molecules to give a required twist angle, thereby preventing reverse twist. A helical pitch can be adjusted by adding the optically active compound thereto. Two or more optically active compounds may be added for the purpose of adjusting temperature dependence of the helical pitch. As a chiral agent to be used in the liquid crystal composition of the invention, a compound having helical twisting power (HTP) is preferred. In the compound having large helical twisting power, an amount of addition required for obtaining a desired pitch can be reduced, and therefore a rise of driving voltage can be suppressed, and such a case is advantageous in practical use. Specifically, a compound represented by compounds (Op-1) to (Op-18) is preferred. In compound (Op-18), ring J is 1,4-cyclohexylene or 1,4-phenylene, and $R^{28}$ is alkyl having 1 to 10 carbons. Moreover, in compounds (Op-17) and (Op-18), a binapthyl group is an optically active site, and chirality of the chiral agent does not matter.

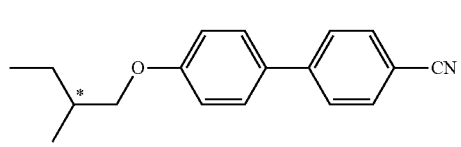

(Op-1)

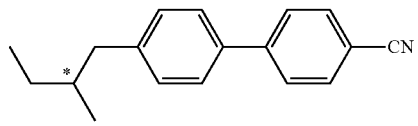

(Op-2)

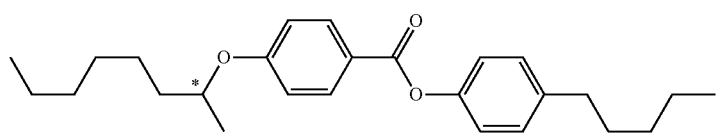

(Op-3)

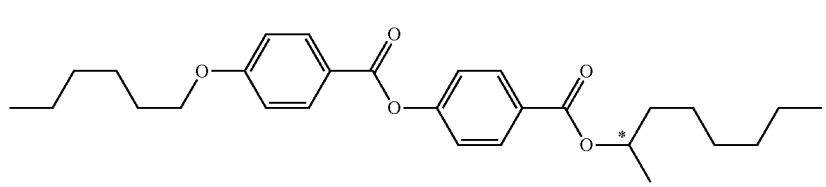

(Op-4)

-continued
(Op-5)
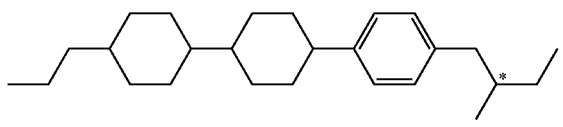
(Op-6)
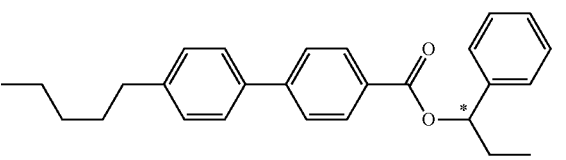
(Op-7)
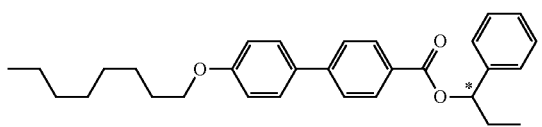
(Op-8)
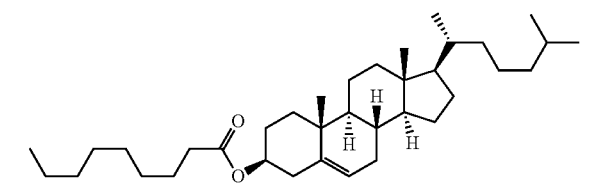
(Op-9)
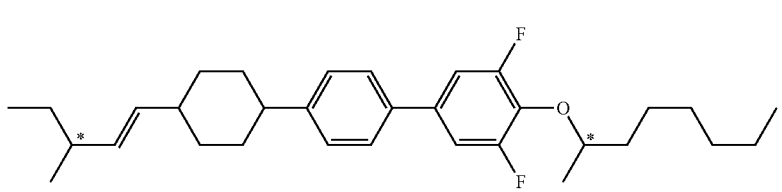
(Op-10)
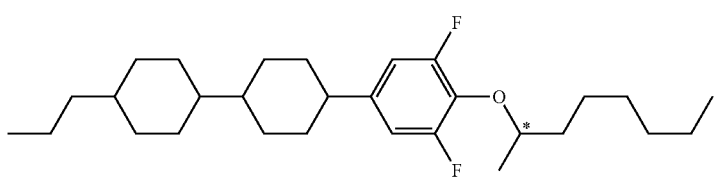
(Op-11)
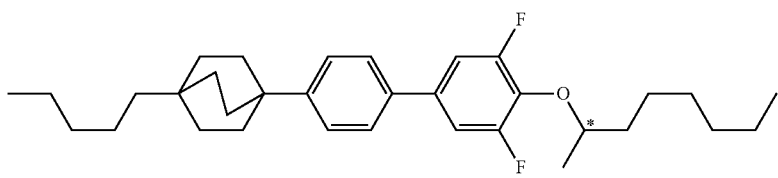
(Op-12)
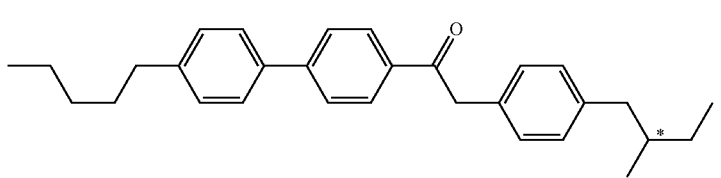
(Op-13)
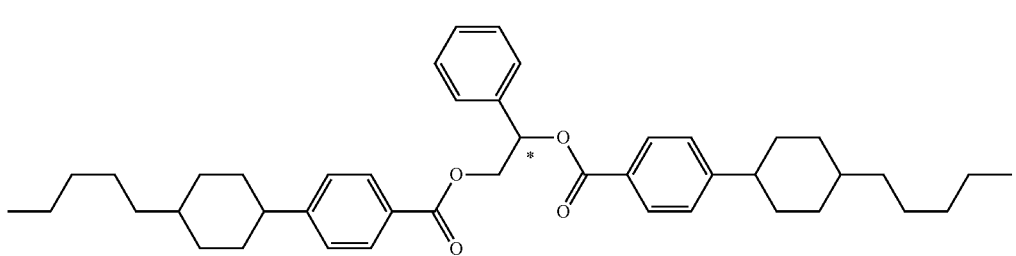
(Op-14)
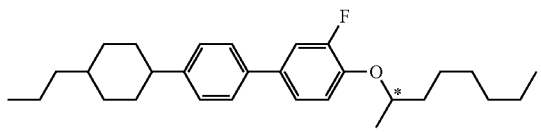
(Op-15)
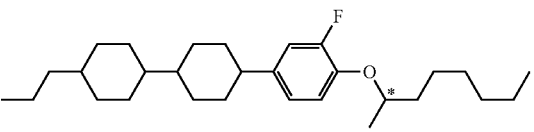

(Op-16)

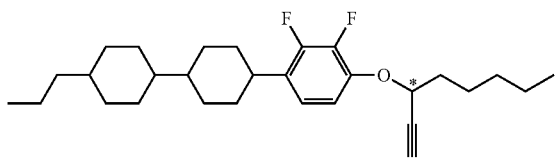

(Op-17)

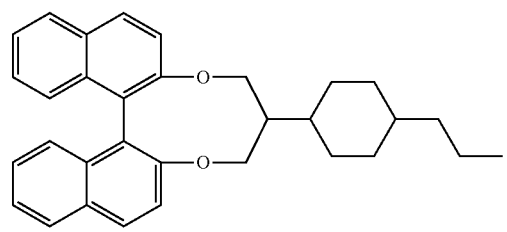

(Op-18)

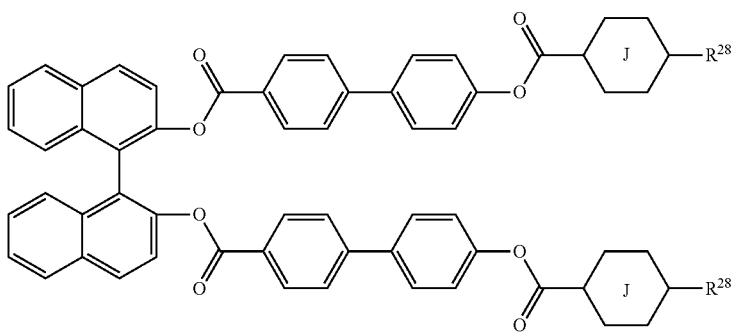

Antioxidant

The antioxidant is effective for maintaining a large voltage holding ratio. Specific preferred examples of the antioxidant include compounds (AO-1) and (AO-2) described below; and Irganox 415, Irganox 565, Irganox 1010, Irganox 1035, Irganox 3114 and Irganox 1098 (trade names; BASF SE). The ultraviolet light absorber is effective for preventing reduction of the maximum temperature. Specific preferred examples of the ultraviolet light absorber include a benzophenone derivative, a benzoate derivative and a triazole derivative. Specific examples include compounds (AO-3) and (AO-4) described below; Tinuvin 329, Tinuvin P, Tinuvin 326, Tinuvin 234, Tinuvin 213, Tinuvin 400, Tinuvin 328 and Tinuvin 99-2 (trade names; BASF SE); and 1,4-diazabicyclo [2.2.2]octane (DABCO).

The light stabilizer such as an amine having steric hindrance is preferred for maintaining the large voltage holding ratio. Specific preferred examples of the light stabilizer include compounds (AO-5) and (AO-6) described below; and Tinuvin 144, Tinuvin 765 and Tinuvin 770DF (trade names: BASF SE). The heat stabilizer is also effective for maintaining the large voltage holding ratio, and specific preferred examples thereof include Irgafos 168 (trade name; BASF SE). The antifoaming agent is effective for preventing foam formation. Specific preferred examples of the antifoaming agent include dimethyl silicone oil and methylphenyl silicone oil.

(AO-1)

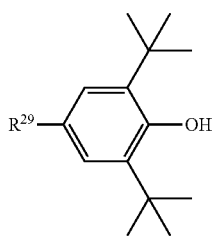

(AO-2)

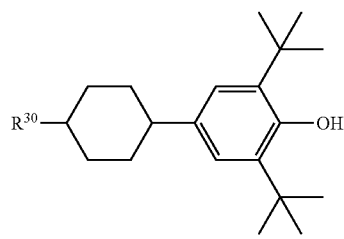

(AO-3)

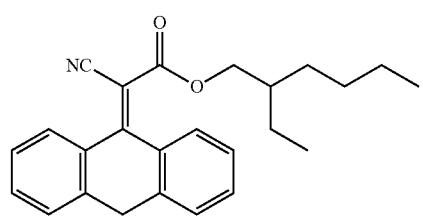

(AO-4)

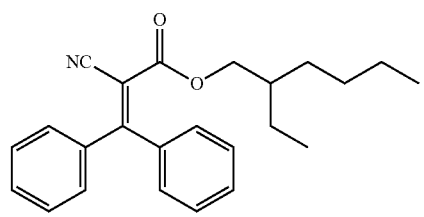

(AO-5)

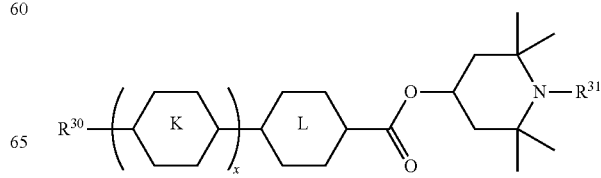

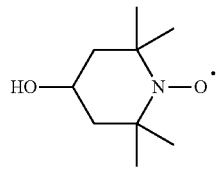

(AO-6)

In compound (AO-1), $R^{29}$ is alkyl having 1 to 20 carbons, alkoxy having 1 to 20 carbons, —COOR$^{32}$ or —CH$_2$CH$_2$COOR$^{32}$, in which $R^{32}$ is alkyl having 1 to 20 carbons. In compounds (AO-2) and (AO-5), $R^{30}$ is alkyl having 1 to 20 carbons. In compound (AO-5), $R^{31}$ is hydrogen, methyl or O. (oxygen radical), ring K and ring L are 1,4-cyclohexylene or 1,4-phenylene, and x is 0, 1 or 2.

Polymerizable Compound

In the polymerizable compound, a response time in the device can be shortened and image persistence can be improved by polymerizing the compound while three-dimensionally controlling the polymerization. Preferred examples of the polymerizable compound include acrylate, methacrylate, a vinyl compound, a vinyloxy compound, propenyl ether, an epoxy compound (oxirane, oxetane) and vinyl ketone. Further preferred examples include a compound having at least one piece of acryloyloxy, and a compound having at least one piece of methacryloyloxy. Still further preferred examples also include a compound having both acryloyloxy and methacryloyloxy.

Additional examples of other polymerizable compounds are compounds (M-1) to (M-12). In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

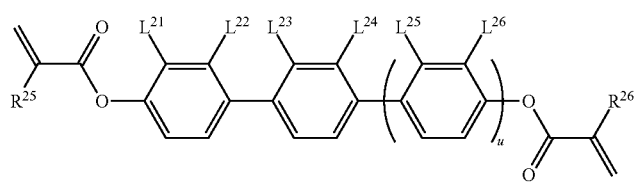

(M-1)

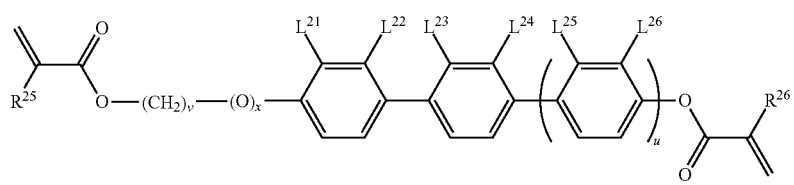

(M-2)

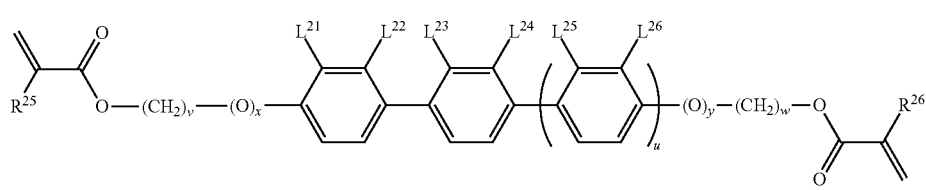

(M-3)

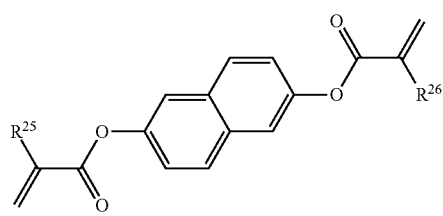

(M-4)

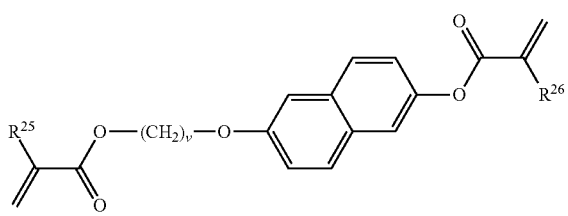

(M-5)

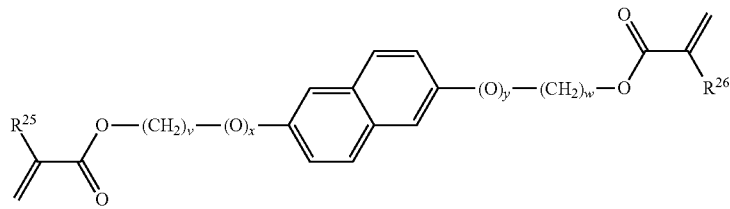

(M-6)

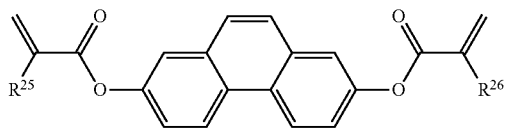 (M-7)

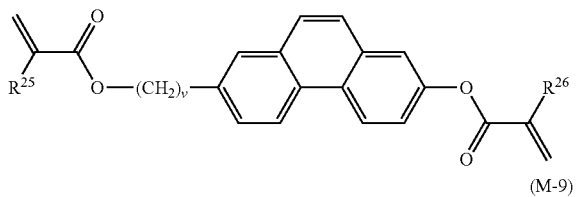 (M-8)

(M-9)

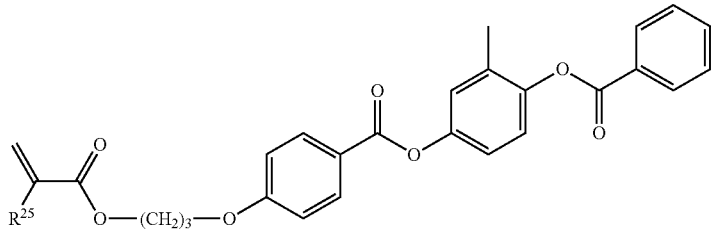

(M-10)

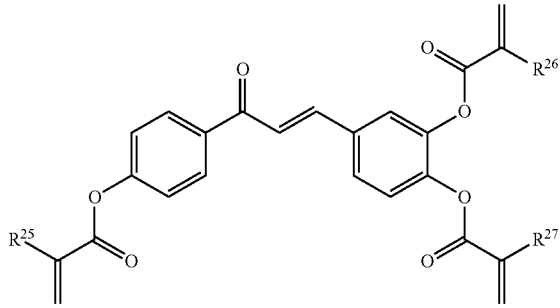

(M-11)

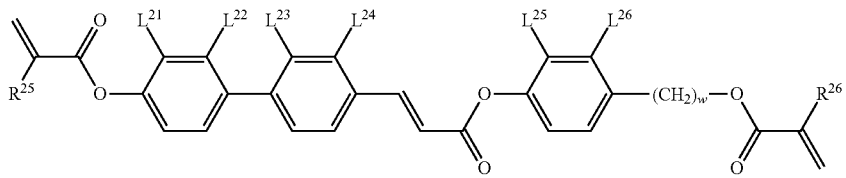

(M-12)

The polymerizable compound can be rapidly polymerized by adding the polymerization initiator thereto. An amount of a remaining polymerizable compound can be reduced by optimizing a reaction temperature. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate and a mixture of benzophenone and methyltriethanolamine.

Upon storing the polymerizable compound, the polymerization inhibitor may be added thereto for preventing polymerization. The polymerizable compound is ordinarily added to the composition without removing the polymerization inhibitor. Specific examples of the polymerization inhibitor include hydroquinone, a hydroquinone derivative such as methylhydroquinone, 4-t-butylcatechol, 4-methoxyphenol and phenothiazine.

Other Components

The liquid crystal composition of the invention can also be used as a liquid crystal composition for a guest-host (GH) mode by adding a dye such as a dichroic dye including a merocyanine type, a styryl type, an azo type, an azomethine type, an azoxy type, a quinophthalone type, an anthraquinone type and a tetrazine type thereto.

Method of Preparing Liquid Crystal Composition and Characteristics Thereof

The liquid crystal composition of the invention can be prepared, when compounds that composing each component are liquid, by mixing each compound, or when one kind or two or more kinds of compounds that compose each component are solid, by mixing each compound and converting each component into liquid by heating and melting each component under a nitrogen atmosphere, and subsequently by shaking the resulting mixture, for example. Moreover, the liquid crystal composition of the invention can also be prepared by other publicly-known methods.

When the liquid crystal composition of the invention is prepared, each component can also be selected in consideration of the dielectric anisotropy of bimesogenic compound (1), for example. The liquid crystal composition in which each component is selected has stability to heat, light or the like, low viscosity, suitable dielectric anisotropy, suitable optical anisotropy, a suitable elastic constant, low threshold voltage, high maximum temperature of the nematic phase and low minimum temperature of the nematic phase. Here, a term "suitable" means that a preferred range of the dielectric anisotropy, the optical anisotropy and the elastic constant is appropriately determined according to an operating mode of the liquid crystal display device including the liquid crystal composition of the invention, for example.

In the liquid crystal composition of the invention, the maximum temperature of the nematic phase can be adjusted to 70° C. or higher, and the minimum temperature of the nematic phase can be adjusted to −20° C. or lower, and the temperature range of the nematic phase is wide. Accordingly, the liquid crystal display device including the liquid crystal composition of the invention can be used in the wide temperature range.

In the liquid crystal composition of the invention, the value of optical anisotropy ($\Delta n$) can be adjusted to an arbitrary range, for example, to the range of 0.10 to 0.13, or to the range of 0.05 to 0.18, by appropriately adjusting the composition or the like.

In the liquid crystal composition of the invention, the value of dielectric anisotropy ($\Delta \varepsilon$) can be adjusted ordinarily to the range of −5.0 to 2.0, and preferably to the range of −4.5 to −2.5, by appropriately adjusting the composition or the like.

In the liquid crystal composition of the invention, the value of dielectric anisotropy ($\Delta \varepsilon$) can be adjusted ordinarily to the range of 1 to 30, and preferably to the range of 2 to 25, by appropriately adjusting the composition or the like. In addition, a method of measuring physical properties each described above is as described in Examples.

Conjugate Fibers with Encapsulated Liquid Crystal

The conjugate fibers with the encapsulated liquid crystal according to the invention are conjugate fibers in which the liquid crystal composition of the invention is encapsulated, and sheath-core conjugate fibers in which the liquid crystal composition is applied as the core component. FIG. 1 shows a perspective view of conjugate fibers 10 with an encapsulated liquid crystal (hereinafter, occasionally referred to as "conjugate fibers 10") to be used in the invention. Conjugate fibers 10 with the encapsulated liquid crystal are the sheath-core conjugate fibers in which the liquid crystal composition is applied as the core component. More specifically, conjugate fibers 10 with the encapsulated liquid crystal contain liquid crystal composition 2a that composes core component 2, and sheath component-forming material 4a that exists in a periphery of core component 2 to compose sheath component 4 being an outer envelope of conjugate fibers 10 with the encapsulated liquid crystal. In addition, a reference numeral 2a schematically shows alignment of the liquid crystal molecules, but a major axis of liquid crystal molecules 2b may be in parallel with fibers as shown in FIG. 1, or the major axis of liquid crystal molecules 2b may be orthogonal to a fiber direction.

Conjugate fibers 10 with the encapsulated liquid crystal are formed by discharging of sheath component-forming material 4 and liquid crystal composition 2a from different discharging devices, namely different nozzles. More specifically, in the conjugate fibers 10 with the encapsulated liquid crystal according to the present embodiment, such a phenomenon is not caused in which sheath component-forming material 4a and liquid crystal composition 2a are once mixed, and then separated into sheath component 4 and core component 2. Each of sheath component-forming material 4a and liquid crystal composition 2a is formed to sheath component 4 and core component 2, individually, from the beginning, and therefore a state is ensured in which sheath component-forming material 4a and liquid crystal composition 2a are substantially separated.

Sheath component-forming material 4a of sheath component 4 of conjugate fibers 10 in the invention is not particularly limited, but is preferably a fiber-formable material. Specific examples of the fiber-forming material include a polymer material such as polyvinyl alcohol, polyethylene glycol, polyethylene oxide, polyvinyl pyrrolidone, polyethylene, polypropylene, polyethylene terephthalate, polylactic acid, polyamide, polyurethane, polystyrene, polysulfone, polyethersulfone, polyfluorovinylidene, polyacrylonitrile, polymethyl methacrylate, polyglycolic acid, polycaprolactone, polyvinyl acetate, polycarbonate, polyimide, polyetherimide, cellulose, a cellulose derivative, chitin, chitosan, collagen, gelatin and a copolymer thereof, and an inorganic material such as alumina, silica, titania, zirconia and hydroxyapatite. The fiber-forming materials described above can be used in one kind, or in combination of two or more kinds. A mixing ratio thereof when such materials are mixed and used is not particularly limited, and can be appropriately set in view of physical properties of the fibers obtained. If sheath component-forming material 4a of sheath component 4 is an amorphous polymer having transparency, a light transmission quantity can be improved, and therefore such conjugate fibers can be preferably used in the form of the liquid crystal display device, and therefore such a case is preferred. Specific examples of such an amorphous polymer include polymethyl methacrylate, polyvinyl acetate, polyvinyl pyrrolidone, polycarbonate, polystyrene and gelatin.

If sheath component-forming material 4a of sheath component 4 according to the invention is a component having a refractive index close to a refractive index of liquid crystal composition 2a, light scattering in an interface can be reduced, and therefore such a case is preferred. Specific examples of such sheath component-forming material 4a of sheath component 4 include polyvinyl pyrrolidone.

Specific examples of a method of manufacturing conjugate fibers 10 of the invention include a melt spinning method, a dry spinning method, a wet spinning method, a spunbond method, a meltblown method, a flash spinning method, an electrospinning method and a force spinning method, and from a viewpoint of obtaining uniform and ultrafine fibers, an electrospinning method is preferred. The electrospinning method will be described below, but not limited thereto.

The electrospinning method means a method in which a spinning solution is discharged therefrom, and simultaneously an electric field is acted thereon to process the discharged spinning solution into fibers to obtain the fibers on a collector. Specific examples thereof include a method of spinning fibers by extruding a spinning solution from a nozzle, and simultaneously acting an electric field thereon, a method of spinning fibers by bubbling a spinning solution, and simultaneously acting an electric field thereon, and a method of spinning fibers by guiding a spinning solution onto a surface of a cylindrical electrode, and simultaneously acting an electric field thereon. According to the methods described above, uniform fibers having a diameter of 10 nanometers to 10 micrometers can be obtained.

Specific examples of the method of manufacturing conjugate fibers 10 in the invention include a method of performing electrospinning of fibers by separately discharging a sheath solution and a liquid crystal material from a double tube nozzle, and a method of performing electrospinning of a spinning solution prepared by mixing a polymer, a liquid crystal material and a solvent, and simultaneously allowing phase separation. From ease of driving the liquid crystal composition, however, a method of performing electrospinning of fibers by separately discharging a sheath solution and a liquid crystal material from a double tube nozzle is preferred. The conjugate fibers with the encapsulated liquid crystal prepared by the method of performing electrospinning of the spinning solution prepared by mixing the polymer, the liquid crystal material and the solvent, and simultaneously allowing phase separation include a state in which the polymer component is mixed with the liquid crystal material, and therefore alignment of the liquid crystals is disturbed, and good characteristics in the form of the liquid crystal display device are unable to be obtained.

The sheath solution is not particularly limited as long as the solution has spinnability, but such a solution can be used as a solution obtained by dissolving a fiber-forming material (sheath component-forming material 4a) in a solvent, and a solution obtained by melting a fiber-forming material by heat or laser irradiation. As the sheath solution used in the invention, the solution obtained by dissolving the fiber-forming material in the solvent is preferably used in view of capability of easily controlling smallness or uniformity of a diameter of conjugate fibers 10, and continuity and alignability of liquid crystal composition 2a.

Specific examples of the fiber-forming material include a polymer material such as polyvinyl alcohol, polyethylene glycol, polyethylene oxide, polyvinyl pyrrolidone, polyethylene, polypropylene, polyethylene terephthalate, polylactic acid, polyamide, polyurethane, polystyrene, polysulfone, polyethersulfone, polyfluorovinylidene, polyacrylonitrile, polymethyl methacrylate, polyglycolic acid, polycaprolactone, polyvinyl acetate, polycarbonate, polyimide, polyetherimide, cellulose, a cellulose derivative, chitin, chitosan, collagen and a copolymer thereof, and an inorganic material such as alumina, silica, titania, zirconia and hydroxyapatite. The fiber-forming materials may be used in one kind, or in combination of two or more kinds. A mixing ratio when such materials are mixed and used is not particularly limited, and can be appropriately set in view of the physical properties of the fibers obtained. If sheath component-forming material 4a of sheath component 4 is an amorphous polymer, conjugate fibers 10 can be used in the form of an optical device, and therefore such a case is preferred. Specific examples of such an amorphous polymer include polymethyl methacrylate, polyvinyl acetate, polyvinylpyrrolidone, polycarbonate and polystyrene.

Specific examples of the solvent in which the fiber-forming material is dissolved include water, methanol, ethanol, propanol, acetone, N,N-dimethylformamide, N,N-dimethylacetamide, dimethyl sulfoxide, N-methyl-2-pyrrolidone, toluene, xylene, pyridine, formic acid, acetic acid, tetrahydrofuran, dichloromethane, chloroform, 1,1,1,3,3,3-hexafluoroisopropanol and a mixture thereof. The continuity and the alignability of liquid crystal composition 2a and the diameter of conjugate fibers 10 or the like can be easily controlled by using the mixtures described above, and therefore such a case is preferred. A formulation of the mixture is not particularly limited, but is preferably a mixture of a polar solvent and a nonpolar solvent. Specific examples of the polar solvent include water, methanol, ethanol, propanol, and specific examples of the nonpolar solvent include toluene, xylene, tetrahydrofuran, chloroform, dichloromethane and dichlorobenzene. Moreover, a mixing ratio thereof is not particularly limited, and specific examples thereof include the range of 5:95 to 95:5 in terms of a weight ratio when two kinds of solvents are mixed.

For the purpose of improving stability and fiber-forming properties of electrospinning, an additive may be further incorporated into the sheath solution. Specific examples of the additive include an anionic surfactant such as dodecyl sodium sulfate, a cationic surfactant such as tetrabutylammonium bromide, a nonionic surfactant such as polyoxyethylene sorbitan monolaurate and inorganic salt such as sodium chloride.

A method of collecting conjugate fibers 10 in the invention is not particularly limited, but a method of rotating a drum-shaped collector or a disc-shaped collector at a high speed, or a method of using a grid-shaped collector is preferably applied. If such a collection method is applied, the fibers can be arranged in any direction. A rotating speed of the drum-shaped collector or the disc-shaped collector is not particularly limited, but a peripheral speed thereof is preferably in the range of 50 to 2,000 m/minute, and further preferably in the range of 100 to 1,000 m/minute. If the peripheral speed is 50 m/minute or more, conjugate fibers 10 can be arranged along a rotating direction, and if the peripheral speed is 100 m/minute or more, conjugate fibers 10 are sufficiently arranged. Moreover, if the peripheral speed is 2,000 m/minute or less, an influence of an air flow caused by rotation can be reduced, and if the peripheral speed is 1,000 m/minute or less, the influence can be sufficiently reduced, and the fibers can be stably collected. When the grid-shaped collector is used, specific examples of a grid interval include the range of 10 to 200 millimeters. Moreover, specific examples of a shape of the grid include a square, a quadrangle, a rhombus, an equilateral triangle, a right hexagon and a waveform.

Conjugate Fiber Composite with Encapsulated Liquid Crystal

Conjugate fiber aggregate 20 in the invention is not particularly limited, but conjugate fibers 10 in which a liquid crystal is encapsulated is preferably uniaxially arranged. When conjugate fibers 10 are uniaxially arranged, various characteristics of conjugate fibers 10 can be anisotropically developed, and conjugate fibers 10 can be preferably used in the form of the liquid crystal display device having high contrast. A degree of arrangement of conjugate fibers 10 can be evaluated by a standard deviation of a fiber arrangement angle, and if the standard deviation of the fiber arrangement angle is small, the degree of arrangement of the fibers may be reasonably maintained to be high. The standard deviation of the fiber arrangement angle is preferably 20° or less, and further preferably 15° or less.

Moreover, conjugate fibers 10 may be randomly arranged. When conjugate fibers 10 are randomly arranged, various characteristics thereof can be isotropically developed.

A thickness of conjugate fiber aggregate 20 is not particularly limited, but is preferably in the range of 1 to 20 micrometers, and further preferably 2 to 10 micrometers. If the thickness thereof is 1 micrometer or more, a function as a liquid crystal device can be sufficiently satisfied, and if the thickness thereof is 20 micrometers or less, the light transmission quantity can be sufficiently increased.

An area proportion of conjugate fibers 10 in conjugate fiber aggregate 20 is preferably 80% or more, and further preferably 95% or more.

Conjugate fiber aggregate 20 can be formed by arranging a plurality of conjugate fibers 10 on substrate 30 and filling binder 40 therein. More specifically, a liquid crystal layer can be formed on substrate 30 without forming an alignment film, which is different from a conventional technology, and a manufacturing cost for the liquid crystal display device can be significantly suppressed.

Conjugate fibers 10 in the invention can be preferably used in the form of a liquid crystal device for display or a liquid crystal device for wavelength selective reflection because the liquid crystals are continuously distributed inside the fibers.

Liquid Crystal Display Device

The liquid crystal display device of the invention includes the liquid crystal composition described above. In the liquid crystal display device of the invention, a response time is quick, power consumption and driving voltage are small, a contrast ratio is large, and the device can be used in a wide temperature range, and therefore can be used in a liquid crystal projector, a liquid crystal television and so forth.

The liquid crystal composition of the invention can be used not only in a liquid crystal display device having an operating mode such as the PC mode, the TN mode, STN mode, the OCB mode, the VA mode, and the IPS mode, and is driven by a passive matrix (PM) mode, but also in a liquid crystal display device having an operating mode such as the PC mode, the TN mode, the STN mode, the OCB mode, the VA mode, the IPS mode, and the PSA mode, and is driven by an active matrix (AM) mode. The liquid crystal display devices having the AM mode and the PM mode can be applied to any liquid crystal display of a reflective type, a transmissive type, a transflective type or the like.

The liquid crystal composition of the invention can also be used in an electrically controlled birefringence (ECB) mode device in which birefringence is controlled, a dynamic scattering (DS) mode device using a liquid crystal composition to which a conducting agent is added, a nematic curvilinear aligned phase (NCAP) device prepared by microencapsulating the liquid crystal composition, a polymer dispersed (PD) device prepared by forming a three-dimensional network polymer in the liquid crystal composition, for example, a polymer network (PN) device, and a phase changed-, a surface stabilized- or a polymer stabilized-cholesteric texture (SSCT, PSCT) device.

Moreover, the structure of the liquid crystal display device driven by the VA mode is published in K. Ohmuro, S. Kataoka, T. Sasaki and Y. Koike, SID' 97 Digest of Technical Papers, 28, 845 (1997), and the structure of the liquid crystal display device driven by the IPS mode is published in WO 91/10936 A (family: U.S. Pat. No. 5,576, 867 B).

Among them, the liquid crystal composition of the invention has the characteristics described above, and therefore can be preferably used in a uniform lying helix (ULH) mode device utilizing the flexo-electric effect that is particularly observed in the cholesteric liquid crystal, as a device in which a high speed response can be achieved. An aspect of use of the composition in the display device is a flexo-electric display device including one or more kinds of bimesogenic compound (1) of the invention of the present application, or composed of the liquid crystal composition containing at least one kind of bimesogenic compound (1), or composed of the conjugate fibers or the conjugate fiber aggregate each in which the liquid crystal composition of the present application is encapsulated, or the fiber composite with the encapsulated liquid crystal.

Next, an embodiment of the invention will be described. Bimesogenic compound (1) of the invention and the composition containing thereof can be arranged into various alignment states in a cholesteric phase by a publicly-known method using surface treatment or an external field such as the electric field. For example, alignment can be made in a planar (Grandjean) state, a focalconic state or a homeotropic state. Further, in bimesogenic compound (1) having a large dipole moment, a flexo-electric response can be made, and therefore such compound (1) can be used in an electrooptical switch or the liquid crystal display device.

Subsequently, with regard to preferred switching between different phase states, bimesogenic compound (1) of the invention will be described in detail below.

For example, a sample is injected into a cell formed of two plane-parallel glass plates each having an electrode layer such as ITO to allow molecules in homogeneous alignment in the cholesteric phase to align a cholesteric helical axis thereof in a normal direction of a cell wall. The state is called a Grandjean state, and an optical texture thereof can be observed as a Grandjean texture by observation using a polarizing microscope. Homogeneousness can be achieved by applying surface treatment to a cell interface (for example, by applying a technique such as rubbing), or by arranging a liquid crystal alignment layer using polyimide or the like, for example.

Further, the Grandjean state having a small amount of defects with high alignment can be achieved by heating the sample an isotropic phase, and then cooling the sample, at a temperature close thereto, to a cholesteric-isotropic phase transition to the cholesteric phase, and by rubbing a cell.

In a planar state, the sample exhibits selective reflection of incident light, and a central wavelength of reflection depends on a helical pitch and average refractive index of a material.

If the electric field is applied to the cell described above, the sample is switched to the homeotropic state, and a helix is loosened, and the molecules are aligned in parallel to the electric field, namely in a direction perpendicular to an electrode surface. In the homeotropic state, light is transmitted through the cell, and when an orthogonal polarizer is placed thereon, a black display is caused.

The sample takes a focalconic texture by reducing or blocking the electric field in the homeotropic state, and the helical axis is aligned perpendicularly to the electric field into a molecular alignment in which the helix is twisted in parallel to the electrode surface. The focalconic state can be achieved by only applying a weak electric field to the sample in the planar state. In the focalconic state, light is scattered, and when the sample is placed between the orthogonal polarizers, a bright display is caused.

Bimesogenic compound (1) can be easily achieved in macroscopically uniform alignment, and therefore is particularly useful for a flexo-electric liquid crystal display device.

Next, an embodiment on the liquid crystal display device using the conjugate fibers with the encapsulated liquid crystal or the conjugate fiber aggregate with the encapsulated liquid crystal each encapsulated with the liquid crystal composition having bimesogenic compound (1) will be described.

Figure 2:
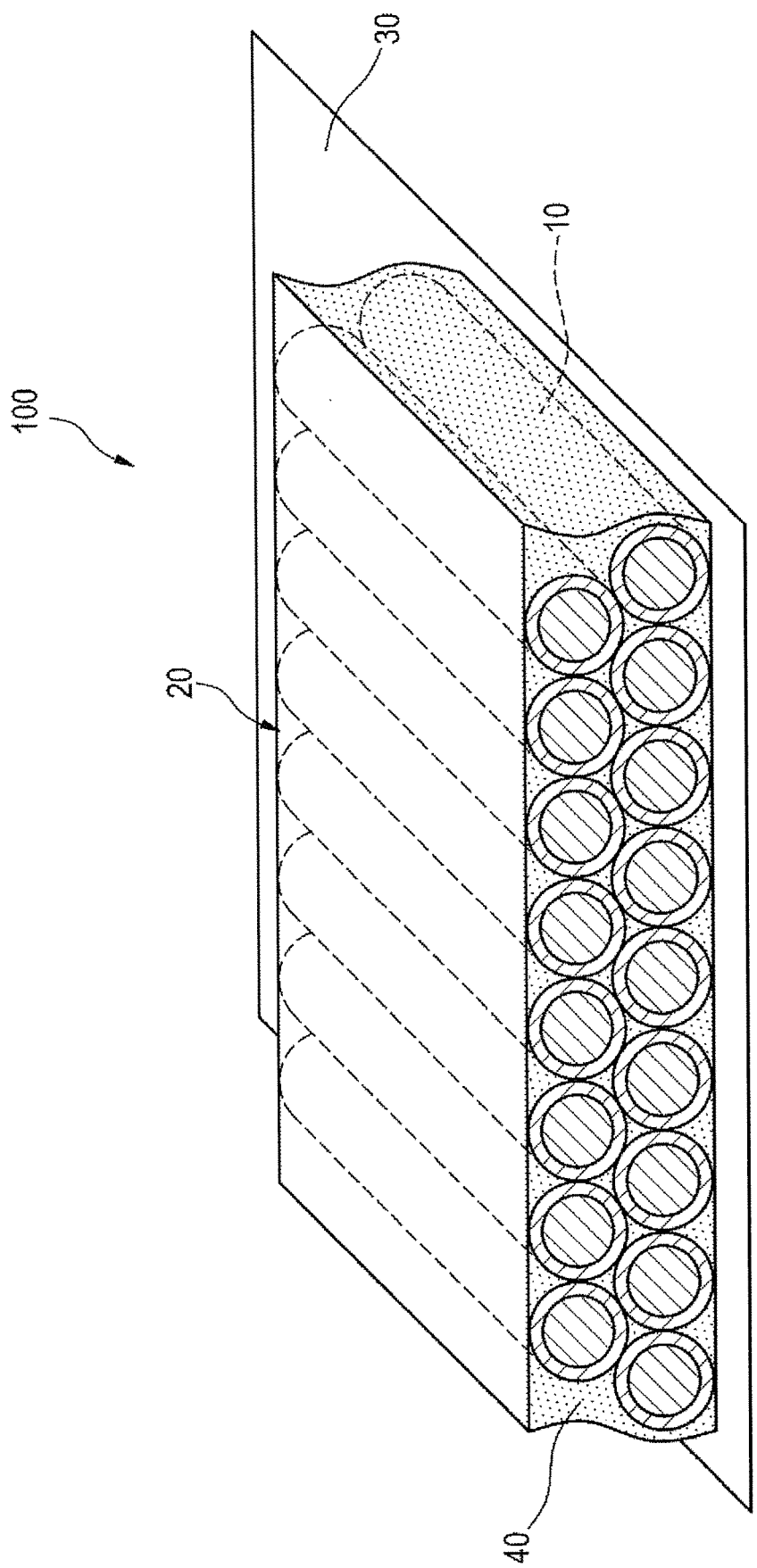
FIG. 2 shows a perspective view of liquid crystal display device 100 of the invention.

FIG. 2 shows a perspective view of liquid crystal display device 100. Liquid crystal display device 100 includes at least one substrate 30 and conjugate fiber aggregate 20 that is arranged on substrate 30, and formed by uniaxially arranging conjugate fibers 10 with the encapsulated liquid crystal. Substrate 30 can be prepared even by a glass substrate, but prepared by using a bendable plastic substrate. Thus, liquid crystal display device 100 can be configured in the form of a bendable flexible liquid crystal display device. Further, liquid crystal display device 100 includes an electrode (not shown) arranged on substrate 30 to apply the electric field or voltage to conjugate fiber aggregate 20 based on a signal from outside. In liquid crystal display device 100, other members such as a thin film transistor device may be further arranged.

Figure 3:
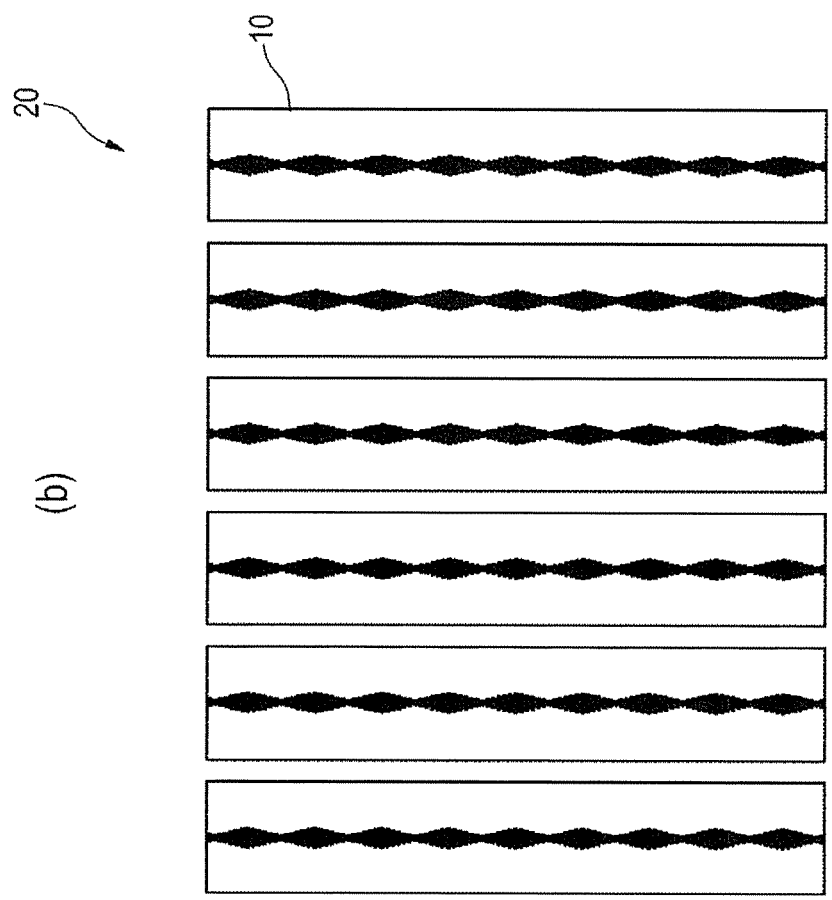
FIG. 3 shows views showing conceptual diagrams of (a) conjugate fibers with an encapsulated liquid crystal and (b) a conjugate fiber aggregate, in a ULH mode liquid crystal display device of the invention.
Figure 3:
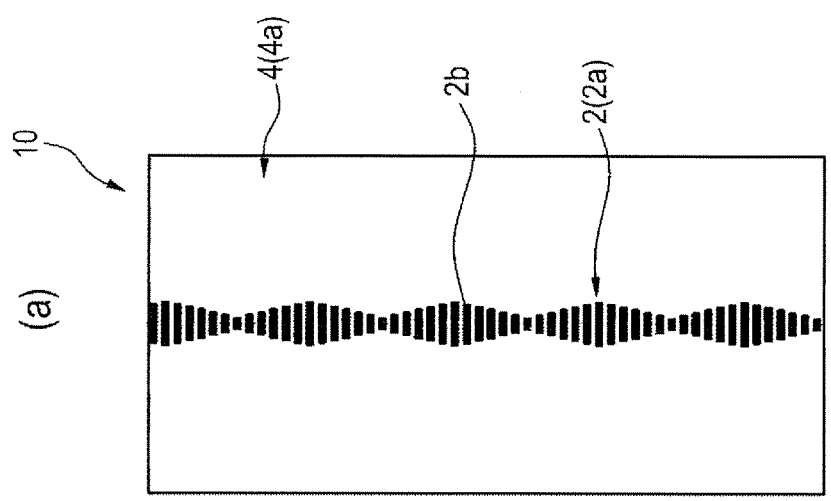

FIG. 3 shows views showing conceptual diagrams of conjugate fibers with an encapsulated liquid crystal and a conjugate fiber aggregate in a ULH mode liquid crystal display device, and FIG. 3(a) is a plan view of the conjugate fibers with the encapsulated liquid crystal, and FIG. 3(b) is a plan view of the conjugate fiber aggregate.

As shown in FIG. 3(b), conjugate fiber aggregate 20 is formed by arranging a plurality of conjugate fibers 10 with the encapsulated liquid crystal, on a substrate (not shown), in a planer shape, preferably also in a height direction (directions on a surface side of a paper surface and on a rear side thereof). A conventional manufacturing method has required the alignment film for aligning the helical axis of the liquid crystal composition in a predetermined direction. The liquid crystal compositions of the present application can be easily arranged in one direction by arranging conjugate fibers 10 with the encapsulated liquid crystal according to the present application in the planer shape, or using conjugate fibers with the encapsulated liquid crystal and or the conjugate fiber aggregate with the encapsulated liquid crystal which is previously arranged in the planer shape. Thus, a large size (large screen) of the ULH mode liquid crystal display device can be achieved.

EXAMPLES

The invention will be described in greater detail by way of Examples. However, the invention is not limited by the Examples.

1. Example of Compound (1)

Compound (1) was prepared according to a method described in Example 1 or the like. The thus prepared compound was identified by a method such as an NMR analysis. Characteristics of the compound were measured by methods described below.

NMR Analysis

For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

HPLC Analysis

For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set at 254 nanometers. A sample was dissolved in acetonitrile and prepared to be a 0.1 weight % solution, and then 1 microliter of the resulting solution was injected into a sample chamber. As a recorder, C-R7A plus made by Shimadzu Corporation was used.

Ultraviolet-Visible Spectrophotometry

For measurement, PharmaSpec UV-1700 made by Shimadzu Corporation was used. A detection wavelength was adjusted in the range from 190 nanometers to 700 nanometers. A sample was dissolved in acetonitrile and prepared to be a 0.01 mmol/L solution, and measurement was carried out by putting the solution in a quartz cell (optical path length: 1 cm).

Sample for Measurement

Upon measuring phase structure and a transition temperature (a clearing point, a melting point, a polymerization start temperature or the like), a compound itself was used as a sample. Upon measuring characteristics such as a maximum temperature of the nematic phase, viscosity, optical anisotropy and dielectric anisotropy, a mixture of a compound and a base liquid crystal was used as a sample.

When the sample prepared by mixing the compound with the base liquid crystal was used, measurement was carried out by the following methods. The sample was prepared by mixing 15% by weight of the compound and 85% by weight of the base liquid crystal. An extrapolated value was calculated from the measured value of the sample according to the extrapolation method represented by the following equation and the calculated value of the sample was described:

{Extrapolated value}={100×(measured value of a sample)−(% by weight of a base liquid crystal)×(measured value of the base liquid crystal)}/(% by weight of the compound).

When crystals (or a smectic phase) precipitated at 25° C. even if the ratio of the compound to the base liquid crystal was in the ratio described above, a ratio of the compound to the base liquid crystal was changed in the order of (10% by weight:90% by weight), (5% by weight:95% by weight) and (1% by weight:99% by weight), and physical properties of the sample were measured at a ratio at which no crystal (or no smectic phase) precipitated at 25° C. In addition, unless otherwise noted, the ratio of the compound to the base liquid crystal was (15% by weight:85% by weight).

When dielectric anisotropy of the compound was positive, base liquid crystal (i) described below was used.

Base Liquid Crystal (i):

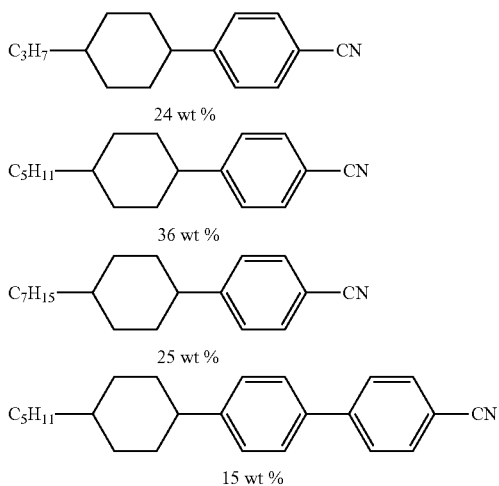

When dielectric anisotropy of the compound was negative, base liquid crystal (ii) described below was used.
Base Liquid Crystal (ii):

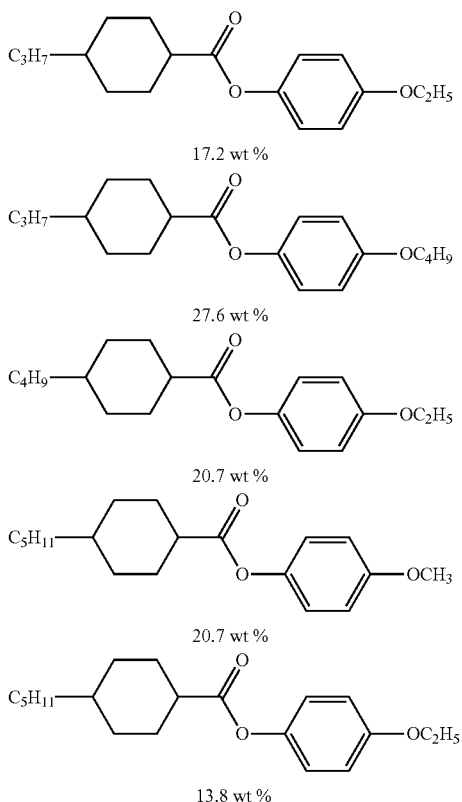

Measuring Method

Characteristics were measured according to the methods described below. Most of the measuring methods are applied as described in the Standard of Japan Electronics and Information Technology Industries Association (JEITA) (JEITA ED-2521B) discussed and established by JEITA, or modified thereon. No thin film transistor (TFT) was attached to a TN device used for measurement.

(1) Phase Structure

A sample was placed on a hot plate in a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A melting point and a polymerization starting temperature of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

A crystal was expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as I. A transition temperature was expressed as "C 50.0 N 100.0 I," for example. The expression indicates that a transition temperature from the crystals to the nematic phase is 50.0° C., and a transition temperature from the nematic phase to the liquid is 100.0° C.

(3) Maximum Temperature of Nematic Phase ($T_{NI}$ or NI; ° C.)

A sample was placed on a hot plate in a melting point measuring apparatus equipped with a polarizing microscope, and heated at a rate of 1° C. per minute. Temperature when part of the sample began to change from a nematic phase to an isotropic liquid was measured. A maximum temperature of the nematic phase may be occasionally abbreviated as "maximum temperature." When the sample was a mixture of compound (1) and the base liquid crystal, the maximum temperature was expressed in terms of a symbol $T_{NI}$. When the sample was a mixture of compound (1) and a compound such as compounds (2) to (15), the measured value was expressed in terms of a symbol NI.

(4) Minimum Temperature of Nematic Phase ($T_C$; ° C.)

Samples each having a nematic phase were kept in freezers at temperatures of 0° C., −10° C., −20° C., −30° C. and −40° C. for 10 days, and then liquid crystal phases were observed. For example, when the sample was maintained the nematic phase at −20° C. and was changed to crystals or a smectic phase at −30° C., $T_C$ was expressed as $T_C \leq -20°$ C. A minimum temperature of the nematic phase may be occasionally abbreviated as "minimum temperature."

(5) Compatibility of Compound

The base liquid crystal having the nematic phase was prepared by mixing several kinds of compounds each having a similar structure. A compound to be measured was added to the base liquid crystal. One example of the ratio to be mixed was (15% by weight:85% by weight) in the compound to the base liquid crystal. The composition obtained was kept at a low temperature such as −20° C. and −30° C. for 30 days. Whether or not a part of the compound was changed to crystals (or the smectic phase was observed. The mixing ratio and the storage temperature were changed when necessary. From thus measured results, a condition where crystals (or a smectic phase) precipitated and a condition where no crystals (or no smectic phase) precipitated were determined. The conditions obtained were a scale of compatibility.

(6) Viscosity (Bulk Viscosity; η; Measured at 20° C.; mPa·s)

Viscosity was measured by using a cone-plate (E type) rotational viscometer made by Tokyo Keiki Inc.

(7) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism.

A refractive index (n∥) was measured when a direction of polarized light was parallel to a direction of rubbing. A refractive index (n⊥) was measured when the direction of polarized light was perpendicular to the direction of rubbing. A value of optical anisotropy (Δn) was calculated from an equation:

$$\Delta n = n\| - n\perp.$$

(8) Specific Resistance (ρ; Measured at 25° C.; Ωcm)

Into a vessel equipped with electrodes, 1.0 milliliter of sample was injected. A direct current voltage (10 V) was applied to the vessel, and a direct current after 10 seconds was measured. Specific resistance was calculated from the following equation:

(specific resistance)={(voltage)×(electric capacity of a vessel)}/{(direct current)×(dielectric constant of vacuum)}.

(9) Voltage Holding Ratio (VHR-1; Measured at 25° C.; %)

A TN device used for measurement had a polyimide alignment film, and a distance (cell gap) between two glass substrates was 5 micrometers. A sample was put in the device, and then the device was sealed with an ultraviolet-curable adhesive. The device was charged by applying a pulse voltage (60 microseconds at 5 V). A decaying voltage was measured for 16.7 milliseconds with a high-speed voltmeter, and area A between a voltage curve and a horizontal axis in a unit cycle was determined. Area B was an area without decay. A voltage holding ratio was expressed in terms of a percentage of area A to area B.

(10) Voltage Holding Ratio (VHR-2; Measured at 80° C.; %)

A voltage holding ratio was measured according to procedures identical with the procedures described above except that measurement was carried out at 80° C. in place of 25° C. The results were expressed in terms of a symbol VHR-2.

The measuring method of the characteristics may be different between a sample having a positive dielectric anisotropy and a sample having a negative dielectric anisotropy. When the dielectric anisotropy was positive, the measuring method was described in sections (11a) to (15a). When the dielectric anisotropy was negative, the measuring methods were described in sections (11b) to (15b).

(11a) Viscosity (Rotational Viscosity; γ1; Measured at 25° C.; mPa·s)

Positive dielectric anisotropy: Measurement was carried out according to a method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) described on page 40 of the paper presented by M. Imai et al. A value of dielectric anisotropy required for the calculation was determined using the device by which the rotational viscosity was measured and by a method described below.

(11b) Viscosity (Rotational Viscosity; γ1; Measured at 25° C.; mPa·s)

Negative dielectric anisotropy: Measurement was carried out according to a method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 39 V to 50 V at an increment of 1 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and calculation equation (8) described on page 40 of the paper presented by M. Imai et al. In dielectric anisotropy required for the calculation, a value measured according to items of dielectric anisotropy described below was used.

(12a) Dielectric Anisotropy (Δε; Measured at 25° C.)

Positive dielectric anisotropy: A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (ε∥) of liquid crystal molecules in a major axis direction was measured. Sine waves (0.5 V, 1 kHz) were applied to the device, and after 2 seconds, a dielectric constant (ε⊥) of liquid crystal molecules in a minor axis direction was measured. A value of dielectric anisotropy was calculated from an equation:

$$\Delta\varepsilon = \varepsilon\| - \varepsilon\perp.$$

(12b) Dielectric Anisotropy (Δε; Measured at 25° C.)

Negative dielectric anisotropy: A value of dielectric anisotropy was calculated from an equation:

$$\Delta\varepsilon = \varepsilon\| - \varepsilon\perp.$$

A dielectric constants (ε∥ and ε⊥) was measured as described below.

(1) Measurement of a dielectric constant (ε∥): An ethanol (20 mL) solution of octadecyltriethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (ε∥) of liquid crystal molecules in a major axis direction was measured.

(2) Measurement of a dielectric constant (($\epsilon\perp$): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant ($\epsilon\perp$) of liquid crystal molecules in a minor axis direction was measured.

(13a) Elastic Constant (K; Measured at 25° C.; pN)

Positive dielectric anisotropy: For measurement, HP4284A LCR Meter made by Yokogawa-Hewlett-Packard Co. was used. A sample was put in a horizontal alignment device in which a distance (cell gap) between two glass substrates was 20 micrometers. An electric charge of 0 V to 20 V was applied to the device, and electrostatic capacity and applied voltage were measured. The measured values of electrostatic capacity (C) and applied voltage (V) were fitted to equation (2.98) and equation (2.101) on page 75 of "Liquid Crystal Device Handbook" (Ekisho Debaisu Handobukku in Japanese; Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed in terms of a mean value of the thus determined $K_{11}$, $K_{22}$ and $K_{33}$.

(13b) Elastic Constant ($K_{11}$ and $K_{33}$; Measured at 25° C.; pN)

Negative dielectric anisotropy: For measurement, Elastic Constant Measurement System Model EC-1 made by TOYO Corporation was used. A sample was put in a vertical alignment device in which a distance (cell gap) between two glass substrates was 20 micrometers. An electric charge of 20 V to 0 V was applied to the device, and electrostatic capacity and applied voltage were measured. Values of electrostatic capacity (C) and applied voltage (V) were fitted to equation (2.98) and equation (2.101) on page 75 of "Liquid Crystal Device Handbook" (Ekisho Debaisu Handobukku in Japanese; Nikkan Kogyo Shimbun, Ltd.), and a value of elastic constant was obtained from equation (2.100).

(14a) Threshold Voltage (Vth; Measured at 25° C.; V)

Positive dielectric anisotropy: For measurement, an LCD-5100 luminance meter made by Otsuka Electronics Co., Ltd. was used. A light source was a halogen lamp. A sample was put in a normally white mode TN device in which a distance (cell gap) between two glass substrates was 0.45/$\Delta$n (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 90% transmittance.

(14b) Threshold Voltage (Vth; Measured at 25° C.; V)

Negative dielectric anisotropy: For measurement, an LCD-5100 luminance meter made by Otsuka Electronics Co., Ltd. was used. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of a voltage at 10% transmittance.

(15a) Response Time ($\tau$; Measured at 25° C.; Ms)

Positive dielectric anisotropy: For measurement, an LCD-5100 luminance meter made by Otsuka Electronics Co., Ltd. was used. A light source was a halogen lamp. A low-pass filter was set to 5 kHz. A sample was put in a normally white mode TN device in which a distance (cell gap) between two glass substrates was 5.0 micrometers and a twist angle was 80 degrees. A voltage (rectangular waves; 60 Hz, 5 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time ($\tau r$; millisecond) was expressed in terms of time required for a change from 90% transmittance to 10% transmittance. A fall time ($\tau f$; millisecond) was expressed in terms of time required for a change from 10% transmittance to 90% transmittance. A response time is expressed by a sum of the rise time and the fall time thus determined.

(15b) Response Time ($\tau$; Measured at 25° C.; Ms)

Negative dielectric anisotropy: For measurement, an LCD-5100 luminance meter made by Otsuka Electronics Co., Ltd. was used. A light source was a halogen lamp. A low-pass filter was set to 5 kHz. A sample was put in a normally black mode PVA device in which a distance (cell gap) between two glass substrates was 3.2 micrometers and a rubbing direction was anti-parallel. The device was sealed with an ultraviolet-curable adhesive. The device was applied with a voltage of a little exceeding a threshold voltage for 1 minute, and then was irradiated with ultraviolet light of 23.5 mW/cm$^2$ for 8 minutes, while applying a voltage of 5.6 V. A voltage (rectangular waves; 60 Hz, 10 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A response time is expressed in terms of time required for a change from 90% transmittance to 10% transmittance (fall time; millisecond).

Examples of Liquid Crystal Compound

Examples of liquid crystal compounds and so forth are described below.

Example 1

Synthesis of 1,9-di(4-(4-fluorophenyl)-3-fluorophenyloxy)-5-nonanone (Compound (1-102))

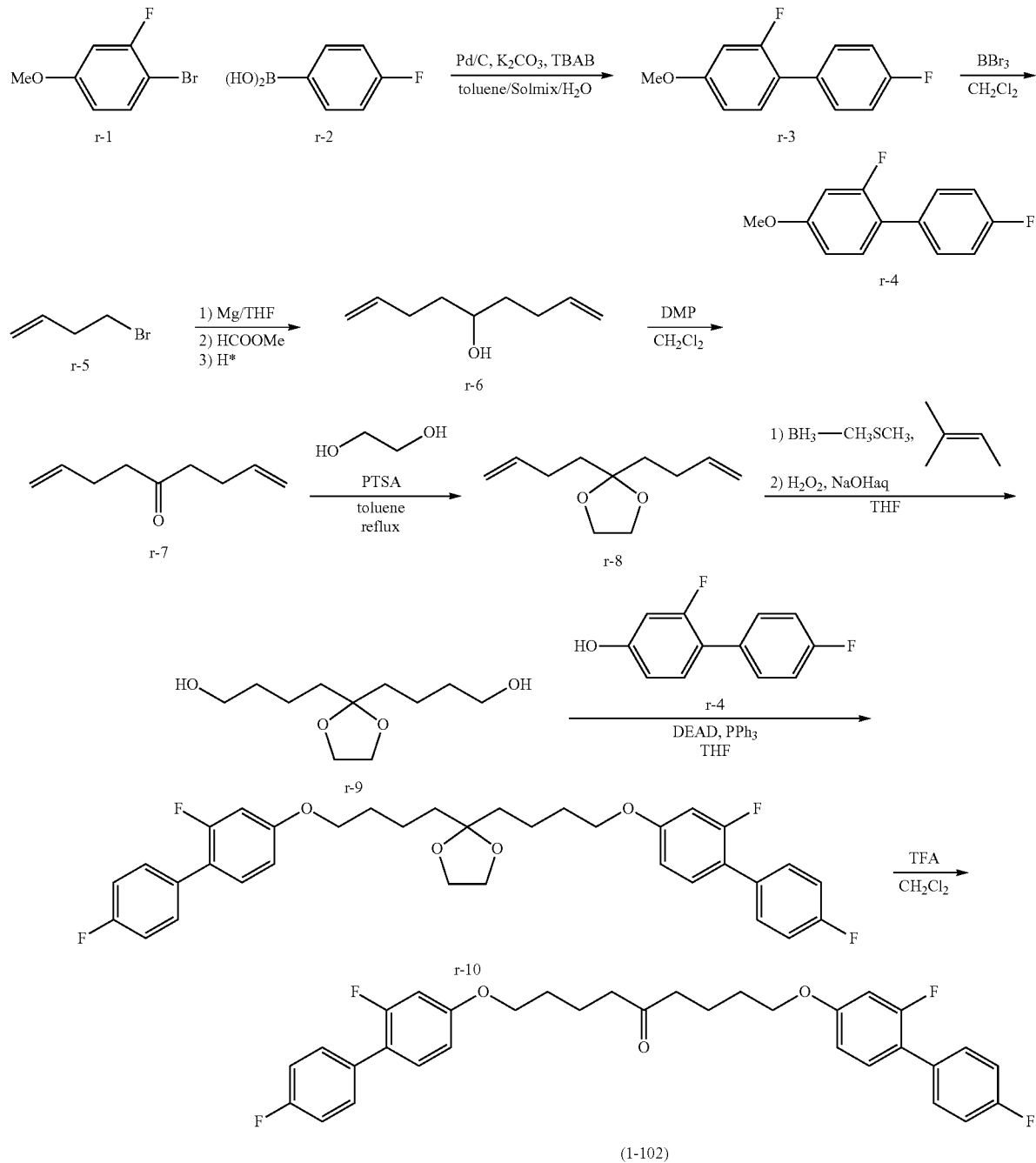

First Step

Then, 25.0 g (121.94 mmol) of compound (r-1), 20.5 g (146.3 mmol) of compound (r-2), 1.3 g of 5 wt %-palladium on carbon (Pd/C), 33.7 g (244 mmol) of potassium carbonate and 7.9 g (322.4 mmol) of tetrabutylammonium bromide (TBAB) were suspended into a mixed solvent of toluene/Solmix/water (75 mL/75 mL/75 mL), and the resulting suspension was refluxed under heating for 20 hours. The resulting reaction mixture was left to cool to room temperature, and then the reaction suspension was filtered by a filter paper, and the resulting solution was subjected to extraction with toluene. The resulting extracted solution was washed with water (150 mL) and saturated brine (150 mL), and dried over anhydrous magnesium sulfate. A solvent was distilled off under reduced pressure, and then the residue was purified by silica gel column chromatography (eluate:heptane/toluene=3/1 (volume ratio) to obtain 23.9 g (108.4 mmol) of compound (r-3) with a yield of 88.9%.

Second Step

A dichloromethane (470 mL) solution of 23.9 g (108.4 mmol) of compound (r-3) was cooled down to −20° C., and 162.7 mL (162.7 mmol) of boron tribromide dichloromethane solution (17% by weight, about 1 mol/L) was added dropwise thereto, and the resulting mixture was heated to room temperature, and stirred overnight. The resulting reaction mixture was poured into 200 mL of ice water, 100 mL of sodium hydrogencarbonate aqueous solution was added thereto, and subjected to extraction with ethyl acetate. The resulting extracted solution was washed with 200 mL of water and 200 mL of saturated brine, and then dried over anhydrous magnesium sulfate. A solvent was distilled off under reduced pressure, and the residue was fractionated by column chromatography (eluate:heptane/ethyl acetate=4/1), and then purified by recrystallization (solvent:heptane/ethyl acetate=10/1) to obtain 15.9 g (77.1 mmol) of compound (r-4) with a yield of 71.1%.

Third Step

Then, 19.80 g (614.8 mmol) of magnesium was suspended into 230 mL of tetrahydrofuran, and a tetrahydrofuran (THF) solution (150 mL) of 100.0 g (740.7 mmol) of compound (r-5) was added dropwise thereto. The resulting mixture was refluxed under heating for 1 hour, left to cool to room temperature, and a solution in which 20.02 g (333.3 mmol) of methyl formate was dissolved in 20 mL of THF was added dropwise thereto, and the resulting mixture was stirred overnight at room temperature. The resulting reaction mixture was poured into 300 mL of aqueous solution of ammonium chloride, and subjected to extraction with dichloroethane. The resulting extracted solution was washed with 200 mL of water and 200 mL of saturated brine, and dried over anhydrous magnesium sulfate. A solvent was distilled off under reduced pressure, and the residue was purified by silica gel column chromatography (eluate:heptane/ethyl acetate=6/1 (volume ratio)) to quantitatively obtain 46.8 g (333.3 mmol) of compound (r-6).

Fourth Step

A solution in which 46.8 g (333.3 mmol) of compound (r-6) was dissolved in 470 mL of dichloromethane was cooled down to 0° C., and 155.5 g (366.7 mmol) of Dess-Martin periodinane was added thereto little by little, and the resulting mixture was heated to room temperature, and stirred for 5 hours. The resulting reaction mixture was poured into 300 mL of sodium hydrogencarbonate aqueous solution, and sodium sulfite was added thereto. The resulting mixture was subjected to extraction with dichloromethane, and then an organic layer was combined, washed with 200 mL of water and 200 mL of saturated brine, and dried over anhydrous magnesium sulfate. A solvent was distilled off under reduced pressure, and the residue was purified by silica gel column chromatography (eluate:heptane/ethyl acetate=8/1 (volume ratio)) to quantitatively obtain 40.1 g (333.3 mmol) of compound (r-7).

Fifth Step

A solution in which 40.1 g (333.3 mmol) of compound (r-7), 22.8 g (366.7 mmol) of ethylene glycol and p-toluenesulfonic acid monohydrate (0.444 g, 2.33 mmol) were dissolved in 900 mL of toluene was refluxed under heating for 8 hours using a Dean-Stark apparatus while water was removed. The resulting reaction mixture was left to cool to room temperature, and then poured into 300 mL of sodium hydrogencarbonate aqueous solution, and subjected to extraction with dichloromethane. The resulting extracted solution was washed with 200 mL of water and 200 mL of saturated brine, and dried over anhydrous magnesium sulfate. A solvent was distilled off under reduced pressure, and the residue was purified by silica gel column chromatography (eluate:heptane/ethyl acetate=20/1 (volume ratio)) to obtain 56.7 g (310.9 mmol) of compound (r-8) with a yield of 93.3%.

Sixth Step

A solution in which 83.7 g (1102 mmol) of borane dimethyl sulfide was dissolved in 200 mL of THF was cooled down to −10° C., and a solution in which 154.6 g (2205 mmol) of 2-methyl-2-butene was dissolved in 600 mL of THF was added dropwise thereto. The resulting mixture was stirred at 0° C. for 2 hours, and then a solution in which 43.1 g (236.9 mmol) of compound (r-8) was dissolved in 310 mL of THF was added dropwise thereto. The resulting mixture was stirred at 0° C. for 2 hours, and then heated to room temperature, stirred overnight at a same temperature, and then 250.5 mL of 6 N sodium hydroxide aqueous solution, 507.2 mL of 30% by weight hydrogen peroxide and 731.4 mL of ethanol were slowly added dropwise thereto, respectively. The resulting mixture was stirred at 50° C. for 3 hours, and the resulting reaction mixture was left to cool to room temperature. The resulting mixture was subjected to extraction with diethyl ether, and then the resulting extracted solution was dried over anhydrous magnesium sulfate. A solvent was distilled off under reduced pressure, and the residue was purified by silica gel column chromatography (eluate:chloroform/methanol=100/5 (volume ratio)) to obtain 51.3 g (234.9 mmol) of compound (r-9) with a yield of 93.8%.

Seventh Step

Then, 240 mL of THF solution of 7.21 g (33.0 mmol) of compound (r-9), 13.6 g (66.1 mmol) of compound (r-4) and 26.0 g (99.1 mmol) of triphenyl phosphine was cooled down to 0° C., and 45.0 mL (99.1 mmol) of diethyl azodicarboxylate (DEAD; 40% by weight toluene solution, about 2.2 mol/L) was added dropwise thereto, and the resulting reaction mixture was heated to room temperature, and then stirred overnight. The resulting mixture was subjected to extraction with ethyl acetate, and the resulting extracted solution was washed with 100 mL of water and 100 mL of saturated brine, and dried over anhydrous magnesium sulfate. A solvent was distilled off under reduced pressure, and the residue was purified by silica gel column chromatography (eluate:heptane/ethyl acetate=4/1 (volume ratio)) to obtain 12.0 g (20.2 mmol) of compound (r-10) with a yield of 61.1%.

Eighth Step

To a solution in which 12.0 g (20.2 mmol) of compound (r-10) was dissolved in 125 mL of dichloroethane, 23.0 g (201.5 mmol) of trifluoroacetic acid was added little by little, and the resulting reaction mixture was stirred overnight. The resulting reaction solution was poured into water, and subjected to extraction with ethyl acetate, and the resulting extracted solution was washed with 100 mL of water and 100 mL of saturated brine, and dried over anhydrous magnesium sulfate. A solvent was distilled off under reduced pressure, and the residue was purified by silica gel column chromatography (eluate:heptane/ethyl acetate=3/1 (volume ratio)) to obtain 10.9 g (19.9 mmol) of compound (1-102) with a yield of 98.6%.

¹H-NMR (CDCl₃; δ ppm): 7.47-7.44 (4H, m), 7.29 (2H, t, J=8.8 Hz), 7.13-7.08 (4H, m), 6.74 (2H, dd, J=2.5 Hz, 8.5 Hz), 6.69 (2H, dd, J=2.5, 12.4), 3.98 (4H, t, J=5.9 Hz), 2.53 (4H, t, J=6.9 Hz), 1.82-1.76 (8H, m), 1.35 (3H, t, J=6.9 Hz).

A transition temperature was expressed using a measured value of compound (1-102) itself, and maximum temperature ($T_{NI}$), a value of dielectric anisotropy (Δε) and a value of optical anisotropy (Δn) each were expressed using an extrapolated value obtained by converting, according to the extrapolation method described above, a measured value of a sample formed by mixing compound (1-102) with base liquid crystal i. Values of physical properties of compound (1-102) were as described below.

Transition temperature: Cr 75.8 Iso.

$T_{NI}$=37.7° C., Δε=5.1, Δn=0.147.

Example 2

Synthesis of 1,9-di(4-(4-fluorophenyl)-3-fluorophenyloxy)-5-propylnonane (Compound (1-104))

tography (eluate:heptane/ethyl acetate=4/1 (volume ratio)) to quantitatively obtain 3.07 g (5.16 mmol) of compound (r-11).

Second Step

A solution in which 2.74 g (4.61 mmol) of compound (r-11) was dissolved in 16 mL of dichloromethane was cooled down to −60° C., and a solution in which 0.54 g (4.61 mmol) of triethylsilane was dissolved in 11 mL of dichloromethane was added dropwise thereto, and the resulting mixture was stirred at −60° C. for 20 minutes. Then, 1.31 g (9.22 mol) of boron trifluoride-ether complex was added dropwise thereto, and the resulting mixture was heated to room temperature, and stirred overnight. The resulting reaction mixture was poured into ice water, and subjected to extraction with ethyl acetate. The resulting extracted solution was washed with 20 mL of water and 20 mL of saturated brine, and dried over anhydrous magnesium sulfate. A solvent was distilled off under reduced pressure, and the residue was purified by silica gel column chromatography

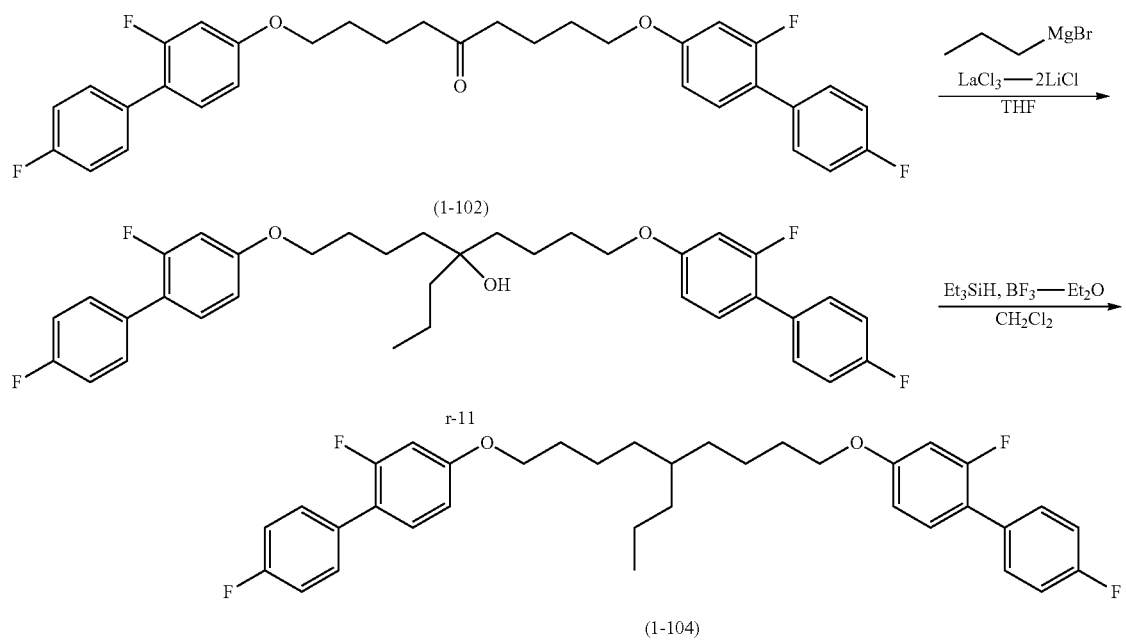

First Step

To 15.01 mL (15.5 mmol) of propylmagnesium bromide tetrahydrofuran solution (1.02 mol/L), 9.45 mL (5.67 mmol) of lanthanum chloride-bislithium chloride complex (0.6 mol/L) was added, and the resulting mixture was cooled down to 0° C., and a solution in which 2.84 g (5.16 mmol) of compound (1-102) was dissolved in 30 mL of THF was added dropwise thereto, and the resulting mixture was stirred overnight at room temperature. The resulting reaction mixture was poured into 20 mL of 1 N hydrochloric acid, and subjected to extraction with ethyl acetate. The resulting extracted solution was washed with 30 mL of water and 30 mL of saturated brine, and dried over anhydrous magnesium sulfate. A solvent was distilled off under reduced pressure, and the residue was purified by silica gel column chroma- (eluate:heptane/ethyl acetate=40/1 (volume ratio)) to obtain 1.65 g (2.85 mmol) of compound (1-104) with a yield of 72.0%.

A transition temperature was expressed using a measured value of compound (1-104) itself, and maximum temperature ($T_{NI}$), a value of dielectric anisotropy (Δε) and a value of optical anisotropy (Δn) each were expressed using an extrapolated value obtained by converting, according to the extrapolation method described above, a measured value of a sample formed by mixing compound (1-104) with base liquid crystal i. Values of physical properties of compound (1-104) were as described below.

Transition temperature: Gr −39.4 Iso.

$T_{NI}$=−34.3° C., Δε=6.5, Δn=0.07.

Example 3

Synthesis of 1,9-di(4-(4-fluorophenyl)-3-fluorophenyloxy)-5,5-difluorononane (Compound (1-103))

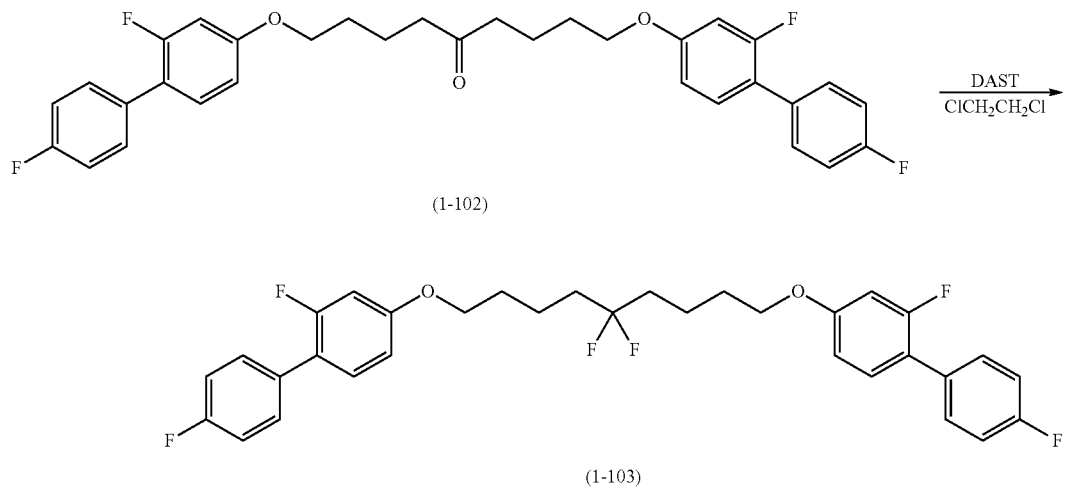

First Step

A solution in which 5.0 g (9.08 mmol) of compound (1-102) was dissolved in 30 mL of dichloroethane was cooled down to 0 to −5° C., and a dichloroethane (30 mL) solution of 14.6 g (90.8 mmol) of diethylaminosulfur trifluoride (DAST) was added dropwise thereto. The resulting mixture was stirred under heating at 80° C. for 26 hours, and then cooled down to room temperature, and then the resulting reaction mixture was poured into a saturated aqueous solution of sodium hydrogencarbonate. The resulting mixture was subjected to extraction with toluene, and then the resulting extracted solution was washed with 40 mL of water and 40 mL of saturated brine, and dried over anhydrous magnesium sulfate. A solvent was distilled off under reduced pressure, and the residue was purified by silica gel column chromatography (eluate:heptane/ethyl acetate=from 8/1 to 4/1 (volume ratio)) to obtain 1.8 g (3.20 mmol) of compound (1-103) with a yield of 35.2%.

$^1$H-NMR (CDCl$_3$; δ ppm): 7.47-7.44 (4H, m), 7.29 (2H, t, J=8.9 Hz), 7.13-7.08 (4H, m), 6.75 (2H, dd, J=2.5 Hz, 8.5 Hz), 6.70 (2H, dd, J=2.4 Hz, 12.4), 4.00 (4H, t, J=6.3 Hz), 1.98-1.81 (8H, m), 1.73-1.67 (4H, m).

A transition temperature was expressed using a measured value of compound (1-103) itself, and maximum temperature (T$_{NI}$), a value of dielectric anisotropy (Δε) and a value of optical anisotropy (Δn) each were expressed using an extrapolated value obtained by converting, according to the extrapolation method described above, a measured value of a sample formed by mixing compound (1-103) with base liquid crystal i. Values of physical properties of compound (1-103) were as described below.

Transition temperature: Cr1 61.7 Cr2 98.0 Iso.

T$_{NI}$=18.4° C., Δε=8.5, Δn=0.104.

Example 4

Synthesis of 1,5-di(4-(4-fluorophenyl)-3-fluorophenyloxy)-3-methylpentane (Compound (1-1))

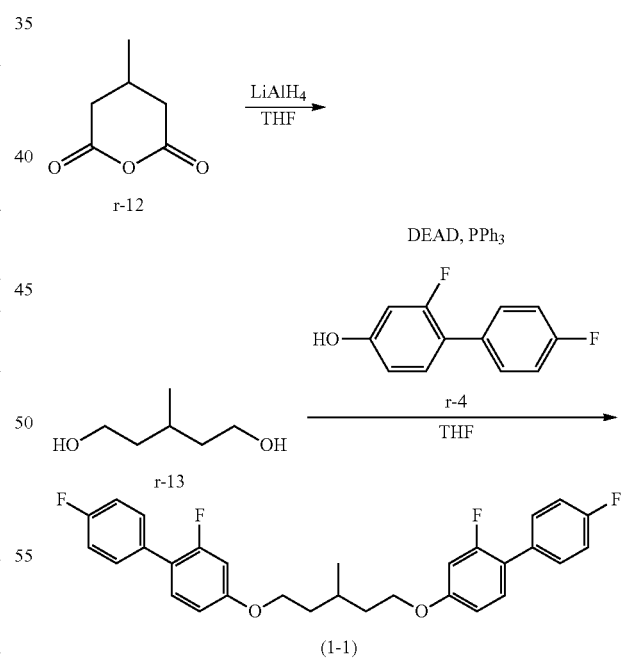

First Step

Under a nitrogen atmosphere, a solution in which 5.0 g of 3-methylglutaric anhydride (r-12) was dissolved in 50 mL of THF under ice cooling was added dropwise to a mixture in which 2.96 g of lithium aluminum hydride was dispersed in 25 mL of THF, and the resulting mixture was stirred at room temperature for 2 hours. To the resulting reaction solution, 100 mL of toluene was added, and a saturated aqueous solution of sodium sulfate was further added dropwise until a gum-shaped deposit was formed. An organic layer and a gum-shaped substance were separated by decantation, and the organic layer was dried over anhydrous magnesium sulfate. A solvent was distilled off to obtain 3.75 g of 3-methyl-1,5-pentanediol (compound (r-13)).

Second Step

Under a nitrogen atmosphere, 3.75 g of compound (r-13), 13.1 g of compound (r-3) and 20.0 g of triphenyl phosphine were dissolved in 200 mL of THF, and 34.6 mL of DEAD toluene solution (2.2 mol/L) was slowly added dropwise thereto under ice cooling, and the resulting mixture was stirred overnight at room temperature. A solvent of the resulting reaction solution was distilled off under reduced pressure, and the residue obtained was purified by fractionation by silica gel column chromatography (eluate: heptane/ ethyl acetate=1/9 (volume ratio)), and further purified by recrystallization from a mixed solvent of heptane/Solmix (registered trademark) A-11=1/2 (volume ratio) to obtain 6.5 g of 1,5-di(4-(4-fluorophenyl)-3-fluorophenyloxy)-3-methylpentane (compound (1-1)).

$^1$H-NMR (CDCl$_3$ δ [ppm]); 7.44 (dd, 4H), 7.27 (t, 2H), 7.08 (dd, 1H), 6.74 (dd, 2H), 6.69 (dd, 2H), 4.07-4.00 (m, 4H), 2.03-1.99 (m, 1H), 1.95-1.88 (m, 2H), 1.73-1.66 (m, 2H), 1.05 (d, 3H).

A transition temperature was expressed using a measured value of compound (1-1) itself, and maximum temperature ($T_{NI}$), a value of dielectric anisotropy (Δε) and a value of optical anisotropy (Δn) each were expressed using an extrapolated value obtained by converting, according to the extrapolation method described above, a measured value of a sample formed by mixing compound (1-1) with base liquid crystal i. Values of physical properties of compound (1-1) were as described below.

Transition temperature: Cr1 66.4 Cr2 93.7 Iso.
$T_{NI}$=−0.3° C., Δε=9.90, Δn=0.117.

Example 5

Synthesis of 1,9-di(4-(4-ethoxy-2,3-difluorophenyl)-3-fluorophenyloxy-5-nonanone (Compound (1-122))

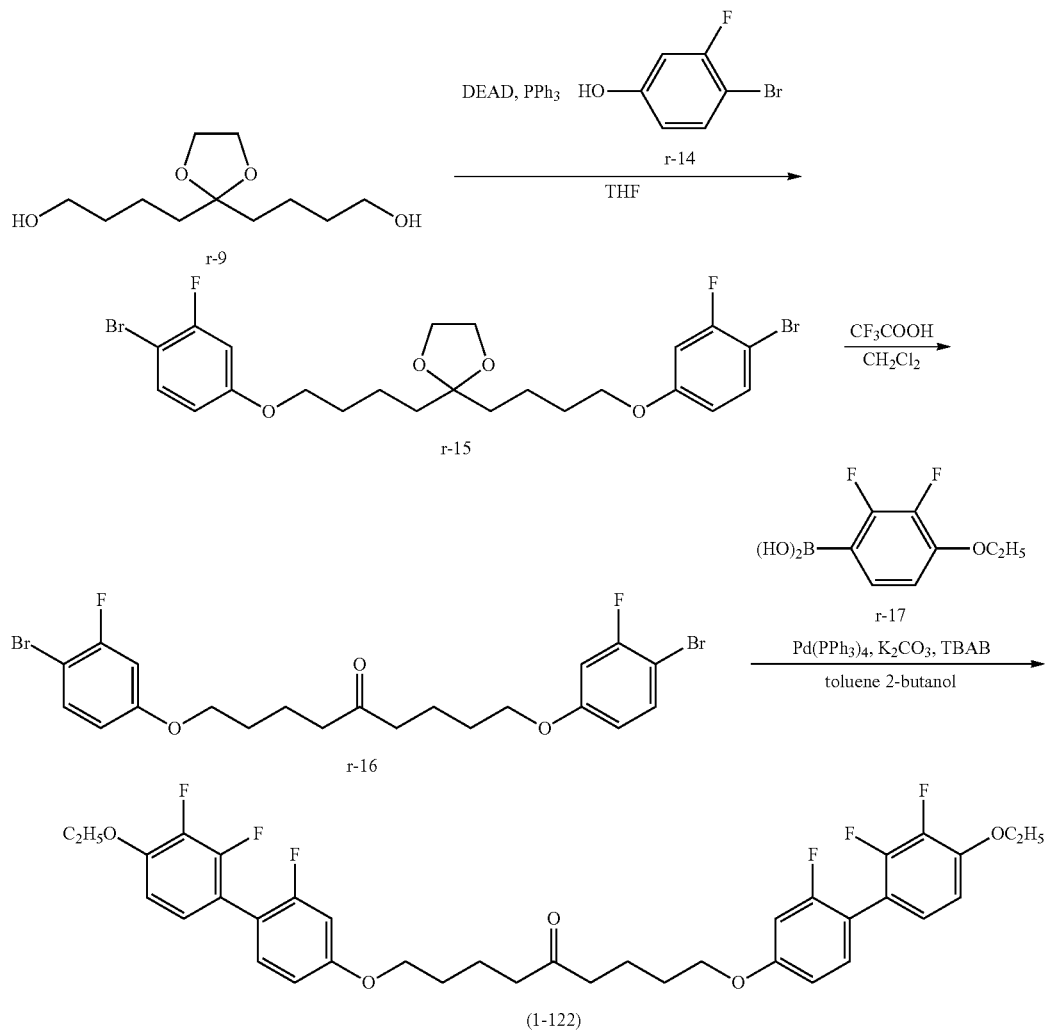

First Step

Under a nitrogen atmosphere, 83.8 g (192.5 mmol) of 40% DEAD toluene solution was added dropwise, under ice cooling, to a solution in which 20.0 g (91.6 mmol) of compound (r-9), 35.2 g (184.0 mmol) of compound (r-14) and 50.67 g (193.2 mmol) of triphenylphosphine were dissolved in 200 mL of THF, and the resulting mixture was stirred overnight at room temperature. A solvent was distilled off under reduced pressure of the resulting reaction solution, and the residue obtained was purified by fractionation by silica gel column chromatography (eluate:toluene) to obtain 27.8 g of compound (r-15).

Second Step

To a solution in which 26.8 g (47.5 mmol) of compound (r-15) was dissolved in 270 mL of dichloroethane, 53.3 g (467.3 mmol) of trifluoroacetic acid was added little by little, and the resulting reaction mixture was stirred overnight. The resulting reaction solution was poured into water, subjected to extraction with ethyl acetate, and the resulting extracted solution was washed with 300 mL of water and 300 mL of saturated brine, and dried over anhydrous magnesium sulfate. A solvent was distilled off under reduced pressure, and the residue was purified by silica gel column chromatography (eluate:heptane/ethyl acetate=2/1 (volume ratio)) to obtain 22.0 g (42.3 mmol) of compound (r-16).

Third Step

Then, 14.0 g (27.0 mmol) of compound (r-16), 16.4 g (51.3 mmol) of compound (r-17), 1.55 g (1.34 mmol) of tetrakistriphenylphosphine palladium, 16.8 g (121 mmol) of potassium carbonate and 4.35 g (13.5 mmol) of tetrabutylammonium bromide (TBAB) were suspended in a mixed solvent of toluene/1-butanol (90 mL/75 mL), and the resulting suspension was refluxed under heating for 5 hours. The resulting reaction mixture was left to cool to room temperature, and then subjected to extraction with toluene. The resulting extracted solution was washed with water (150 mL) and saturated brine (150 mL), and dried over anhydrous magnesium sulfate. A solvent was distilled off under reduced pressure, and then the residue was purified by fractionation by silica gel column chromatography (eluate:heptane/ethyl acetate=2/1 (volume ratio)), and further purified by recrystallization to obtain 5.7 g of 1,9-di(4-(4-ethoxy-2,3-difluorophenyl)-3-fluorophenyloxy)-5-nonanone (Compound (1-122)).

$^1$H-NMR (CDCl$_3$ δ [ppm]); 7.23 (t, 2H), 7.00 (td, 2H), 6.78 (td, 2H), 6.74 (dd, 2H), 6.69 (dd, 2H), 4.15 (q, 4H), 3.98 (t, 4H), 2.53, (t, 4H), 1.84-1.76 (m, 8H), 1.48, (t, 3H).

A transition temperature was expressed using a measured value of compound (1-122) itself, and maximum temperature ($T_{NI}$), a value of dielectric anisotropy (Δε) and a value of optical anisotropy (Δn) each were expressed using an extrapolated value obtained by converting, according to the extrapolation method described above, a measured value of a sample formed by mixing compound (1-122) with base liquid crystal ii. Values of physical properties of compound (1-122) were as described below.

Transition temperature: Cr 122 Iso.

$T_{NI}$=74.3° C., Δε=−7.71, Δn=0.187.

Example 6

Synthesis of 1,9-di(4-(3,5-difluoro-4-((3,4,5-trifluorophenoxy)difluoromethyl)phenyl)-3-fluorophenyloxy)-5-nonanone (Compound (1-367))

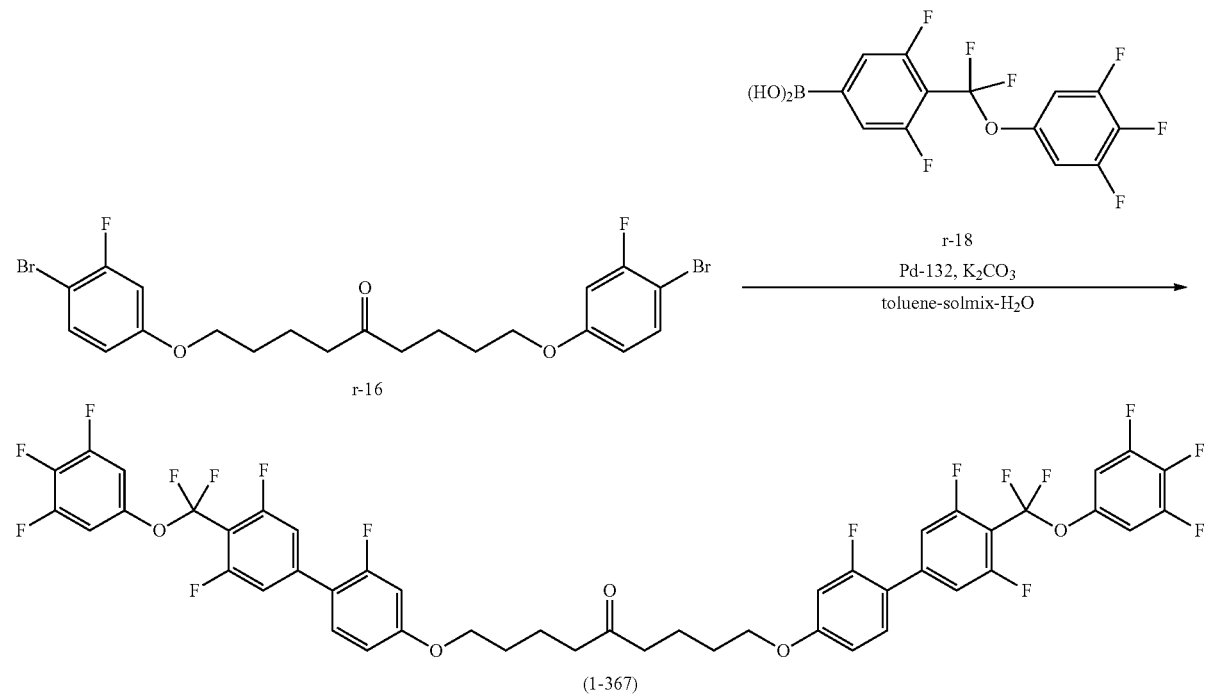

Third Step

Then, 7.36 g (14.1 mmol) of compound (r-16), 11.0 g (31.1 mmol) of compound (r-18), 0.072 g (0.10 mmol) of bis(di-tert-butyl(4-dimethylaminophenyl)phosphine)dichloropalladium (II) (Pd-132) and 5.87 g (42.4 mmol) of potassium carbonate were suspended into a mixed solvent of toluene/Solmix/water (30 mL/5 mL/10 mL), and the resulting mixture was refluxed under heating for 5 hours. The resulting reaction mixture was left to cool to room temperature, and subjected to extraction with toluene. The resulting extracted solution was washed with water (150 mL) and saturated brine (150 mL), and dried over anhydrous magnesium sulfate. A solvent was distilled off under reduced pressure, and the residue was purified by fractionation by silica gel column chromatography (eluate:heptane/ethyl acetate=2/1 (volume ratio)), and further purified by recrystallization from a mixed solvent of heptane/ethyl acetate=9/1 (volume ratio) to obtain 5.92 g of 1,9-di(4-(3,5-difluoro-4-((3,4,5-trifluorophenoxy)(difluoromethyl)phenyl)-3-fluorophenyloxy)-5-nonanone (Compound (1-367)).

$^1$H-NMR (CDCl$_3$ δ [ppm]); 7.34 (t, 2H), 7.17 (d, 4H), 7.00 (td, 4H), 6.77 (dd, 2H), 6.70 (dd, 2H), 4.00 (t, 4H), 2.53 (t, 4H), 1.85-1.75 (m, 8H).

A transition temperature was expressed using a measured value of compound (1-367) itself, and maximum temperature ($T_{NI}$), a value of dielectric anisotropy (Δε) and a value of optical anisotropy (Δn) each were expressed using an extrapolated value obtained by converting, according to the extrapolation method described above, a measured value of a sample formed by mixing compound (1-367) with base liquid crystal ii. Values of physical properties of compound (1-367) were as described below.

Transition temperature: Cr1 87.7 Cr2 97.2 Iso.
$T_{NI}$=57.7° C., Δε=9.7, Δn=0.157.

Example 7

Synthesis of 1,9-di(4-(4-fluorophenyl)-3-fluorophenyloxy)-5-nonanol (Compound (1-361))

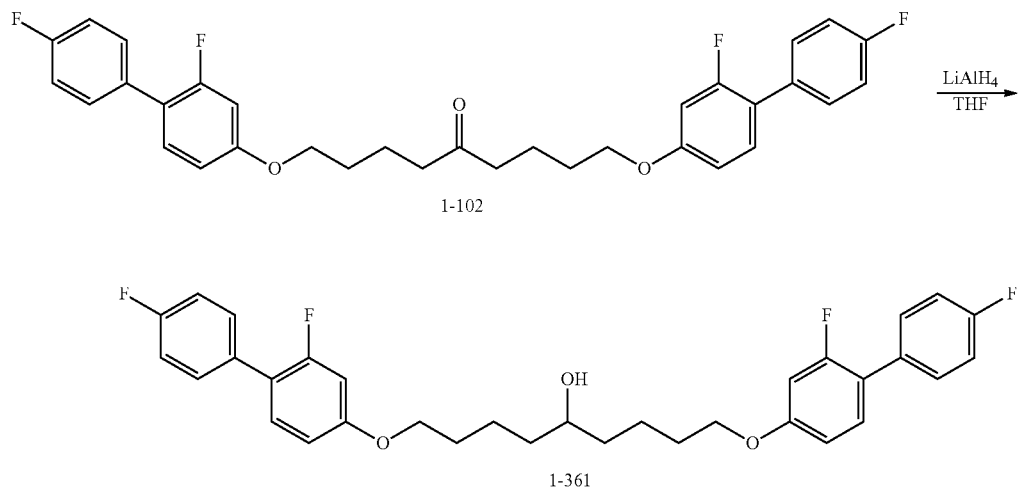

First Step

Under a nitrogen atmosphere, a solution in which 2.19 g (3.98 mmol) of compound (1-102) was dissolved in 10 mL of THF under ice cooling was added dropwise to a dispersion liquid in which 0.234 g (6.17 mmol) of lithium aluminum hydride was dispersed into 10 mL of THF, and the resulting mixture was stirred at room temperature for 2 hours. To the resulting reaction solution, 20 mL of toluene was added, and a saturated aqueous solution of sodium sulfate was further added dropwise thereto until a gum-shaped deposit was formed. An organic layer and a gum-shaped substance were separated by decantation, and the organic layer obtained was dried over anhydrous magnesium sulfate. A solvent was distilled off under reduced pressure, and then the residue was purified by fractionation by silica gel column chromatography (eluate:heptane/ethyl acetate=2/1 (volume ratio)), and further purified by recrystallization from heptane to obtain 1.85 g of 1,9-di(4-(4-fluorophenyl)-3-fluorophenyloxy)-5-nonanol (compound (1-361)).

$^1$H-NMR (CDCl$_3$; δ ppm): 7.47-7.44 (m, 4H), 7.29 (2H, t, J=8.8 Hz), 7.10 (tt, 4H, m), 6.74 (dd, 2H, J=2.5 Hz, 8.5 Hz), 6.69 (dd, 2H, J=2.5 Hz, 12.4 Hz), 3.99 (t, 4H, J=6.4 Hz), 3.68 (1H, s), 1.83 (sex, 4H), 1.67-1.50 (8H, m), 1.39 (1H, d, J=11.5 Hz).

A transition temperature was expressed using a measured value of compound (1-367) itself, and maximum temperature ($T_{NI}$), a value of dielectric anisotropy (Δε) and a value of optical anisotropy (Δn) each were expressed using an extrapolated value obtained by converting, according to the extrapolation method described above, a measured value of a sample formed by mixing compound (1-367) with base liquid crystal i. Values of physical properties of compound (1-367) were as described below.

Transition temperature: Cr 80.5 Iso.
$T_{NI}$=46.7° C., Δε=11.7, Δn=0.147.

Example 8

Synthesis of 1,9-di(4-(4-ethoxy-2,3-difluorophenyl)-3-fluorophenyloxy)-5-ethenylnonane (Compound (1-124))

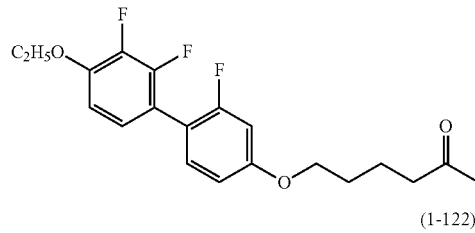

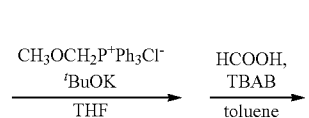

(1-122)

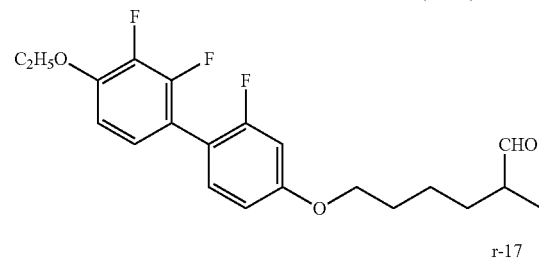

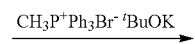

r-17

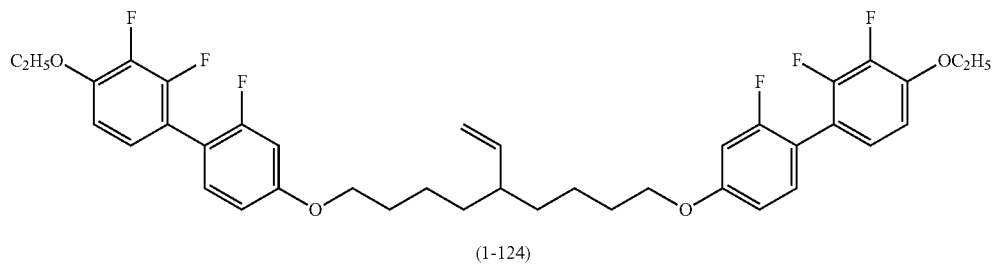

(1-124)

First Step

Under a nitrogen atmosphere, 0.65 g (5.78 mmol) of potassium tert-butoxide was added, at −30° C., to a suspension in which 1.98 g (5.78 mmol) of methoxymethyltriphenylphosphonium chloride was suspended into 20 mL of THF, and the resulting mixture was stirred at a same temperature for 1 hour. A solution in which 3.00 g (4.45 mmol) of compound (1-122) was dissolved in 20 mL of THF was added dropwise thereto at a same temperature, and then the resulting mixture was heated to room temperature, and stirred for 20 hours. The resulting reaction solution was poured into water, and subjected to extraction with toluene, and then an organic phase was washed with saturated brine, and dried over anhydrous magnesium sulfate. A solvent was distilled off under reduced pressure, and the residue obtained was purified by fractionation by silica gel column chromatography (eluate:toluene) to obtain 3.12 g of a residual material.

To a solution in which 3.12 g (4.45 mmol) of the residual material was dissolved in 30 mL of toluene, 0.27 g (0.87 mmol) of TBAB and 6.10 mL of formic acid were added, and the resulting mixture was stirred at room temperature for 40 hours. An organic phase was separated, and the organic phase obtained was washed with water, a saturated aqueous solution of sodium hydrogencarbonate, water and saturated brine, and then dried over anhydrous magnesium sulfate. A solvent was distilled off under reduced pressure, and the residue was purified by silica gel column chromatography (eluate:toluene) to obtain 3.0 g (4.34 mmol) of compound (r-17).

Second Step

Under a nitrogen atmosphere, 0.53 g (4.76 mmol) of potassium tert-butoxide was added, at −30° C., to a suspension in which 1.70 g (4.76 mmol) of methyltriphenylphosphonium bromide was suspended into 20 mL of THF, and the resulting mixture was stirred at a same temperature for 1 hour. A solution in which 2.73 g (3.96 mmol) of compounds (r-17) was dissolved in 30 mL of THF was added dropwise thereto at a same temperature, and the resulting mixture was heated to room temperature, and stirred for 15 hours. The resulting reaction solution was poured into water, and subjected to extraction with toluene, and then an organic phase was washed with saturated brine, and dried over anhydrous magnesium sulfate. A solvent was distilled off under reduced pressure, and the residue was purified by fractionation by silica gel column chromatography (eluate: heptane/toluene=1/2 (volume ratio)), and further purified by recrystallization from a mixed solvent of heptane/toluene=7/1 (volume ratio) to obtain 2.72 g of 1,9-di(4-(4-ethoxy-2,3-difluorophenyl)-3-fluorophenyloxy)-5-ethenylnonane (Compound (1-124)).

$^1$H-NMR (CDCl$_3$ δ [ppm]); 7.23 (t, 2H), 7.00 (td, 2H), 6.76 (td, 2H), 6.75 (dd, 2H), 6.70 (dd, 2H), 5.54 (qd, 1H), 5.01 (td, 2H), 4.15 (q, 4H), 3.97 (t, 4H), 2.03-12.00 (m, 1H), 1.84-1.73 (m, 4H), 1.54-1.29 (m, 8H), 1.48 (t, 3H).

A transition temperature was expressed using a measured value of compound (1-124) itself, and maximum temperature ($T_{NI}$), a value of dielectric anisotropy (Δε) and a value of optical anisotropy (Δn) each were expressed using an extrapolated value obtained by converting, according to the extrapolation method described above, a measured value of a sample formed by mixing compound (1-124) with base liquid crystal ii. Values of physical properties of compound (1-124) were as described below.

Transition temperature: SmC 5.2 Iso.
$T_{NI}$=23.6° C., $\Delta\varepsilon$=−6.30, $\Delta n$=0.140.

Example 9

Synthesis of 1,9-di(4-(3,5-difluoro-4-((3,4,5-trifluorophenoxy)difluoromethyl)phenyl)-3-fluorophenyloxy)-5-nonanol (Compound (1-363))

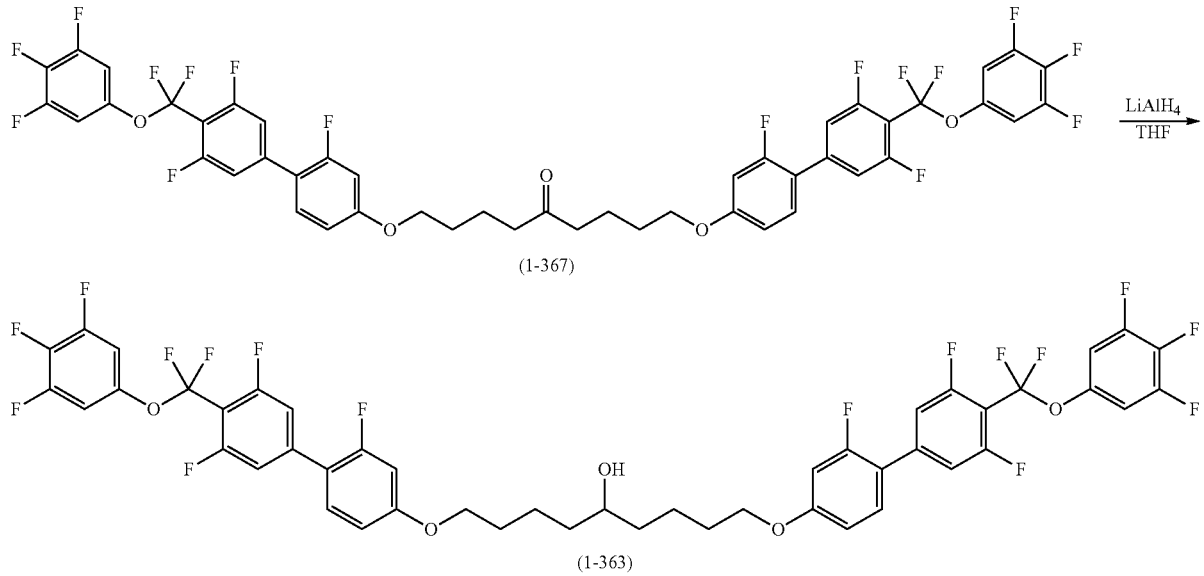

First Step

Under a nitrogen atmosphere, a solution in which 3.00 g (3.07 mmol) of compound (1-367) was dissolved in 45 mL of THF was added dropwise, under ice cooling, to a mixture in which 0.175 g (4.60 mmol) of lithium aluminum hydride was dispersed into 15 mL of THF, and the resulting mixture was stirred at room temperature for 2 hours. Then, 20 mL of toluene was added to the resulting reaction solution, and a saturated aqueous solution of sodium sulfate was further added dropwise thereto until a gum-shaped deposit was formed. An organic layer and a gum-shaped substance were separated in decantation, and the organic layer obtain was dried over anhydrous magnesium sulfate. A solvent was distilled off under reduced pressure, and the residue was purified by fractionation by silica gel column chromatography (eluate:heptane/ethyl acetate=1/1 (volume ratio)), and further purified by recrystallization from heptane to obtain 1.80 g of 1,9-di(4-(3,5-difluoro-4-(3,4,5-trifluorophenoxy)difluoromethyl)phenyl)-3-fluorophenyloxy-5-nonanol (Compound (1-363)).

$^1$H-NMR (CDCl$_3$ δ [ppm]): 7.34 (t, 2H), 7.17 (d, 4H), 6.98 (td, 4H), 6.79 (dd, 2H), 6.72 (dd, 2H), 4.01 (t, 4H), 3.69 (s, 1H), 1.92-1.81 (m, 4H), 1.71-1.48 (m, 8H), 1.38 (s, 1H).

A transition temperature was expressed using a measured value of compound (1-363) itself, and maximum temperature ($T_{NI}$), a value of dielectric anisotropy ($\Delta\varepsilon$) and a value of optical anisotropy ($\Delta n$) each were expressed using an extrapolated value obtained by converting, according to the extrapolation method described above, a measured value of a sample formed by mixing compound (1-363) with base liquid crystal i. Values of physical properties of compound (1-367) were as described below.

Transition temperature: Cr 71.2 N 74.3 Iso.
$T_{NI}$=63.0° C., $\Delta\varepsilon$=8.57, $\Delta n$=0.157.

Example 10

Synthesis of 1,9-di(4-(4-ethoxy-2,3-difluorophenyl)-3-fluorophenyloxy-5-(2-propenyl)nonane (Compound (1-366))

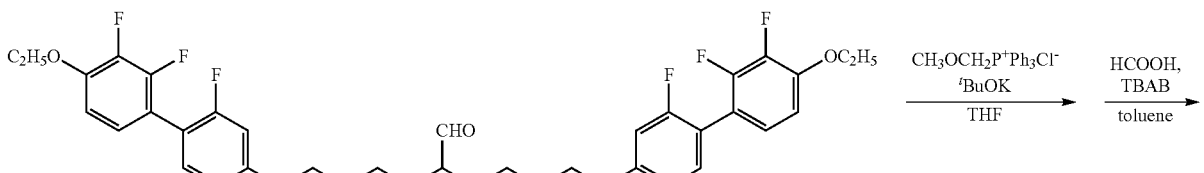

-continued

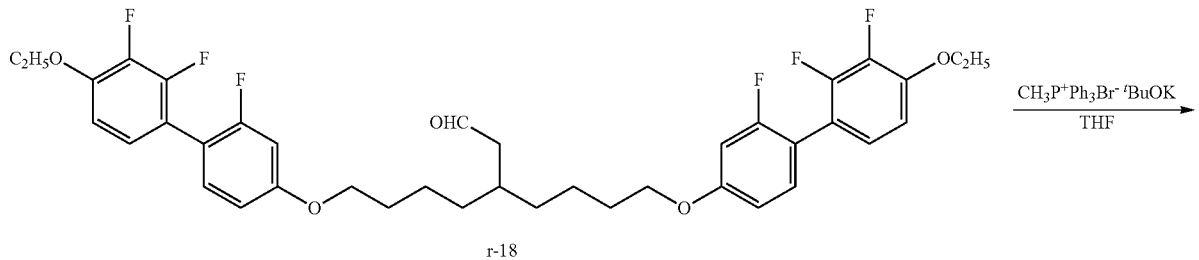

r-18

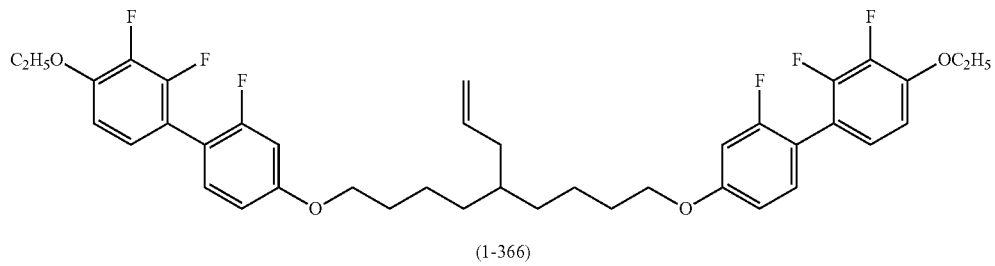

(1-366)

First Step

Under a nitrogen atmosphere, 2.26 g (20.1 mmol) of potassium tert-butoxide was added, at −30° C., to a suspension in which 6.90 g (20.1 mmol) of methoxymethyltriphenylphosphonium chloride was suspended into 60 mL of THF, and the resulting mixture was stirred at a same temperature for 1 hour. A solution in which 9.24 g (13.4 mmol) of compound (r-17) was dissolved in 60 mL of THF was added dropwise thereto at a same temperature, and the resulting mixture was heated to room temperature, and stirred for 2 hours. The resulting reaction solution was poured into water, and subjected to extraction with toluene, and then an organic phase was washed with saturated brine, and dried over anhydrous magnesium sulfate. A solvent was distilled off under reduced pressure, and the residue obtained was purified by fractionation by silica gel column chromatography (eluate:toluene) to obtain 9.62 g of a residual material. Then, to a solution in which 6.54 g (9.12 mmol) of the residual material was dissolved in 65 mL of toluene, 0.88 g (2.74 mmol) of TBAB and 19.6 mL of formic acid was added, and the resulting mixture was stirred at room temperature for 18 hours. An organic phase was separated, and the organic phase obtained was washed with water, a saturated aqueous solution of sodium hydrogencarbonate, water and saturated brine, and then dried over anhydrous magnesium sulfate. A solvent was distilled off under reduced pressure, and the residue was purified by silica gel column chromatography (eluate: toluene/ethyl acetate=19/1 (volume ratio)) to obtain 6.41 g (9.12 mmol) of compound (r-18).

Second Step

Under a nitrogen atmosphere, 1.22 g (10.9 mmol) of potassium tert-butoxide was added, at −30° C., to a suspension in which 3.91 g (10.9 mmol) of methyltriphenylphosphonium bromide was suspended into 60 mL of THF, and the resulting mixture was stirred at a same temperature for 1 hour. A solution in which 6.41 g (9.12 mmol) of compound (r-18) was dissolved in 30 mL of THF was added dropwise thereto at a same temperature, and then the resulting mixture was heated to room temperature and stirred for 15 hours. The resulting reaction solution was poured into water, and subjected to extraction with toluene, and then an organic phase was washed with saturated brine, and dried over anhydrous magnesium sulfate. A solvent was distilled off under reduced pressure, and the residue was purified by fractionation by silica gel column chromatography (eluate: heptane/toluene=1/2 (volume ratio)), to obtain 5.64 g of 1,9-di(4-(4-ethoxy-2,3-difluorophenyl)-3-fluorophenyloxy-5-(2-propenyl)nonane (compound (1-366)).

$^1$H-NMR (CDCl$_3$ δ [ppm]); 7.23 (t, 2H), 7.00 (td, 2H), 6.76 (td, 2H), 6.75 (dd, 2H), 6.70 (dd, 2H), 5.81-5.74 (m, 1H), 5.03-5.00 (m, 2H), 4.15 (q, 4H), 3.98 (t, 4H), 2.07 (t, 2H), 1.79 (quin, 4H), 1.52-1.43 (m, 5H), 1.48 (t, 6H), 1.37-1.33 (m, 4H).

A transition temperature was expressed using a measured value of compound (1-366) itself, and maximum temperature ($T_{NI}$), a value of dielectric anisotropy (Δε) and a value of optical anisotropy (Δn) each were expressed using an extrapolated value obtained by converting, according to the extrapolation method described above, a measured value of a sample formed by mixing compound (1-366) with base liquid crystal ii. Values of physical properties of compound (1-366) were as described below.

Transition temperature: Cr<−50° C.

$T_{NI}$=7.6° C., Δε=−6.00, Δn=0.127.

Exemplification of Bimesogenic Compound

Compounds (1-1) to (1-370) as described below can be prepared in a manner similar to the synthesis methods described in Examples 1 to 10. In addition, Examples of the liquid crystal compounds prepared in Examples 1 to 10 are also shown.

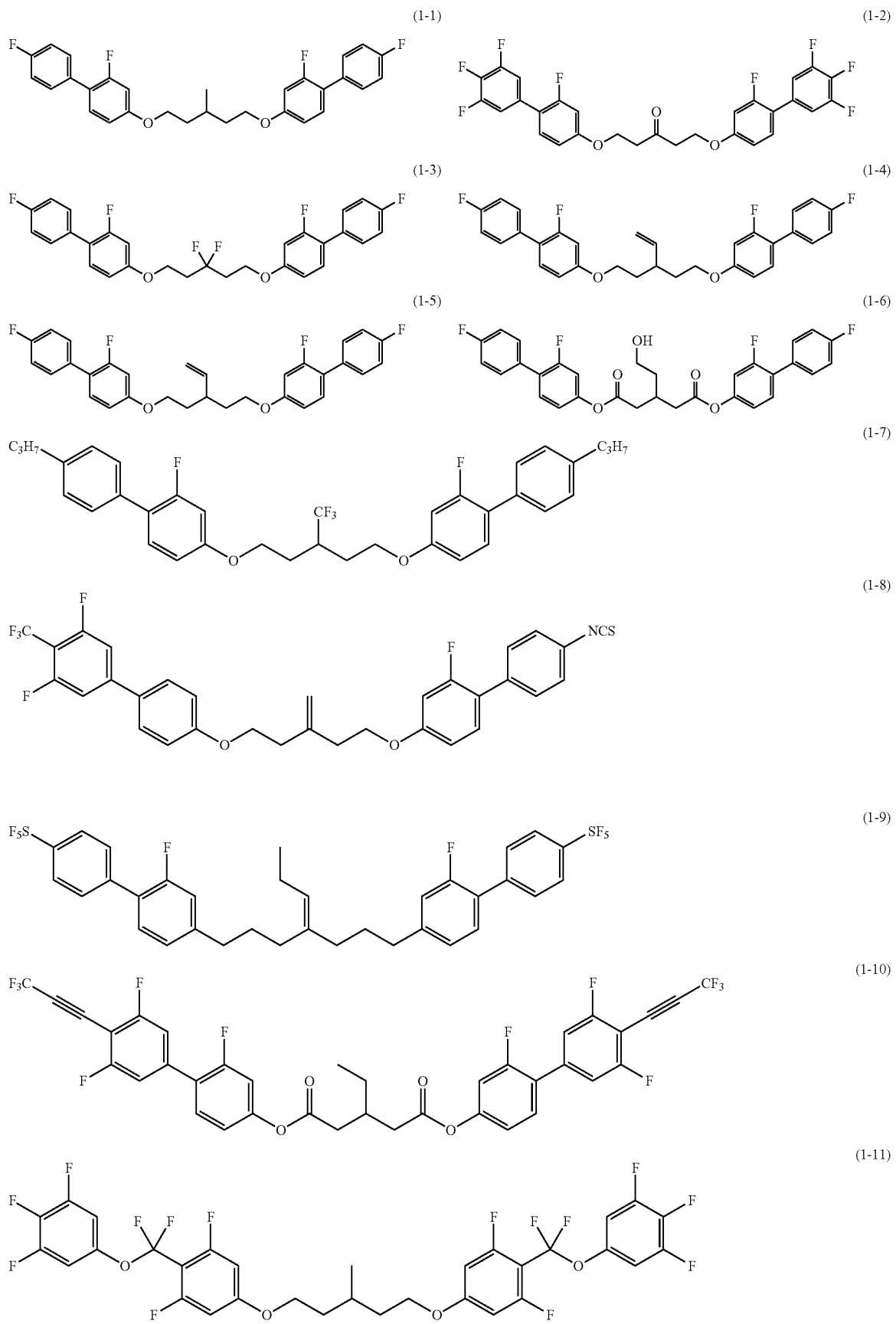

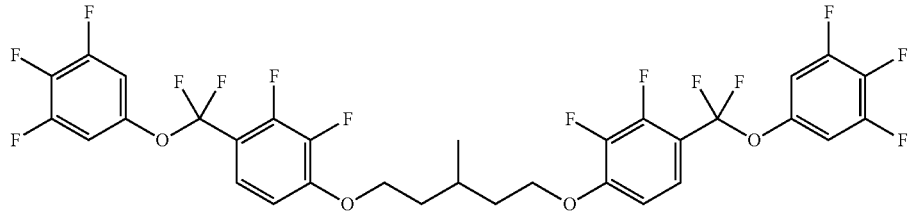
(1-12)
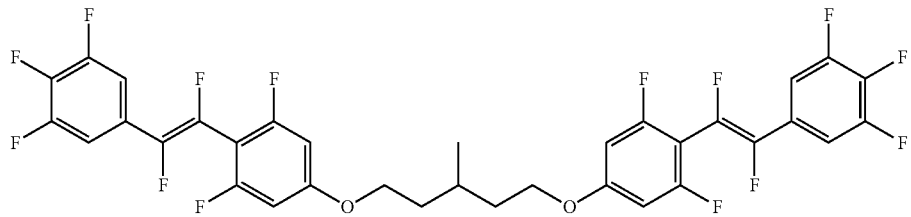
(1-13)
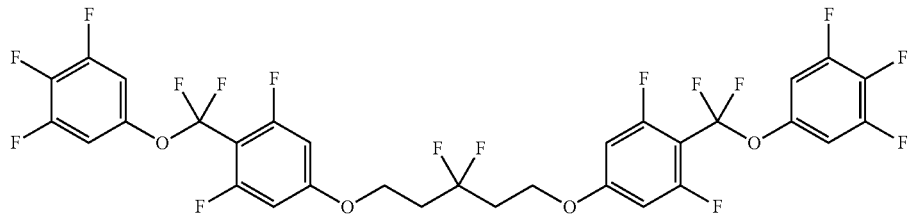
(1-14)
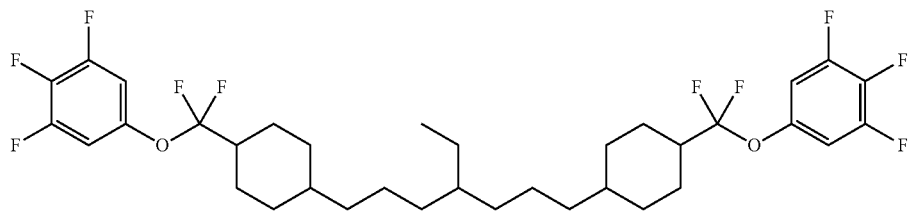
(1-15)
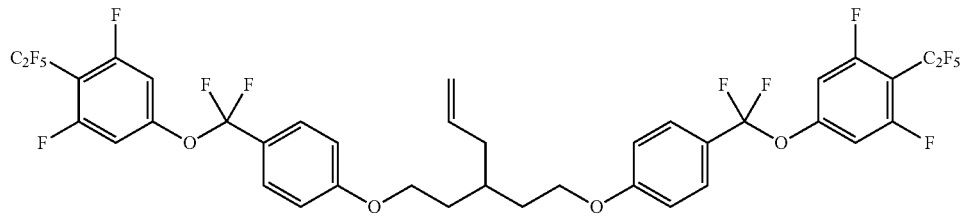
(1-16)
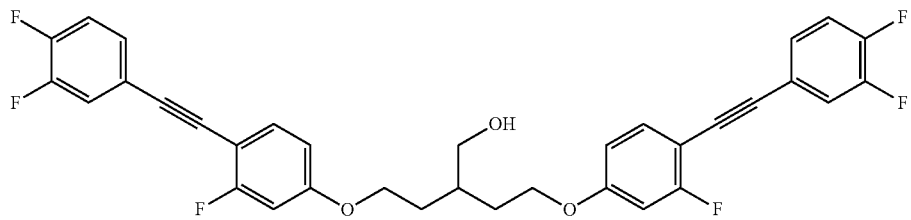
(1-17)
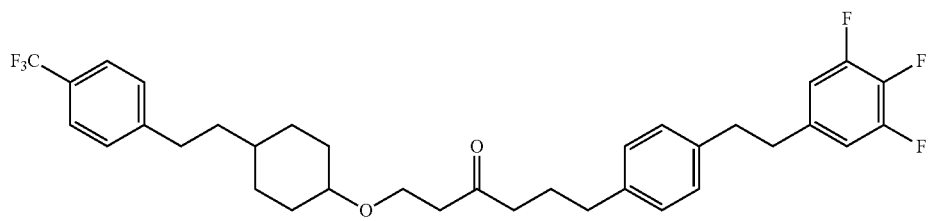
(1-18)

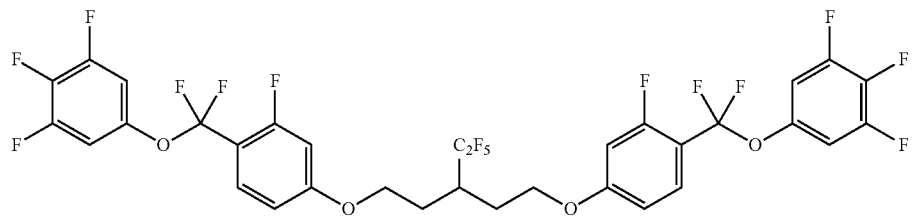
(1-19)
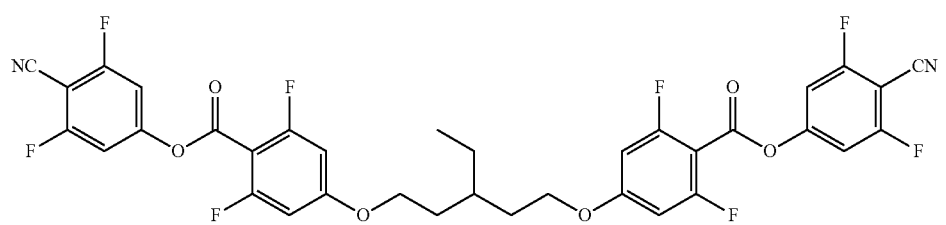
(1-20)
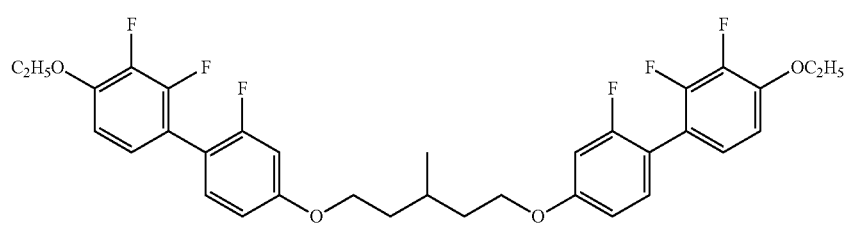
(1-21)
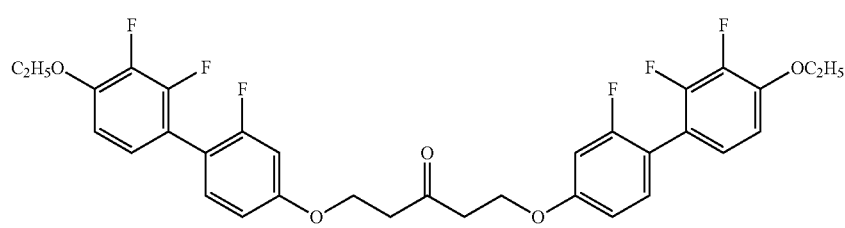
(1-22)
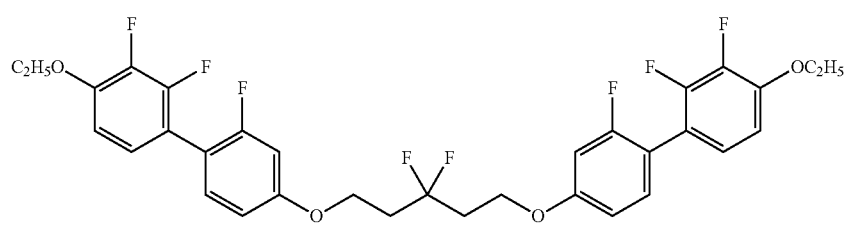
(1-23)
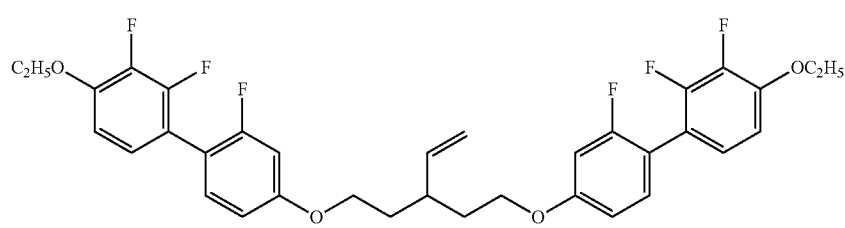
(1-24)
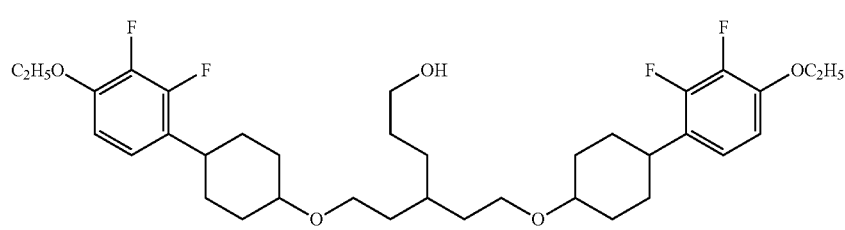
(1-25)

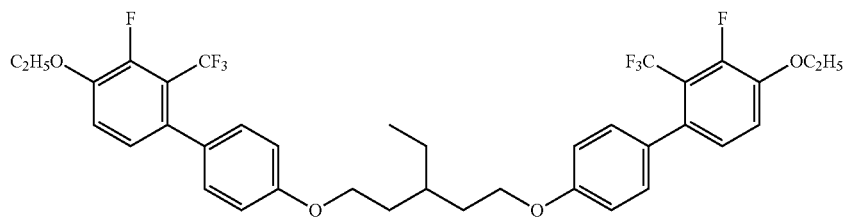
(1-26)
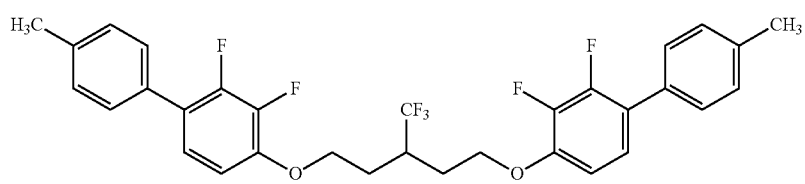
(1-27)
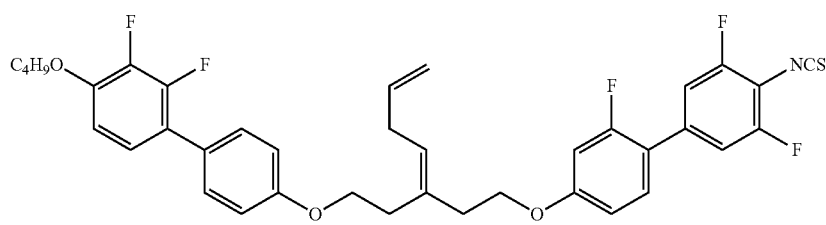
(1-28)
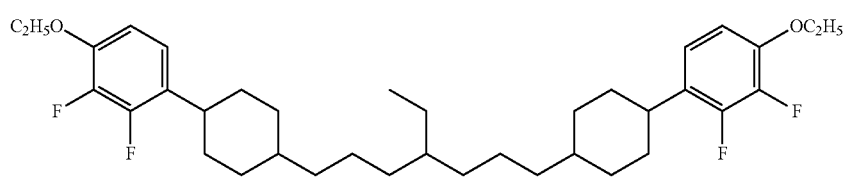
(1-29)
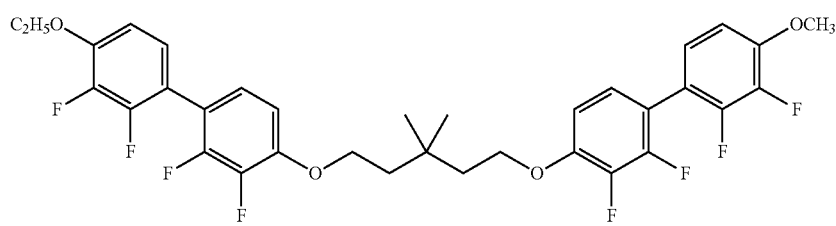
(1-30)
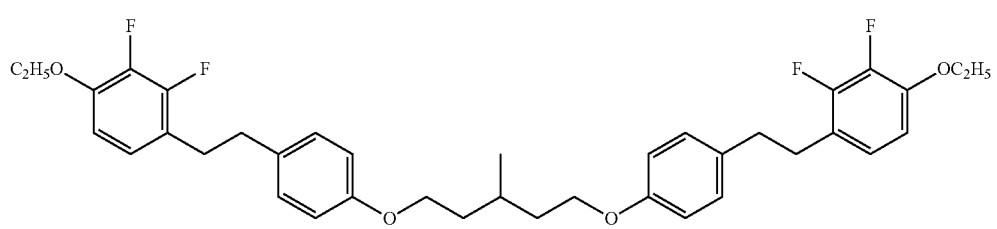
(1-31)
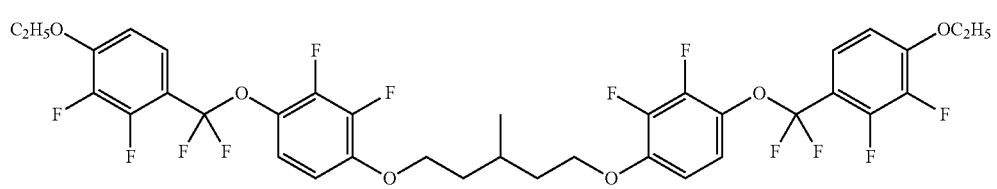
(1-32)
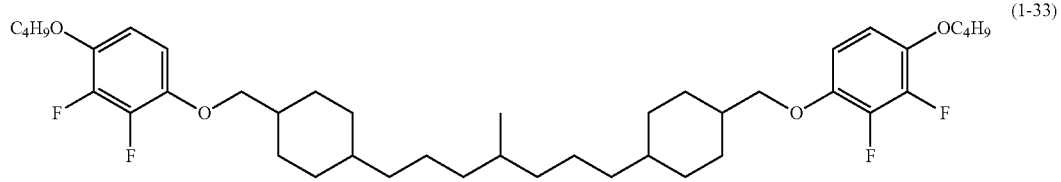
(1-33)

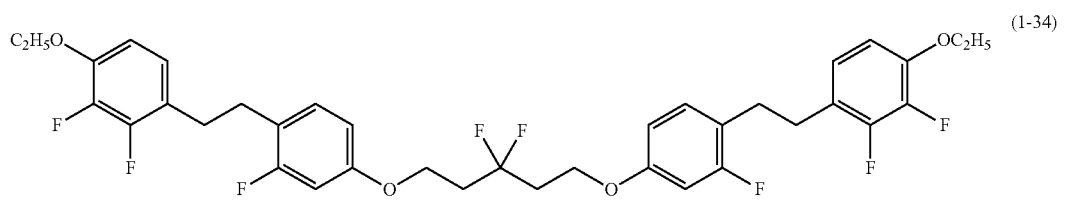
(1-34)
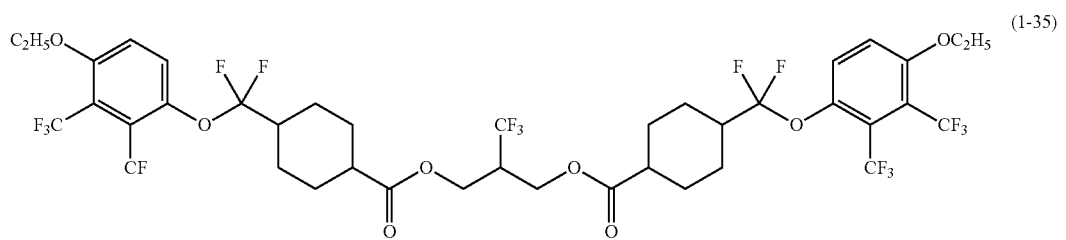
(1-35)
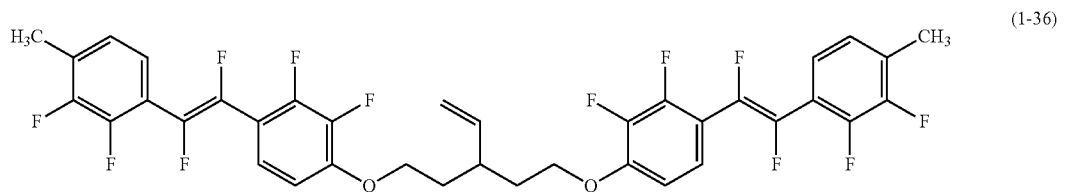
(1-36)
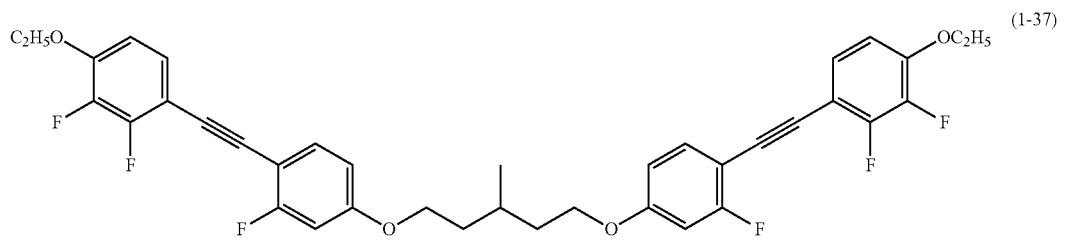
(1-37)
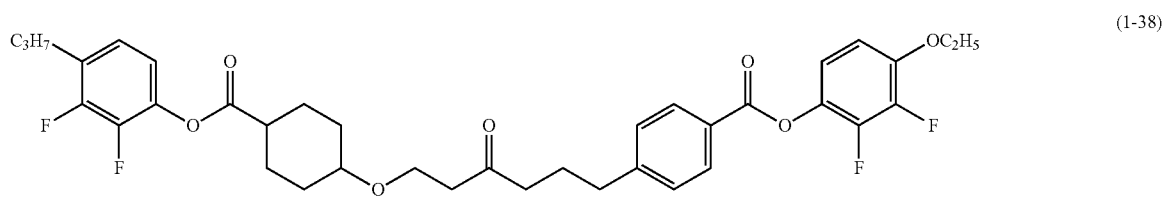
(1-38)
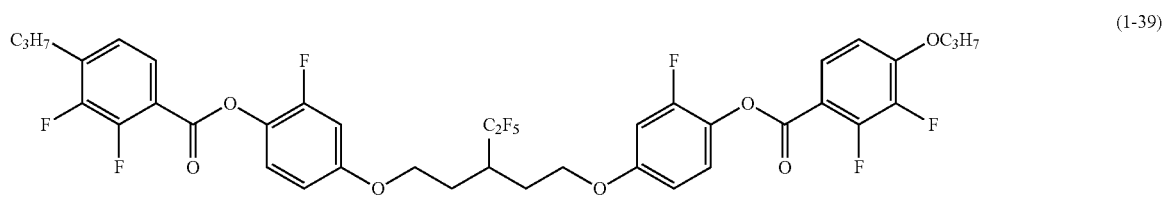
(1-39)
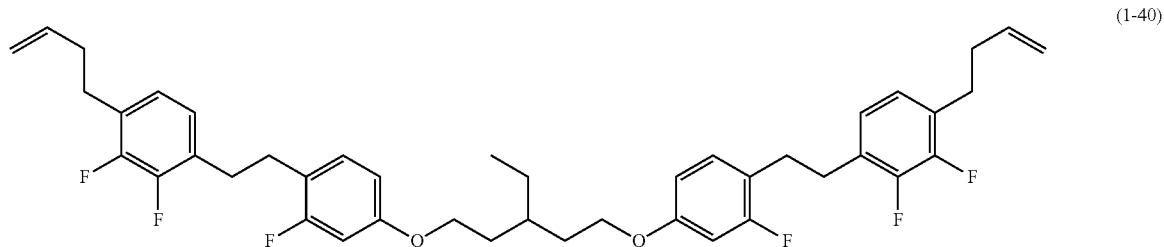
(1-40)

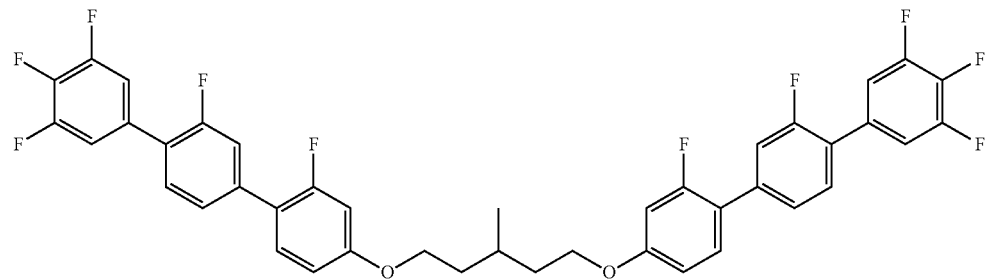
(1-41)
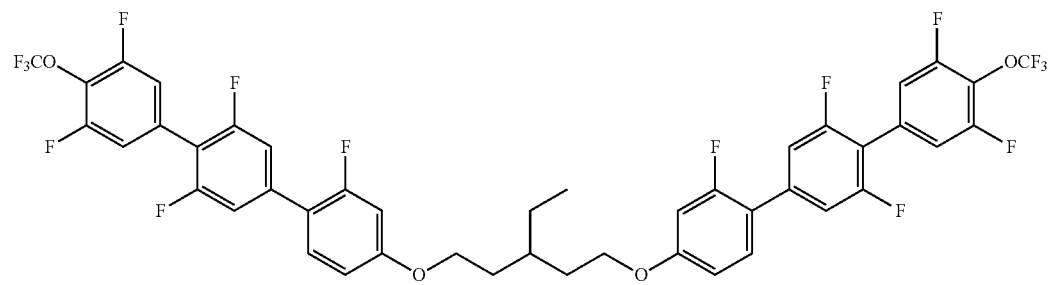
(1-42)
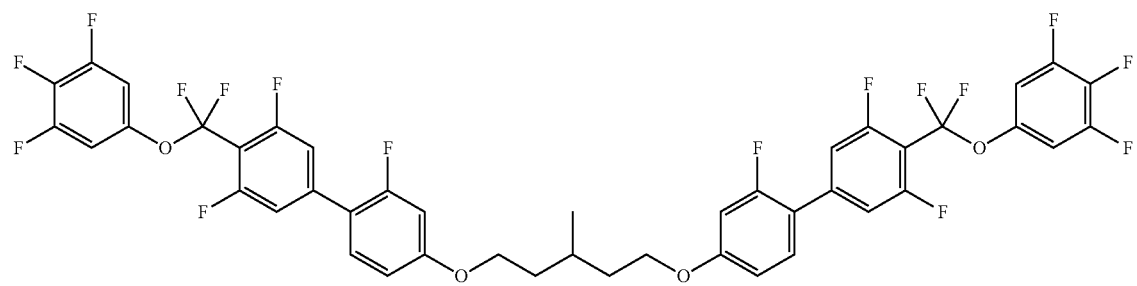
(1-43)
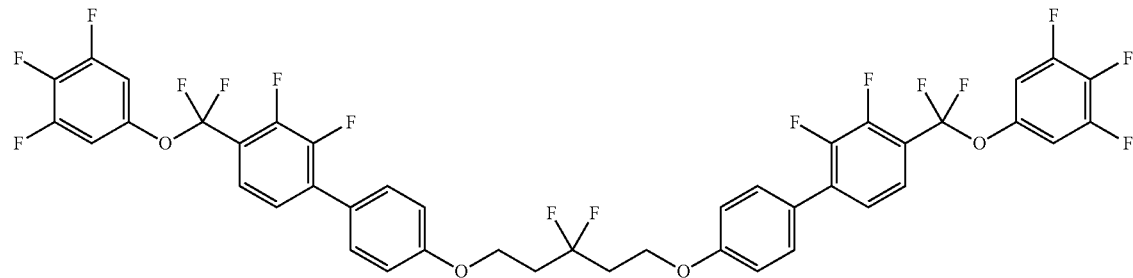
(1-44)
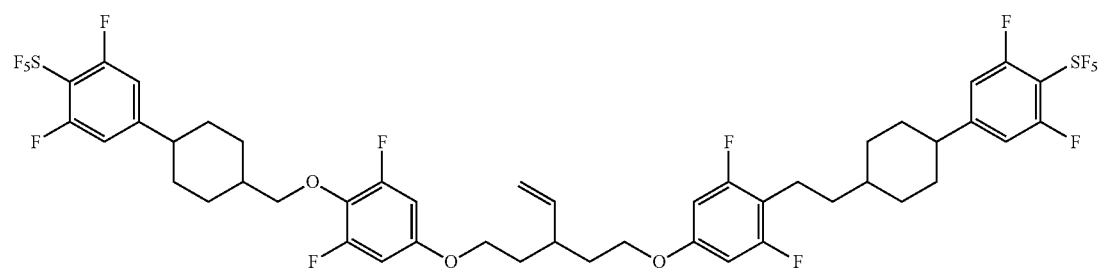
(1-45)

-continued
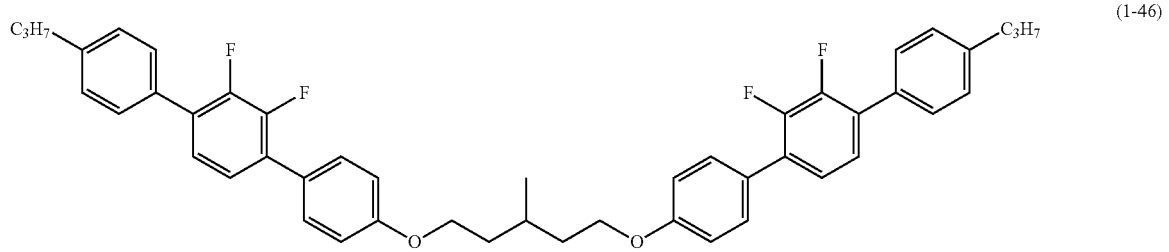
(1-46)
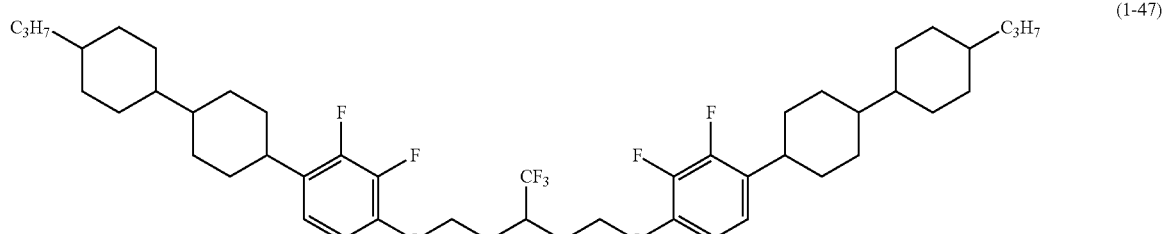
(1-47)
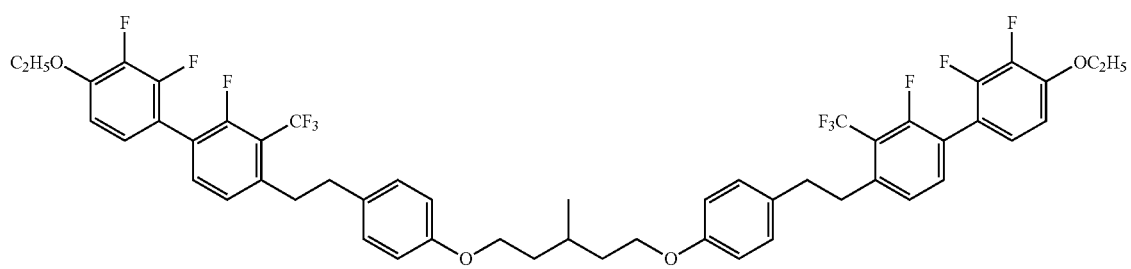
(1-48)
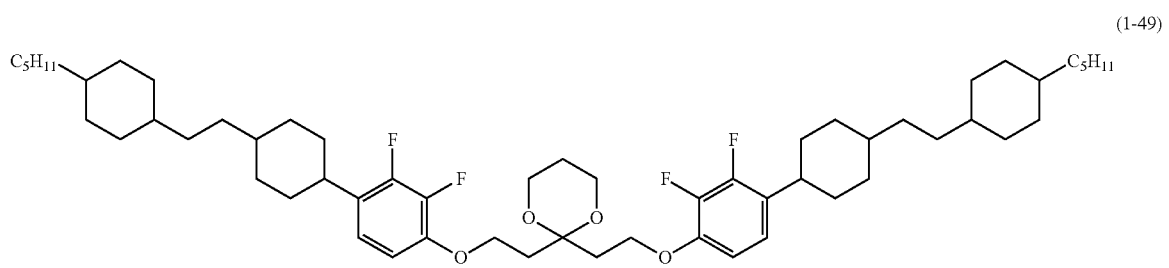
(1-49)
(1-50)
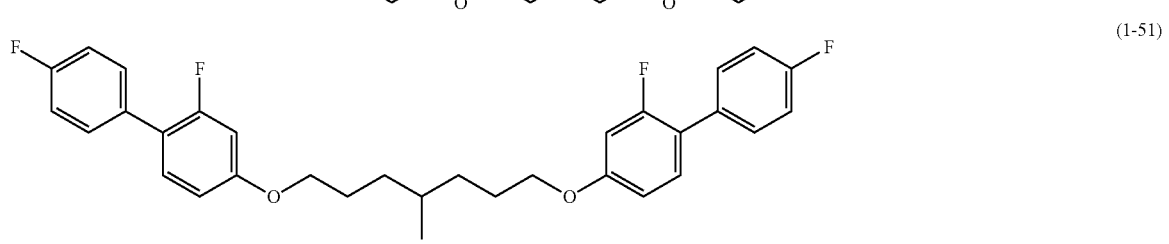
(1-51)

-continued
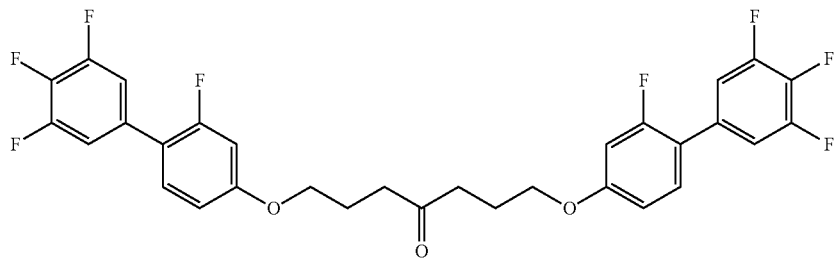
(1-52)
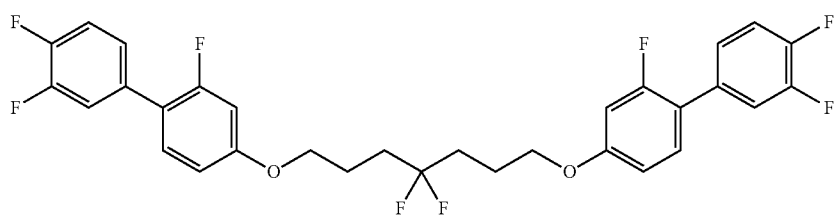
(1-53)
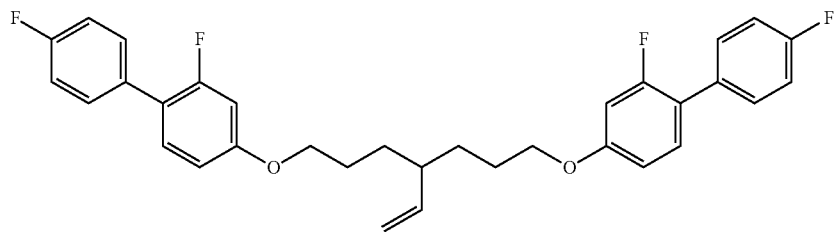
(1-54)
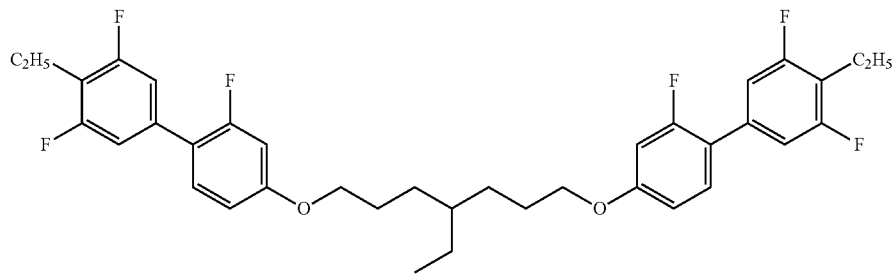
(1-55)
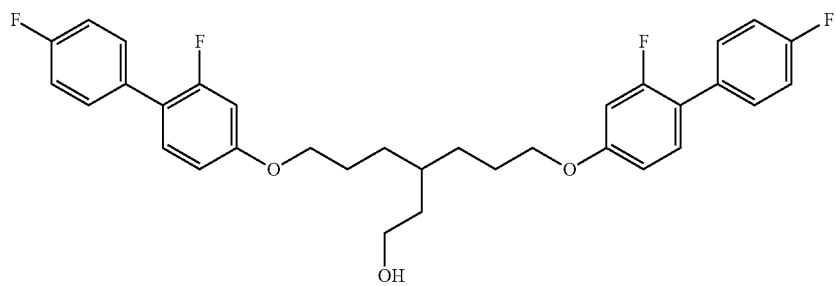
(1-56)
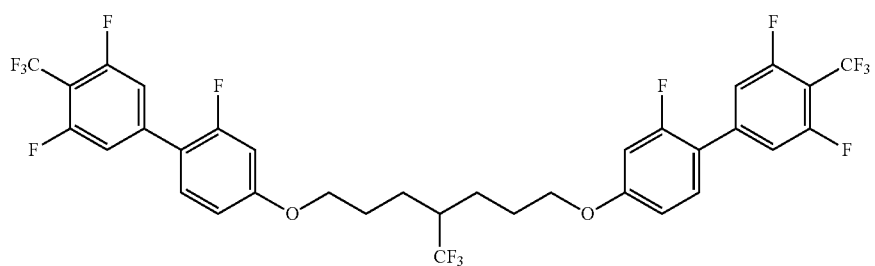
(1-57)

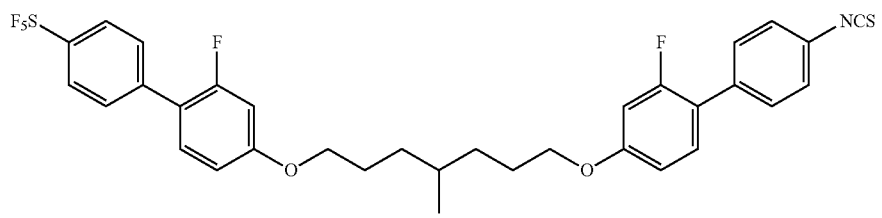
(1-58)
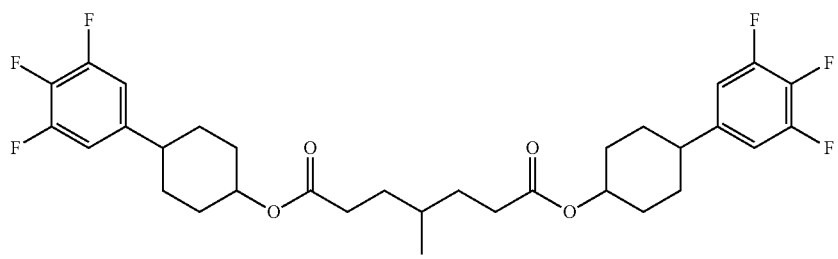
(1-59)
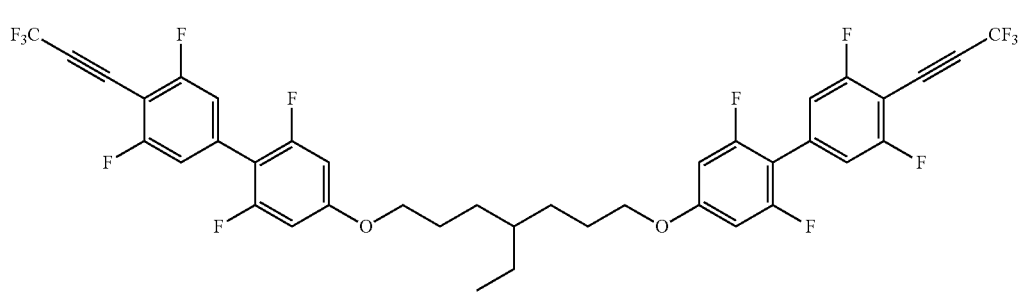
(1-60)
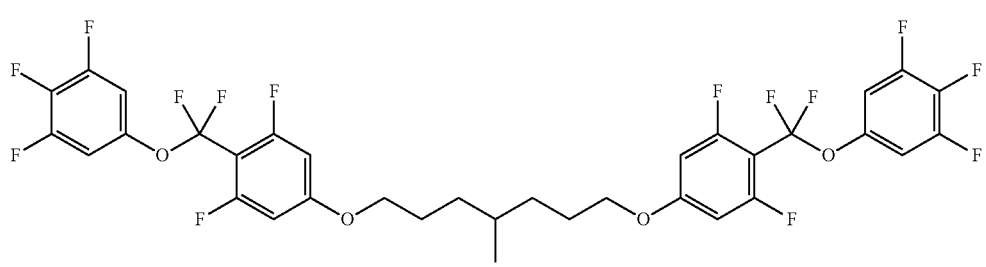
(1-61)
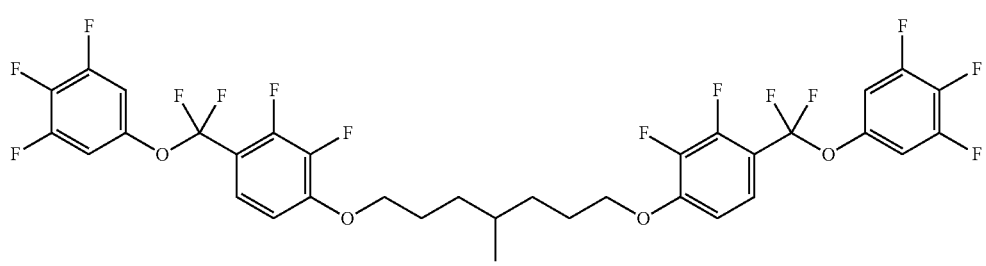
(1-62)
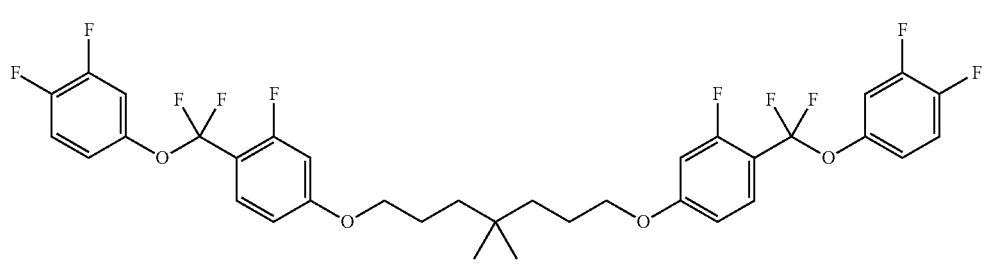
(1-63)

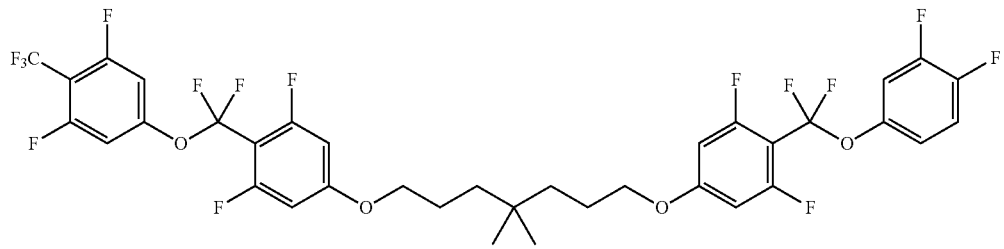
(1-64)
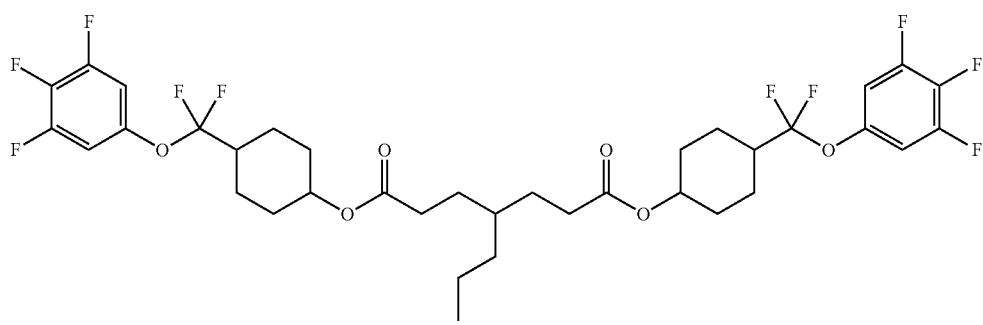
(1-65)
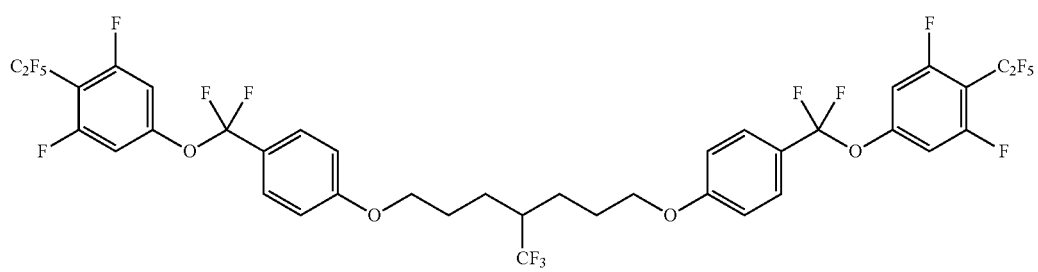
(1-66)
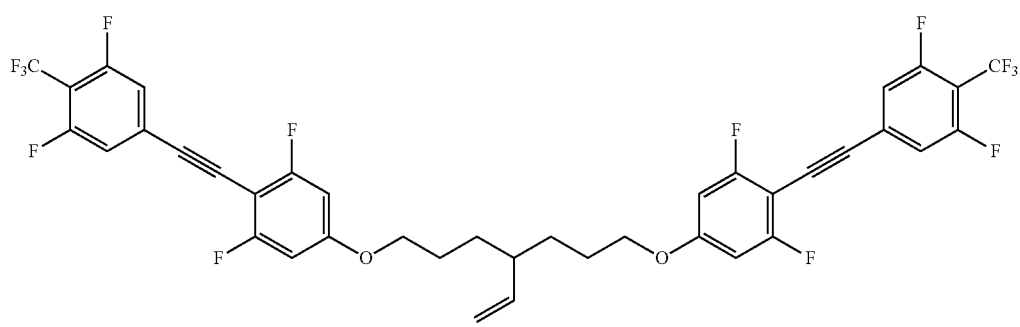
(1-67)
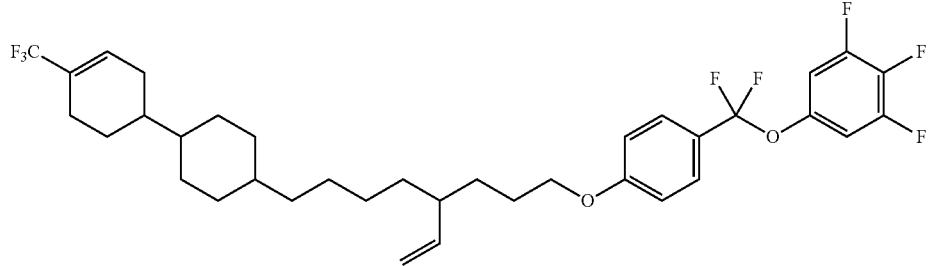
(1-68)

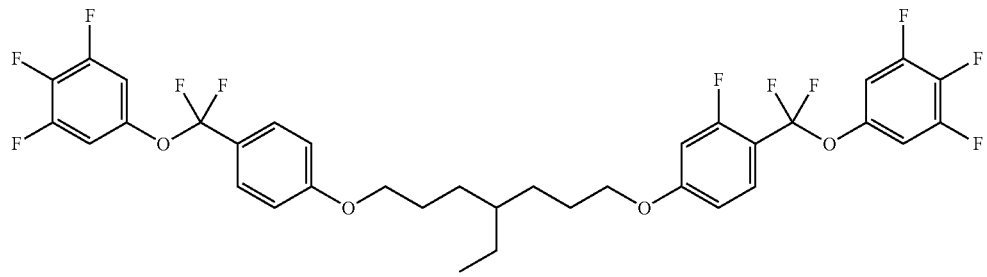 (1-69)
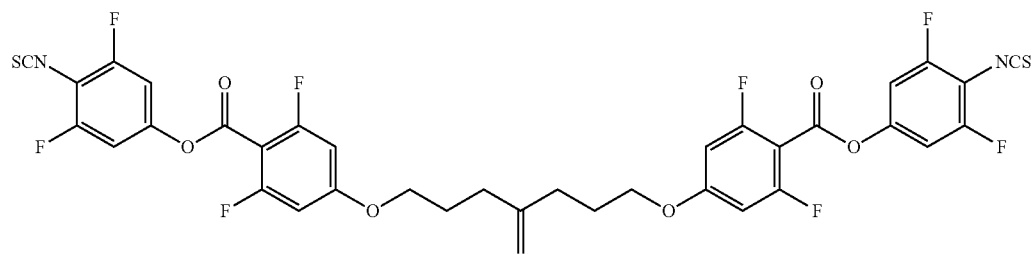 (1-70)
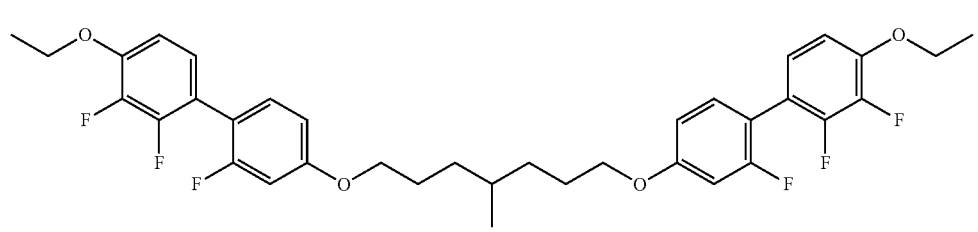 (1-71)
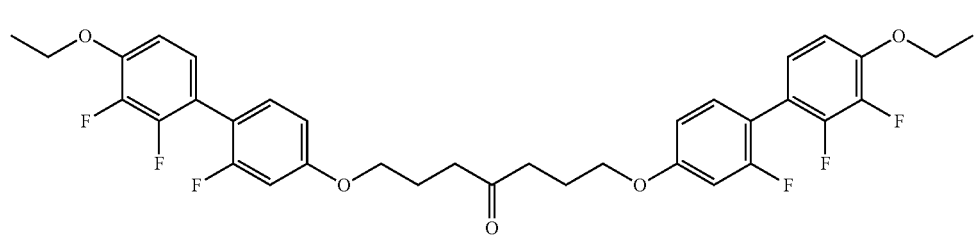 (1-72)
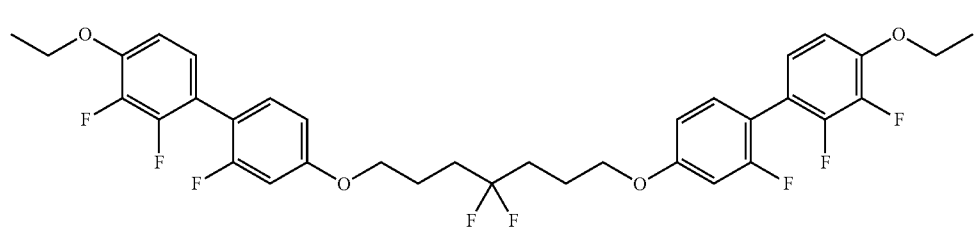 (1-73)
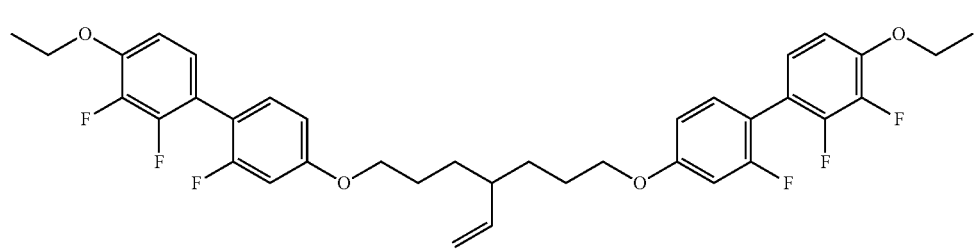 (1-74)

-continued
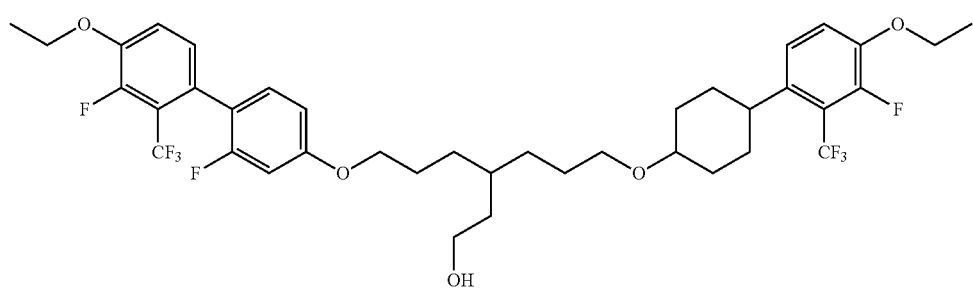
(1-75)
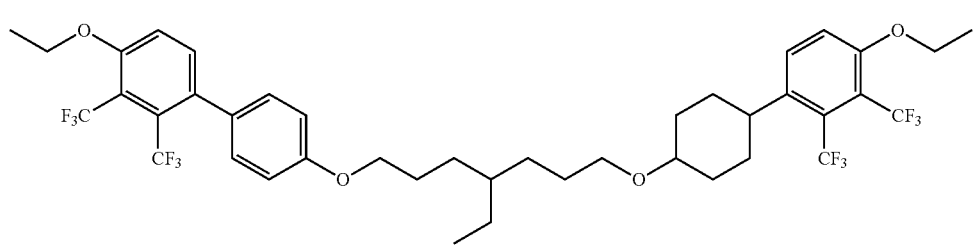
(1-76)
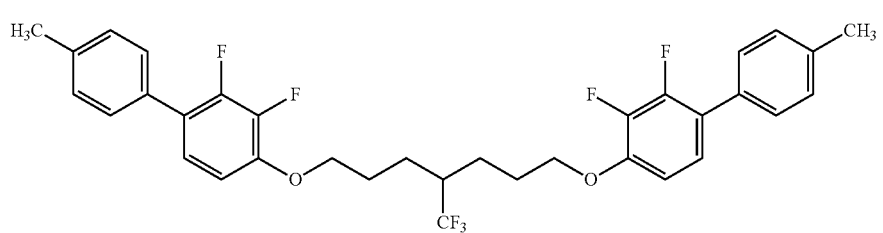
(1-77)
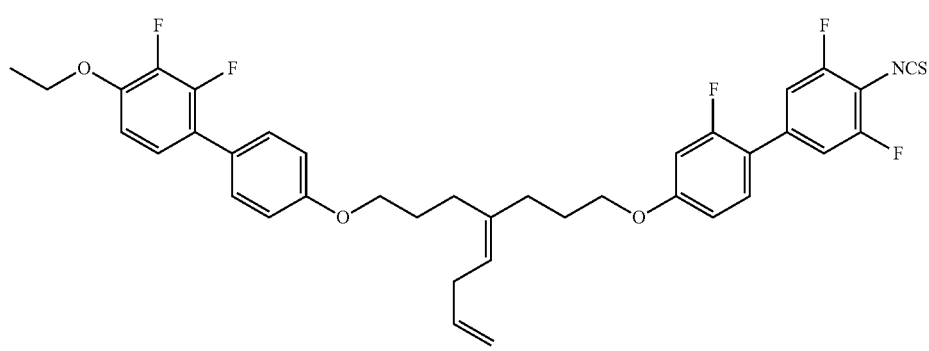
(1-78)
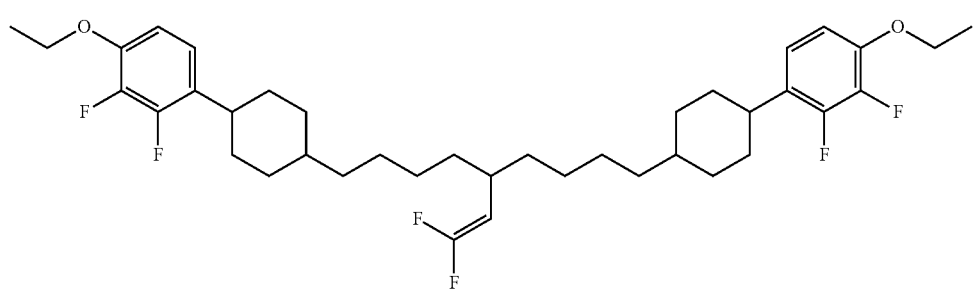
(1-79)
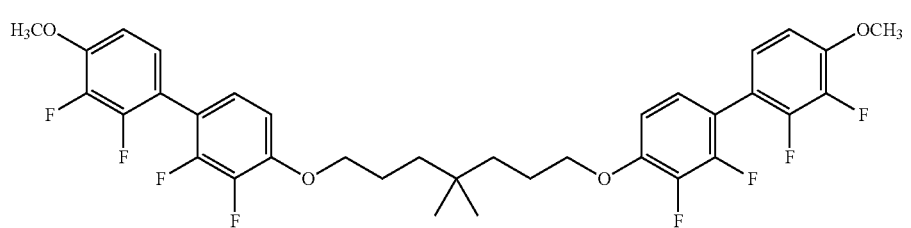
(1-80)

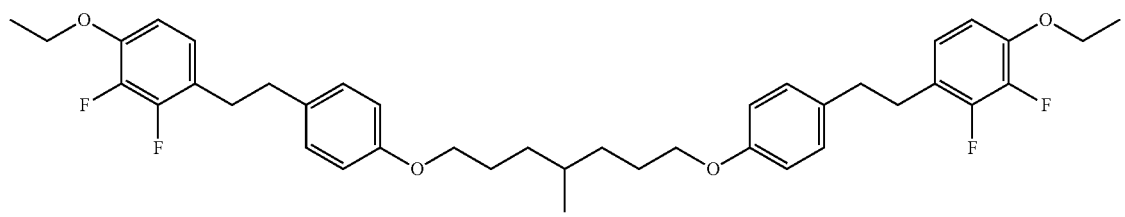
(1-81)
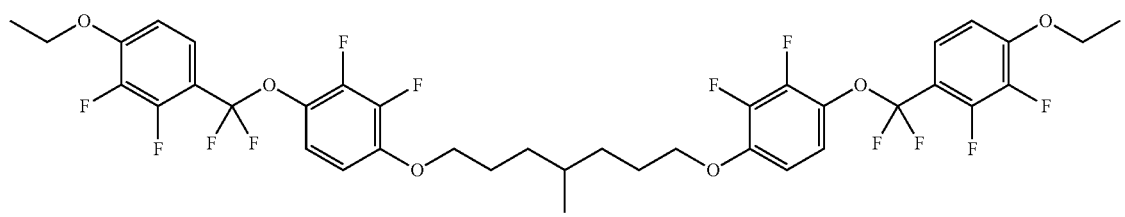
(1-82)
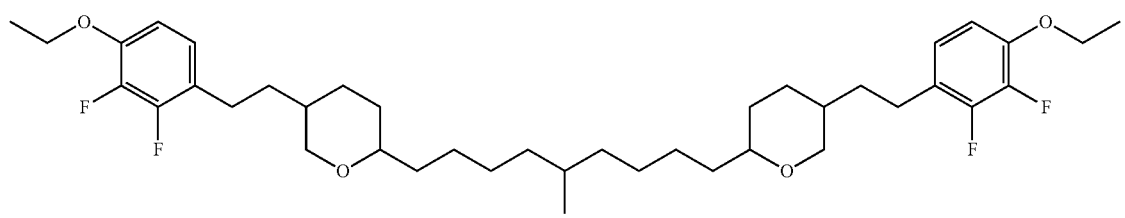
(1-83)
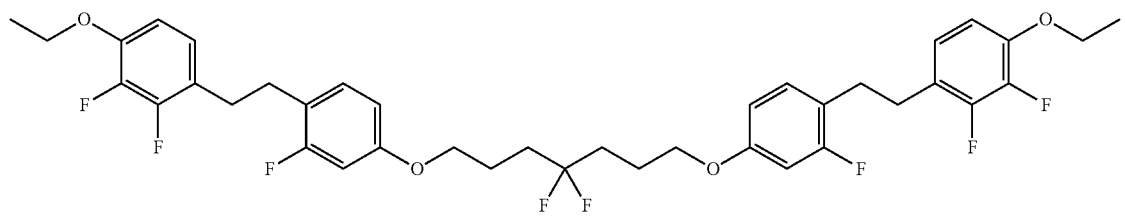
(1-84)
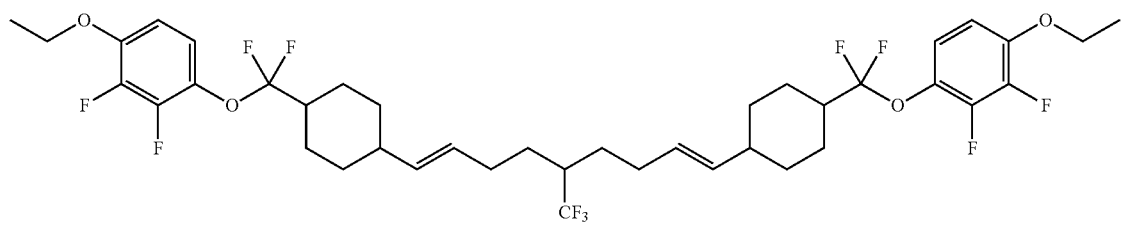
(1-85)
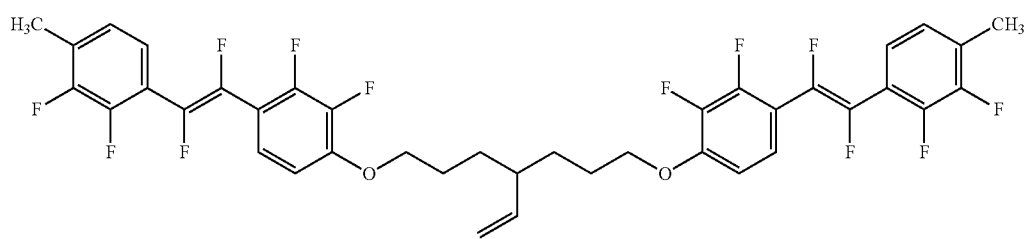
(1-86)

(1-87)
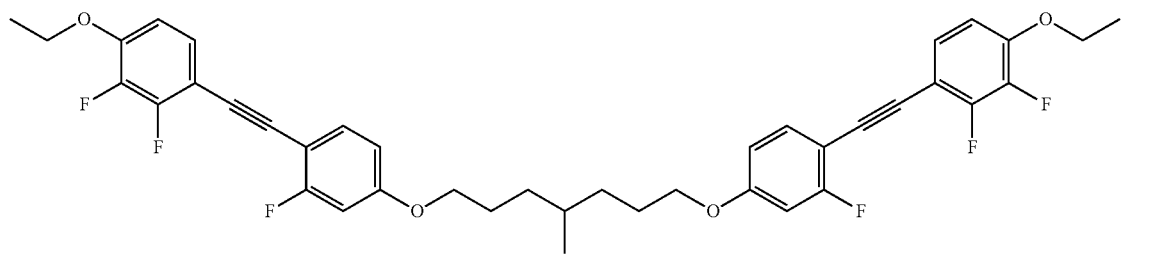
(1-88)
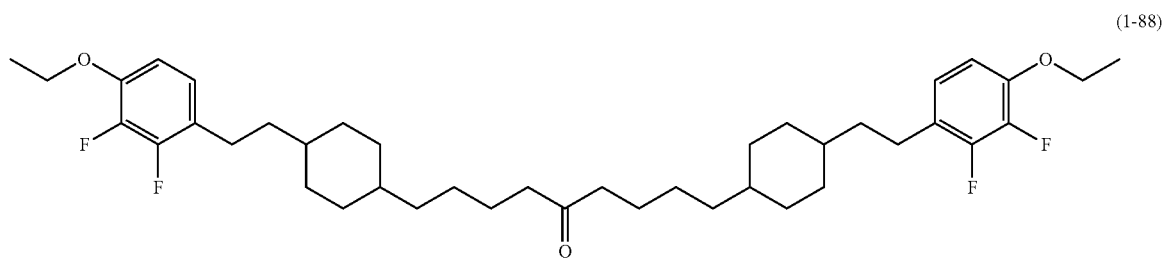
(1-89)
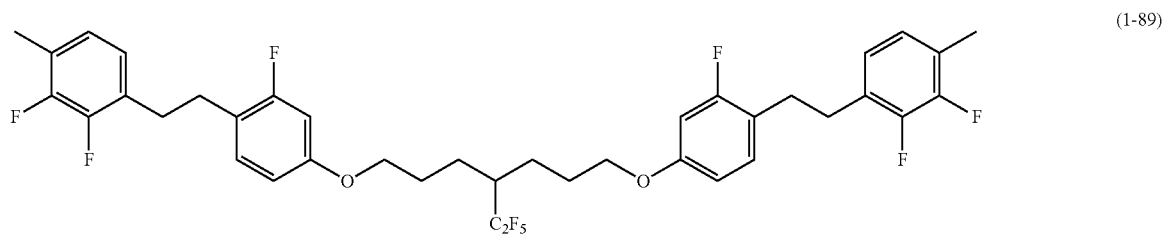
(1-90)
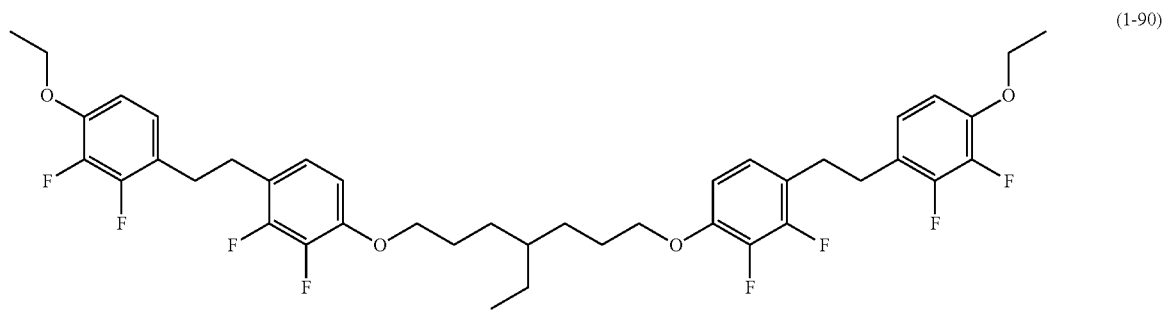
(1-91)
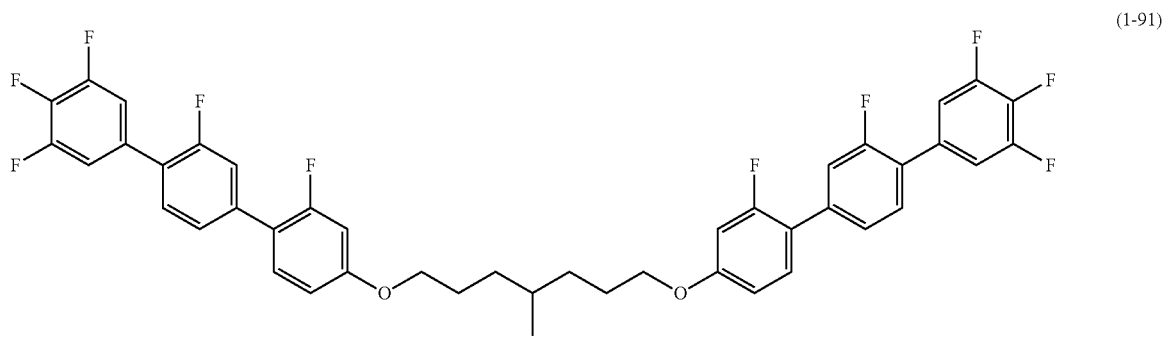

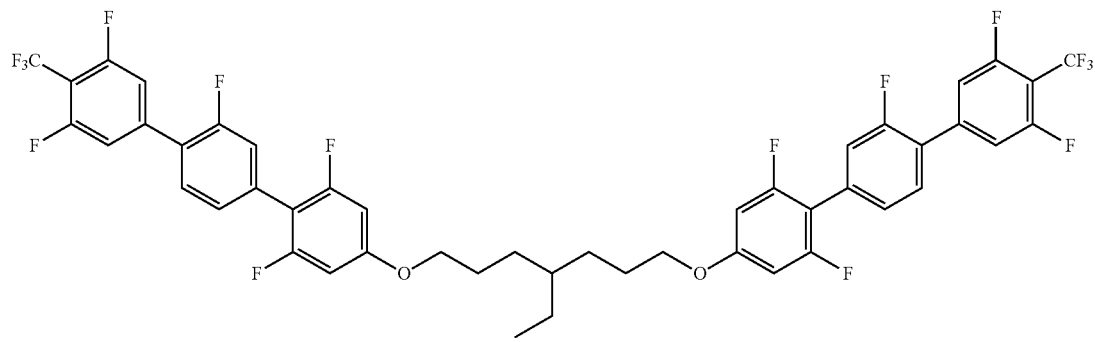
(1-92)
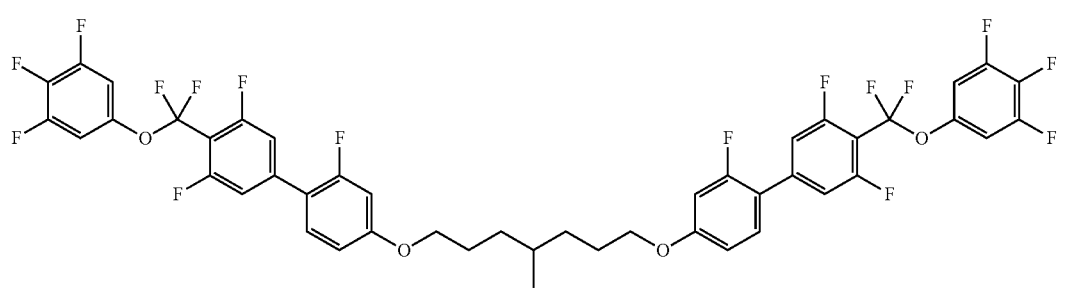
(1-93)
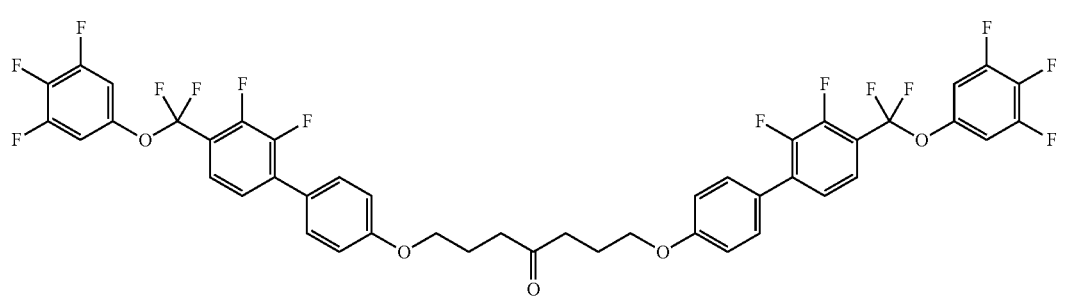
(1-94)
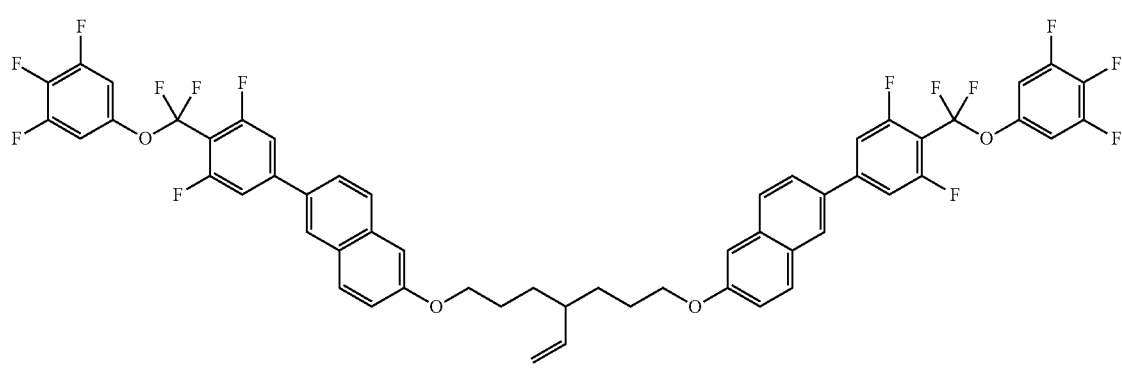
(1-95)
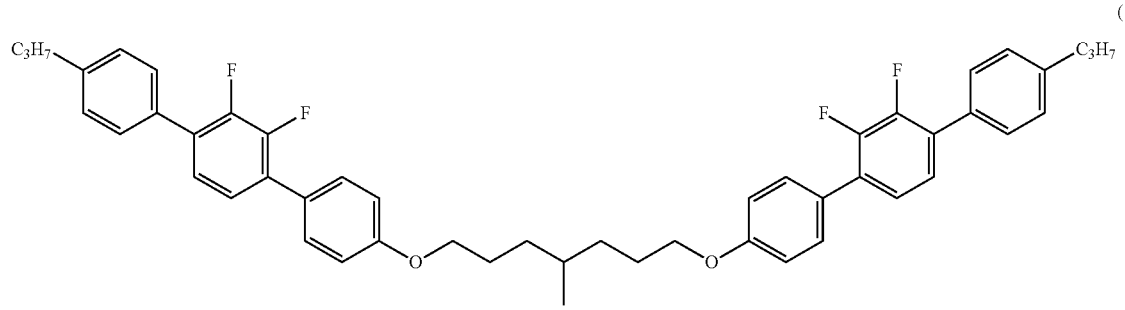
(1-96)

-continued
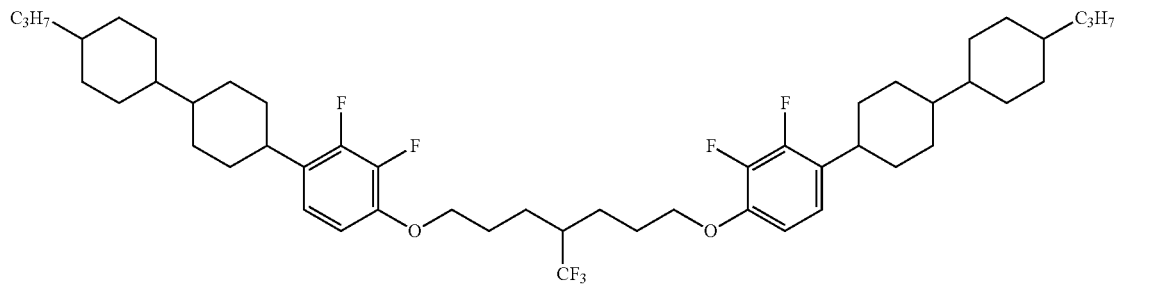
(1-97)
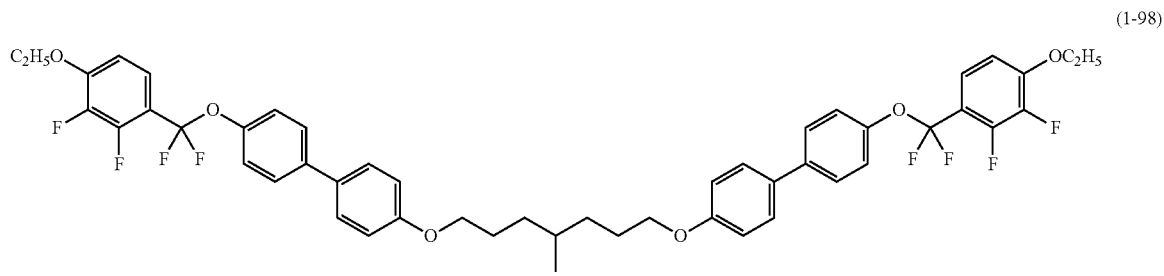
(1-98)
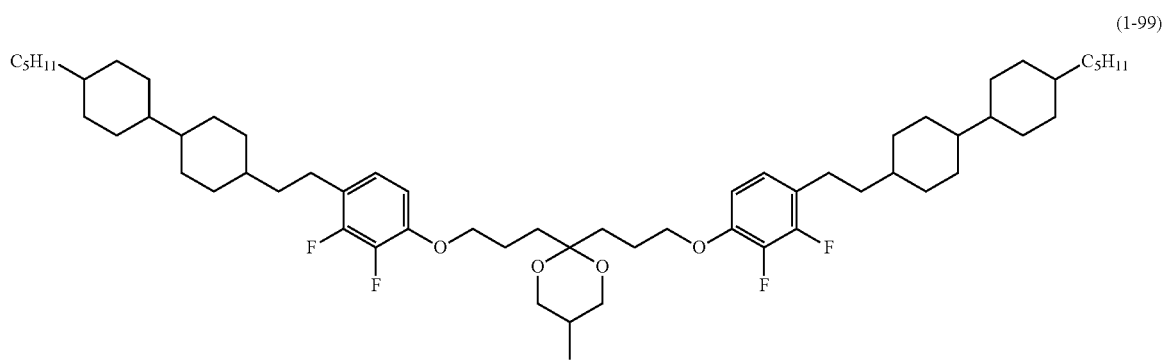
(1-99)
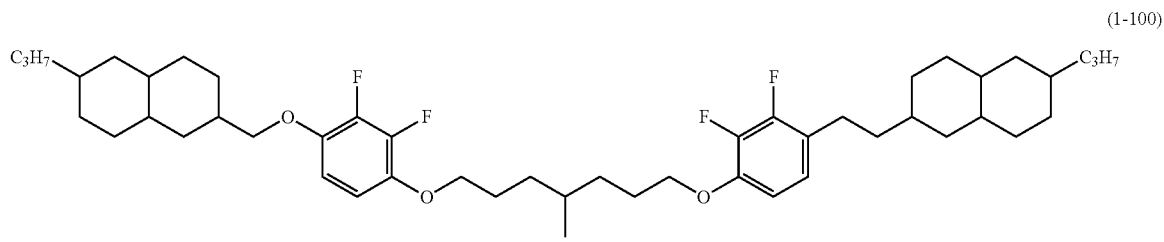
(1-100)
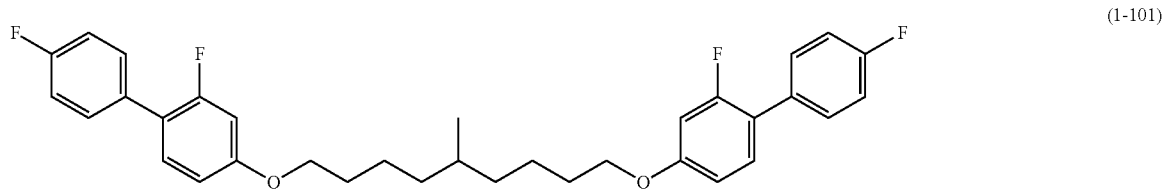
(1-101)
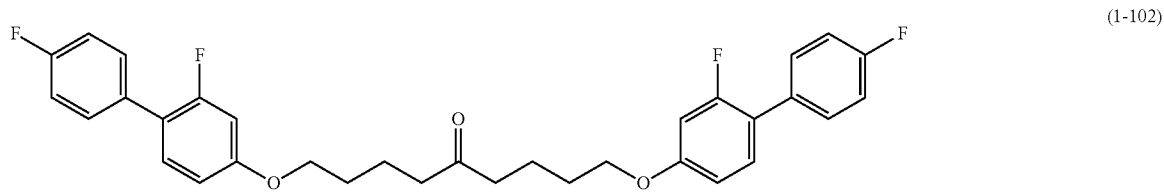
(1-102)

-continued
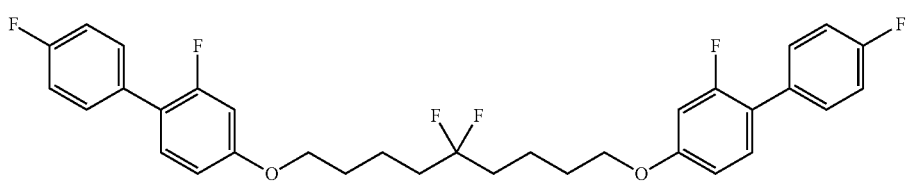
(1-103)
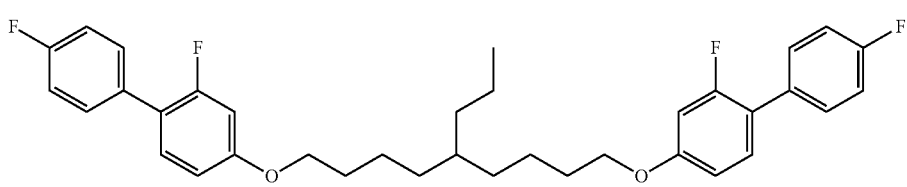
(1-104)
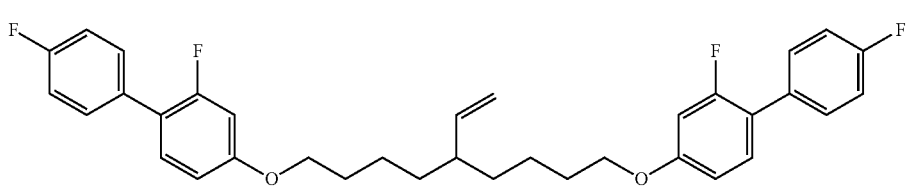
(1-105)
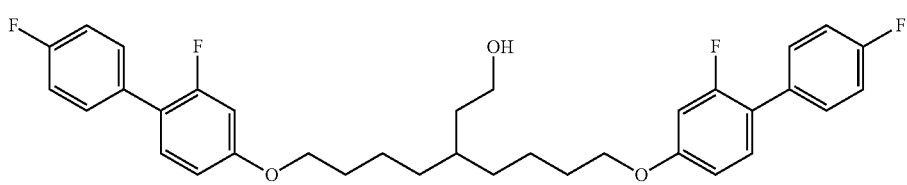
(1-106)
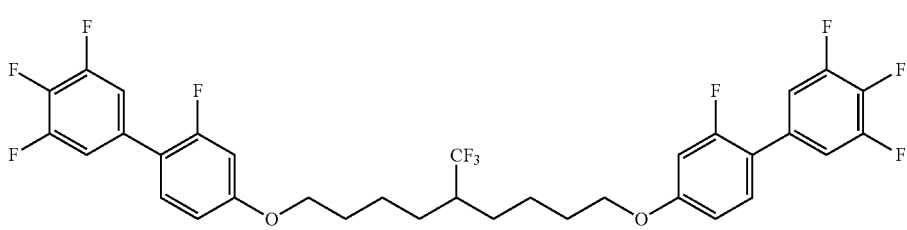
(1-107)
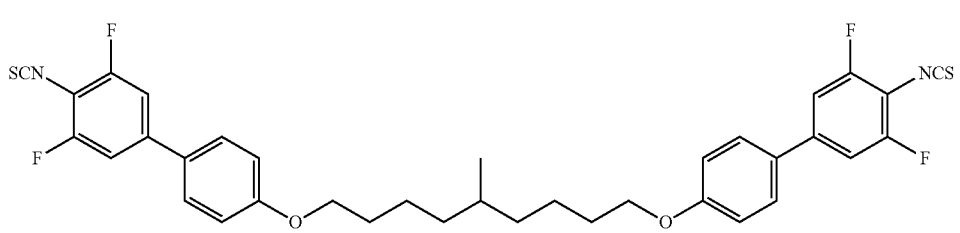
(1-108)
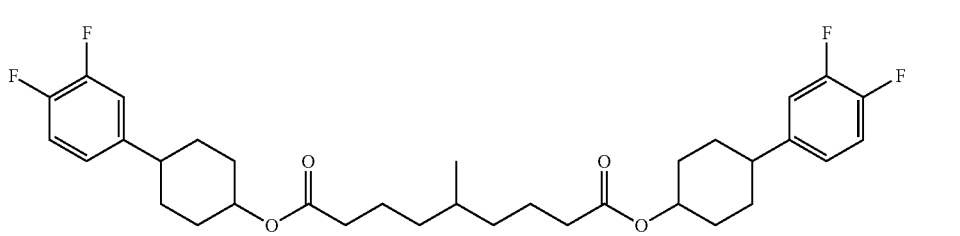
(1-109)

-continued
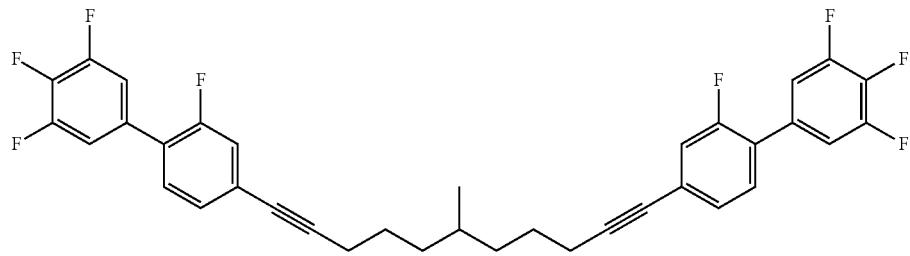
(1-110)
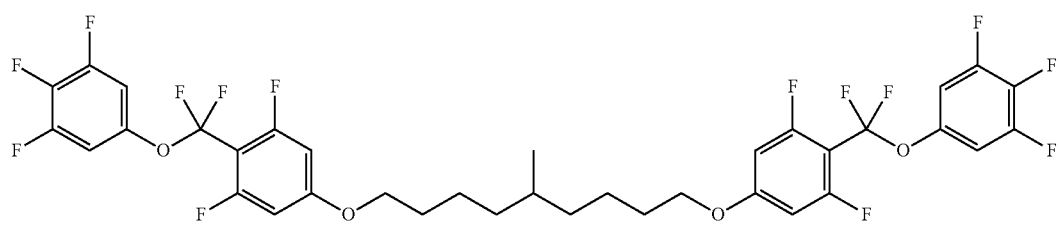
(1-111)
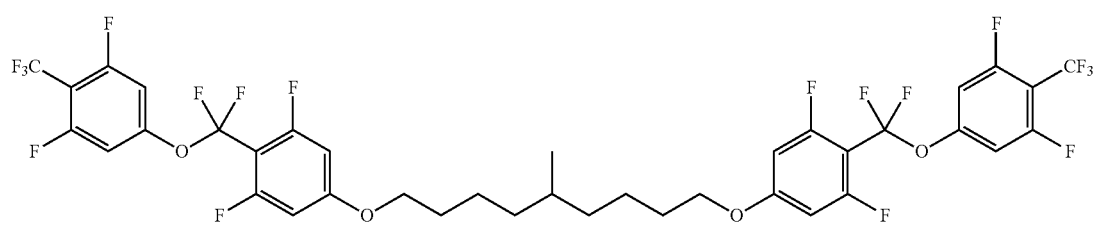
(1-112)
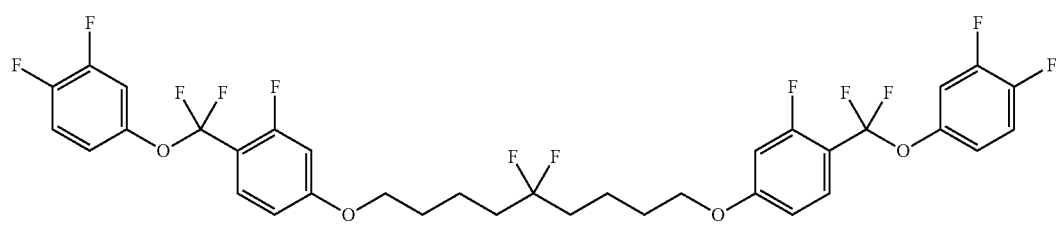
(1-113)
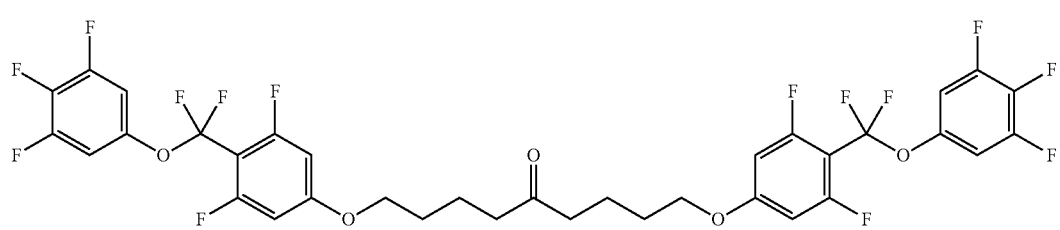
(1-114)
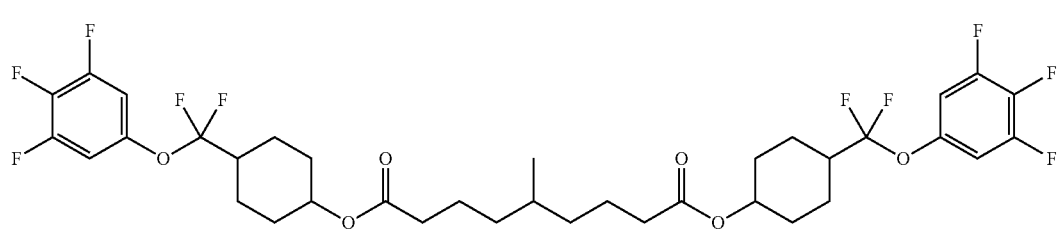
(1-115)
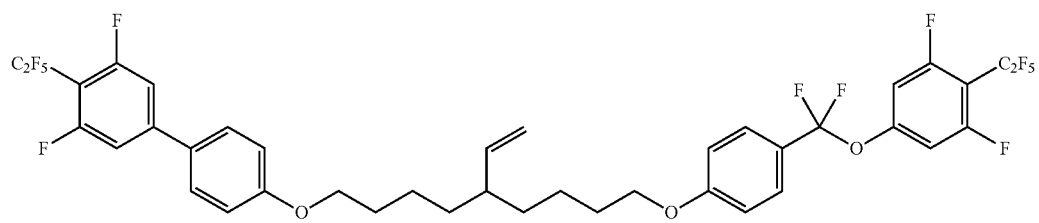
(1-116)

-continued
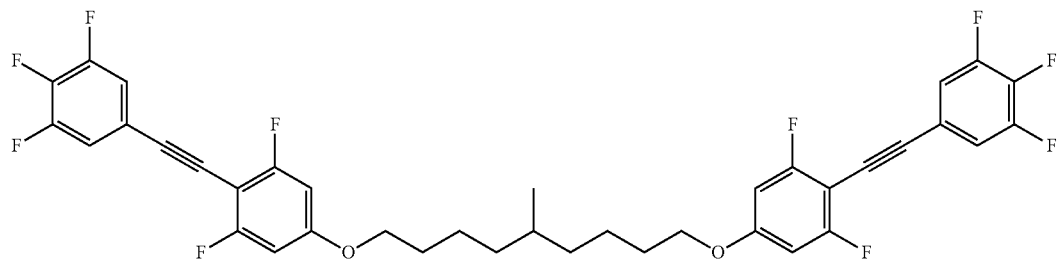
(1-117)
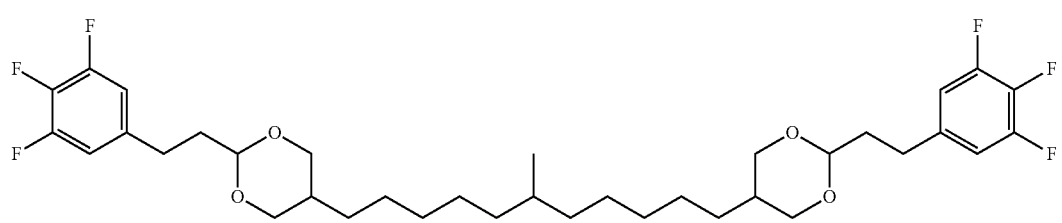
(1-118)
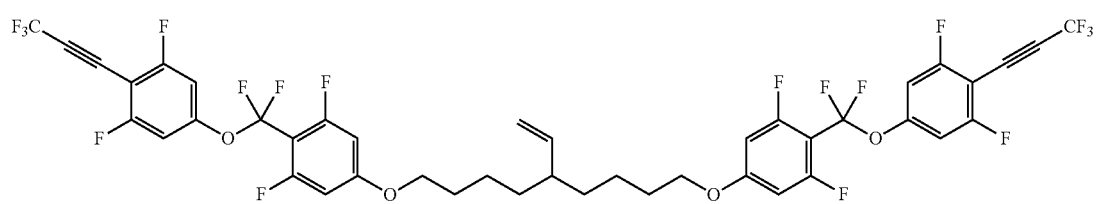
(1-119)
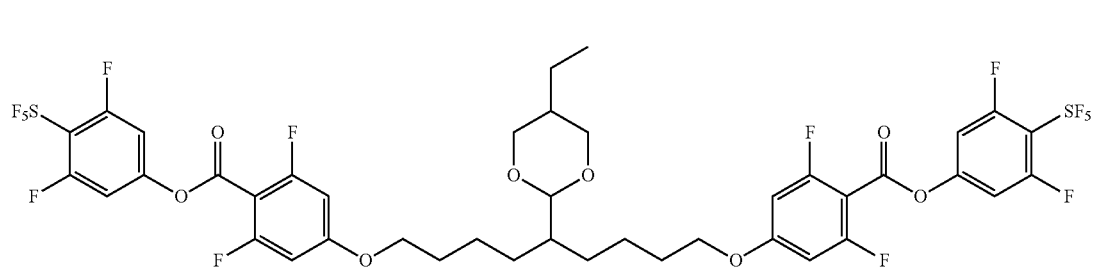
(1-120)
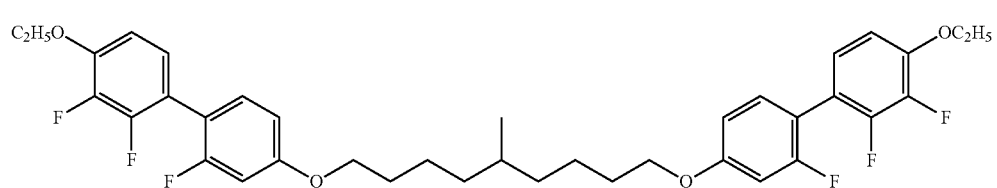
(1-121)
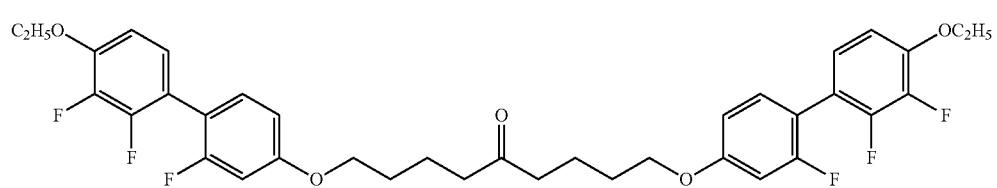
(1-122)
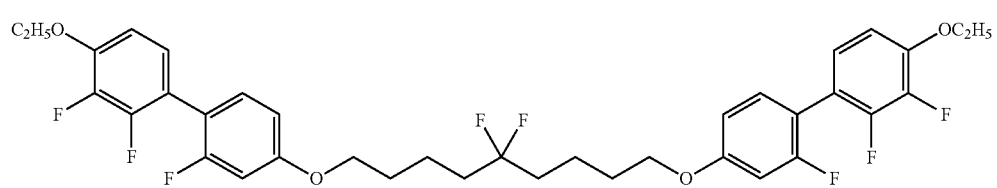
(1-123)

-continued
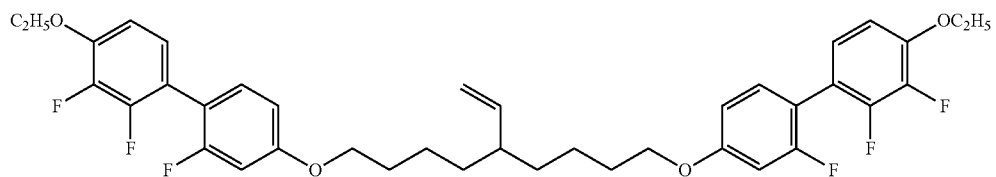
(1-124)
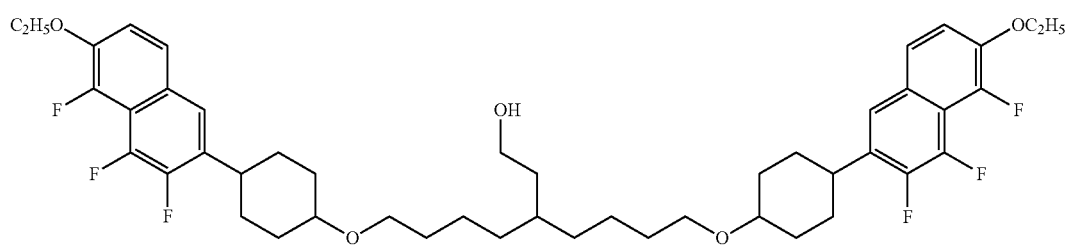
(1-125)
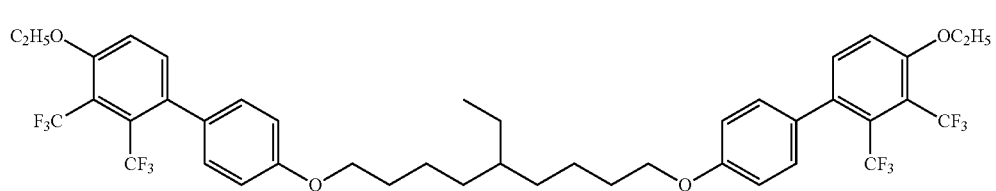
(1-126)
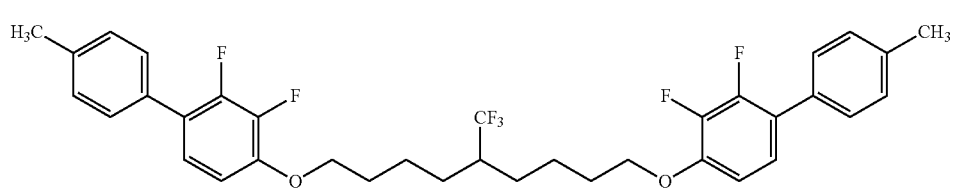
(1-127)
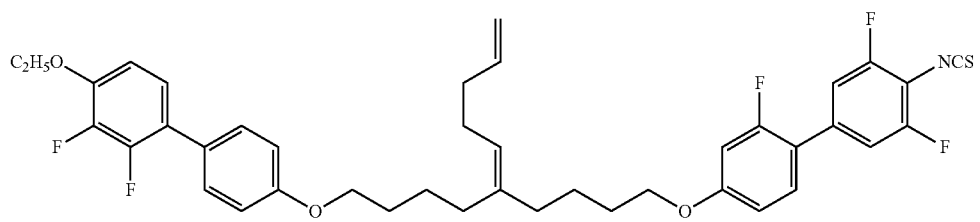
(1-128)
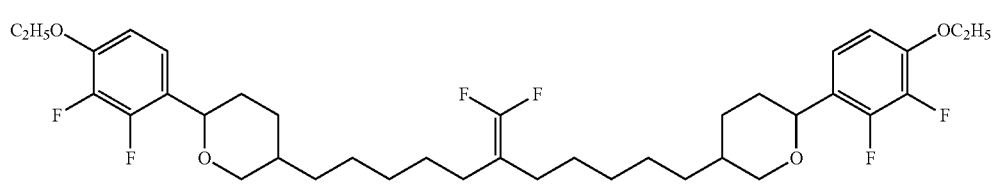
(1-129)
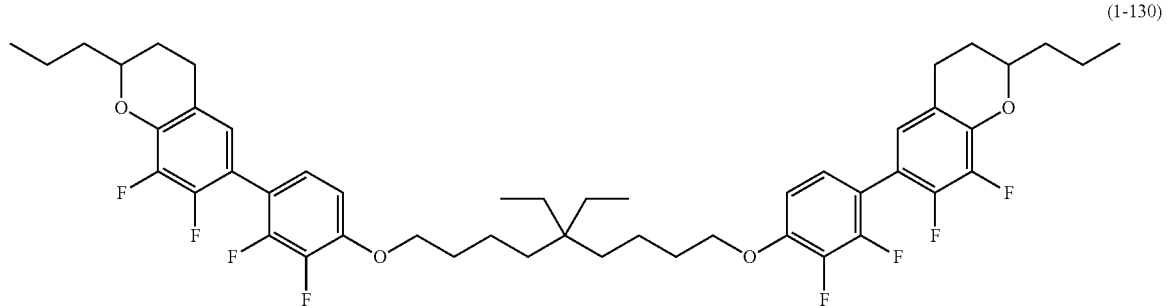
(1-130)

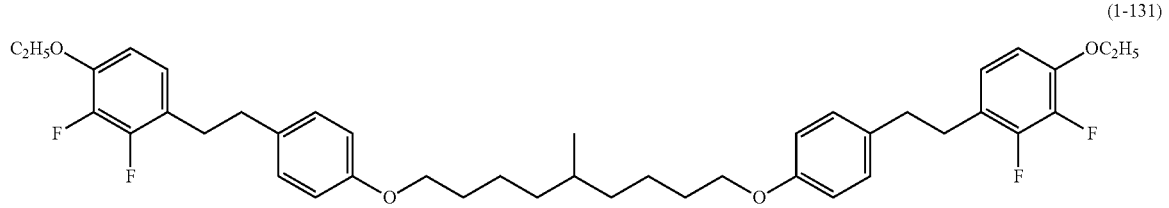
(1-131)
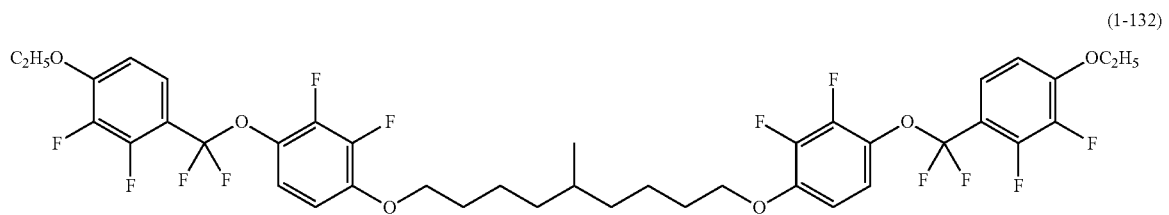
(1-132)
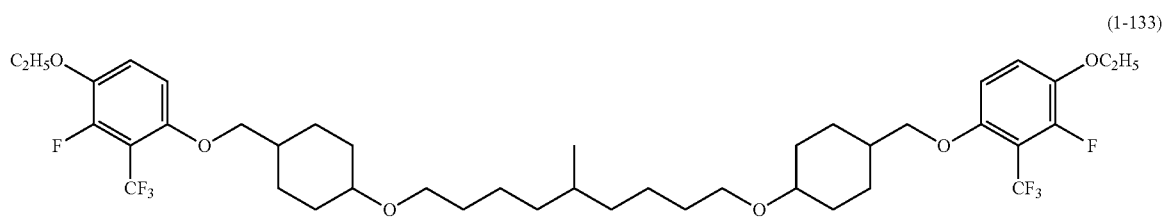
(1-133)
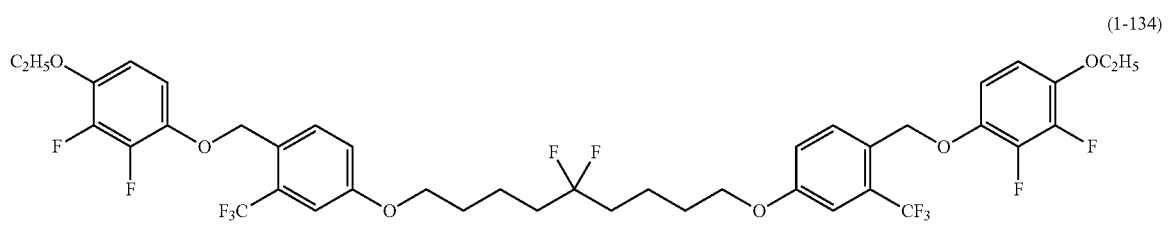
(1-134)
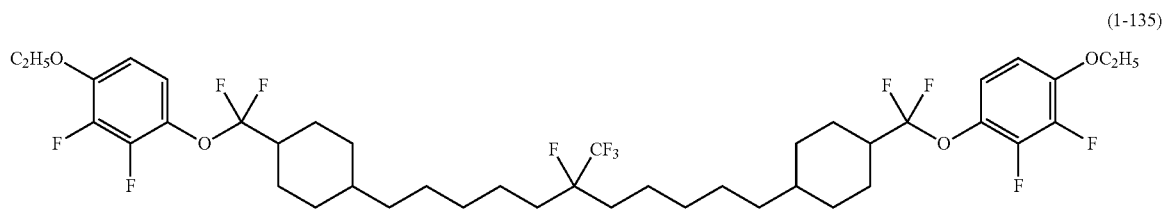
(1-135)
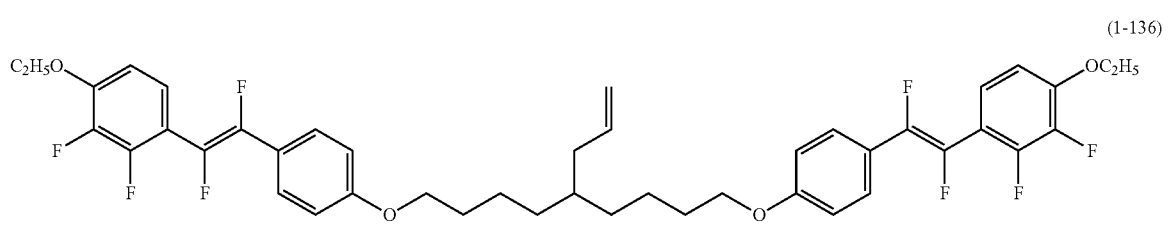
(1-136)
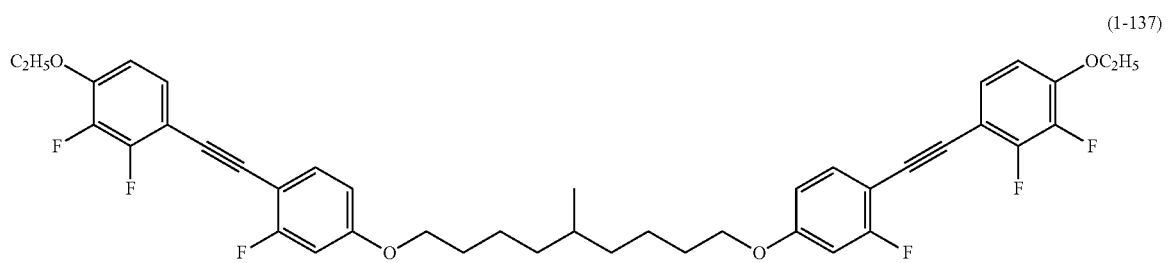
(1-137)

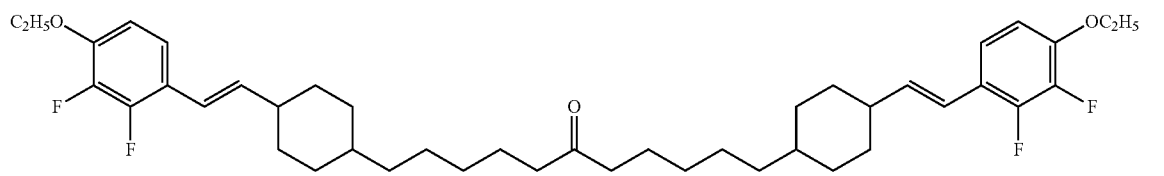
(1-138)
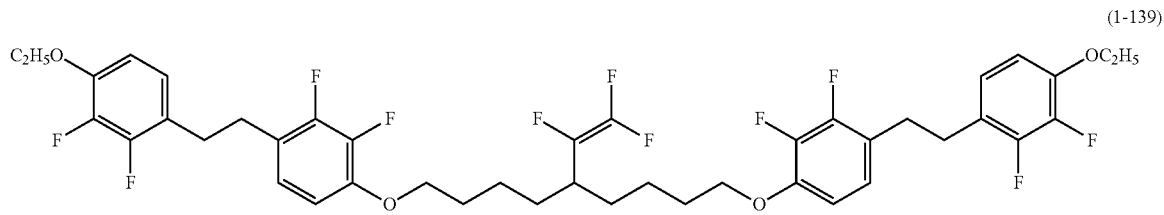
(1-139)
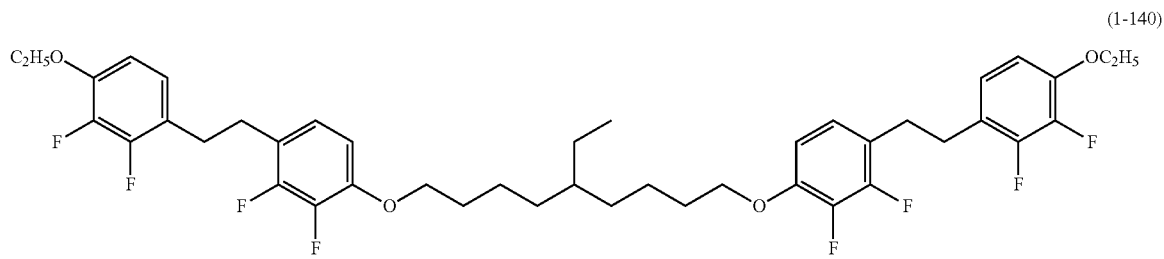
(1-140)
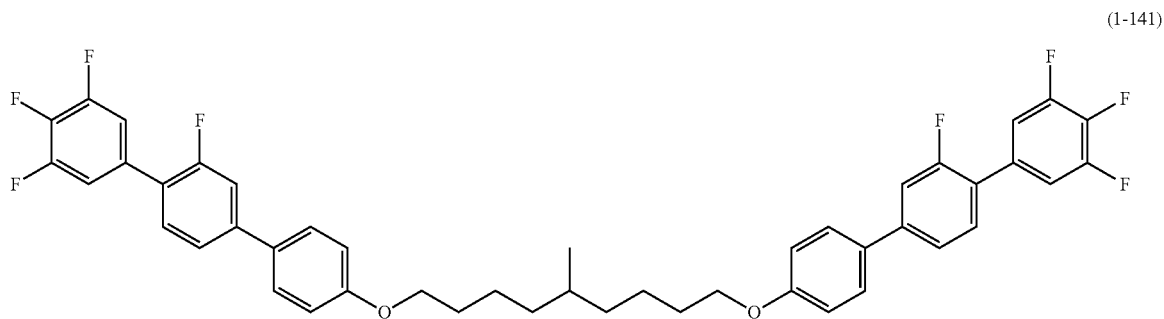
(1-141)
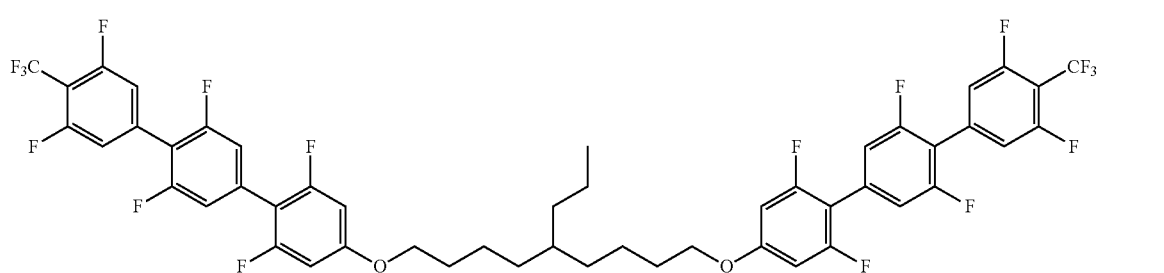
(1-142)
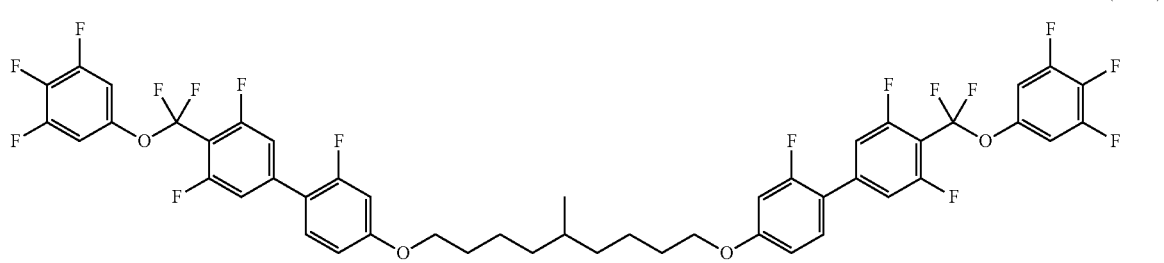
(1-143)

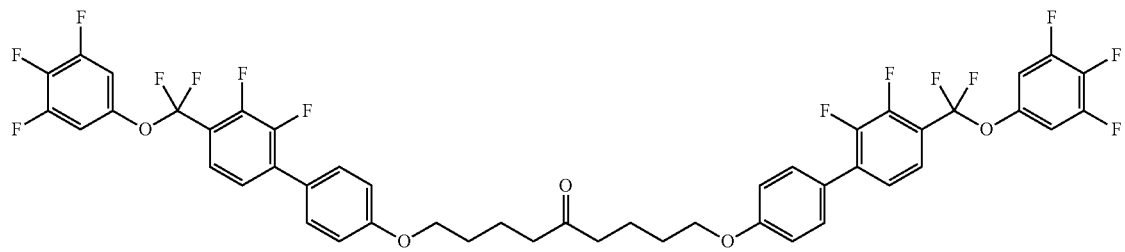
(1-144)
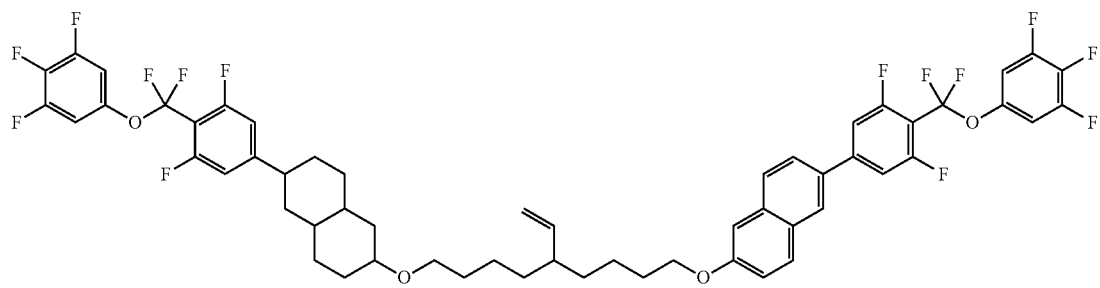
(1-145)
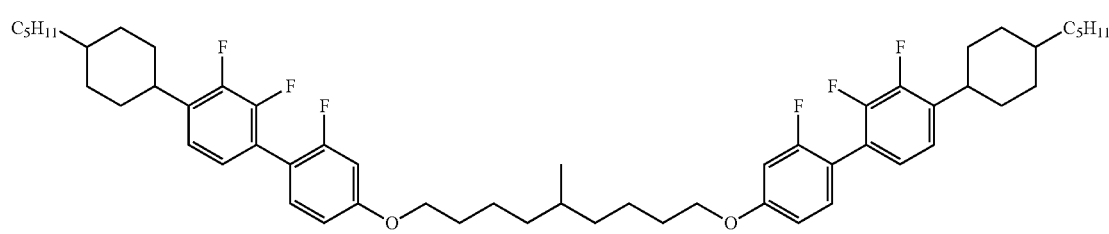
(1-146)
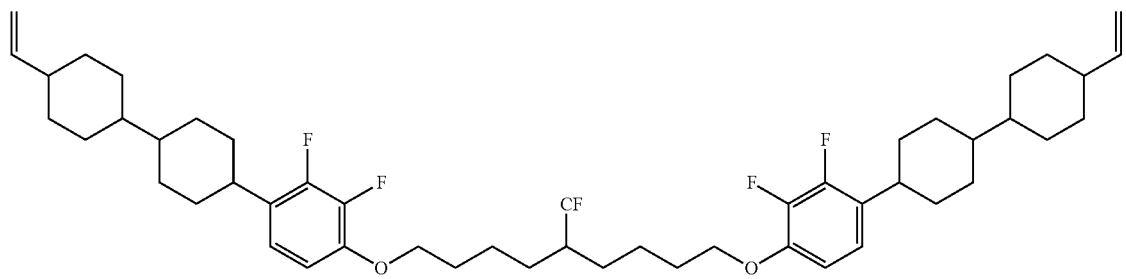
(1-147)
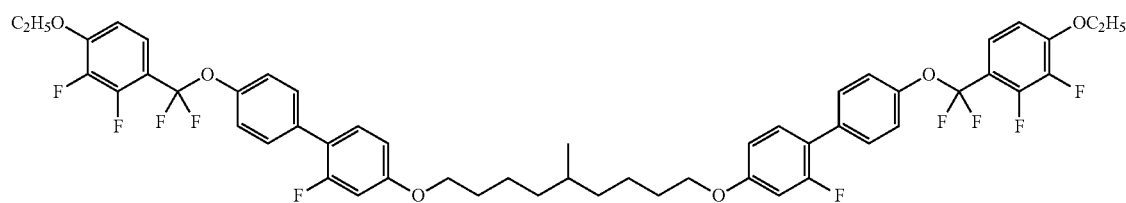
(1-148)
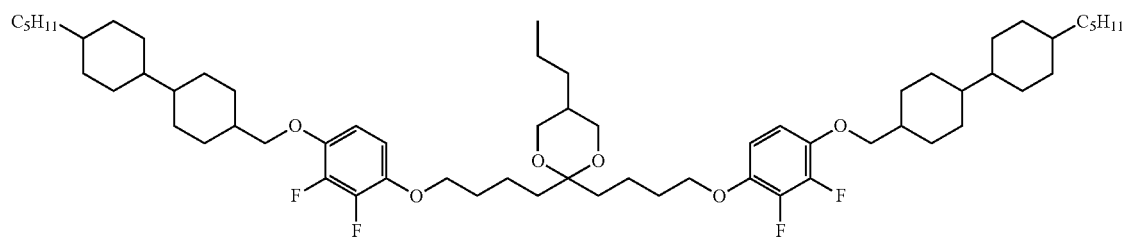
(1-149)

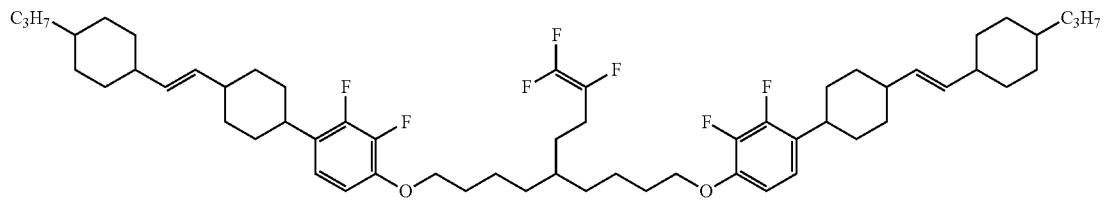
(1-150)
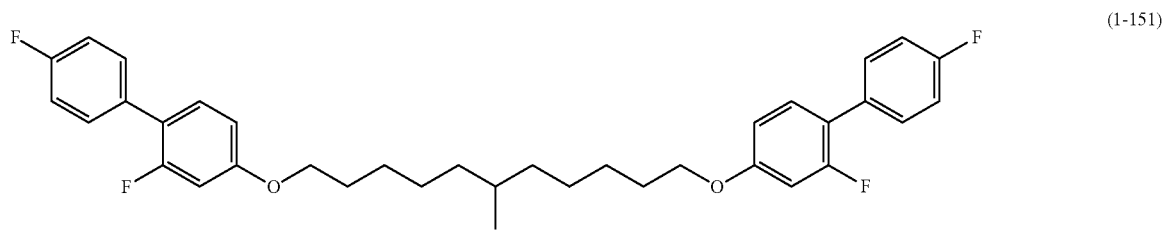
(1-151)
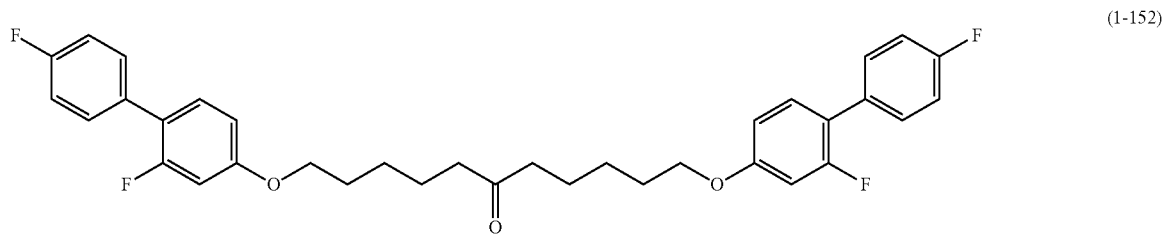
(1-152)
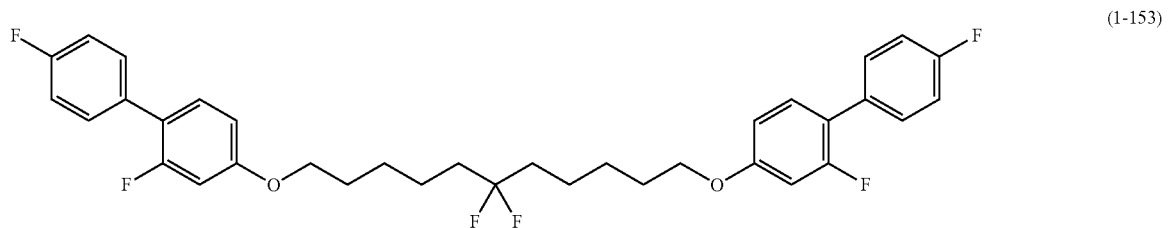
(1-153)
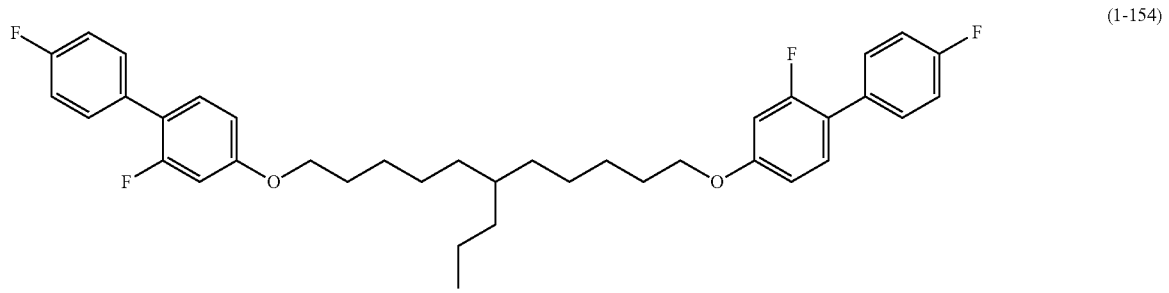
(1-154)
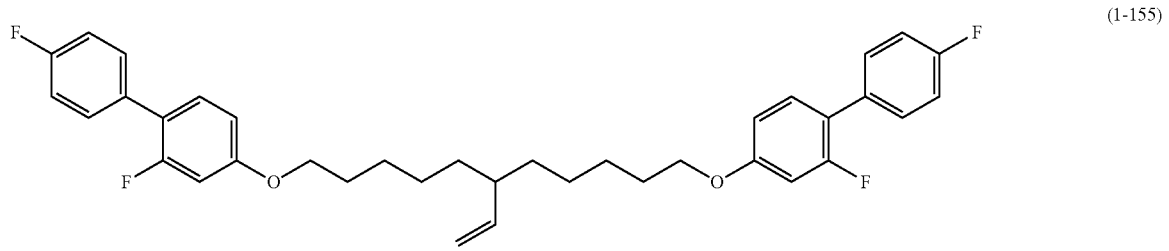
(1-155)

-continued
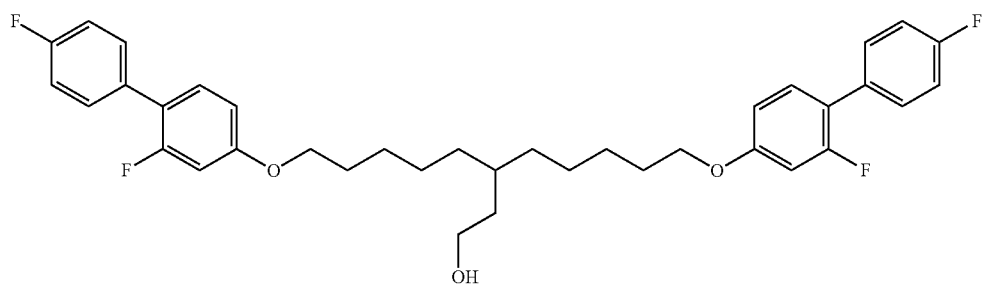
(1-156)
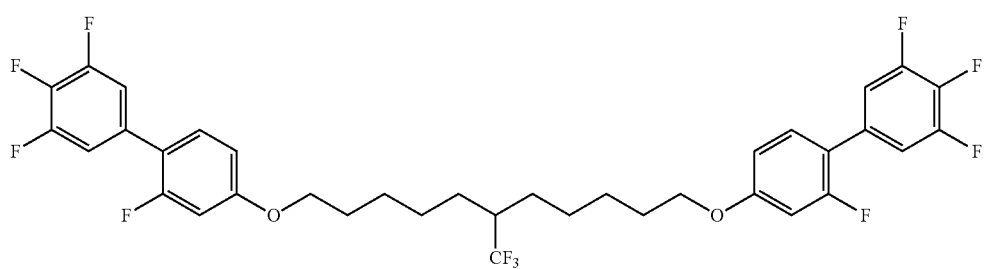
(1-157)
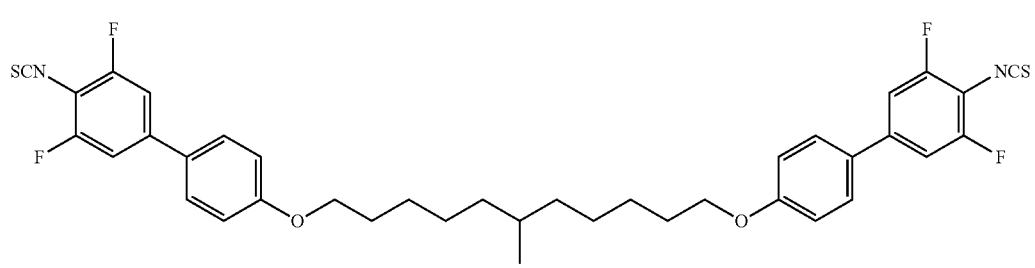
(1-158)
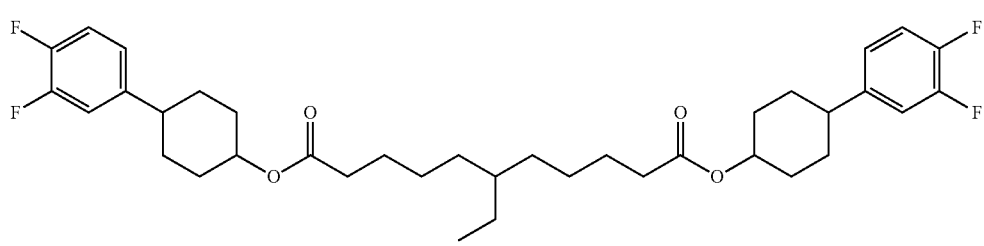
(1-159)
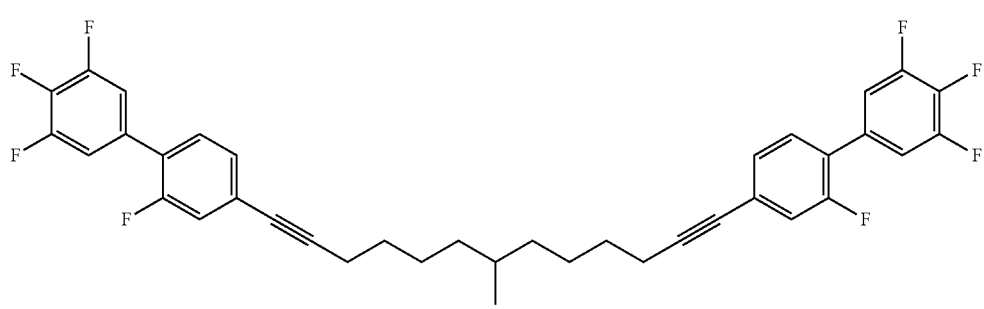
(1-160)
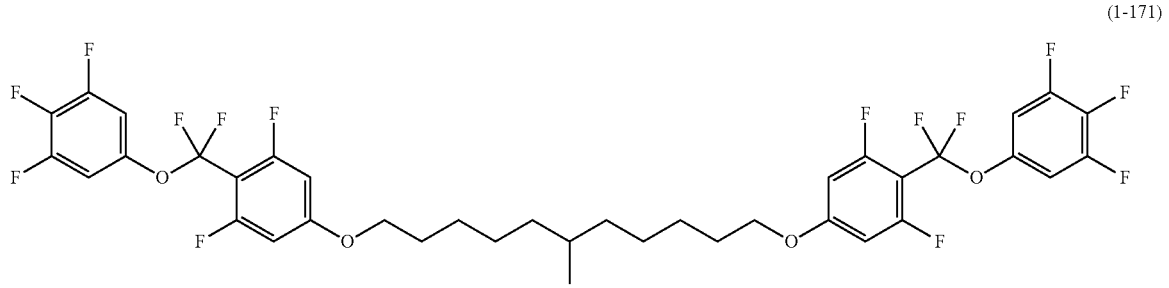
(1-171)

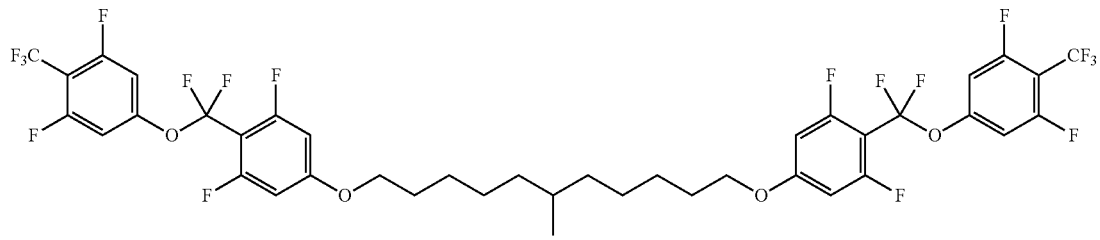
(1-172)
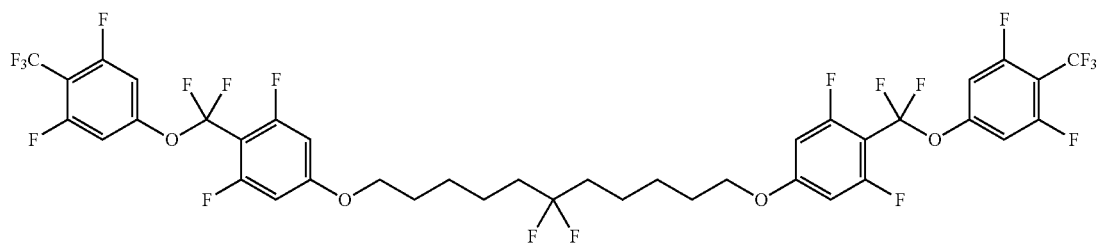
(1-173)
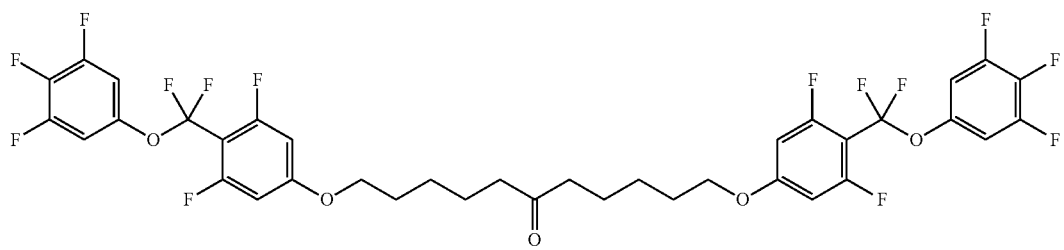
(1-174)
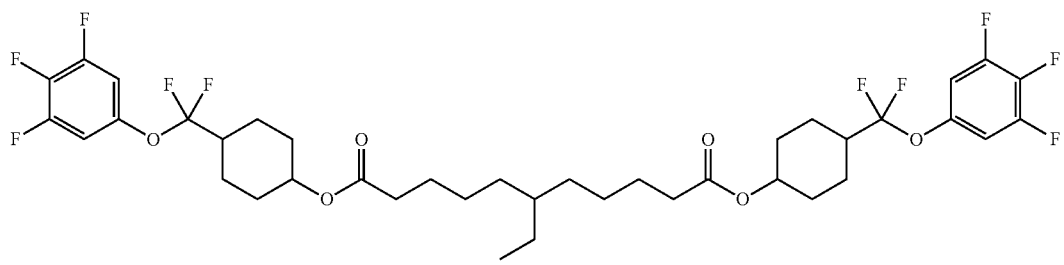
(1-175)
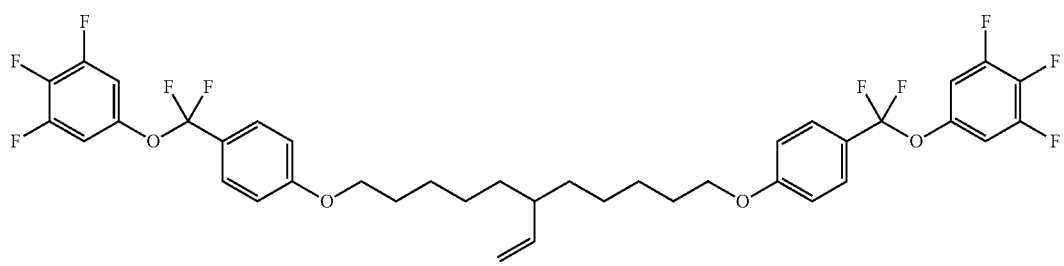
(1-176)
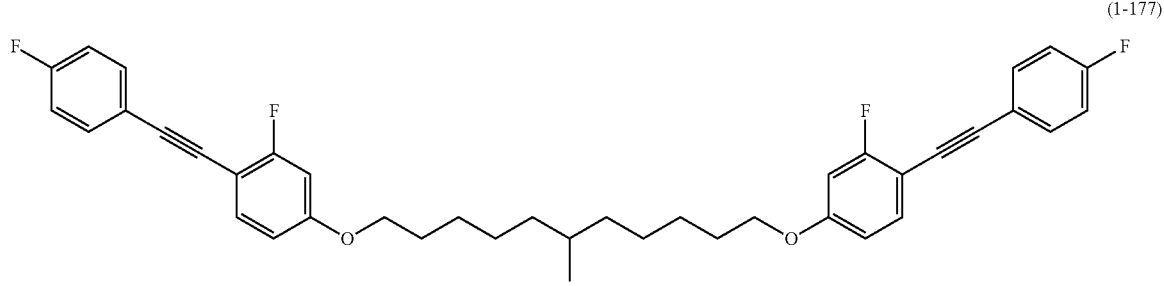
(1-177)

(1-178)
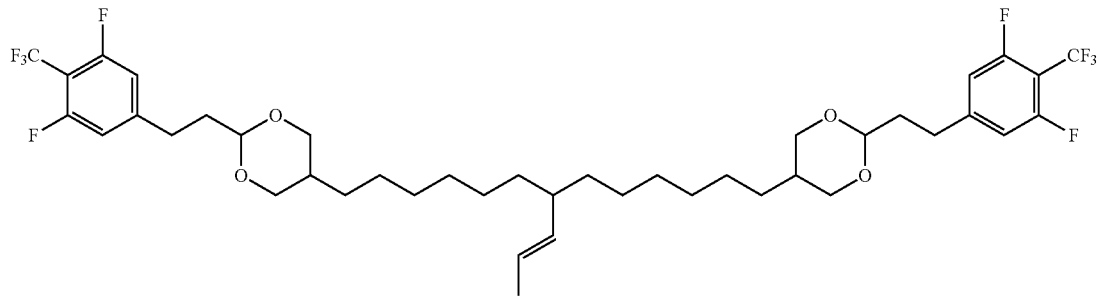
(1-179)
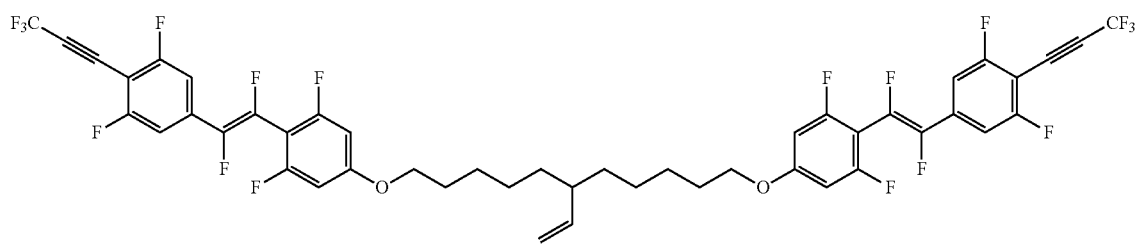
(1-180)
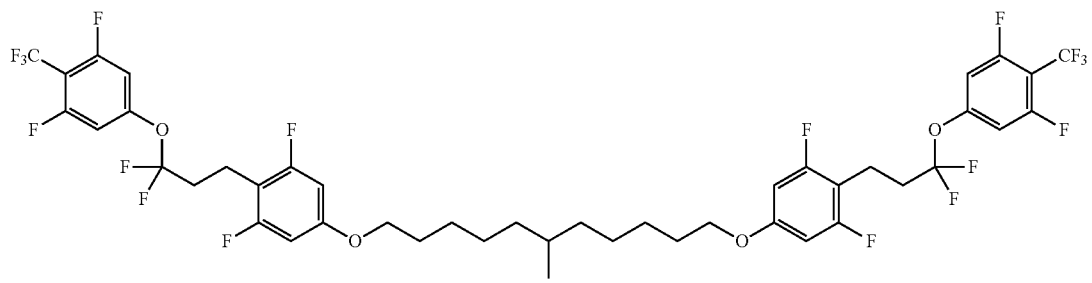
(1-181)
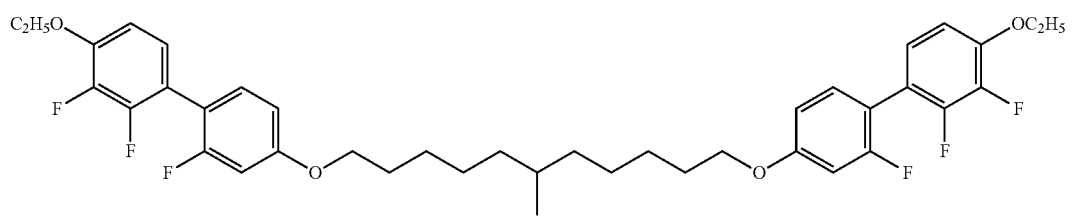
(1-182)
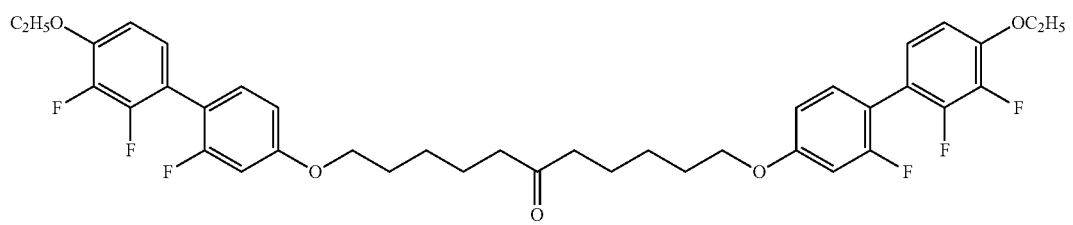
(1-183)
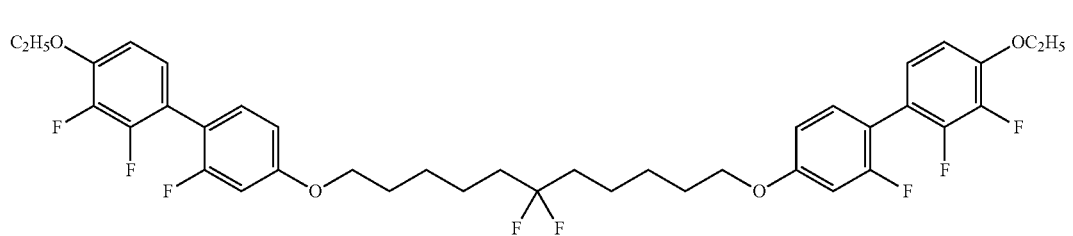

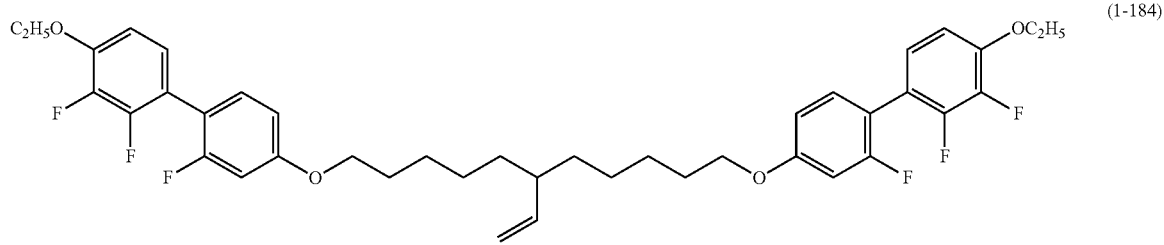
(1-184)
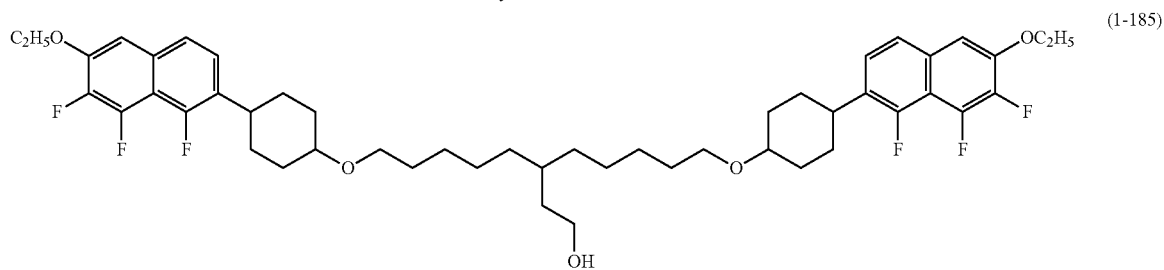
(1-185)
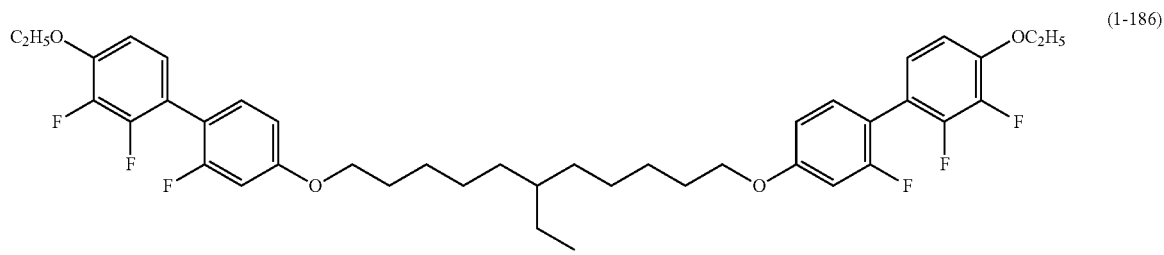
(1-186)
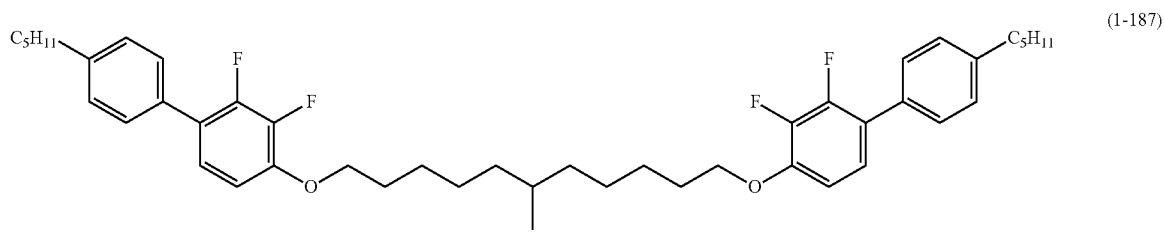
(1-187)
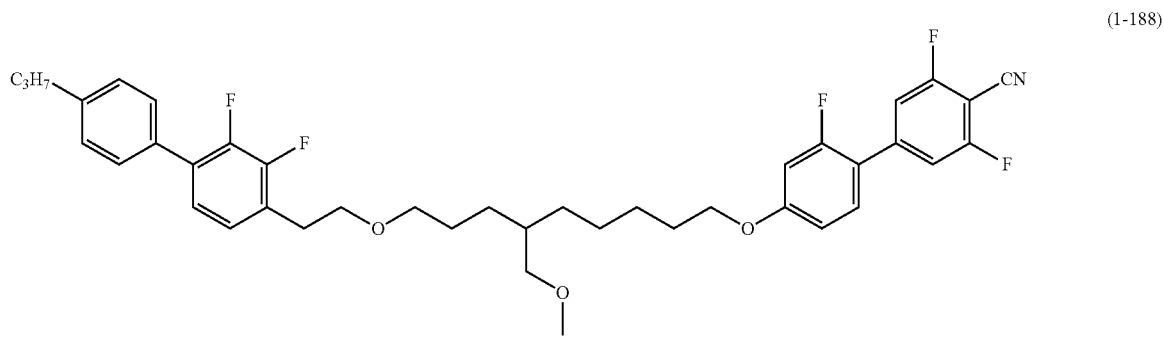
(1-188)
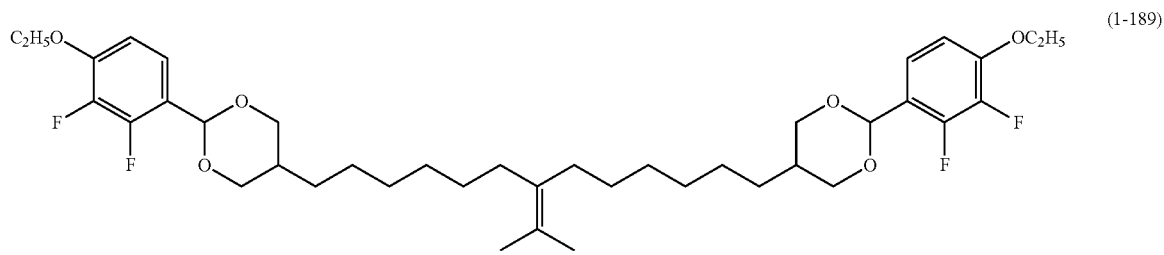
(1-189)

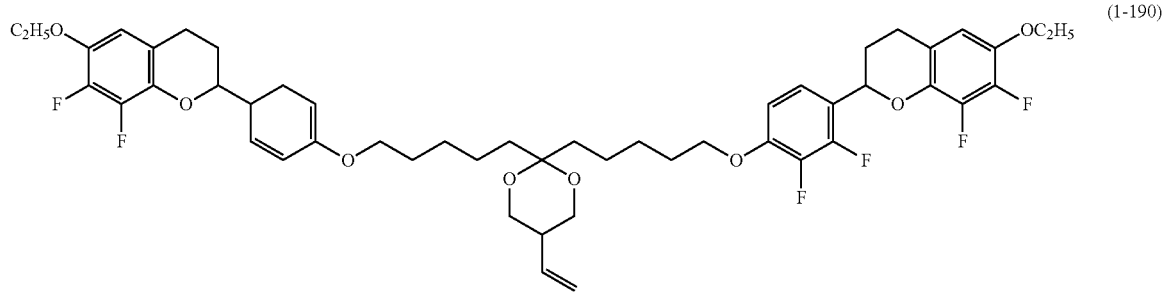
(1-190)
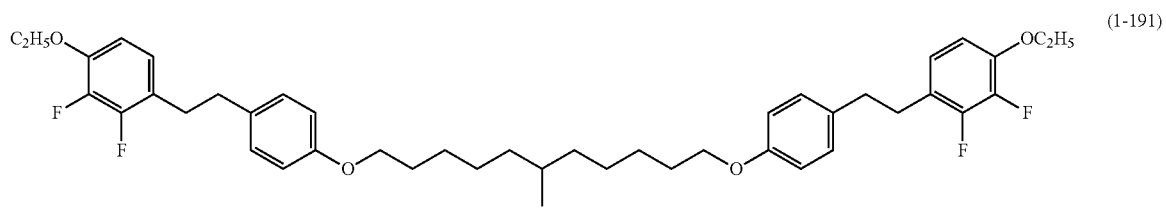
(1-191)
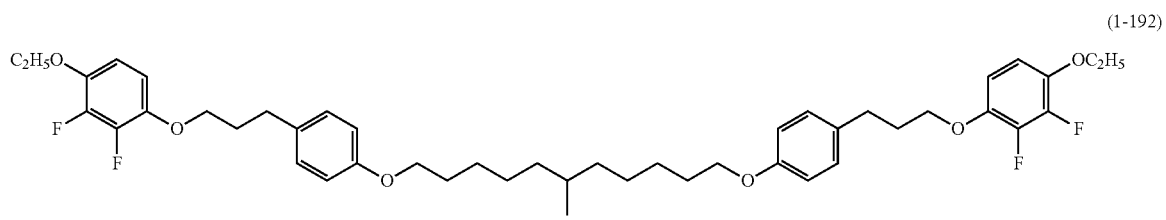
(1-192)
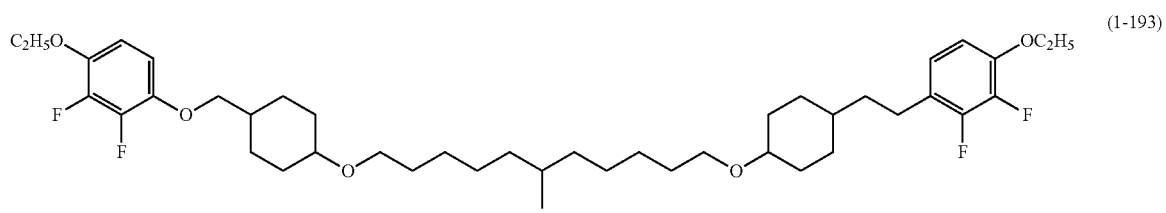
(1-193)
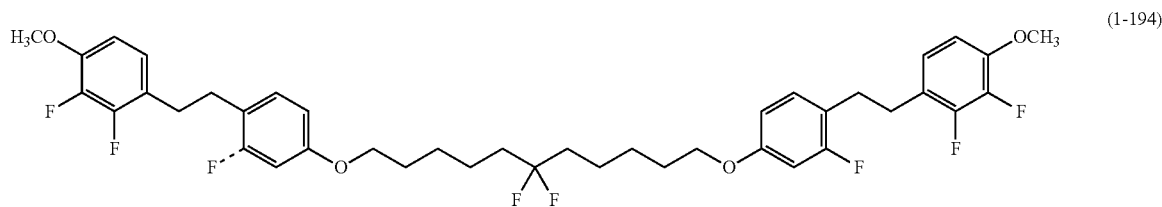
(1-194)
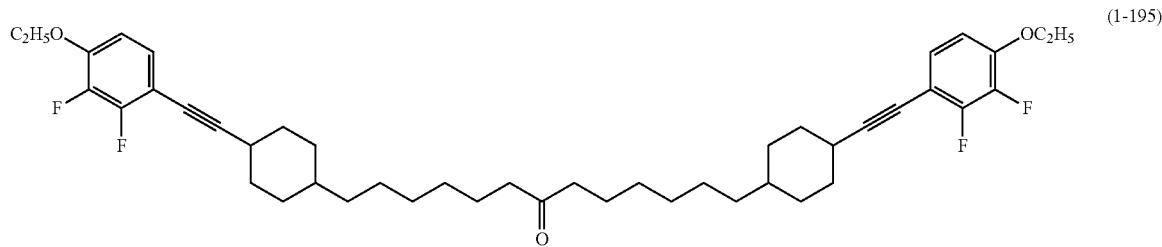
(1-195)
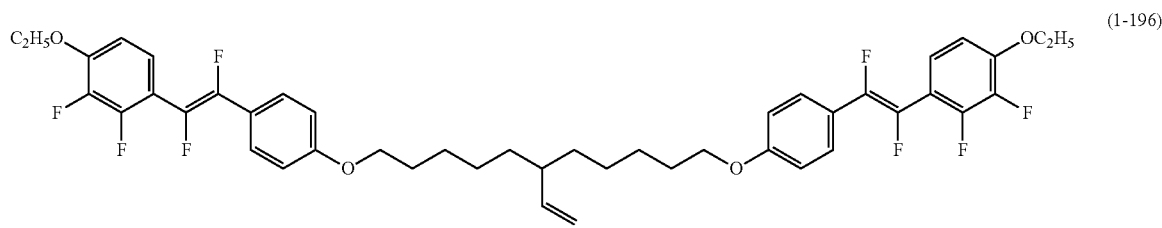
(1-196)

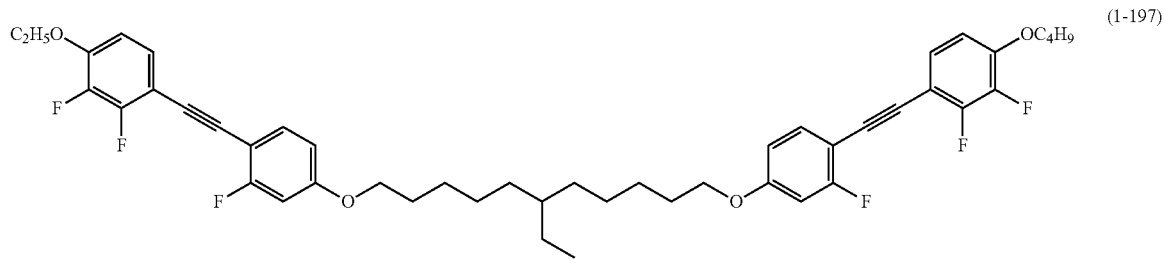
(1-197)
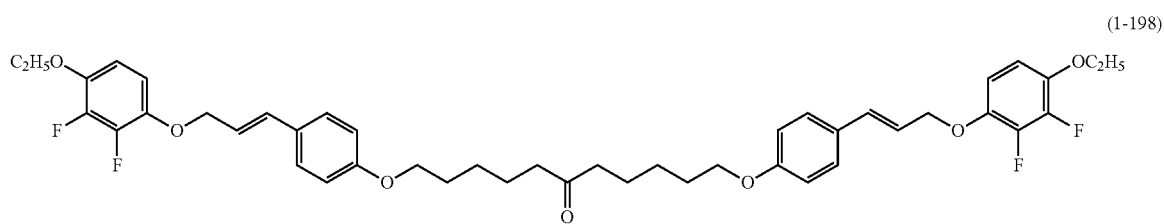
(1-198)
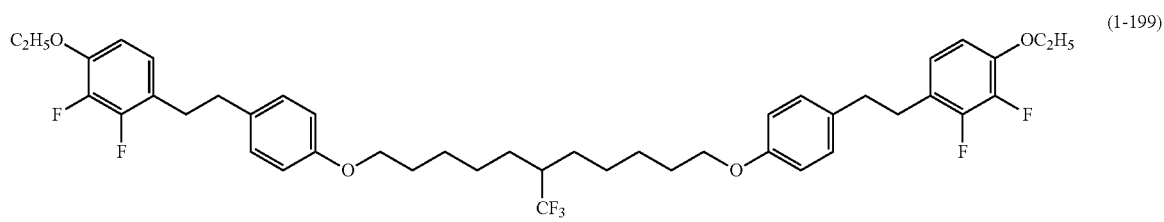
(1-199)
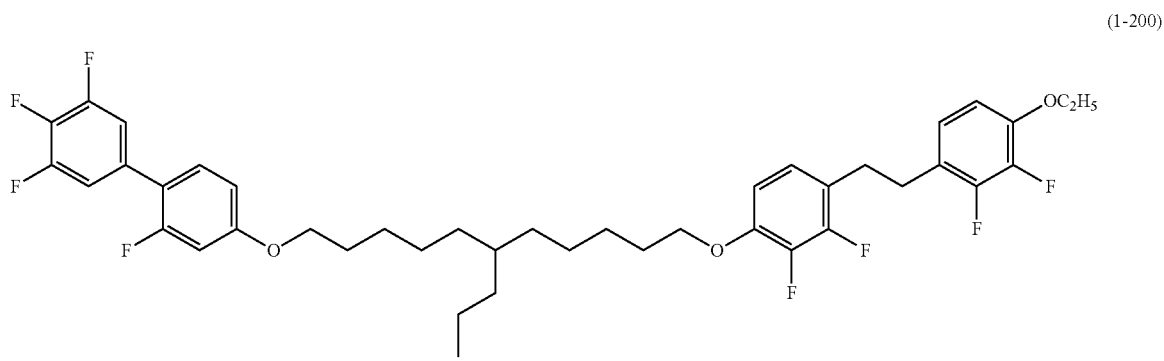
(1-200)
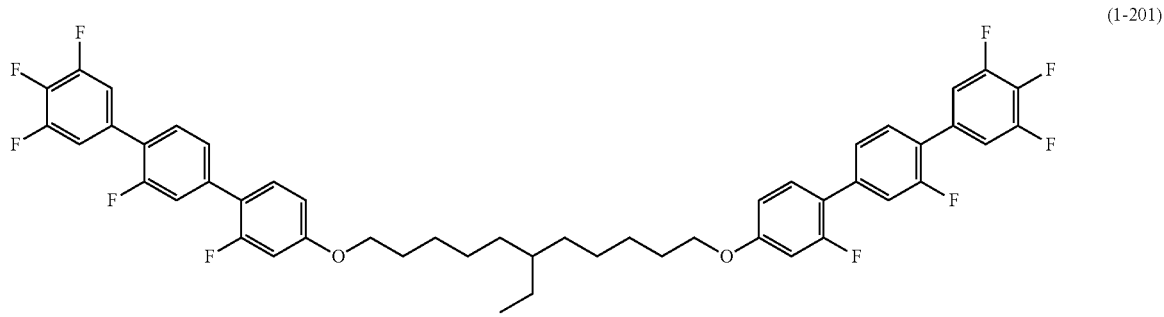
(1-201)

(1-202)
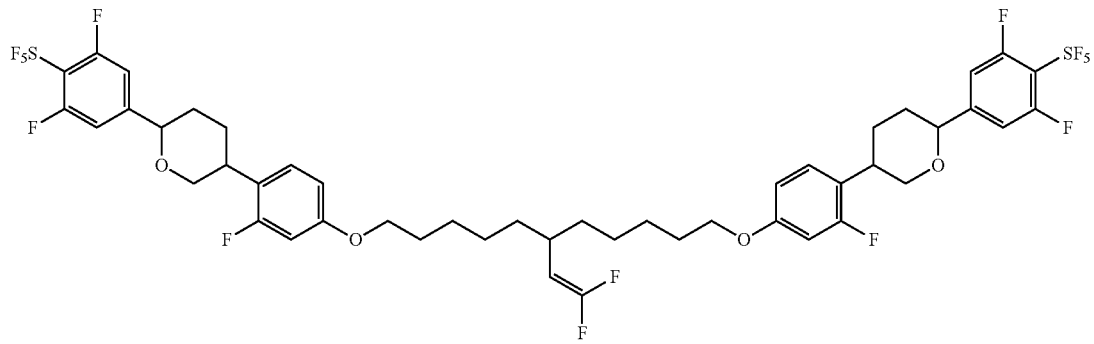
(1-203)
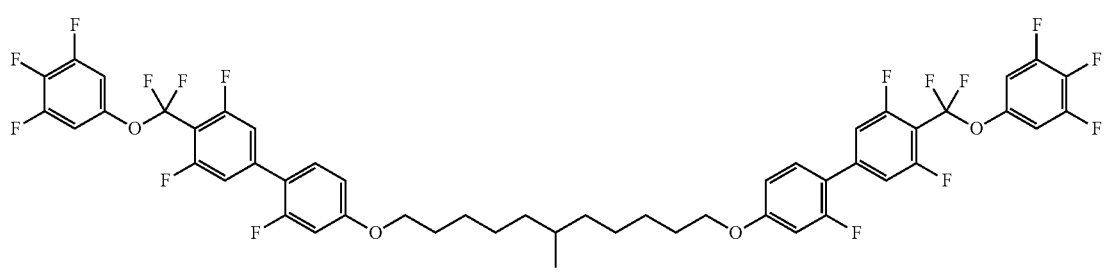
(1-204)
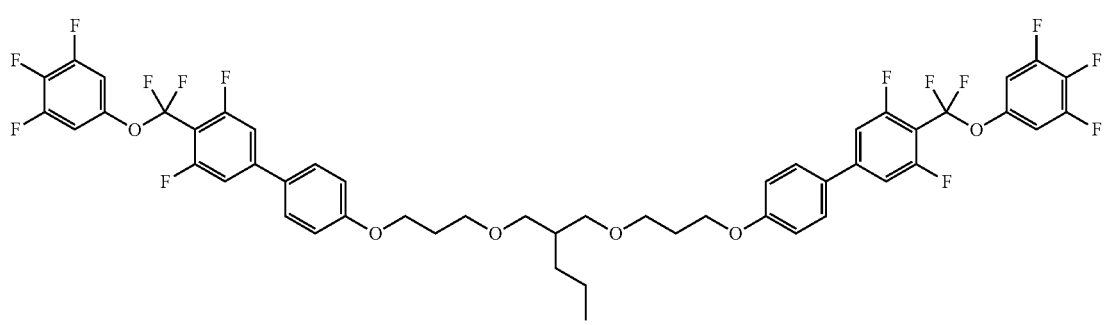
(1-205)
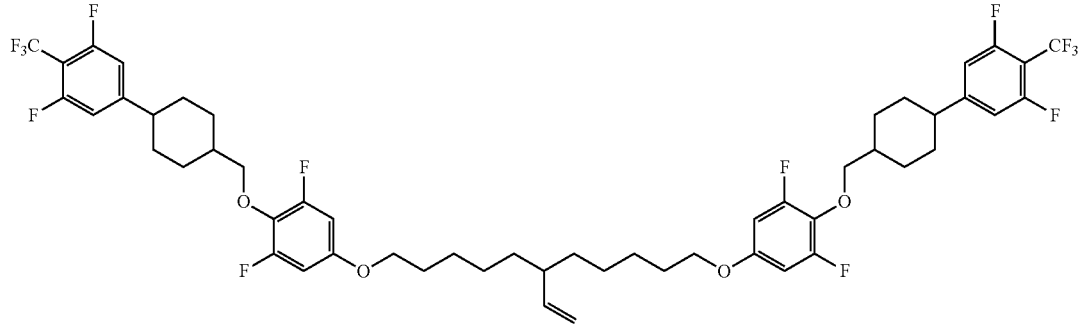
(1-206)
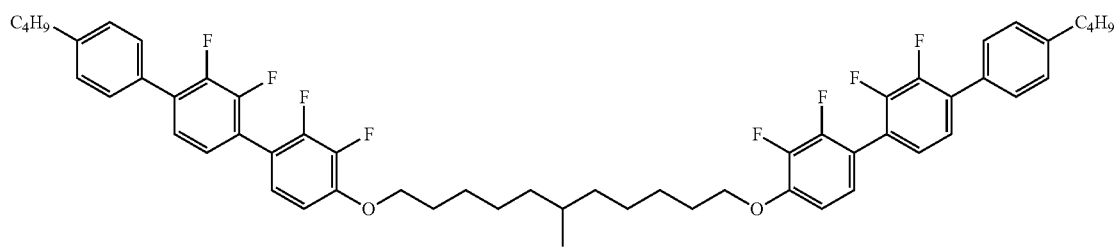

-continued
(1-207)
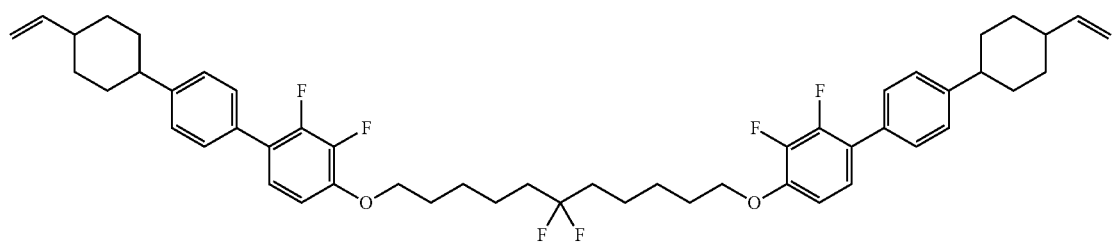
(1-208)
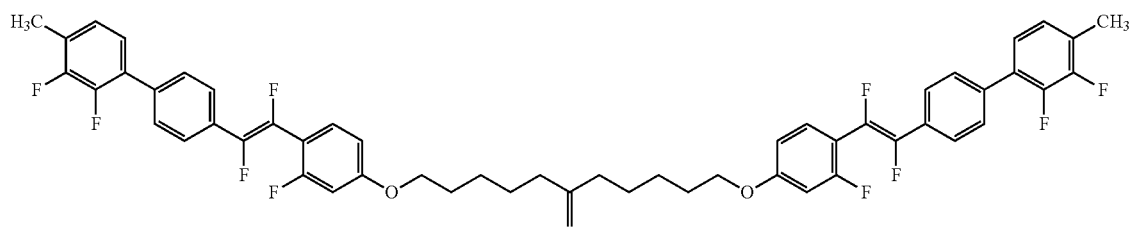
(1-209)
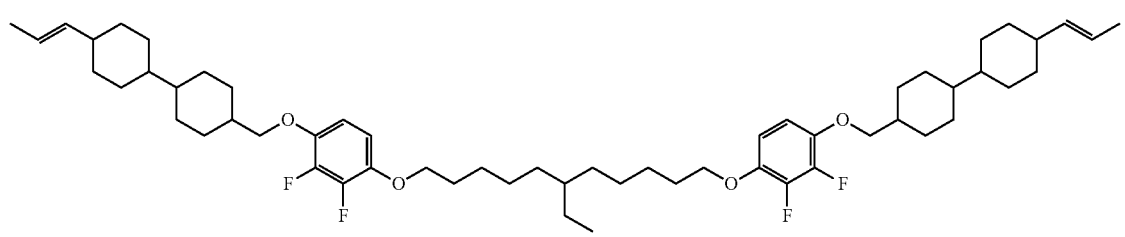
(1-210)
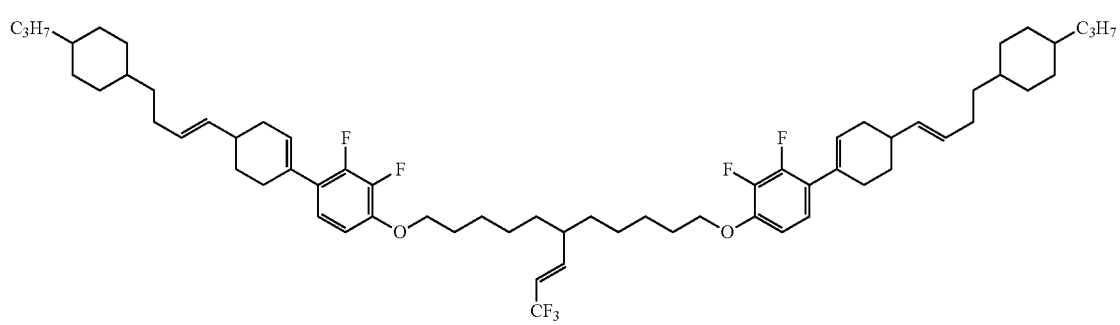
(1-211)
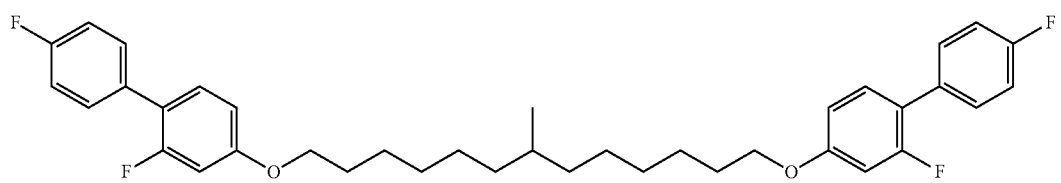
(1-212)
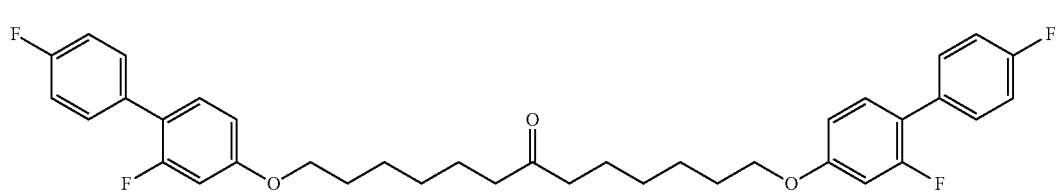

-continued
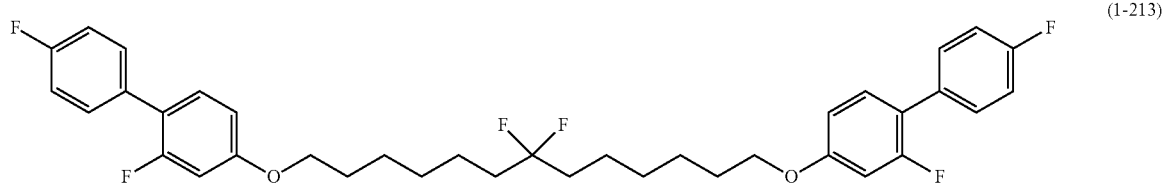
(1-213)
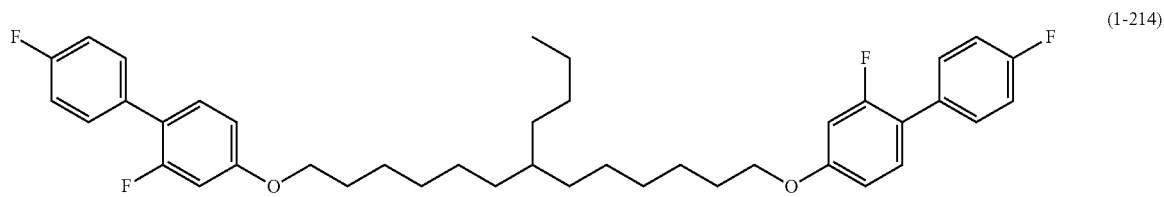
(1-214)
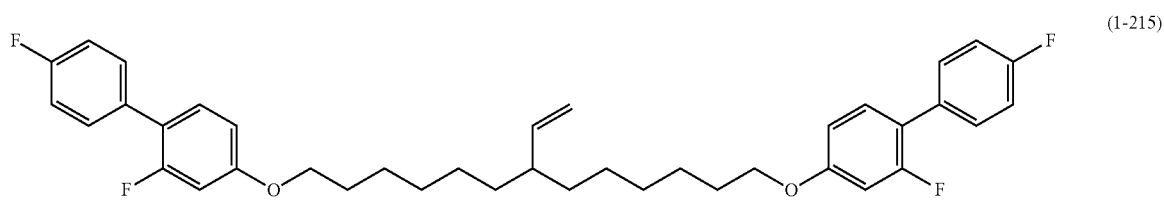
(1-215)
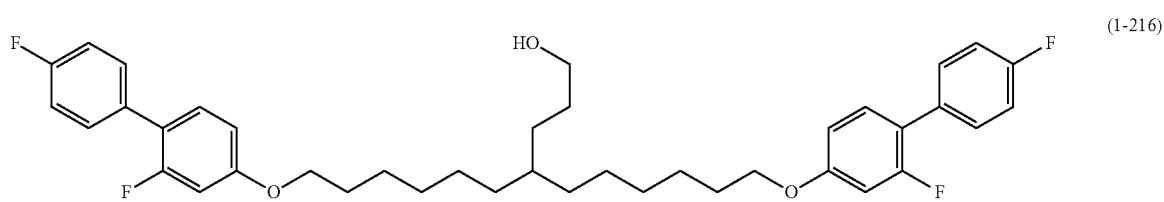
(1-216)
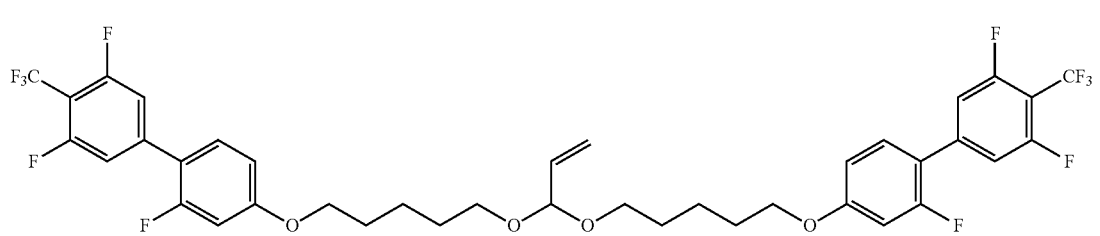
(1-217)
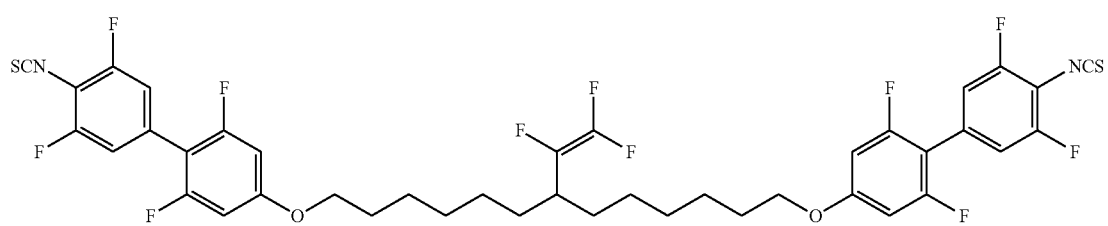
(1-218)
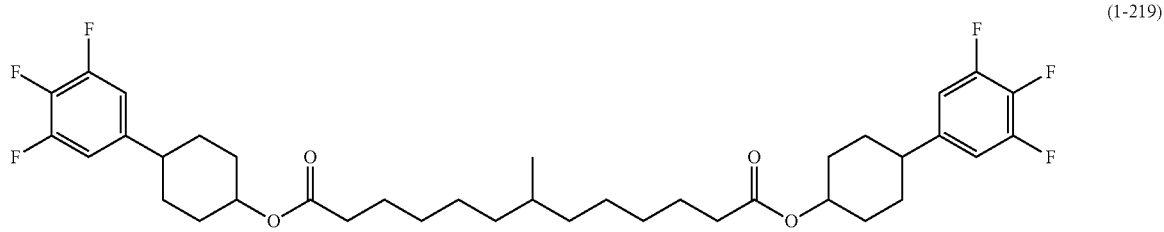
(1-219)

(1-220)
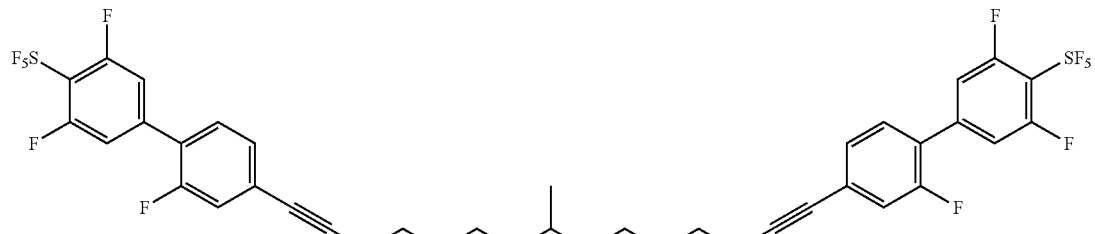
(1-221)
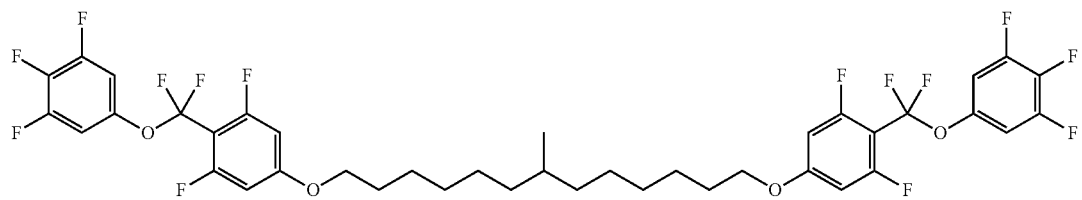
(1-222)
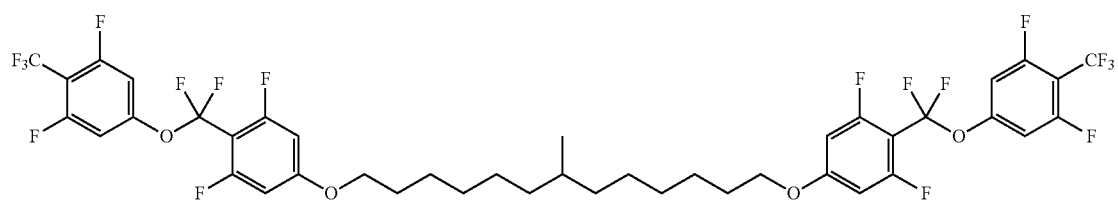
(1-223)
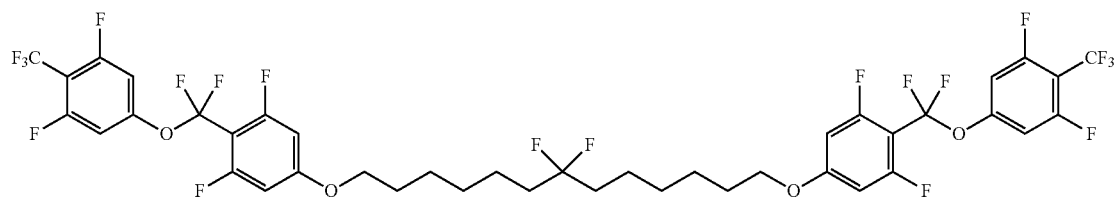
(1-224)
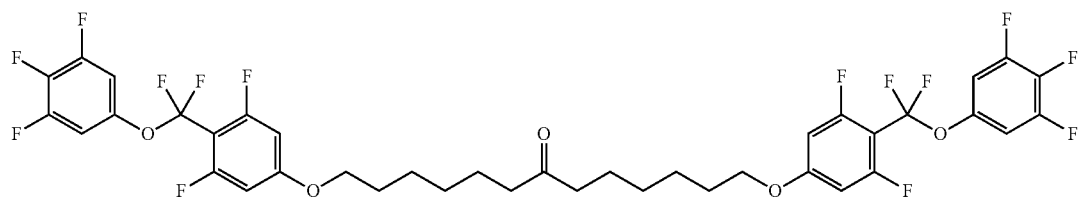
(1-225)
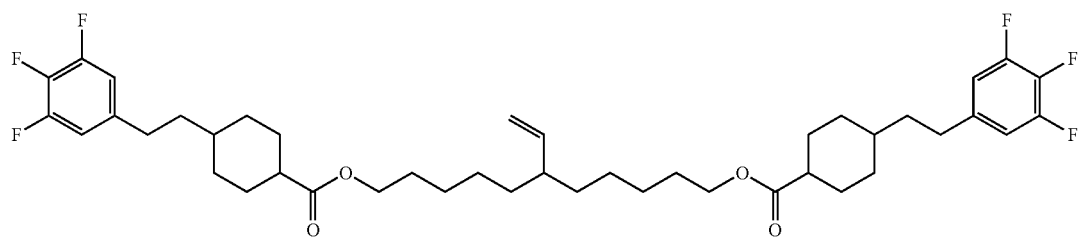
(1-226)
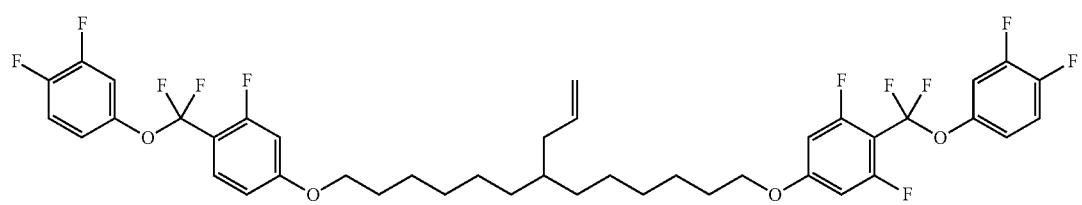

-continued
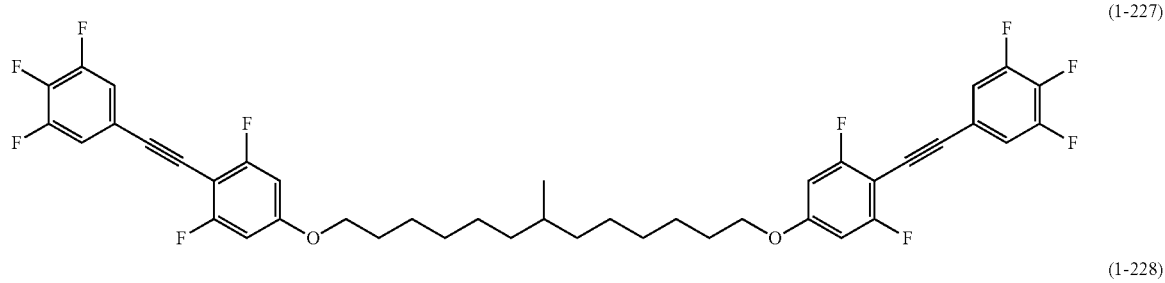
(1-227)
(1-228)
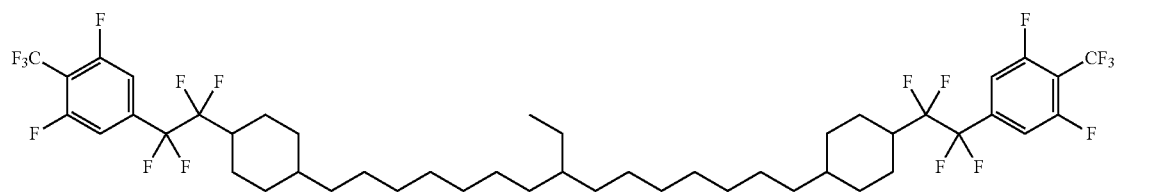
(1-229)
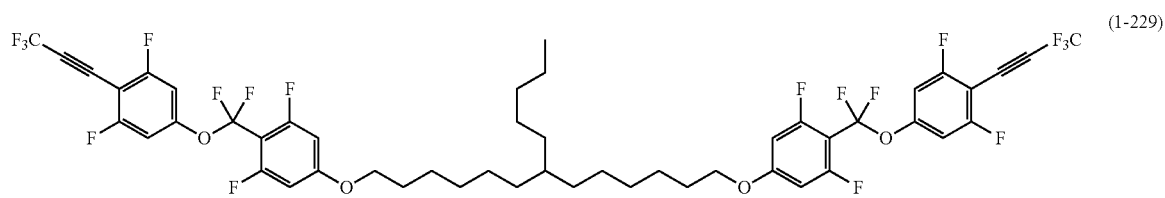
(1-230)
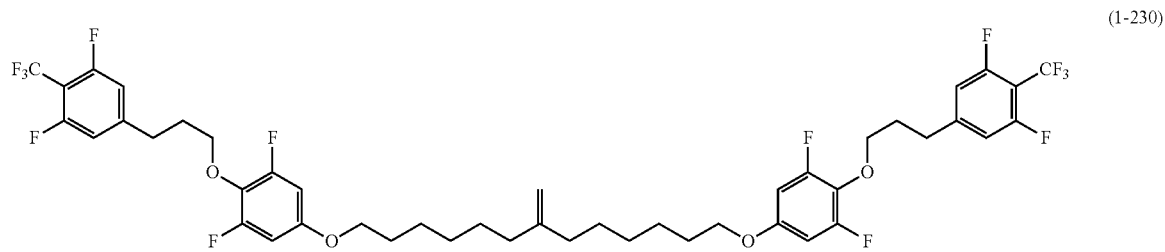
(1-231)
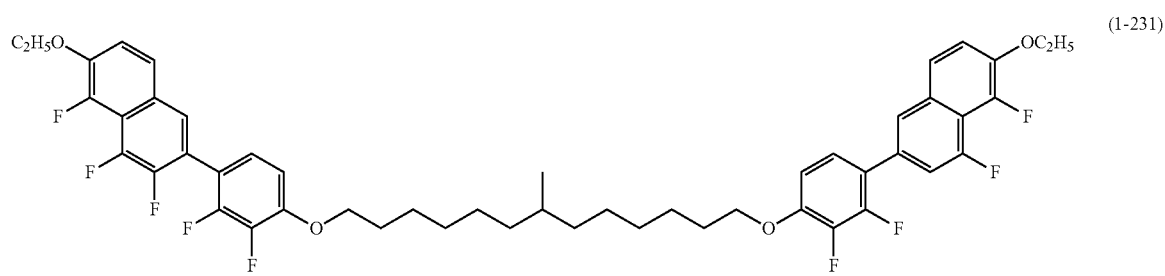
(1-232)
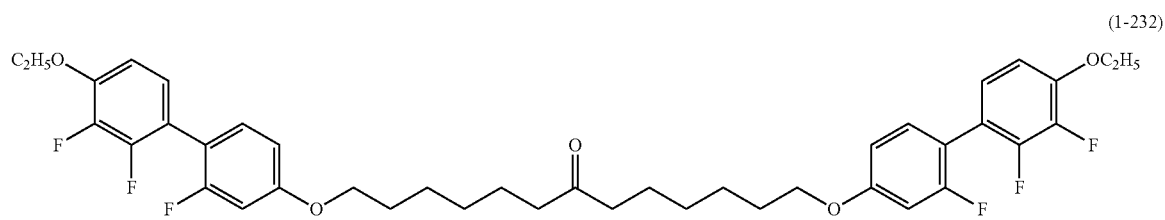
(1-233)
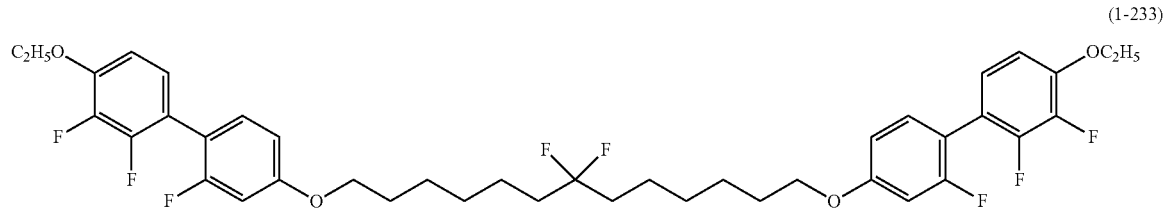

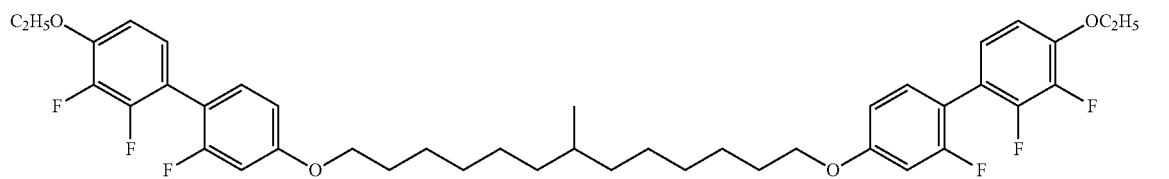
(1-234)
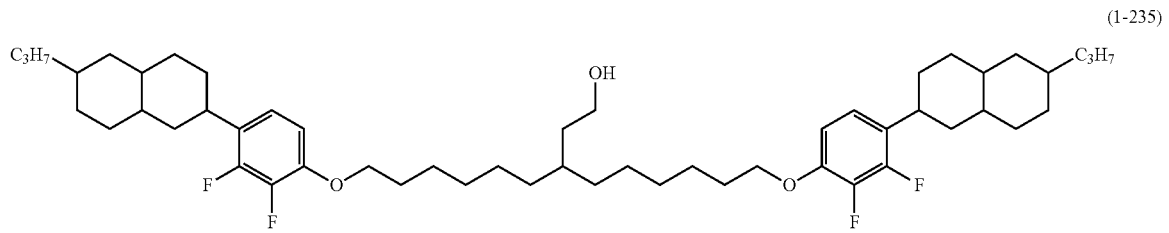
(1-235)
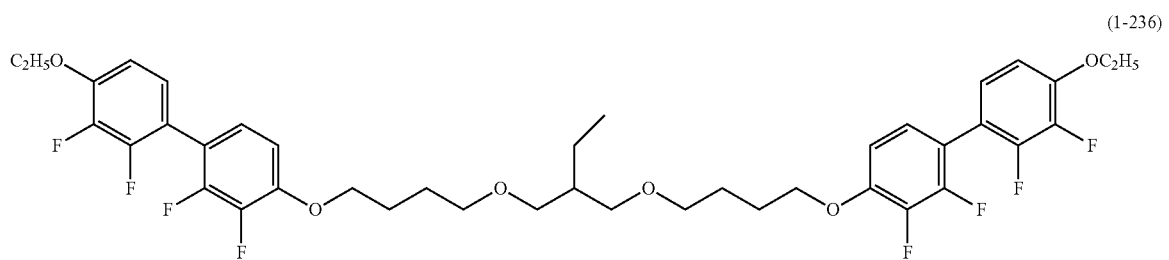
(1-236)
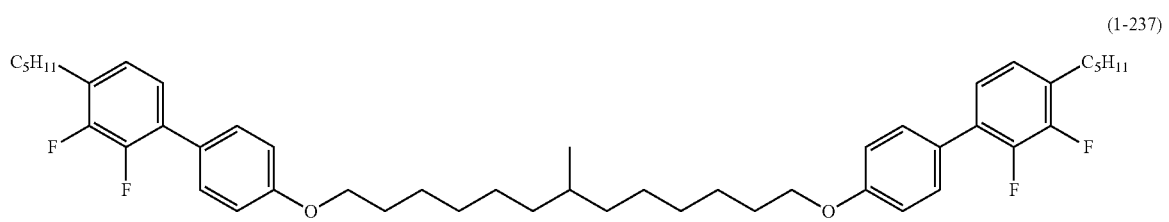
(1-237)
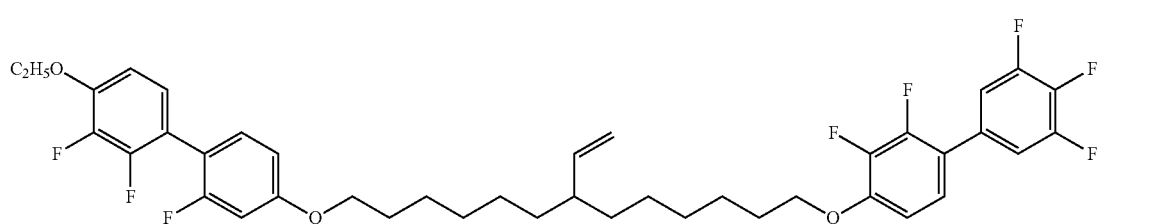
(1-238)
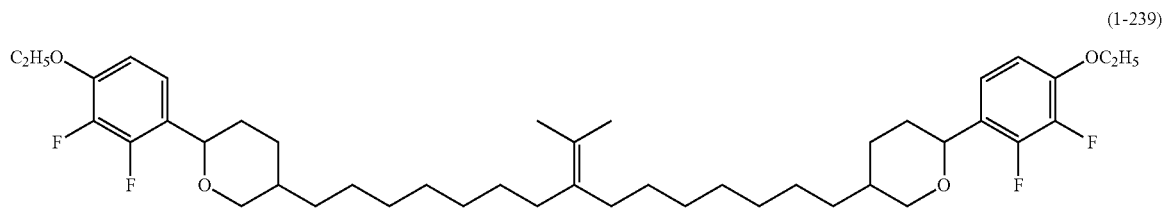
(1-239)
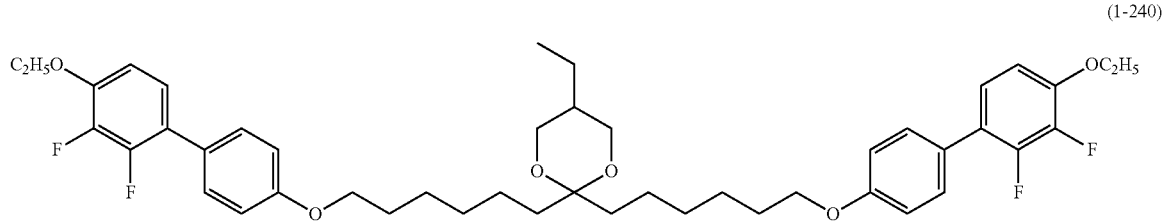
(1-240)

-continued
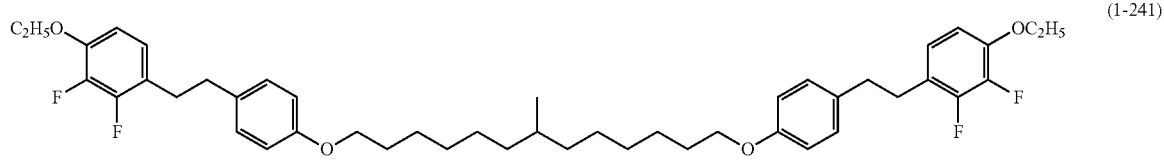
(1-241)
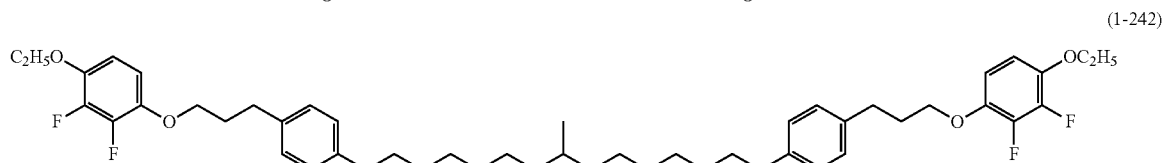
(1-242)
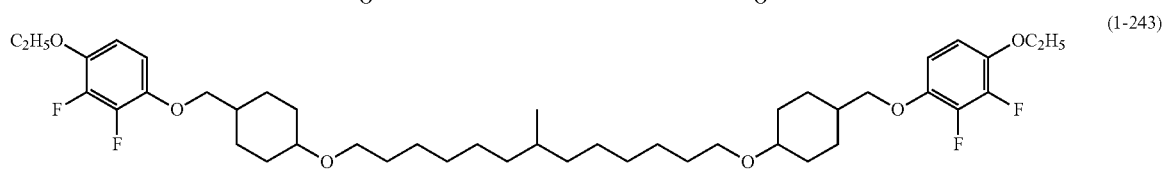
(1-243)
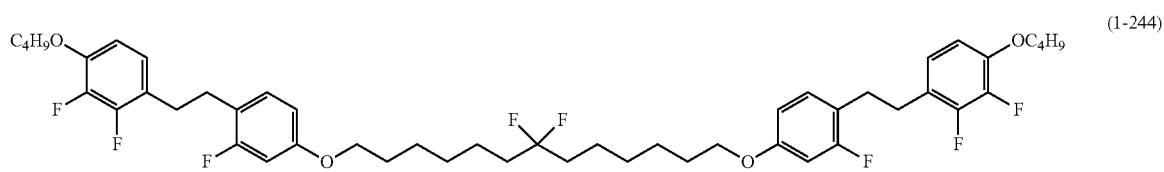
(1-244)
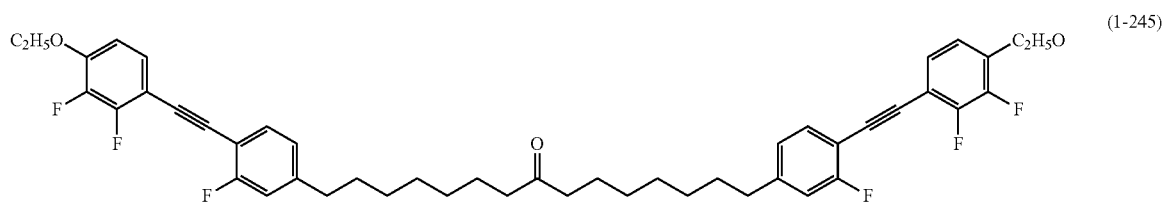
(1-245)
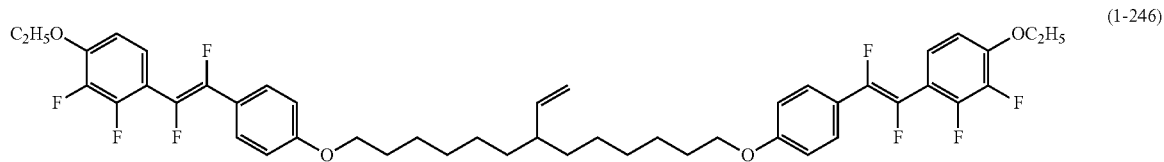
(1-246)
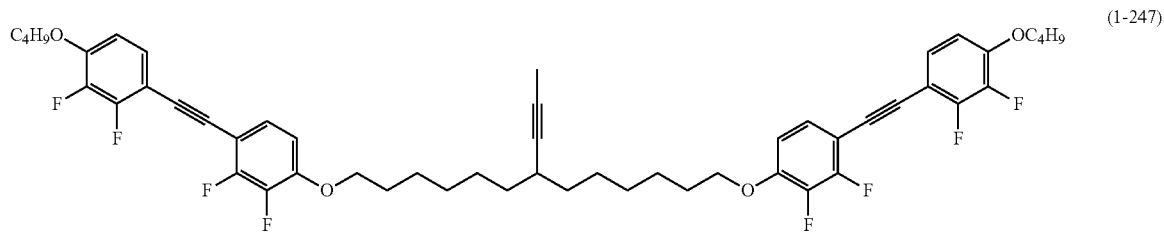
(1-247)
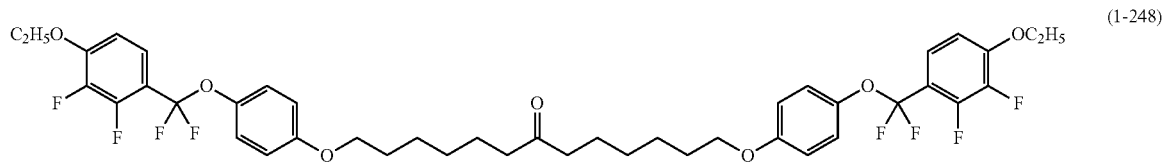
(1-248)
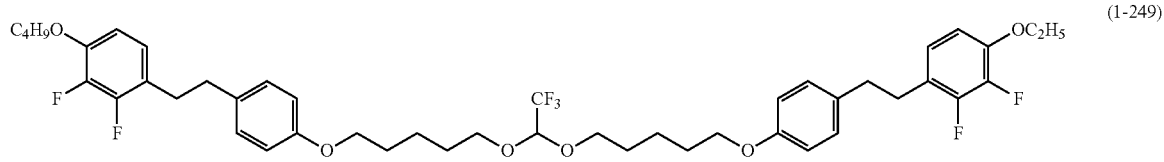
(1-249)

-continued
(1-250)
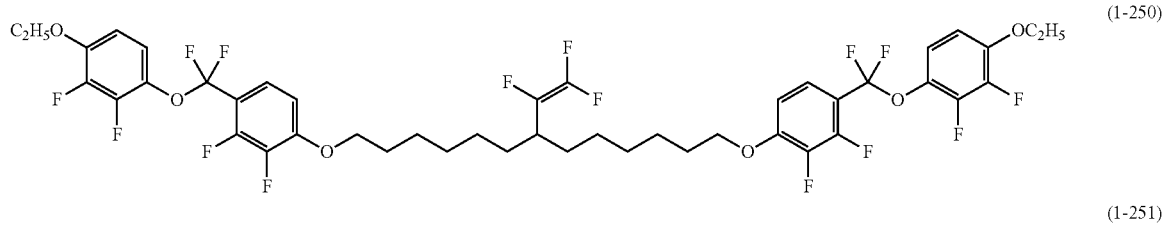
(1-251)
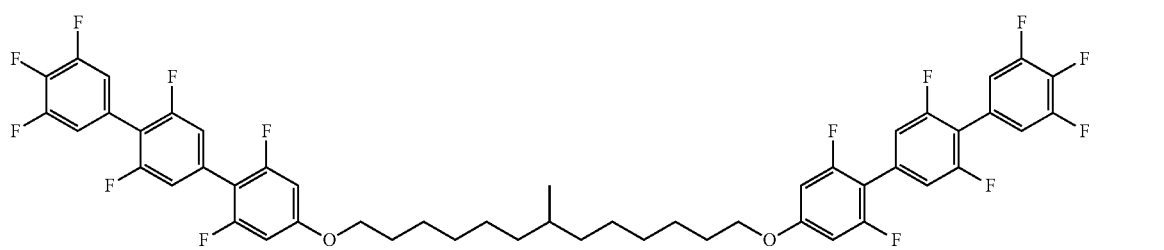
(1-252)
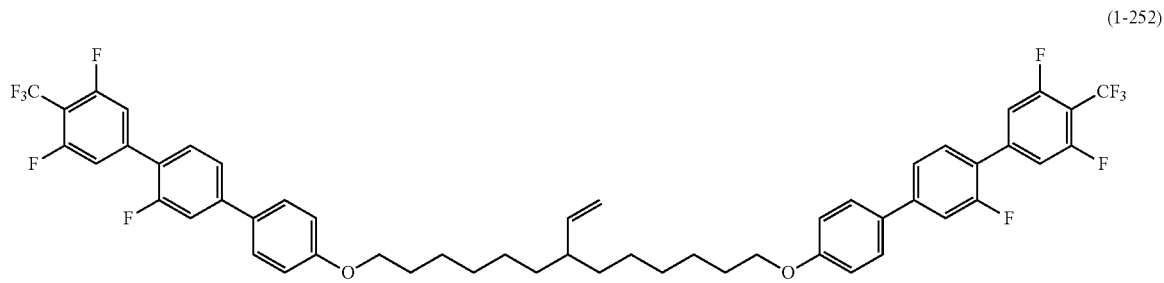
(1-253)
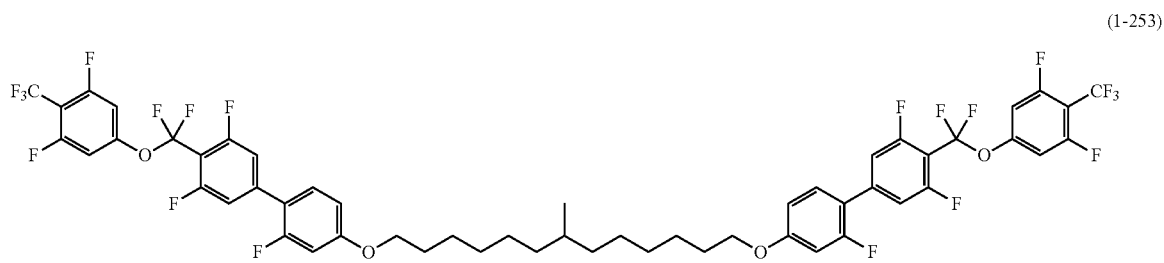
(1-254)
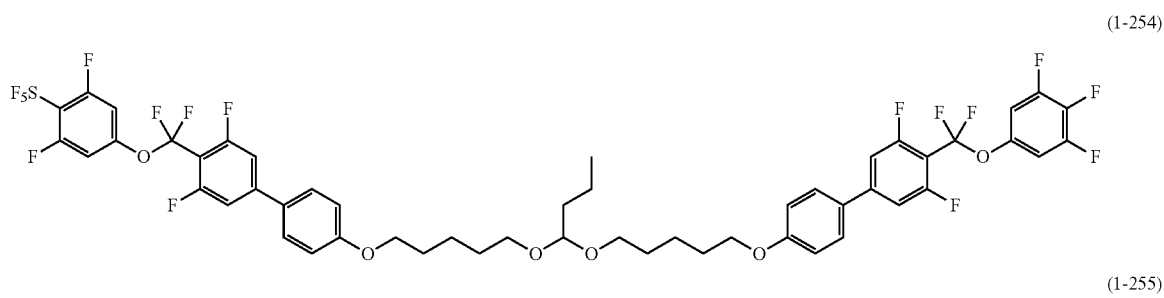
(1-255)
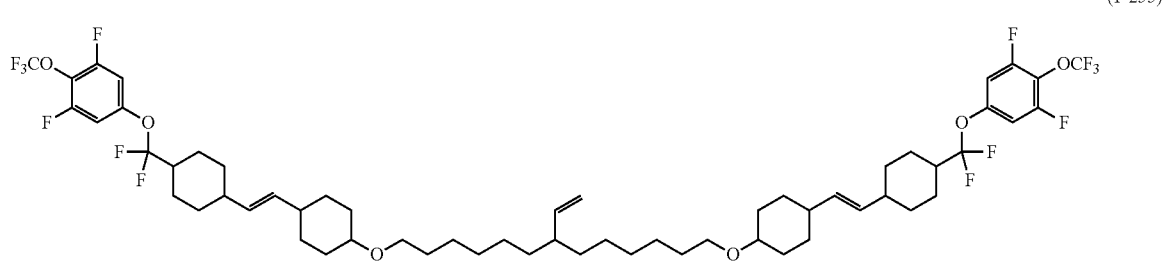

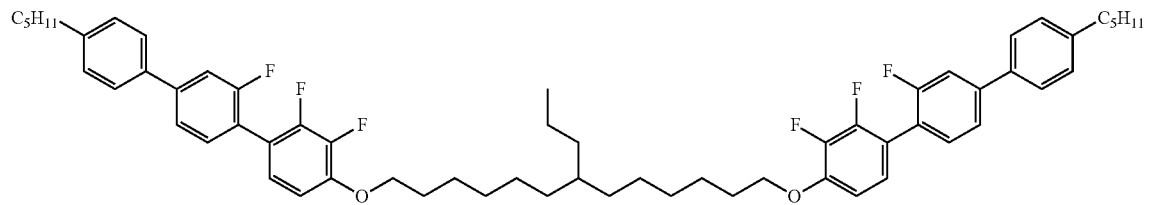
(1-256)
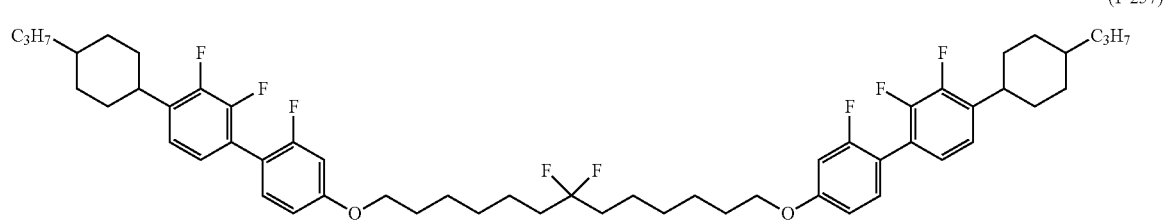
(1-257)
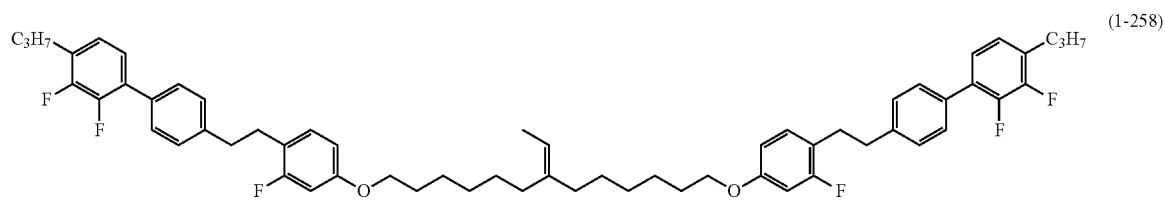
(1-258)
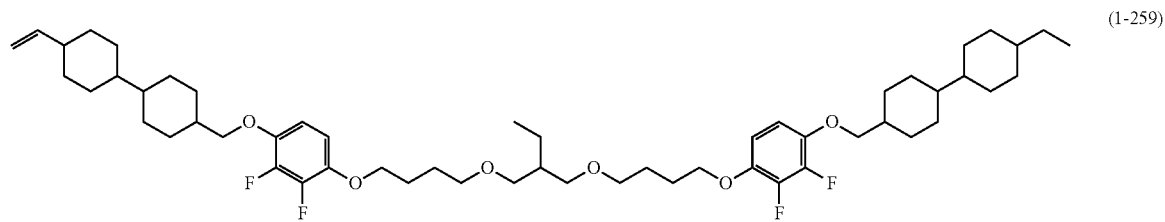
(1-259)
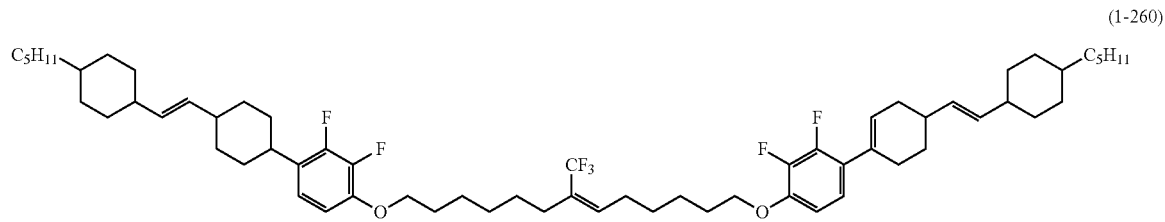
(1-260)
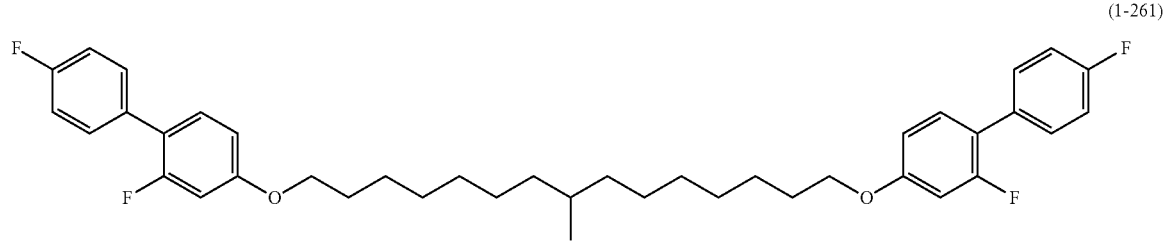
(1-261)
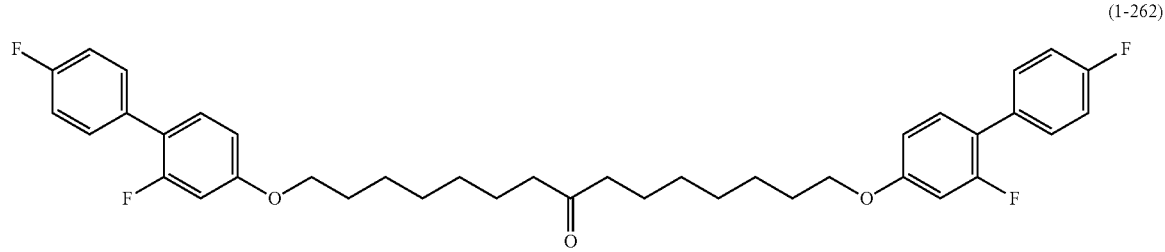
(1-262)

-continued
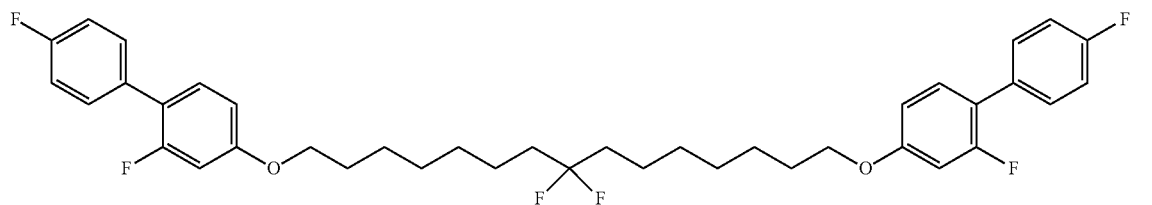
(1-263)
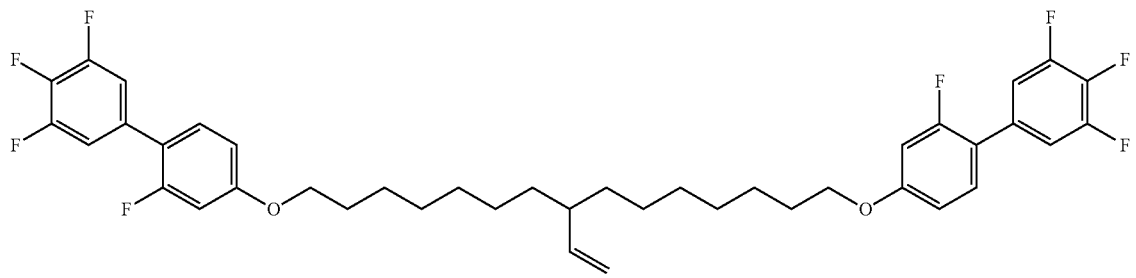
(1-264)
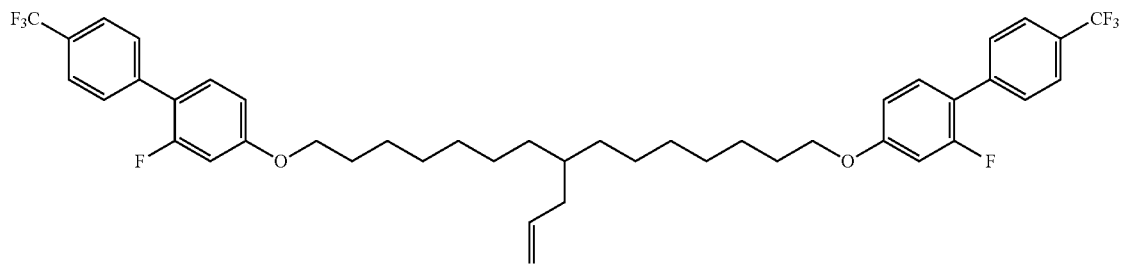
(1-265)
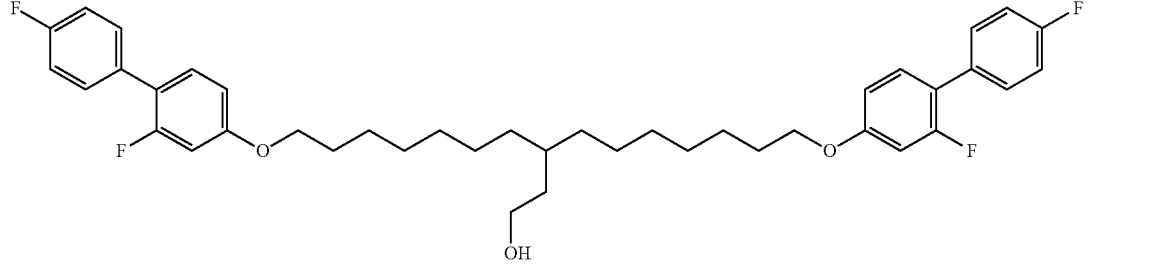
(1-266)
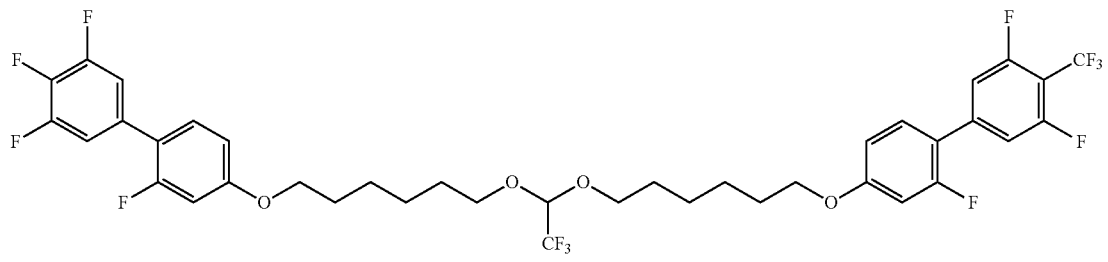
(1-267)
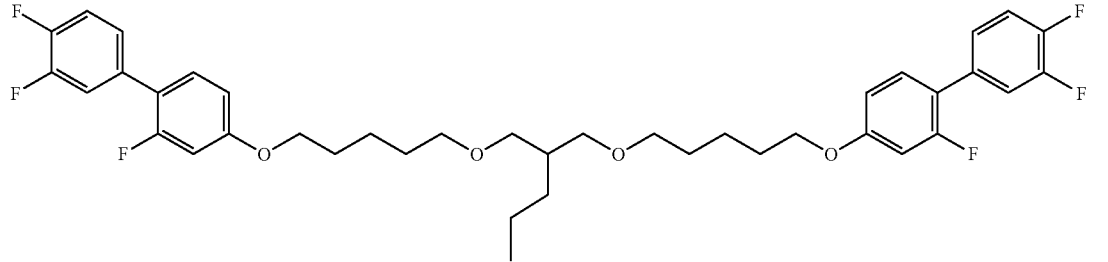
(1-268)

-continued
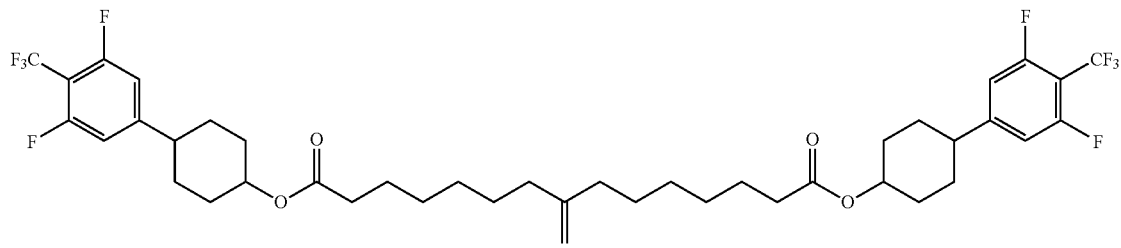
(1-269)
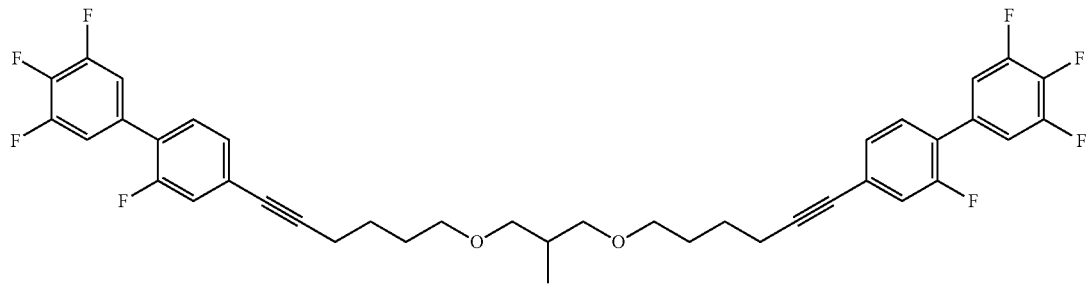
(1-270)
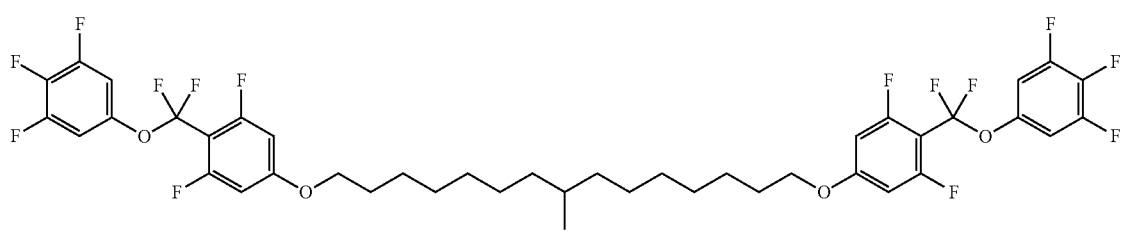
(1-271)
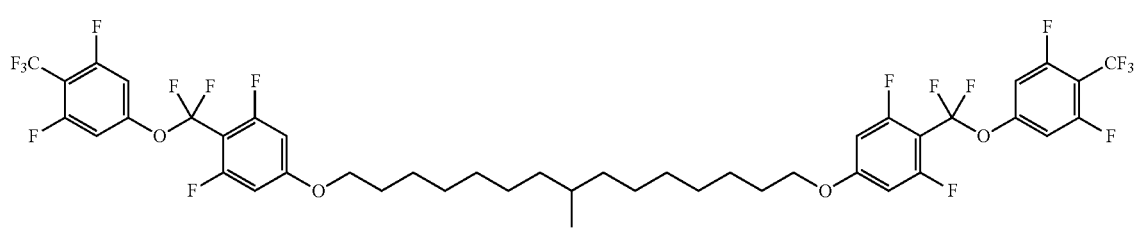
(1-272)
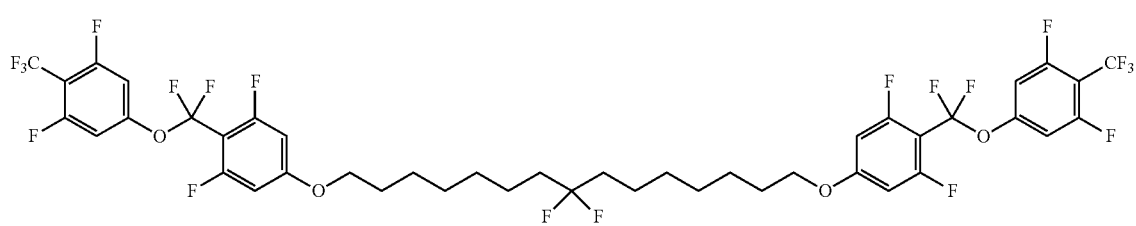
(1-273)
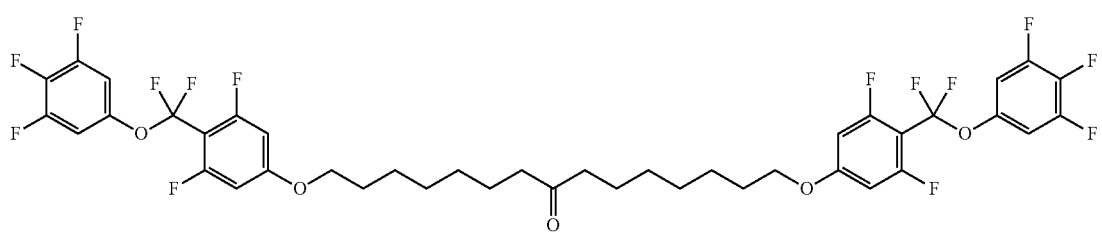
(1-274)

-continued
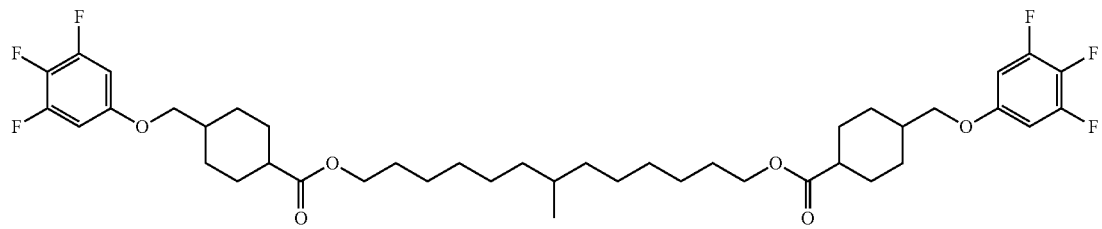
(1-275)
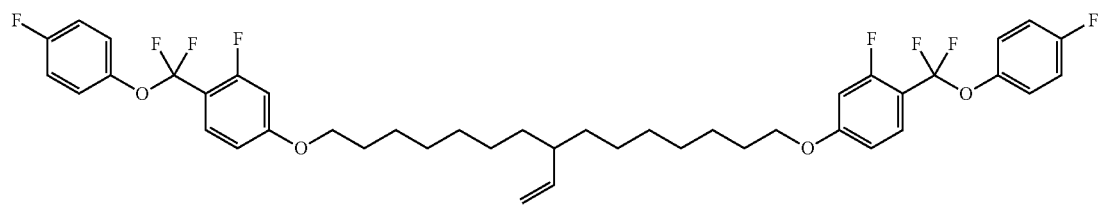
(1-276)
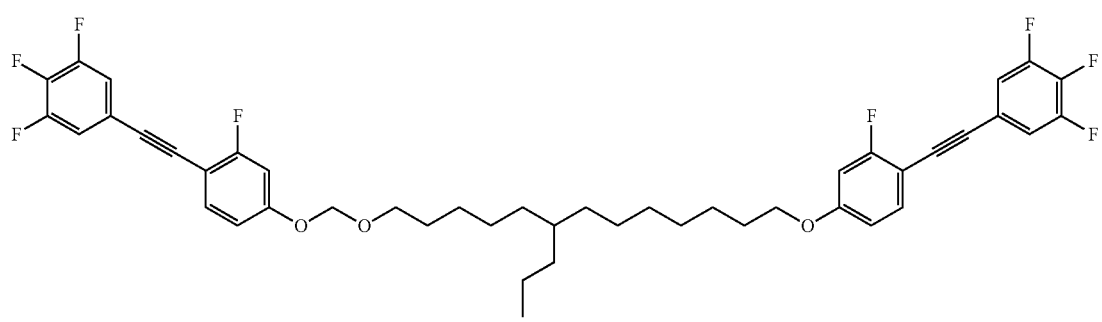
(1-277)
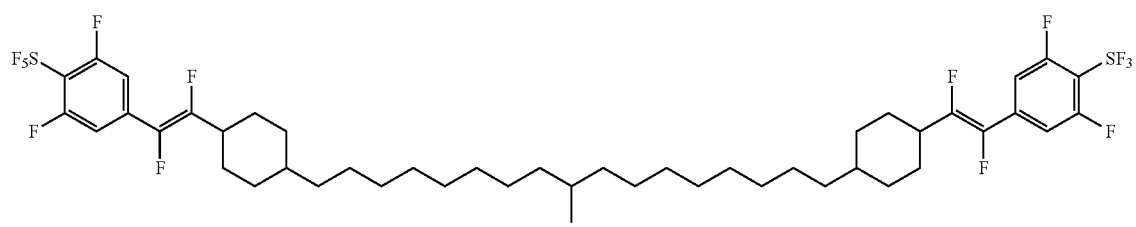
(1-278)
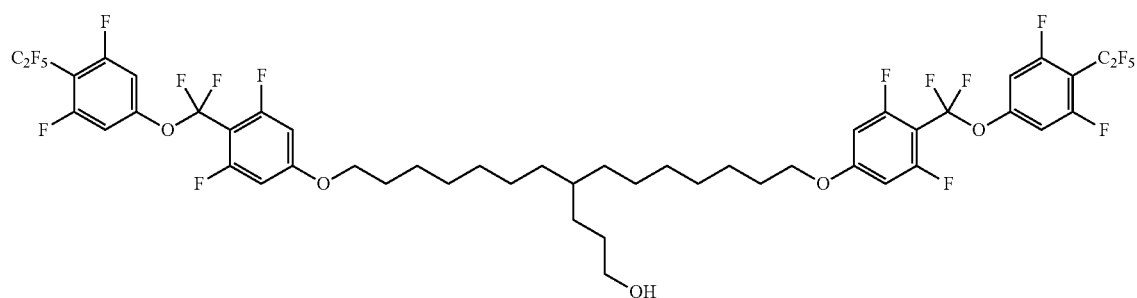
(1-279)
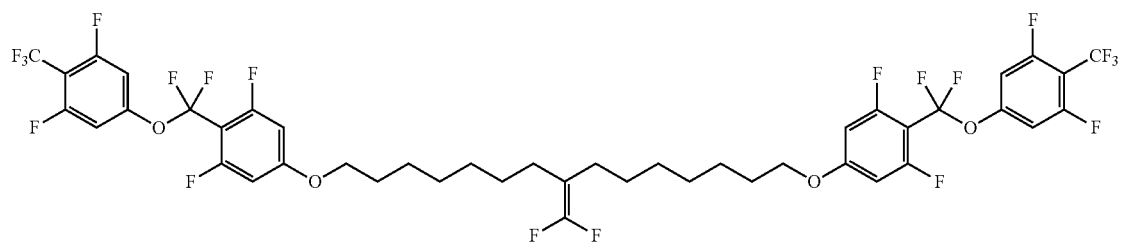
(1-280)

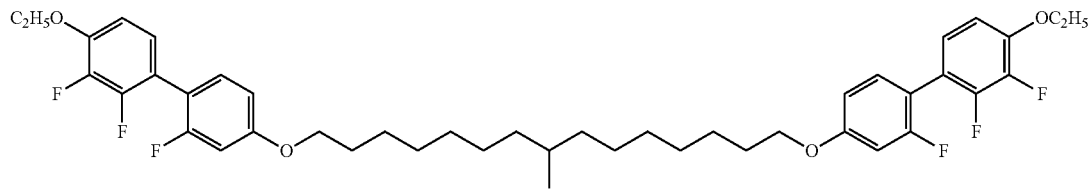
(1-281)
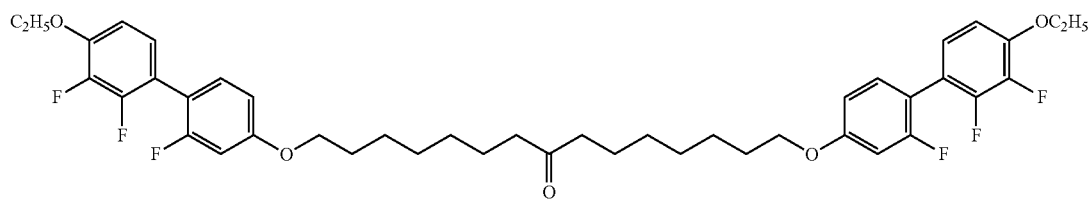
(1-282)
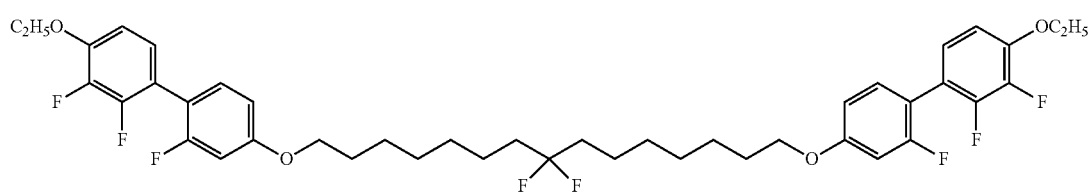
(1-283)
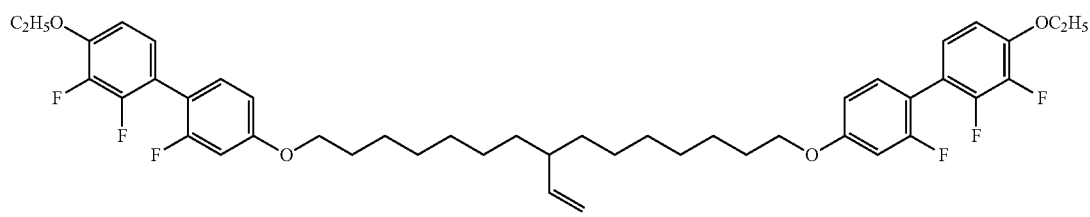
(1-284)
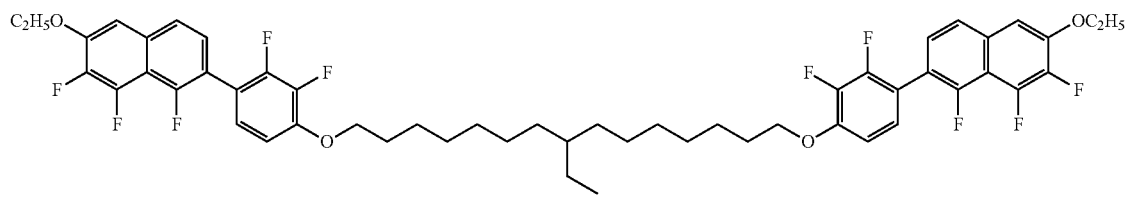
(1-285)
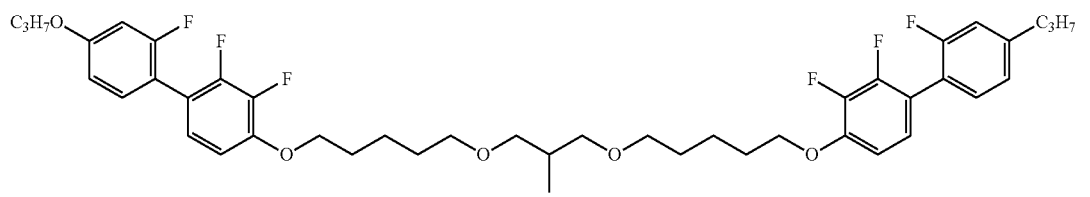
(1-286)
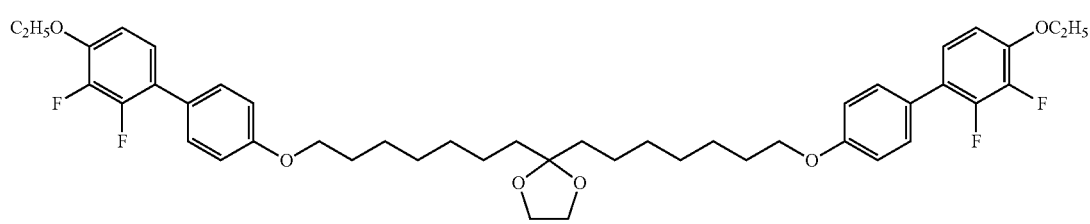
(1-287)

-continued
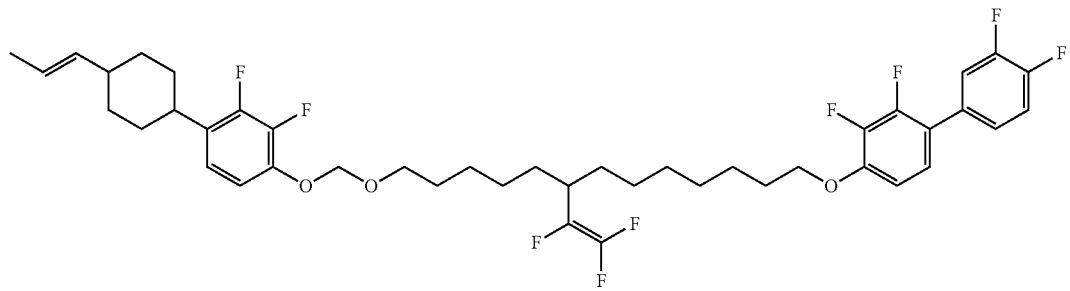
(1-288)
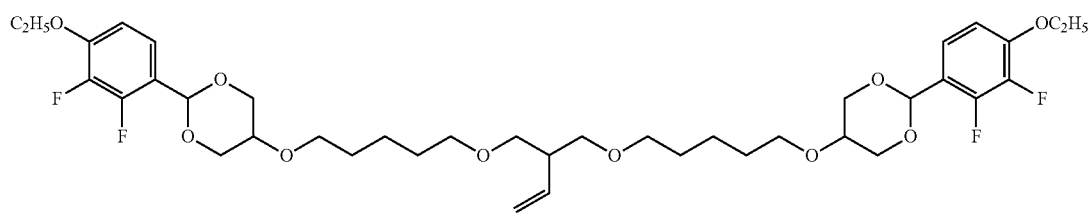
(1-289)
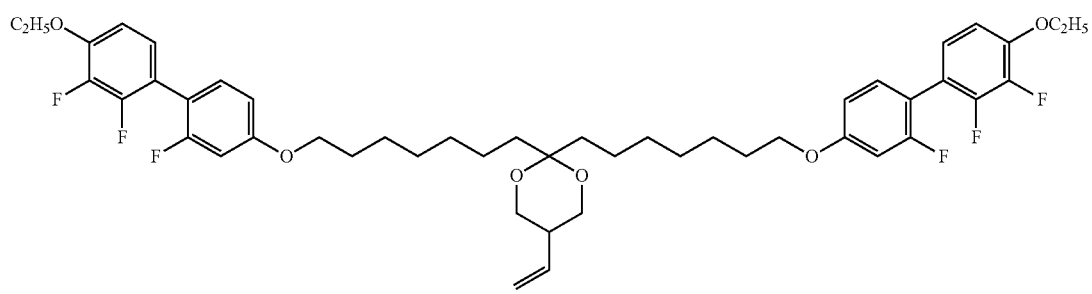
(1-290)
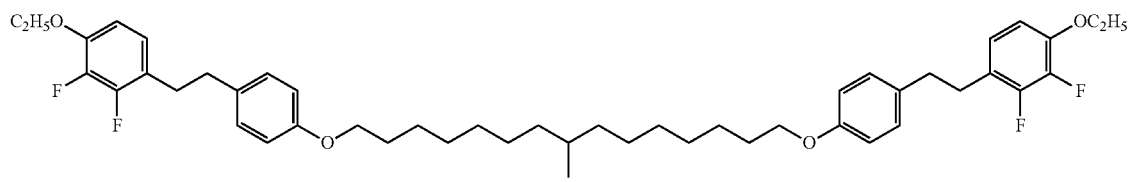
(1-291)
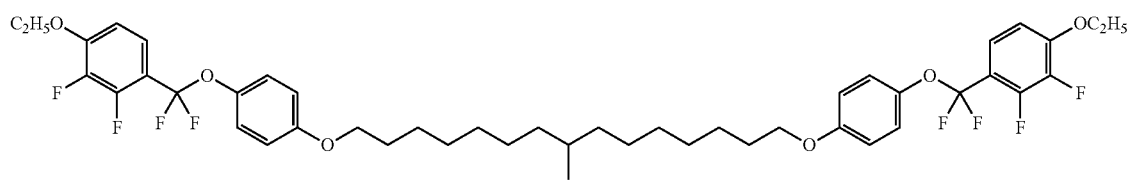
(1-292)
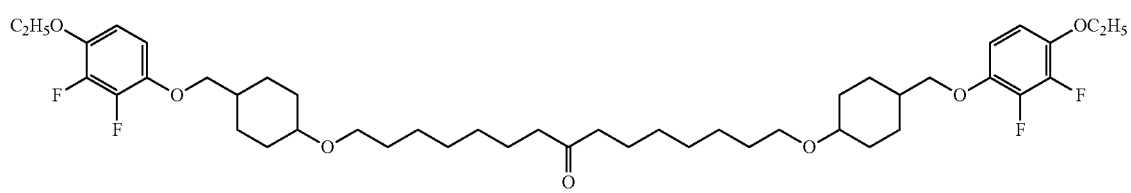
(1-293)
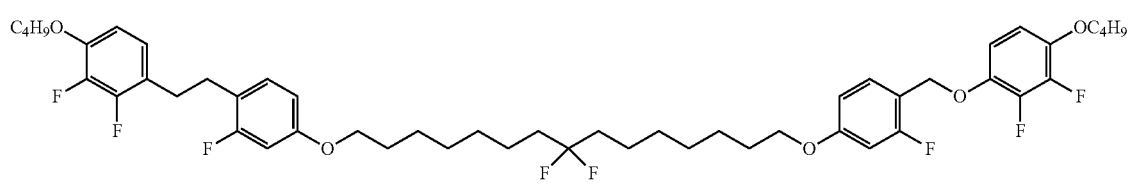
(1-294)

-continued
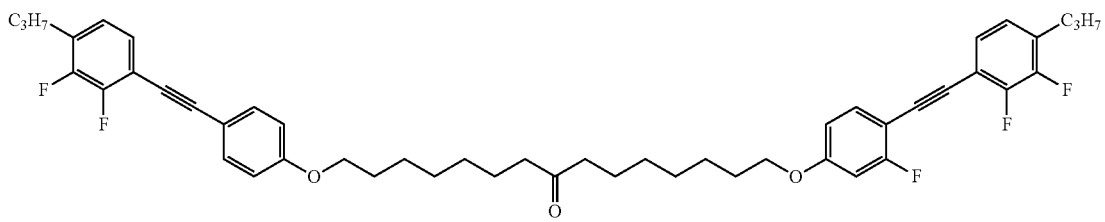
(1-295)
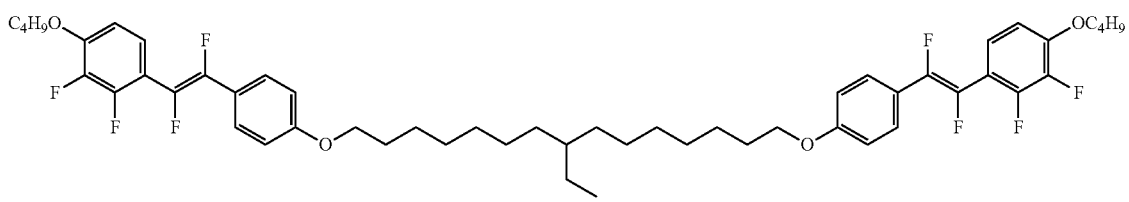
(1-296)
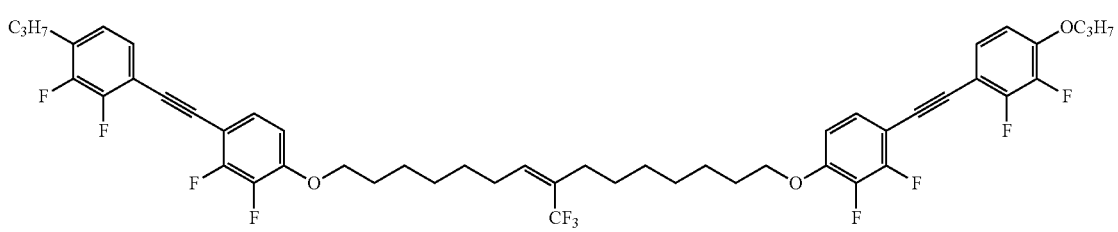
(1-297)
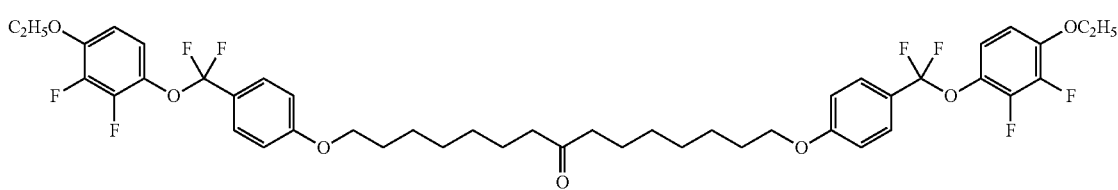
(1-298)
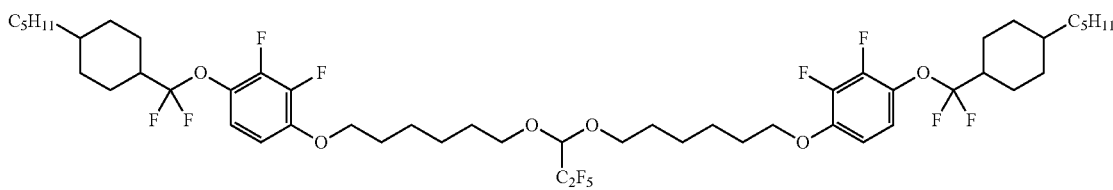
(1-299)
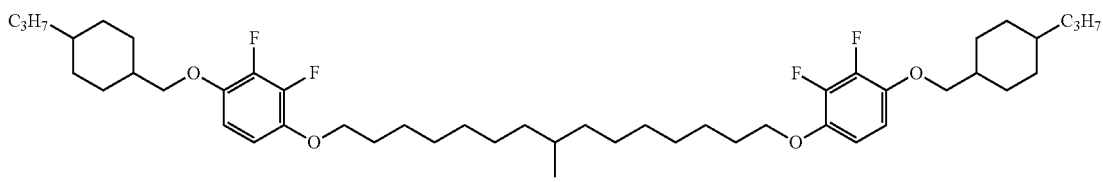
(1-300)
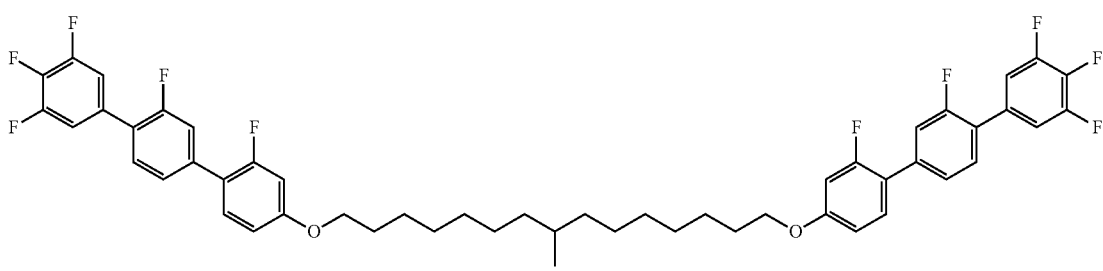
(1-301)

-continued
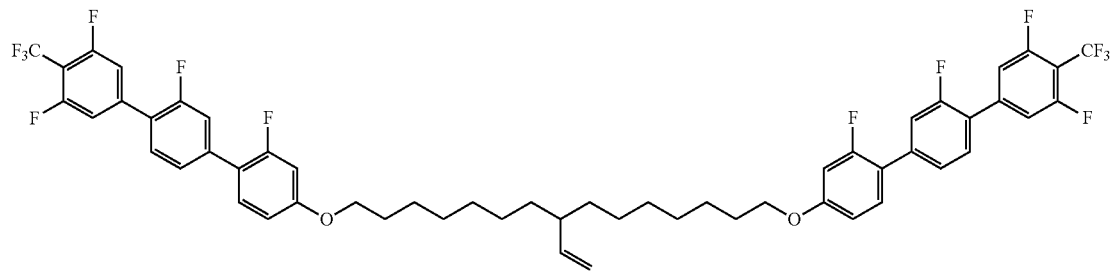
(1-302)
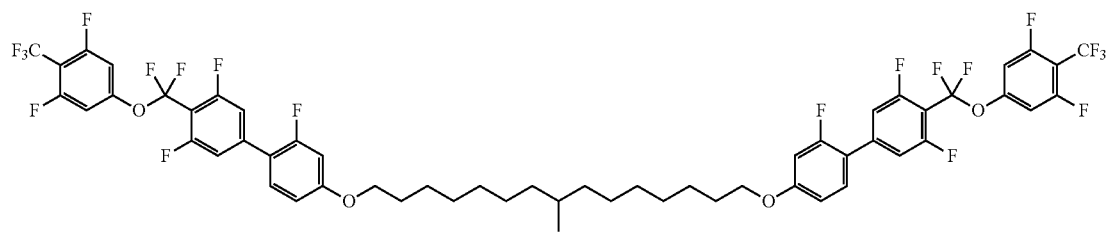
(1-303)
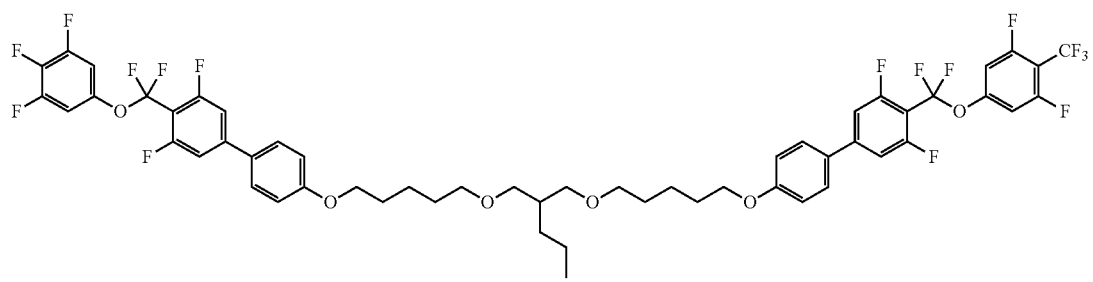
(1-304)
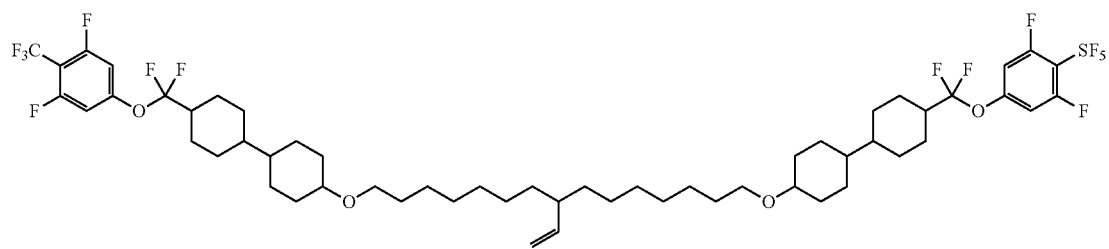
(1-305)
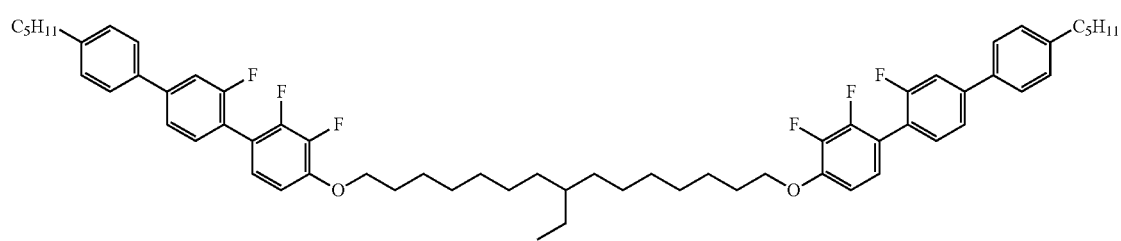
(1-306)
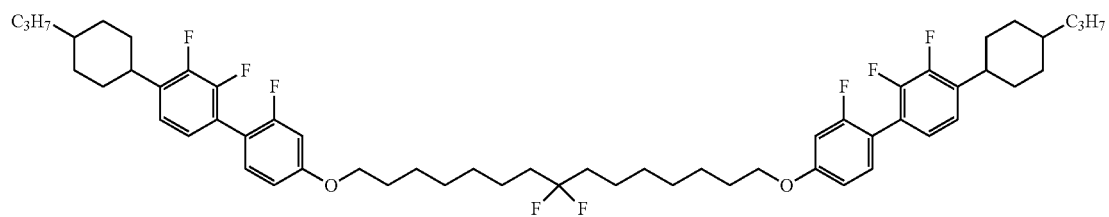
(1-307)

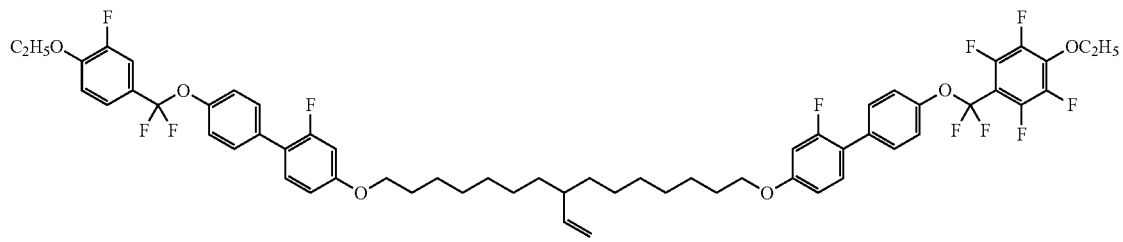
(1-308)
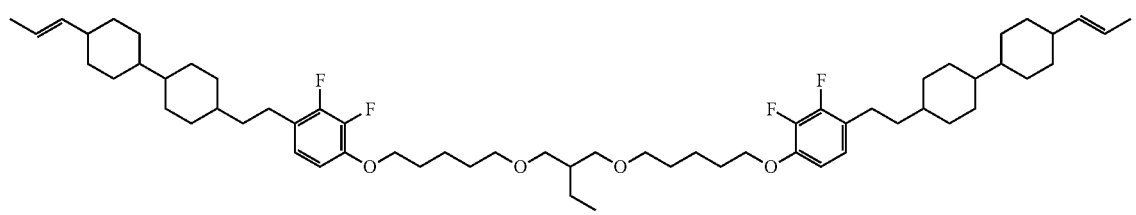
(1-309)
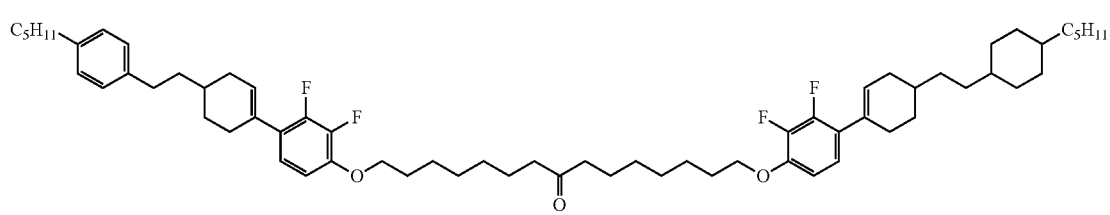
(1-310)
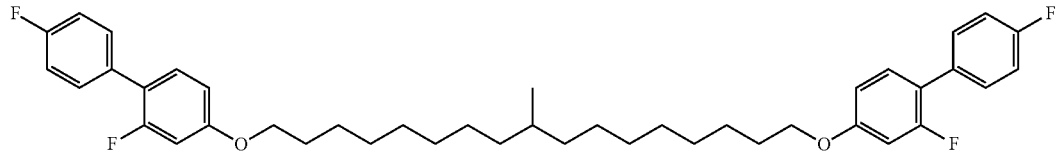
(1-311)
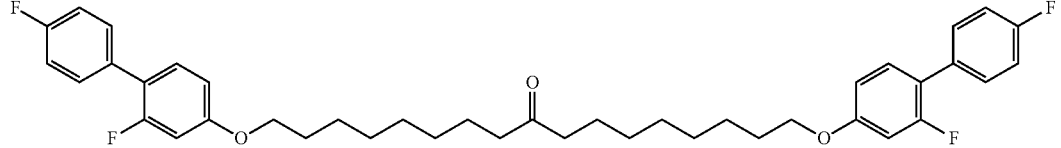
(1-312)
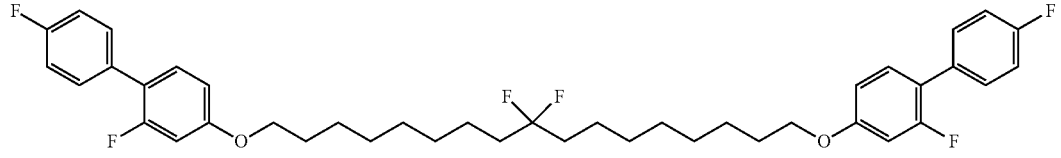
(1-313)
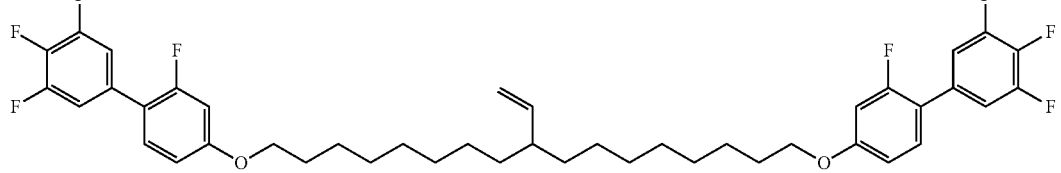
(1-314)
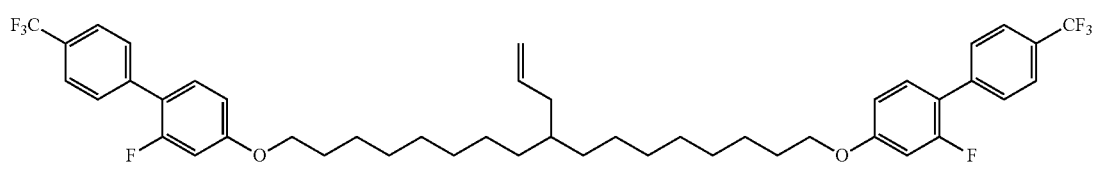
(1-315)

-continued
(1-316)
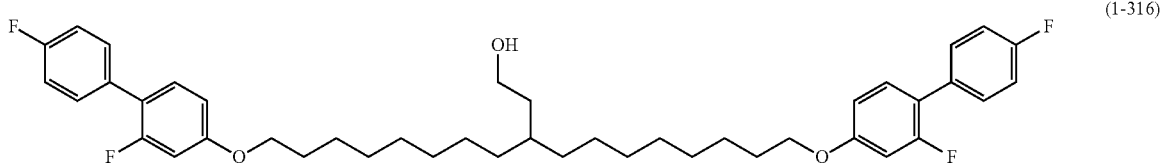
(1-317)
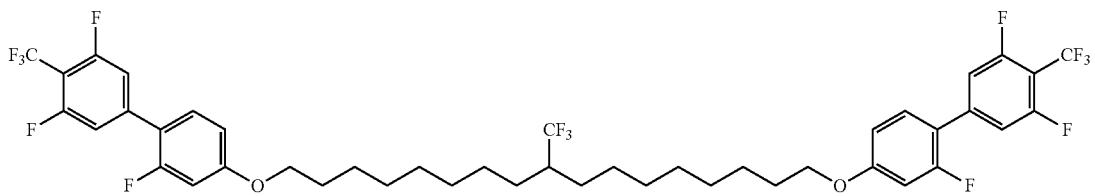
(1-318)
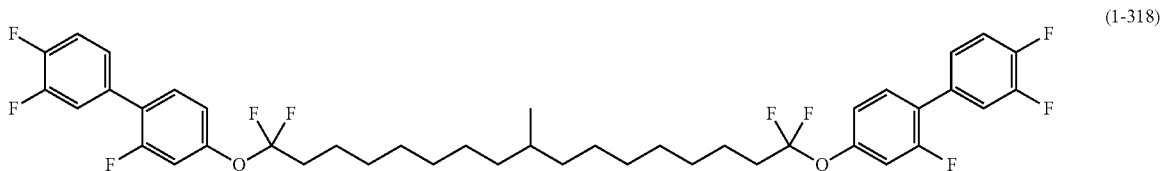
(1-319)
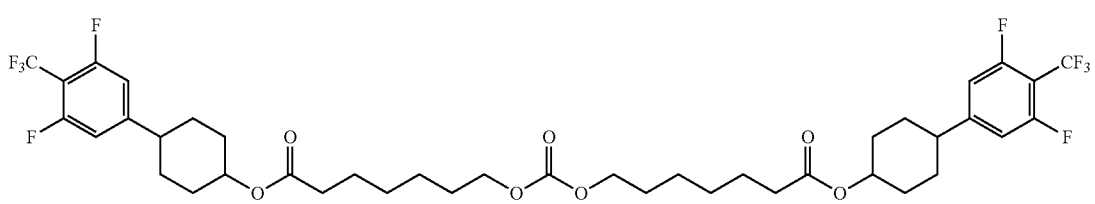
(1-320)
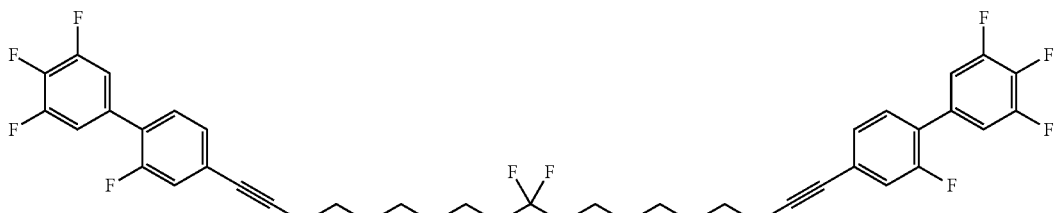
(1-321)
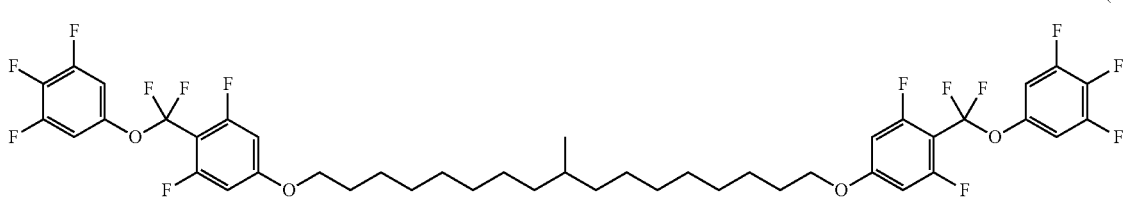
(1-322)
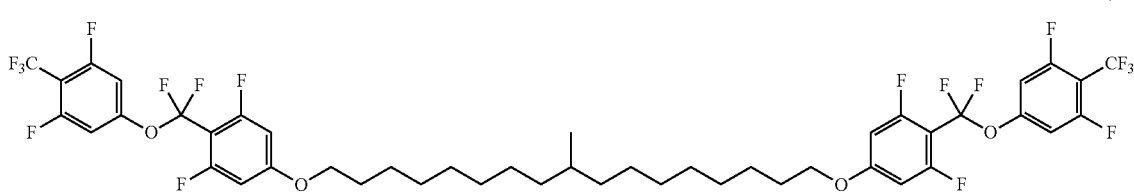
(1-323)
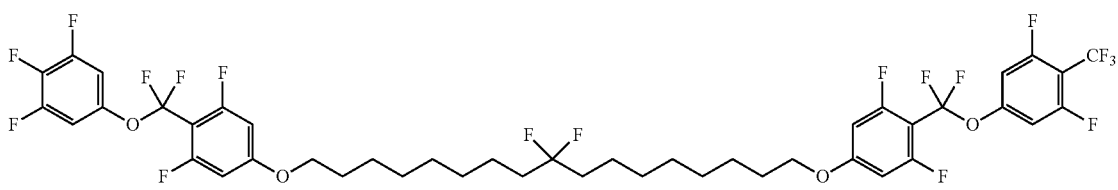

(1-324)
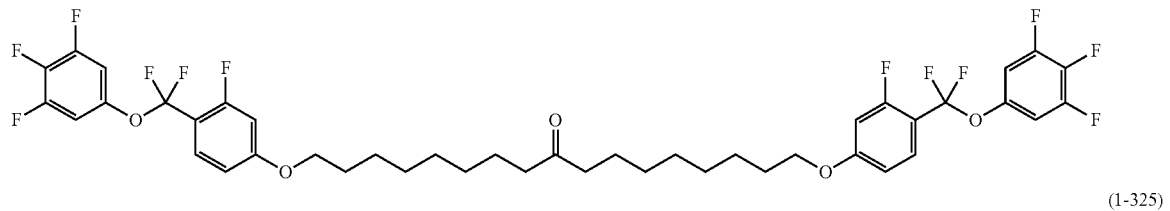
(1-325)
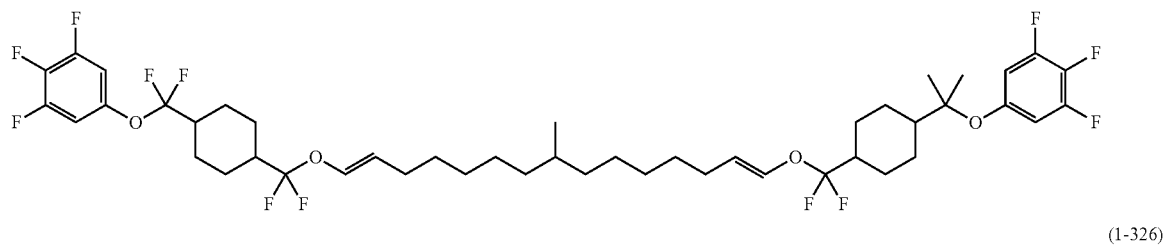
(1-326)
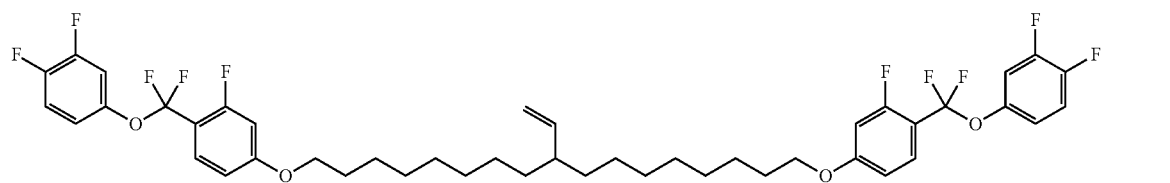
(1-327)
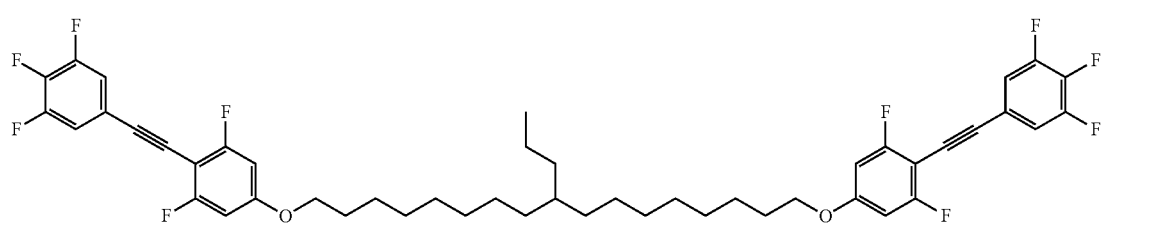
(1-328)
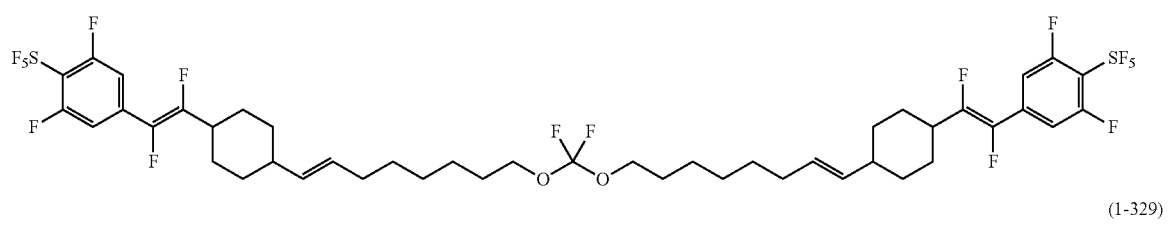
(1-329)
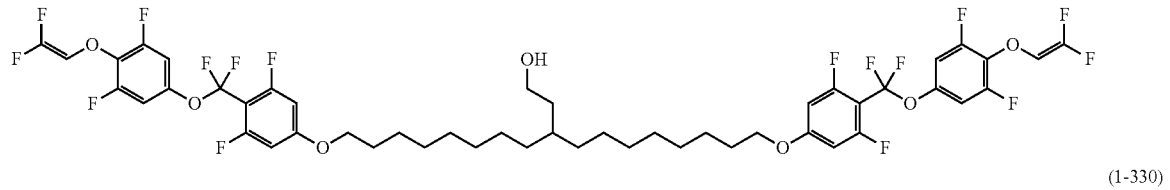
(1-330)
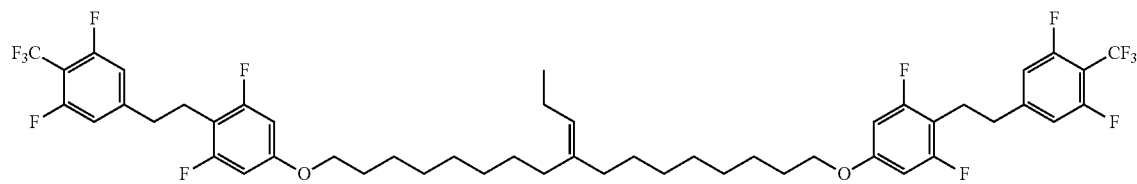

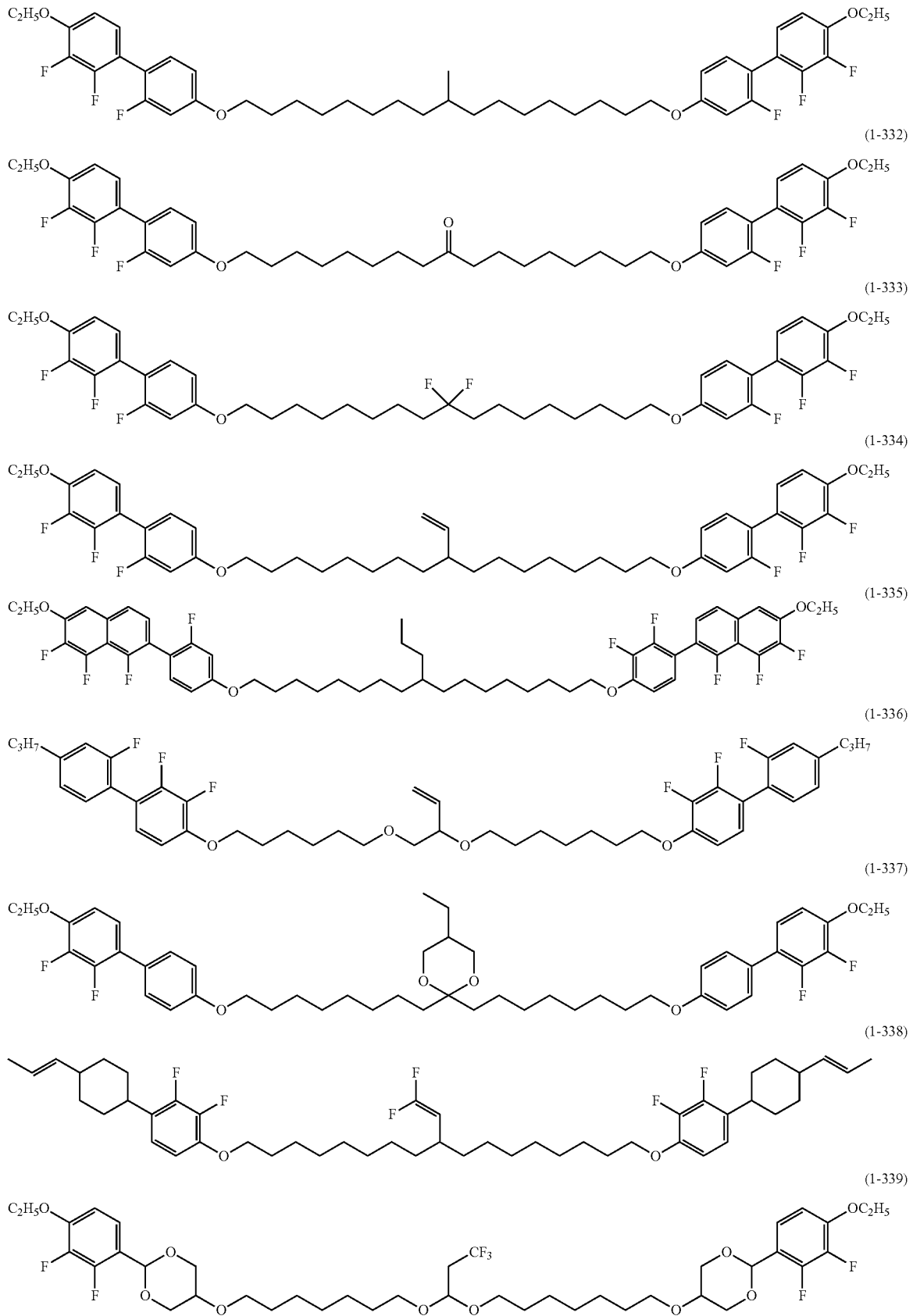

-continued
(1-340)
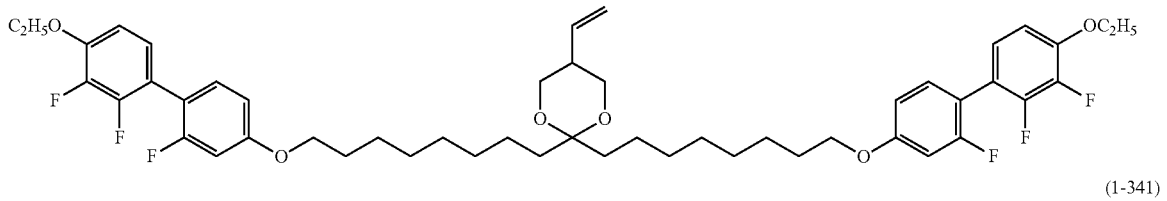
(1-341)
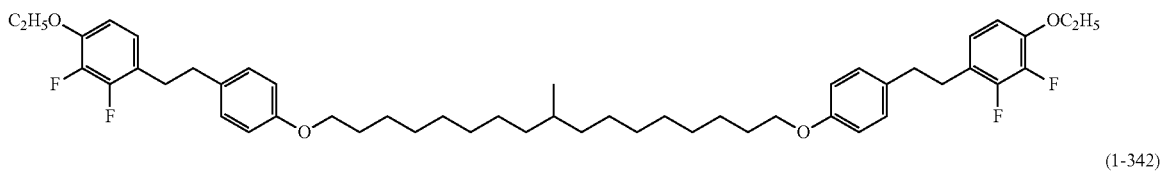
(1-342)
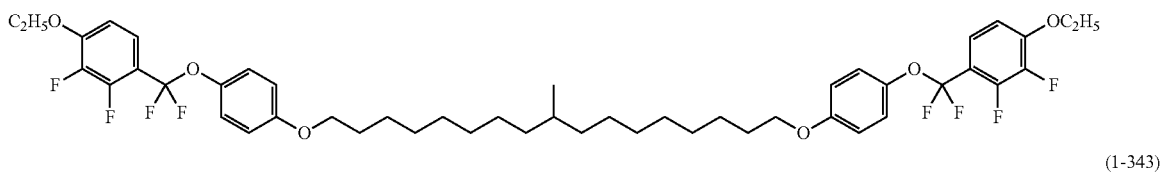
(1-343)
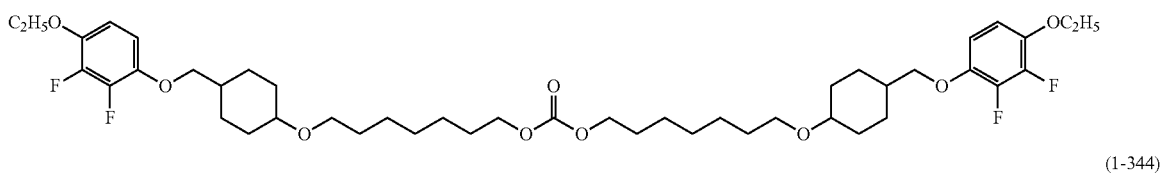
(1-344)
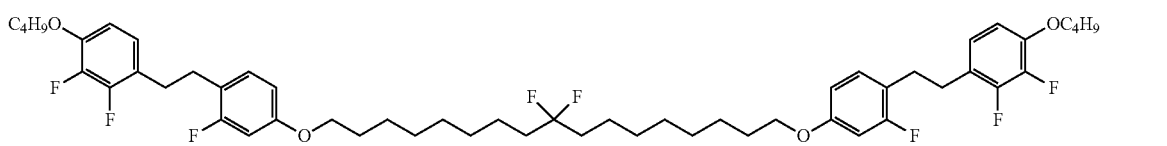
(1-345)
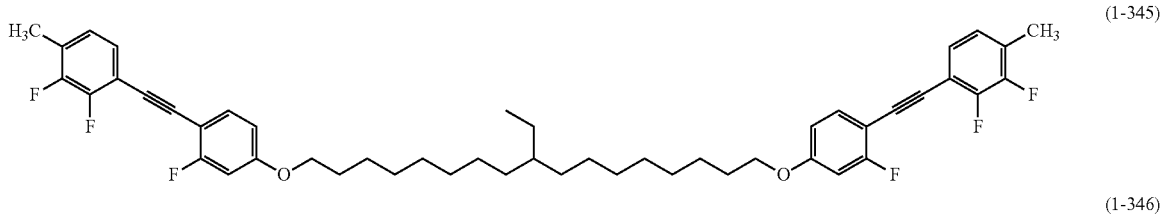
(1-346)
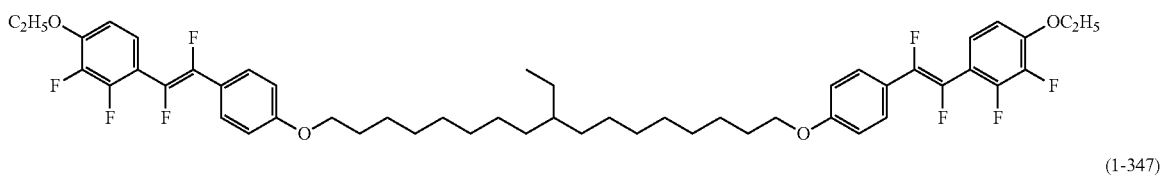
(1-347)
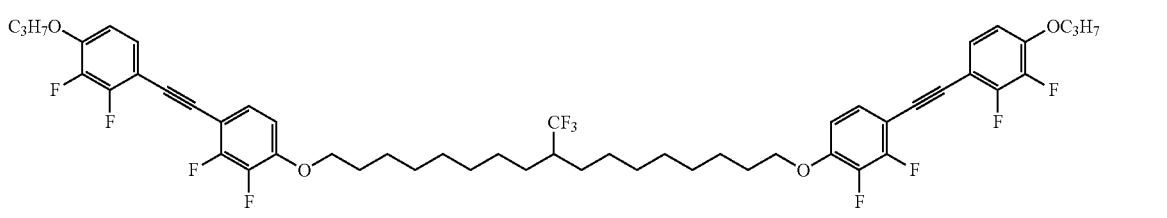
(1-348)
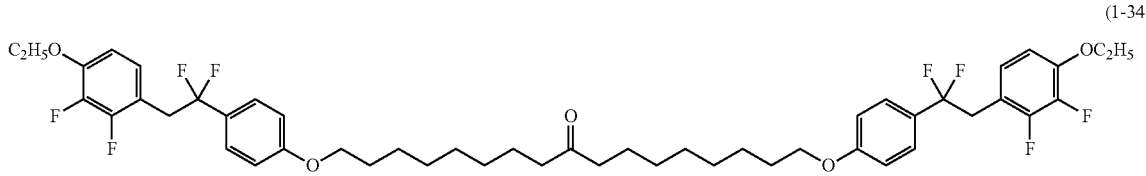

(1-349)
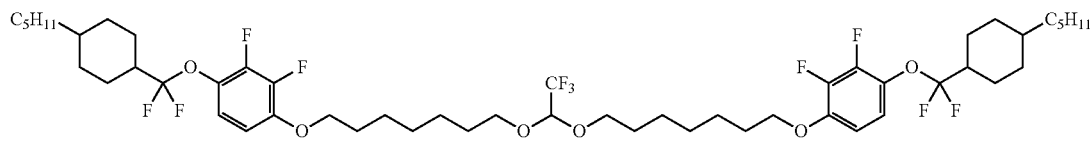
(1-350)
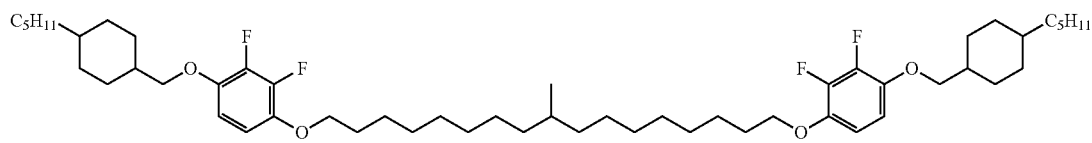
(1-351)
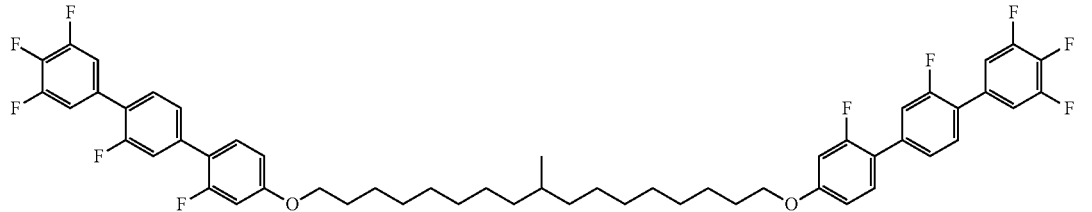
(1-352)
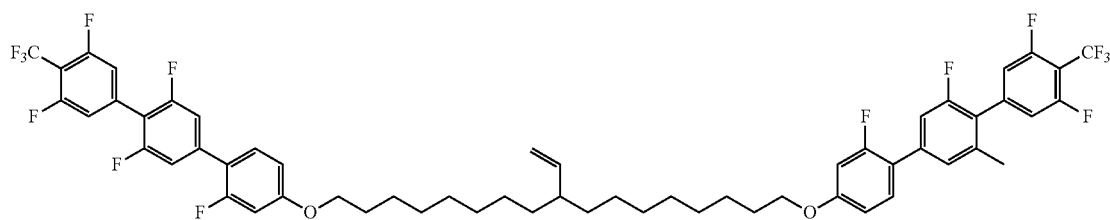
(1-353)
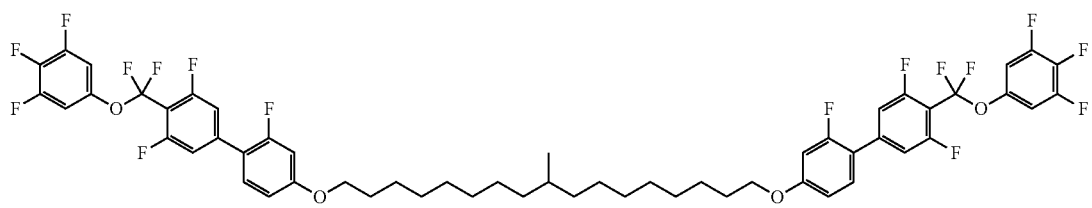
(1-354)
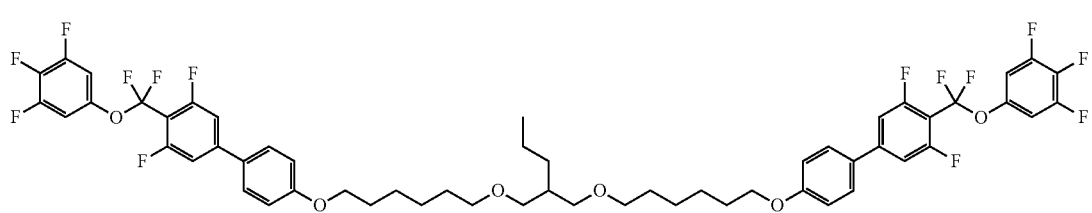
(1-355)
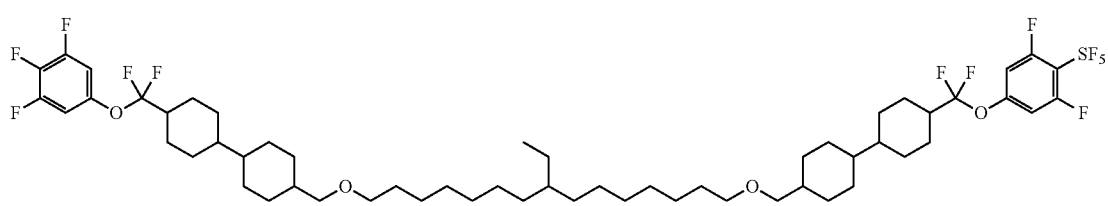

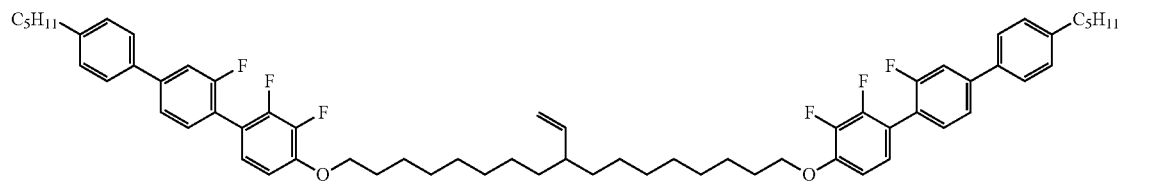
(1-356)
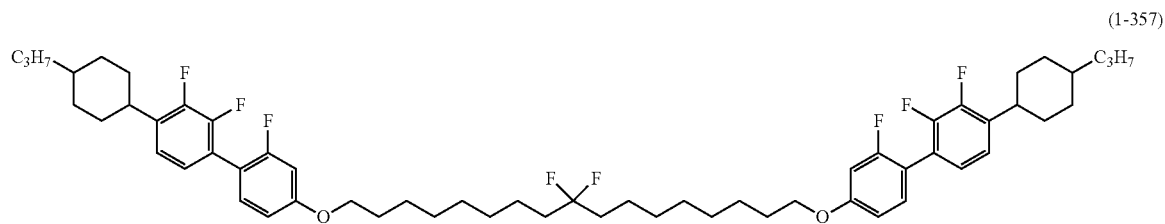
(1-357)
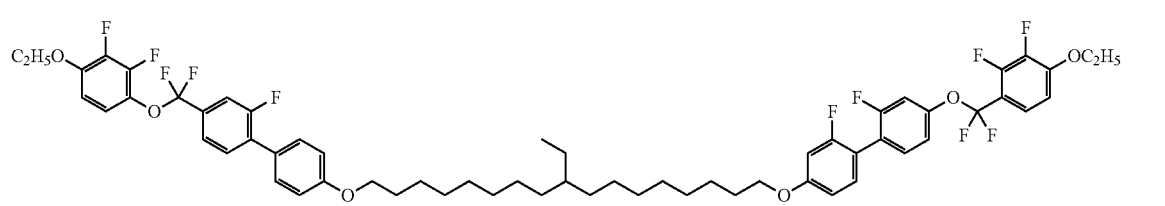
(1-358)
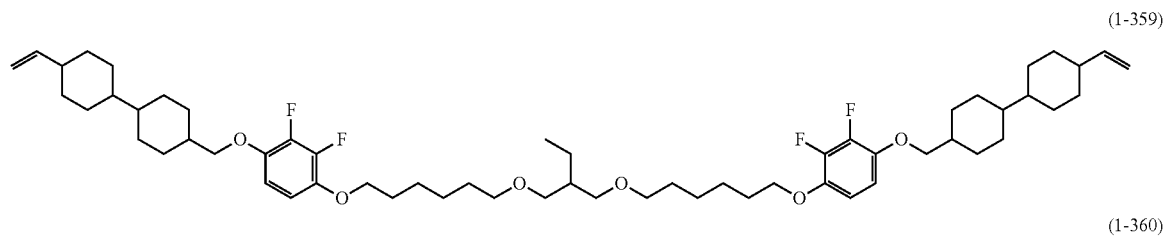
(1-359)
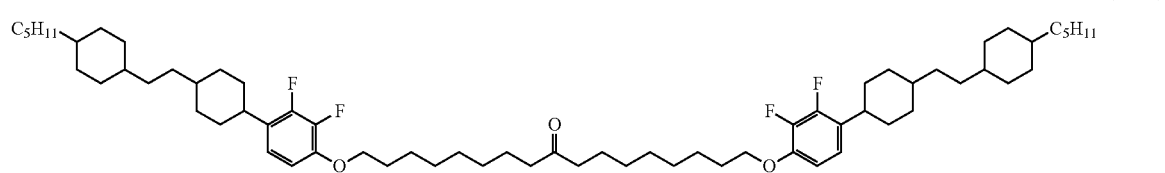
(1-360)
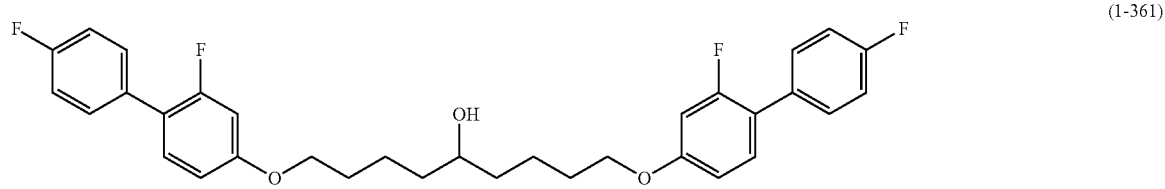
(1-361)
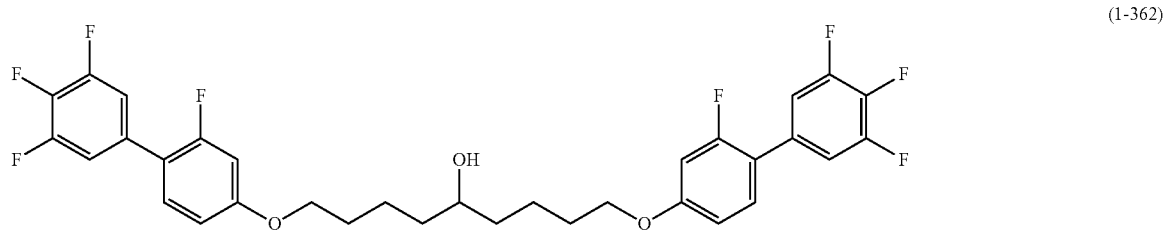
(1-362)

-continued
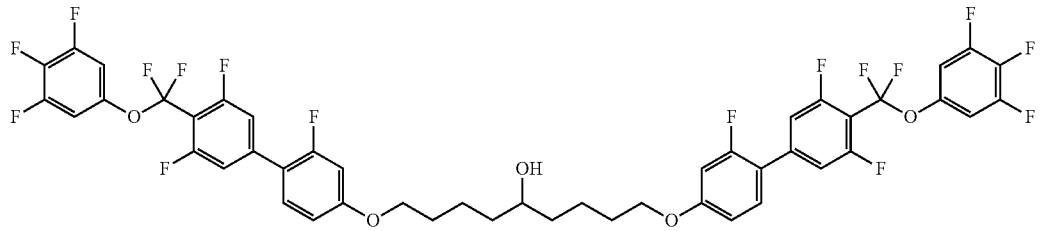
(1-363)
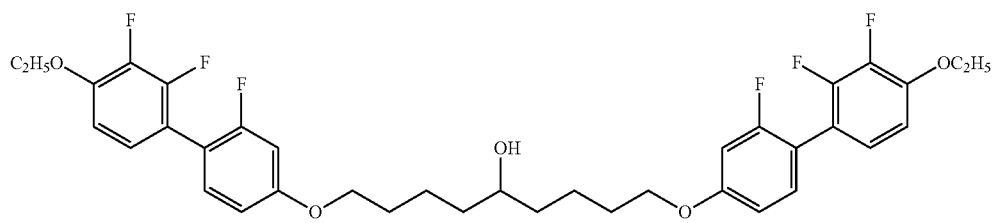
(1-364)
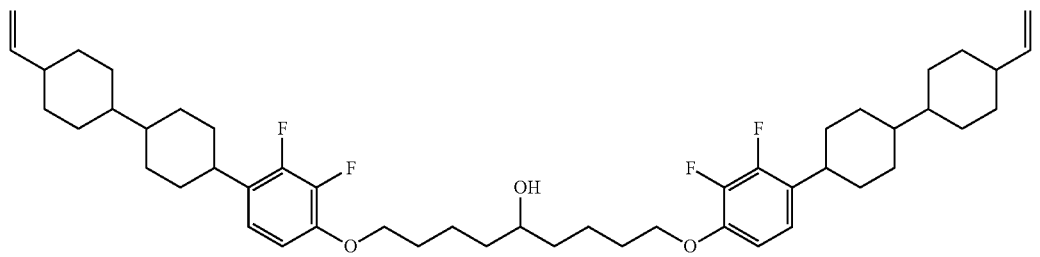
(1-365)
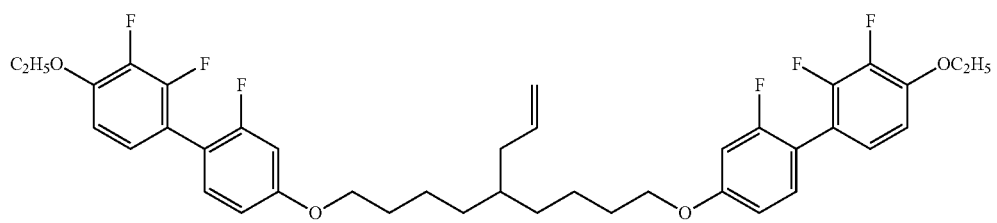
(1-366)
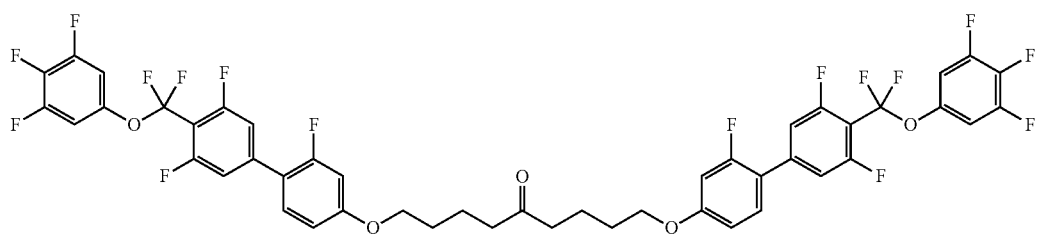
(1-367)
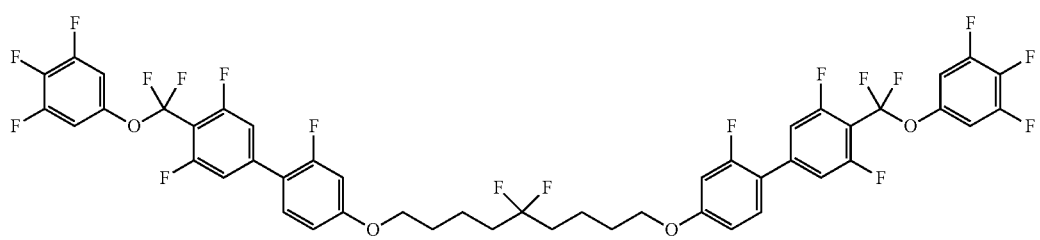
(1-368)
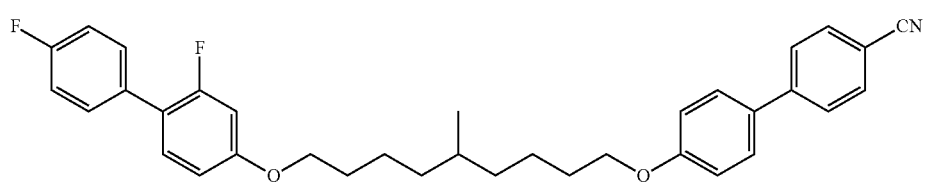
(1-369)

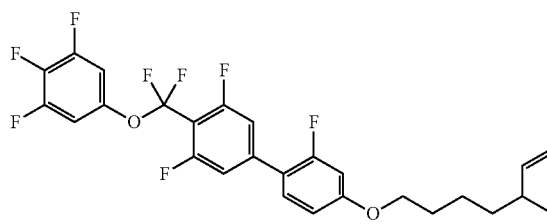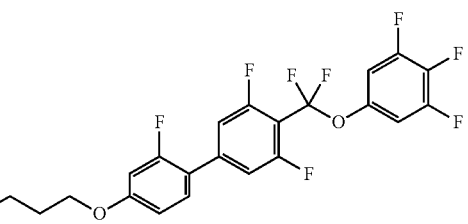

(1-370)

Examples of Liquid Crystal Composition

Examples and the like of liquid crystal compositions are described below.

A method for description of each compound being a component of the liquid crystal composition using symbols is shown in Table 1. In the Table, a configuration of 1,4-cyclohexylene is trans. A proportion (percentage) of each compound is expressed in terms of mass percent (% by weight) based on the total mass of the liquid crystal composition unless otherwise noted.

In addition, the numbers described in a part of the liquid crystal compound used in each Example correspond to the compound numbers of components A to E described above. A case where a symbol (–) is simply described without any description of the compound number means that the compound is any other compound not in corresponding to the components.

TABLE 1

| Teble Method for Description of Compounds using Symbols R—($A_1$)—$Z_1$— ... —$Z_n$—($A_n$)—R' | |
|---|---|
| 1) Left-terminal Group R— | Symbol |
| $C_nH_{2n+1}$— | n— |
| $C_nH_{2n+1}$O— | nO— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |
| 2) Right-terminal Group —R' | Symbol |
| —$C_nH_{2n+1}$ | —n |
| —O$C_nH_{2n+1}$ | —On |
| —COOCH$_3$ | —EMe |
| —CH=CH$_2$ | —V |
| —CH=CH—$C_nH_{2n+1}$ | —Vn |
| —$C_nH_{2n}$—CH=CH$_2$ | —nV |
| —$C_mH_{2m}$—CH=CH—$C_nH_{2n+1}$ | —mVn |
| —CH=CF$_2$ | —VFF |
| —F | —F |
| —Cl | —CL |
| —OCF$_3$ | —OCF3 |
| —OCF$_2$H | —OCF2H |
| —CF$_3$ | —CF3 |
| —OCH=CH—CF$_3$ | —OVCF3 |
| —C≡N | —C |
| 3) Bonding Group —$Z_n$— | Symbol |
| —$C_nH_{2n}$— | n |
| —COO— | E |
| —CH=CH— | V |
| —CH$_2$O— | 1O |
| —OCH$_2$— | O1 |
| —CF$_2$O— | X |
| —C≡C— | T |
| 4) Ring Structure —$A_n$— | Symbol |

| Structure | Symbol |
|---|---|
| cyclohexylene | H |
| phenylene | B |
| 3-fluoro-phenylene | B(F) |
| 2-fluoro-phenylene | B(2F) |
| 2,3-difluoro-phenylene | B(F,F) |
| 2,5-difluoro-phenylene | B(2F,5F) |
| 2,3-difluoro-phenylene | B(2F,3F) |
| pyrimidine | Py |

TABLE 1-continued

Teble Method for Description of Compounds using Symbols
R—(A₁)—Z₁— . . . —Zₙ—(Aₙ)—R'

| | |
|---|---|
| 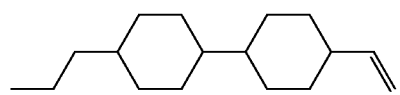 [SMILES: C=CC1CCC(C2CCC(CCC)CC2)CC1] ...skip... | G |

(Structures with labels G, Dh, Cro, B(2F,3CL))

5) Examples of description

Example 1. 3—HH—V

Example 2. 3—BB(F,F)XB(F,F)—F

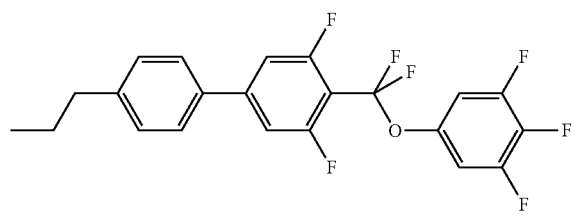 [SMILES: CCCc1ccc(-c2cc(F)c(C(F)(F)Oc3cc(F)c(F)c(F)c3)c(F)c2)cc1]

Example 3. 3—HH—4

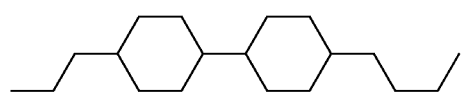 [SMILES: CCCCC1CCC(C2CCC(CCC)CC2)CC1]

Example 4. 3—HBB(2F,3F)—O2

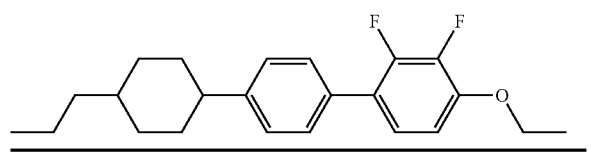

Use Example 1

| | | |
|---|---|---|
| 3-HB-O2 | (2-5) | 10% |
| 5-HB-CL | (5-2) | 13% |
| 3-HBB(F,F)-F | (6-24) | 7% |
| 3-PyB(F)-F | (5-15) | 10% |
| 5-PyB(F)-F | (5-15) | 10% |
| 3-PyBB-F | (6-80) | 10% |
| 4-PyBB-F | (6-80) | 10% |
| 5-PyBB-F | (6-80) | 10% |
| 5-HBB(F)B-2 | (4-5) | 7% |
| 5-HBB(F)B-3 | (4-5) | 8% |
| Compound (1-1) | | 8% |

NI=87.6° C.; η=43.8 mPa·s; Δn=0.184; Δε=8.3.

Use Example 2

| | | |
|---|---|---|
| 2-HB-C | (8-1) | 5% |
| 3-HB-C | (8-1) | 12% |
| 3-HB-O2 | (2-5) | 15% |
| 2-BTB-1 | (2-10) | 3% |
| 3-HHB-F | (6-1) | 4% |
| 3-HHB-1 | (3-1) | 8% |
| 3-HHB-O1 | (3-1) | 5% |
| 3-HHB-3 | (3-1) | 12% |
| 3-HHEB-F | (6-11) | 3% |
| 5-HHEB-F | (6-11) | 2% |
| 2-HHB(F)-F | (6-2) | 6% |
| 3-HHB(F)-F | (6-2) | 6% |
| 5-HHB(F)-F | (6-2) | 6% |
| 3-HHB(F,F)-F | (6-3) | 5% |
| Compound (1-102) | | 8% |

NI=90.5° C.; η=24.5 mPa·s; Δn=0.103; Δε=4.6.

Use Example 3

| | | |
|---|---|---|
| 7-HB(F,F)-F | (5-4) | 3% |
| 3-HB-O2 | (2-5) | 7% |
| 2-HHB(F)-F | (6-2) | 10% |
| 3-HHB(F)-F | (6-2) | 10% |
| 5-HHB(F)-F | (6-2) | 9% |
| 2-HBB(F)-F | (6-2) | 9% |
| 3-HBB(F)-F | (6-2) | 8% |
| 5-HBB(F)-F | (6-2) | 14% |
| 2-HBB-F | (6-22) | 4% |
| 3-HBB-F | (6-22) | 4% |
| 5-HBB-F | (6-22) | 3% |
| 3-HBB(F,F)-F | (6-24) | 3% |
| 5-HBB(F,F)-F | (6-24) | 6% |
| Compound(1-104) | | 10% |

NI=74.8° C.; η=38.5 mPa·s; Δn=0.110; Δε=5.5.

Use Example 4

| | | |
|---|---|---|
| 5-HB-CL | (5-2) | 16% |
| 3-HH-4 | (2-1) | 12% |
| 3-HH-5 | (2-1) | 4% |
| 3-HHB-F | (6-1) | 4% |
| 3-HHB-CL | (6-1) | 3% |
| 4-HHB-CL | (6-1) | 4% |
| 3-HHB(F)-F | (6-2) | 10% |
| 4-HHB(F)-F | (6-2) | 8% |
| 5-HHB(F)-F | (6-2) | 7% |
| 7-HHB(F)-F | (6-2) | 8% |
| 5-HBB(F)-F | (6-23) | 4% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |

| | | |
|---|---|---|
| 3-HH2BB(F,F)-F | (7-15) | 3% |
| 4-HH2BB(F,F)-F | (7-15) | 3% |
| Compound(1-103) | | 3% |

Use Example 5

| | | |
|---|---|---|
| 3-HHB(F,F)-F | (6-3) | 8% |
| 3-H2HB(F,F)-F | (6-15) | 7% |
| 4-H2HB(F,F)-F | (6-15) | 8% |
| 5-H2HB(F,F)-F | (6-15) | 7% |
| 3-HBB(F,F)-F | (6-23) | 20% |
| 5-HBB(F,F)-F | (6-23) | 20% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 4% |
| 1O1-HBBH-5 | (4-1) | 4% |
| Compound(1-105) | | 4% |

Use Example 6

| | | |
|---|---|---|
| 5-HB-F | (5-1) | 12% |
| 6-HB-F | (5-1) | 9% |
| 7-HB-F | (5-1) | 7% |
| 2-HHB-OCF3 | (6-1) | 7% |
| 3-HHB-OCF3 | (6-1) | 7% |
| 4-HHB-OCF3 | (6-1) | 7% |
| 5-HHB-OCF3 | (6-1) | 5% |
| 3-HH2B-OCF3 | (6-4) | 4% |
| 5-HH2B-OCF3 | (6-4) | 4% |
| 3-HHB(F,F)-OCF2H | (6-3) | 3% |
| 3-HHB(F,F)-OCF3 | (6-3) | 5% |
| 3-HH2B(F)-F | (6-5) | 3% |
| 3-HBB(F)-F | (6-23) | 10% |
| 5-HBB(F)-F | (6-23) | 10% |
| 5-HBBH-3 | (4-1) | 3% |
| 3-HB(F)BH-3 | (4-2) | 3% |
| Compound (1-106) | | 1% |

Use Example 7

| | | |
|---|---|---|
| 5-HB-CL | (5-2) | 11% |
| 3-HH-4 | (2-1) | 7% |
| 3-HHB-1 | (3-1) | 5% |
| 3-HHB(F,F)-F | (6-3) | 8% |
| 3-HBB(F,F)-F | (6-24) | 20% |
| 5-HBB(F,F)-F | (6-24) | 13% |
| 3-HHEB(F,F)-F | (6-12) | 10% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 4% |
| 5-HBEB(F,F)-F | (6-39) | 3% |
| 3-HHBB(F,F)-F | (7-6) | 5% |
| Compound(1-102) | | 5% |

Use Example 8

| | | |
|---|---|---|
| 3-HB-CL | (5-2) | 6% |
| 5-HB-CL | (5-2) | 4% |
| 3-HHB-OCF3 | (6-1) | 5% |
| 3-H2HB-OCF3 | (6-13) | 5% |
| 5-H4HB-OCF3 | (6-19) | 15% |
| V-HHB(F)-F | (6-2) | 5% |
| 3-HHB(F)-F | (6-2) | 5% |
| 5-HHB(F)-F | (6-2) | 5% |
| 3-H4HB(F,F)-CF3 | (6-21) | 7% |
| 5-H4HB(F,F)-CF3 | (6-21) | 8% |
| 5-H2HB(F,F)-F | (6-15) | 5% |
| 5-H4HB(F,F)-F | (6-21) | 7% |
| 2-H2BB(F)-F | (6-26) | 5% |
| 3-H2BB(F)-F | (6-26) | 10% |
| 3-HBEB(F,F)-F | (6-39) | 5% |
| Compound(1-107) | | 3% |

Use Example 9

| | | |
|---|---|---|
| 5-HB-CL | (5-2) | 15% |
| 7-HB(F,F)-F | (5-4) | 3% |
| 3-HH-4 | (2-1) | 7% |
| 3-HH-5 | (2-1) | 5% |
| 3-HB-O2 | (2-5) | 15% |
| 3-HHB-1 | (3-1) | 8% |
| 3-HHB-O1 | (3-1) | 5% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 6% |
| 3-H2HB(F,F)-F | (6-15) | 5% |
| 4-H2HB(F,F)-F | (6-15) | 5% |
| Compound (1-51) | | 5% |

Use Example 10

| | | |
|---|---|---|
| 5-HB-CL | (5-2) | 3% |
| 7-HB(F)-F | (5-3) | 7% |
| 3-HH-4 | (2-1) | 8% |
| 3-HH-EMe | (2-2) | 23% |
| 3-HHEB-F | (6-10) | 6% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 4% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 7% |
| Compound (1-121) | | 4% |

Use Example 11

| | | |
|---|---|---|
| 3-HB-O1 | (2-5) | 15% |
| 3-HH-4 | (2-1) | 5% |
| 3-HB(2F,3F)-O2 | (9-1) | 12% |
| 5-HB(2F,3F)-O2 | (9-1) | 12% |
| 2-HHB(2F,3F)-1 | (10-1) | 11% |
| 3-HHB(2F,3F)-1 | (10-1) | 12% |
| 3-HHB(2F,3F)-O2 | (10-1) | 10% |
| 5-HHB(2F,3F)-O2 | (10-1) | 13% |
| 3-HHB-1 | (3-1) | 6% |
| Compound (1-111) | | 4% |

Use Example 12

| | | |
|---|---|---|
| 2-HH-5 | (2-1) | 3% |
| 3-HH-4 | (2-1) | 15% |
| 3-HH-5 | (2-1) | 4% |
| 3-HB-O2 | (2-5) | 10% |
| 3-H2B(2F,3F)-O2 | (9-4) | 15% |
| 5-H2B(2F,3F)-O2 | (9-4) | 14% |
| 3-HHB(2F,3CL)-O2 | (10-12) | 5% |
| 2-HBB(2F,3F)-O2 | (10-7) | 3% |
| 3-HBB(2F,3F)-O2 | (10-7) | 8% |
| 5-HBB(2F,3F)-O2 | (10-7) | 9% |
| 3-HHB-1 | (3-1) | 3% |
| 3-HHB-3 | (3-1) | 3% |
| 3-HHB-O1 | (3-1) | 3% |
| Compound (1-114) | | 4% |

Use Example 13

| | | |
|---|---|---|
| 2-HH-3 | (2-1) | 17% |
| 3-HH-4 | (2-1) | 9% |
| 1-BB-3 | (2-8) | 7% |
| 3-HB-O2 | (2-5) | 2% |
| 3-BB(2F,3F)-O2 | (9-3) | 9% |
| 5-BB(2F,3F)-O2 | (9-3) | 5% |
| 2-HH1OB(2F,3F)-O2 | (10-5) | 11% |
| 3-HH1OB(2F,3F)-O2 | (10-5) | 21% |
| 3-HHB-1 | (3-1) | 4% |
| 3-HHB-O1 | (3-1) | 3% |
| 5-B(F)BB-2 | (3-8) | 2% |
| Compound (1-1) | | 4% |
| Compound (1-102) | | 6% |

NI=71.9° C.; η=27.4 mPa·s; Δn=0.102; Δε=−3.0.

Use Example 14

| | | |
|---|---|---|
| 2-HH-3 | (2-1) | 13% |
| 7-HB-1 | (2-5) | 10% |
| 5-HB-O2 | (2-5) | 8% |
| 3-HB(2F,3F)-O2 | (9-1) | 17% |
| 5-HB(2F,3F)-O2 | (9-1) | 13% |
| 3-HHB(2F,3CL)-O2 | (10-12) | 3% |
| 5-HHB(2F,3CL)-O2 | (10-12) | 2% |
| 3-HH1OCro(7F,8F)-5 | (13-6) | 5% |
| 5-HBB(F)B-2 | (4-5) | 9% |
| 5-HBB(F)B-3 | (4-5) | 9% |
| Compound (1-104) | | 8% |
| Compound (1-103) | | 3% |

Use Example 15

| | | |
|---|---|---|
| 1-BB-3 | (2-8) | 9% |
| 3-HH-V | (2-1) | 26% |
| 3-BB(2F,3F)-O2 | (9-3) | 13% |
| 2-HH1OB(2F,3F)-O2 | (10-5) | 20% |
| 3-HH1OB(2F,3F)-O2 | (10-5) | 13% |
| 3-HHB-1 | (3-1) | 7% |
| 5-B(F)BB-2 | (3-8) | 6% |
| Compound (1-105) | | 3% |
| Compound (1-106) | | 3% |

Use Example 16

| | | |
|---|---|---|
| 2-HH-3 | (2-1) | 6% |
| 3-HH-V1 | (2-1) | 8% |
| 1V2-HH-1 | (2-1) | 8% |
| 1V2-HH-3 | (2-1) | 7% |
| 3-BB(2F,3F)-O2 | (9-3) | 7% |
| 5-BB(2F,3F)-O2 | (9-3) | 4% |
| 3-H1OB(2F,3F)-O2 | (9-5) | 7% |
| 2-HH1OB(2F,3F)-O2 | (10-5) | 8% |
| 3-HH1OB(2F,3F)-O2 | (10-5) | 16% |
| 3-HDhB(2F,3F)-O2 | (—) | 7% |
| 3-HHB-1 | (3-1) | 3% |
| 3-HHB-3 | (3-1) | 2% |
| 2-BB(2F,3F)B-3 | (11-1) | 10% |
| Compound (1-101) | | 3% |
| Compound (1-107) | | 4% |

Use Example 17

| | | |
|---|---|---|
| 1V2-BEB(F,F)-C | (8-15) | 6% |
| 3-HB-C | (8-1) | 15% |
| 2-BTB-1 | (2-10) | 9% |
| 5-HH-VFF | (2-1) | 27% |
| 3-HHB-1 | (3-1) | 4% |
| VFF-HHB-1 | (3-1) | 8% |
| VFF2-HHB-1 | (3-1) | 11% |
| 3-H2BTB-2 | (3-17) | 4% |
| 3-H2BTB-3 | (3-17) | 4% |
| 3-H2BTB-4 | (3-17) | 4% |
| Compound (1-71) | | 5% |
| Compound (1-121) | | 3% |

Use Example 18

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 39% |
| 3-HH-V1 | (2-1) | 6% |
| 3-HHEH-5 | (3-13) | 3% |
| 3-HHB-1 | (3-1) | 3% |
| V-HHB-1 | (3-1) | 5% |
| V2-BB(F)B-1 | (3-6) | 4% |
| 1V2-BB-F | (5-1) | 3% |
| 3-BB(F,F)XB(F,F)-F | (6-97) | 11% |
| 3-HHBB(F,F)-F | (7-6) | 3% |
| Compound (1-111) | | 5% |

Use Example 19

| | | |
|---|---|---|
| 3-GB(F)B(F,F)XB(F,F)-F | (7-57) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 40% |
| 3-HH-V1 | (2-1) | 6% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 4% |
| 1V2-BB-F | (5-1) | 3% |
| 3-BB(F,F)XB(F,F)-F | (6-97) | 6% |
| 3-GB(F,F)XB(F,F)-F | (6-113) | 4% |

-continued

| | | |
|---|---|---|
| 3-HHBB(F,F)-F | (7-6) | 3% |
| Compound (1-114) | | 4% |

Use Example 20

| | | |
|---|---|---|
| 7-HB(F,F)-F | (5-4) | 3% |
| 3-HB-O2 | (2-5) | 7% |
| 2-HHB(F)-F | (6-2) | 8% |
| 3-HHB(F)-F | (6-2) | 8% |
| 5-HHB(F)-F | (6-2) | 10% |
| 2-HBB(F)-F | (6-23) | 10% |
| 3-HBB(F)-F | (6-23) | 10% |
| 5-HBB(F)-F | (6-23) | 14% |
| 2-HBB-F | (6-22) | 4% |
| 3-HBB-F | (6-22) | 4% |
| 5-HBB-F | (6-22) | 3% |
| 3-HBB(F,F)-F | (6-24) | 3% |
| 5-HBB(F,F)-F | (6-24) | 6% |
| Compound (1-361) | | 10% |

NI=82.6° C.; η=39.3 mPa·s; Δn=0.119; Δε=6.0.

Use Example 21

| | | |
|---|---|---|
| 3-HB-O1 | (2-5) | 15% |
| 3-HH-4 | (2-1) | 5% |
| 3-HB(2F,3F)-O2 | (9-1) | 11% |
| 5-HB(2F,3F)-O2 | (9-1) | 12% |
| 2-HHB(2F,3F)-1 | (10-1) | 12% |
| 3-HHB(2F,3F)-1 | (10-1) | 12% |
| 3-HHB(2F,3F)-O2 | (10-1) | 12% |
| 5-HHB(2F,3F)-O2 | (10-1) | 12% |
| 3-HHB-1 | (3-1) | 6% |
| Compound (1-122) | | 3% |

NI=85.5° C.; η=38.7 mPa·s; Δn=0.093; Δε=−3.5.

Use Example 22

| | | |
|---|---|---|
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 6% |
| 5-BB(F)B(F,F)XB(F,F)-F | (7-47) | 3% |
| 3-HH-V | (2-1) | 40% |
| 3-HH-V1 | (2-1) | 6% |
| 3-HHEH-5 | (3-13) | 3% |
| 3-HHB-1 | (3-1) | 3% |
| V-HHB-1 | (3-1) | 5% |
| V2-BB(F)B-1 | (3-6) | 4% |
| 1V2-BB-F | (5-1) | 3% |
| 3-BB(F,F)XB(F,F)-F | (6-97) | 11% |
| 3-HHBB(F,F)-F | (7-6) | 3% |
| Compound (1-367) | | 5% |

NI=81.0° C.; η=18.5 mPa·s; Δn=0.109; Δε=6.5.

Use Example 23

| | | |
|---|---|---|
| 2-HH-5 | (2-1) | 3% |
| 3-HH-4 | (2-1) | 15% |
| 3-HH-5 | (2-1) | 4% |
| 3-HB-O2 | (2-5) | 10% |
| 3-H2B(2F,3F)-O2 | (9-4) | 15% |
| 5-H2B(2F,3F)-O2 | (9-4) | 14% |
| 3-HHB(2F,3CL)-O2 | (10-12) | 5% |
| 2-HBB(2F,3F)-O2 | (10-7) | 4% |
| 3-HBB(2F,3F)-O2 | (10-7) | 8% |
| 5-HBB(2F,3F)-O2 | (10-7) | 9% |
| 3-HHB-1 | (3-1) | 3% |
| 3-HHB-3 | (3-1) | 3% |
| 3-HHB-O1 | (3-1) | 4% |
| Compound (1-124) | | 3% |

Use Example 24

| | | |
|---|---|---|
| 5-HB-CL | (2-5) | 3% |
| 7-HB(F)-F | (5-3) | 7% |
| 3-HH-4 | (2-1) | 8% |
| 3-HH-EMe | (2-2) | 23% |
| 3-HHEB-F | (6-10) | 5% |
| 5-HHEB-F | (6-10) | 8% |
| 3-HHEB(F,F)-F | (6-12) | 10% |
| 4-HHEB(F,F)-F | (6-12) | 5% |
| 4-HGB(F,F)-F | (6-103) | 4% |
| 5-HGB(F,F)-F | (6-103) | 6% |
| 2-H2GB(F,F)-F | (6-106) | 4% |
| 3-H2GB(F,F)-F | (6-106) | 5% |
| 5-GHB(F,F)-F | (6-109) | 7% |
| Compound (1-366) | | 5% |

INDUSTRIAL APPLICABILITY

A liquid crystal compound, a liquid crystal composition and a composite material with an encapsulated liquid crystal according to the invention can be used for a liquid crystal display device.

REFERENCE SIGNS LIST

2 Core component
2a Liquid crystal composition
2b Liquid crystal molecule
4 Sheath component
4a Sheath component-forming material
10 Conjugate fibers with an encapsulated liquid crystal (conjugate fibers)
20 Conjugate fiber aggregate
30 Substrate
40 Binder
100 Liquid crystal display device

What is claimed is:
1. A compound, represented by formula (1):

$$MG^1\text{-}Z^a\text{-}Sp\text{-}Z^b\text{-}MG^2 \quad (1)$$

wherein, in formula (1), $MG^1$ and $MG^2$ are each independently a mesogenic group;
$Z^a$ and $Z^b$ are independently a single bond or alkylene having 1 to 4 carbons, and in the $Z^a$ and the $Z^b$, at least one piece of —$CH_2$— may be replaced by —O—, —S—, —CO— or —$SiH_2$—, at least one piece of —$(CH_2)_2$— may be replaced by —CH=CH— or —C≡C—, and at least one piece of hydrogen may be replaced by fluorine;
Sp has an achiral structure represented by formula (sp-1):

$$\text{-}\alpha\text{-X-}\alpha\text{-} \quad (\text{sp-1})$$

wherein, in formula (sp-1), α is each independently straight-chain alkylene having 1 to 20 carbons, and in the α, at least one piece of —CH$_2$— may be replaced by —O—, —S—, —CO— or —SiH$_2$—, at least one piece of —(CH$_2$)$_2$— may be replaced by —CH═CH— or —C≡C—, and at least one piece of hydrogen may be replaced by fluorine;

X is represented by formula (I), formula (II) or formula (III):

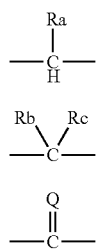

wherein, in formula (I), Ra is a hydroxyl group or alkyl having 1 to 10 carbons, and in the Ra, at least one piece of —CH$_2$— may be replaced by —O—, —S—, —CO— or —SiH$_2$—, at least one piece of —(CH$_2$)$_2$— may be replaced by —CH═CH— or —C≡C—, and at least one piece of hydrogen may be replaced by fluorine;

in formula (II), Rb and Rc are each independently fluorine, chlorine or alkyl having 1 to 10 carbons, and in the Rb and the Rc, at least one piece of —CH$_2$— may be replaced by —O—, —S—, —CO— or —SiH$_2$—, at least one piece of —(CH$_2$)$_2$— may be replace by —CH═CH— or —C≡C—, and at least one piece of hydrogen may be replaced by fluorine; and in formula (III), Q is an oxygen atom, a sulfur atom or alkylidene having 1 to 10 carbons, and in the Q, at least one piece of —CH$_2$— may be replaced by —O—, —S—, —CO— or —SiH$_2$—, at least one piece of —(CH$_2$)$_2$— may be replaced by —CH═CH— or —C≡C—, and at least one piece of hydrogen may be replaced by fluorine.

2. The compound according to claim 1, wherein, in formula (1), MG$^1$ and MG$^2$ are represented by formula (IV):

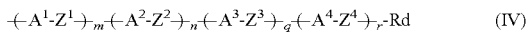

wherein, in formula (IV), Rd is independently —CN, —NCS, —C≡C—CN, —SF$_5$, fluorine, chlorine or straight-chain alkyl having 1 to 20 carbons, and in the Rd, at least one piece of —CH$_2$— may be replaced by —O—, —S—, —CO— or —SiH$_2$—, and at least one piece of —(CH$_2$)$_2$— may be replaced by —CH═CH— or —C≡C—; A$^1$, A$^2$, A$^3$ and A$^4$ are independently 1,4-cyclohexylene, 1,4-phenylene, cyclohexene-1,4-diyl, naphthalene-2,6-diyl, and in the rings, one piece of —CH$_2$— may be replaced by —O—, —S—, —CO— or —SiH$_2$—, and at least one piece of —(CH$_2$)$_2$— may be replaced by —CH═CH— or —CH═N—, and in the rings, at least one piece of hydrogen may be replaced by fluorine, chlorine, —CF$_3$, —CHF$_2$, —CH$_2$F, —OCF$_3$, —OCHF$_2$ or —OCH$_2$F;

Z$^1$, Z$^2$, Z$^3$ and Z$^4$ are independently a single bond or alkylene having 1 to 4 carbons, and in the Z$^1$, the Z$^2$, the Z$^3$ and the Z$^4$, at least one piece of —CH$_2$— may be replaced by —O—, —S—, —CO— or —SiH$_2$—, at least one piece of —(CH$_2$)$_2$— may be replaced by —CH═CH— or —C≡C—, and at least one piece of hydrogen may be replaced by fluorine; and m, n, q and r are independently 0 or 1, and a sum of m, n, q and r is 2, 3 or 4.

3. The compound according to claim 2, wherein, in formula (IV), Rd is fluorine, chlorine or straight-chain alkyl having 1 to 10 carbons, straight-chain alkenyl having 2 to 10 carbons, straight-chain alkoxy having 1 to 9 carbons, straight-chain alkoxyalkyl having 2 to 9 carbons, straight-chain alkenyloxy having 3 to 9 carbons, straight-chain polyfluoroalkyl having 1 to 10 carbons, straight-chain polyfluoroalkoxy having 1 to 9 carbons or straight-chain polyfluoroalkenyl having 2 to 10 carbons;

A$^1$, A$^2$, A$^3$ and A$^4$ are independently 1,4-cyclohexylene, 1,4-phenylene, cyclohexene-1,4-diyl, decahydronaphthalene-2,6-diyl, 1,2,3,4-tetrahydronaphthalene-2,6-diyl or naphthalene-2,6-diyl, and in the rings, at least one piece of hydrogen may be replaced by fluorine, chlorine, —CF$_3$ or —CHF$_2$; and Z$^1$, Z$^2$ and Z$^4$ are independently a single bond, —(CH$_2$)$_2$—, —COO—, —OCO—, —CH$_2$O—, —OCH$_2$—, —CF$_2$O—, —OCF$_2$—, —CH═CH—, —CF═CF—, —C≡C—, —CH$_2$CO—, —COCH$_2$—, —CH$_2$SiH$_2$—, —SiH$_2$CH$_2$—, —(CH$_2$)$_2$COO—, —OCO(CH$_2$)$_2$—, —(CH$_2$)$_2$CF$_2$O—, —OCF$_2$(CH$_2$)$_2$—, —(CH$_2$)$_3$O—, —O(CH$_2$)$_3$— or —(CH$_2$)$_4$—.

4. The compound according to claim 1, wherein, in formula (1), Z$_a$ and Z$^b$ are independently a single bond, —COO—, —OCO—, —CH$_2$O—, —OCH$_2$—, —CF$_2$O—, —OCF$_2$—, —CF═CF—, —CH$_2$CO—, —C≡C—, —COCH$_2$—, —CH$_2$SiH$_2$— or —SiH$_2$CH$_2$—;

in formula (sp-1), α is straight-chain alkylene having 1 to 10 carbons, and in the α, at least one piece of —(CH$_2$)$_2$— may be replaced by —CH═CH— or —C≡C—, and at least one piece of hydrogen may be replaced by fluorine;

in formula (I), Ra is a hydroxyl group, alkyl having 1 to 5 carbons, alkenyl having 2 to 5 carbons, alkoxy having 1 to 4 carbons, alkoxyalkyl having 2 to 4 carbons, alkenyloxy having 3 to 4 carbons, polyfluoroalkyl having 1 to 5 carbons, polyfluoroalkoxy having 1 to 4 carbons or polyfluoroalkenyl having 2 to 5 carbons;

in formula (II), Rb and Rc are each independently fluorine, alkyl having 1 to 5 carbons, alkenyl having 2 to 5 carbons, alkoxy having 1 to 4 carbons, alkoxyalkyl having 2 to 4 carbons, alkenyloxy having 3 to 4 carbons, polyfluoroalkyl having 1 to 5 carbons, polyfluoroalkoxy having 1 to 4 carbons or polyfluoroalkenyl having 2 to 5 carbons; and in formula (III), Q is an oxygen atom or alkylidene having 1 to 5 carbons.

5. The compound according to claim 4, wherein, in formula (1), Z$^a$ and Z$^b$ are independently a single bond, —COO—, —OCO—, —CH$_2$O—, —OCH$_2$—, —CF$_2$O—, —OCF$_2$—, —CH═CH—, —CF═CF— or —C≡C—; and in formula (sp-1), α is straight-chain alkylene having 1 to 10 carbons;

in formula (I), Ra is alkyl having 1 to 5 carbons, alkenyl having 2 to 5 carbons or polyfluoroalkyl having 1 to 5 carbons;

in formula (II), Rb and Rc are each independently fluorine, alkyl having 1 to 5 carbons, alkenyl having 2 to 5 carbons or polyfluoroalkyl having 1 to 5 carbons; and in formula (III), Q is an oxygen atom or alkylidene having 1 to 3 carbons.

6. The compound according to claim 1, wherein, in formula (1), $MG^1$ and $MG^2$ are represented by formula (IV-1):

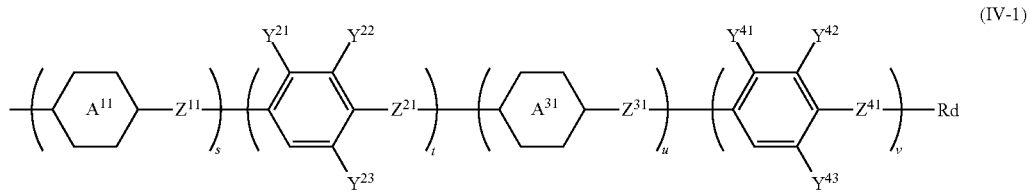

(IV-1)

wherein, Rd is independently —CN, —NCS, —C≡C—CN, —SF$_5$, fluorine, chlorine, straight-chain alkyl having 1 to 6 carbons, straight-chain alkenyl having 2 to 6 carbons, straight-chain alkoxy having 1 to 5 carbons, straight-chain polyfluoroalkyl having 1 to 6 carbons, straight-chain polyfluoroalkoxy having 1 to 5 carbons or straight-chain polyfluoroalkenyl having 2 to 6 carbons;

$A^{11}$ and $A^{31}$ are 1,4-cyclohexylene or 1,4-phenylene;

$Y^{21}, Y^{22}, Y^{23}, Y^{41}, Y^{42}$ and $Y^{43}$ are independently hydrogen, fluorine, —CF$_3$ or —CF$_2$H;

$Z^{11}, Z^{21}, Z^{31}$ and $Z^{41}$ are independently a single bond, —(CH$_2$)$_2$—, —CH$_2$O—, —OCH$_2$—, —CF$_2$O—, —OCF$_2$—, —CH=CH—, —CF=CF—, or —C≡C—; and s, t, u and v are independently 0, 1 or 2, and a sum of s, t and u is 2, 3 or 4, in which t is 1 without exception, and when any one of s, t, u and v is 2, a plurality of ring structures may be an identical group or a different group, and a plurality of $Z^{11}, Z^{21}, Z^{31}$ and $Z^{41}$ may be an identical group or a different group.

7. The compound according to claim 1, wherein, in formula (1), $MG^1$ and $MG^2$ are represented by formulas (IV-1-1-1) to (IV-1-1-55):

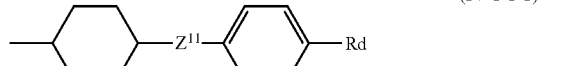
(IV-1-1-1)

(IV-1-1-2)

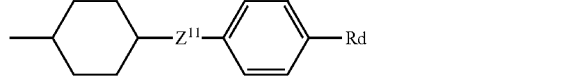
(IV-1-1-3)

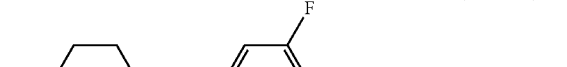
(IV-1-1-4)

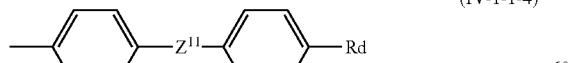
(IV-1-1-5)

-continued

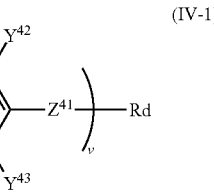
(IV-1-1-6)

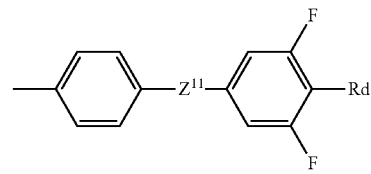
(IV-1-1-7)

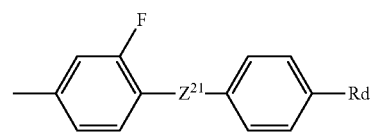
(IV-1-1-8)

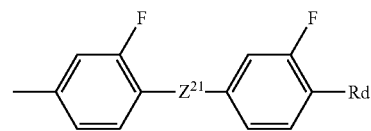
(IV-1-1-9)

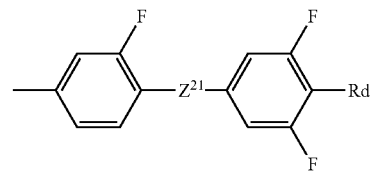
(IV-1-1-10)

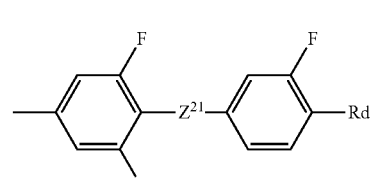
(IV-1-1-11)

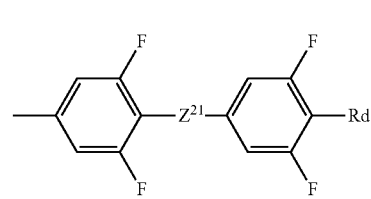
(IV-1-1-12)

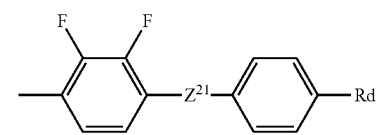
(IV-1-1-13)
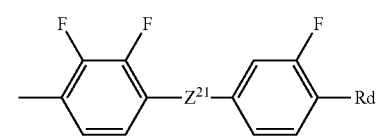
(IV-1-1-14)
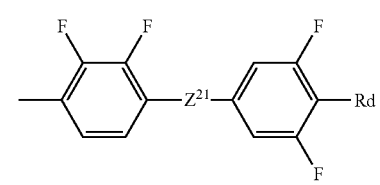
(IV-1-1-15)
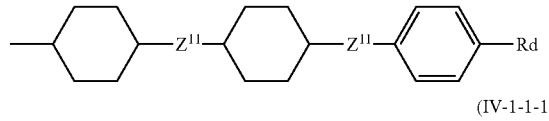
(IV-1-1-16)
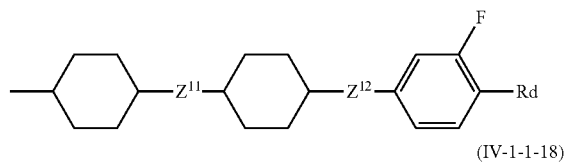
(IV-1-1-17)
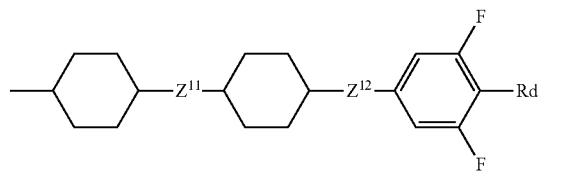
(IV-1-1-18)
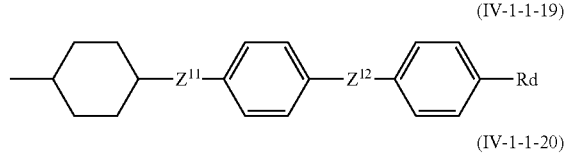
(IV-1-1-19)
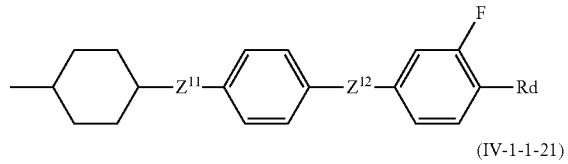
(IV-1-1-20)
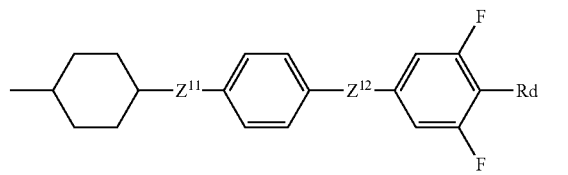
(IV-1-1-21)
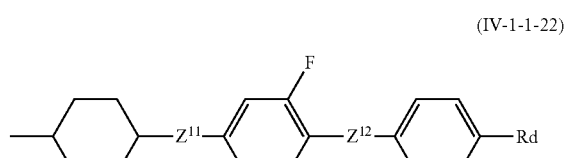
(IV-1-1-22)
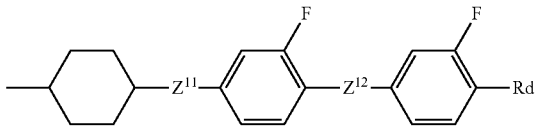
(IV-1-1-23)
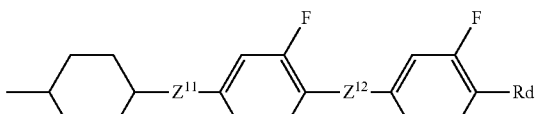
(IV-1-1-24)
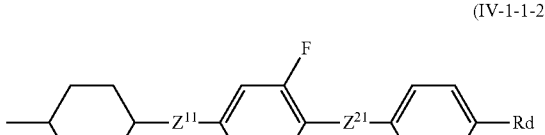
(IV-1-1-25)
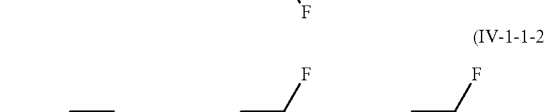
(IV-1-1-26)
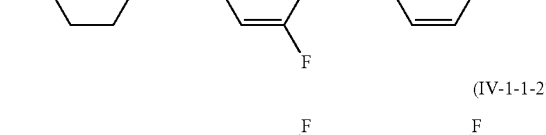
(IV-1-1-27)
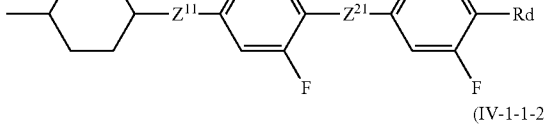
(IV-1-1-28)
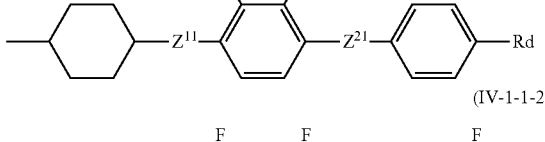
(IV-1-1-29)
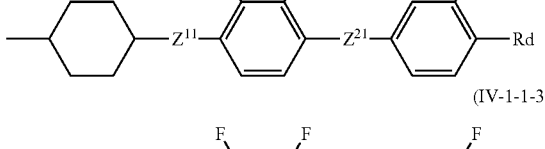
(IV-1-1-30)
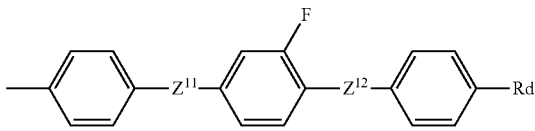
(IV-1-1-31)

(IV-1-1-32)
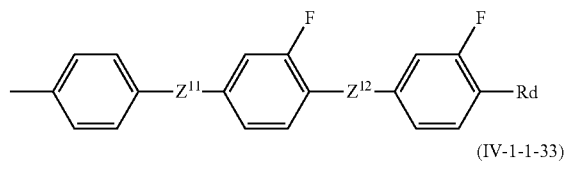
(IV-1-1-33)
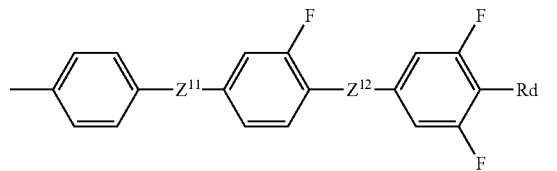
(IV-1-1-34)
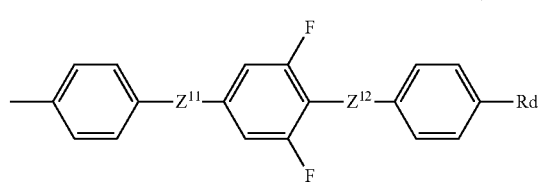
(IV-1-1-35)
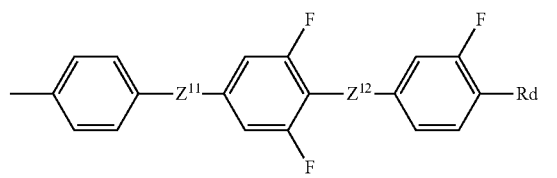
(IV-1-1-36)
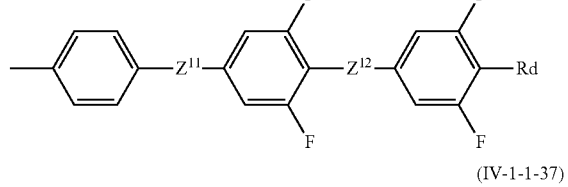
(IV-1-1-37)
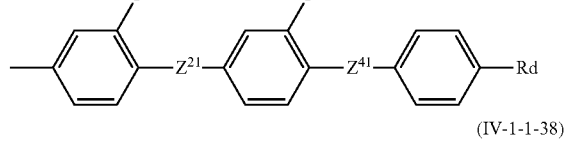
(IV-1-1-38)
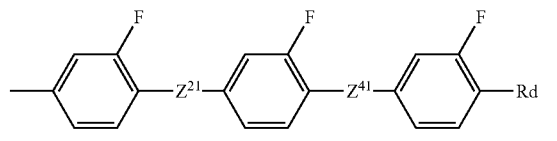
(IV-1-1-39)
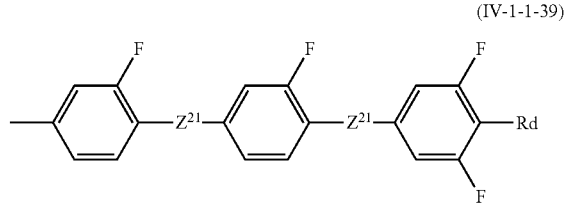
(IV-1-1-40)
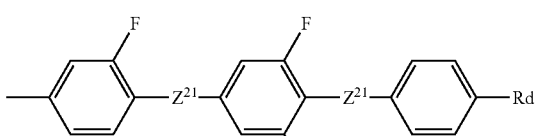
(IV-1-1-41)
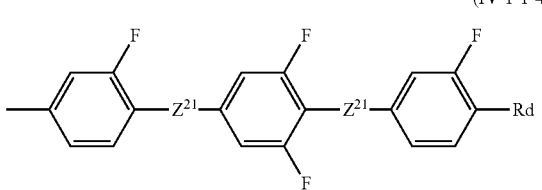
(IV-1-1-42)
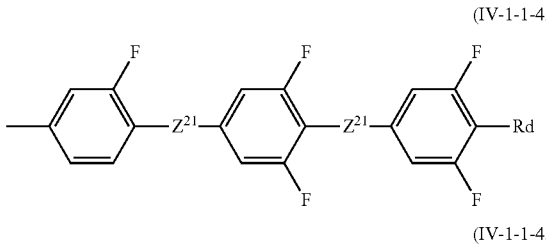
(IV-1-1-43)
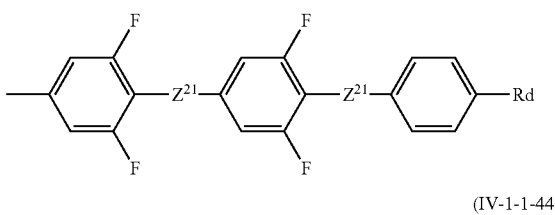
(IV-1-1-44)
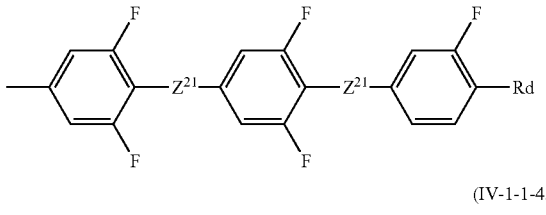
(IV-1-1-45)
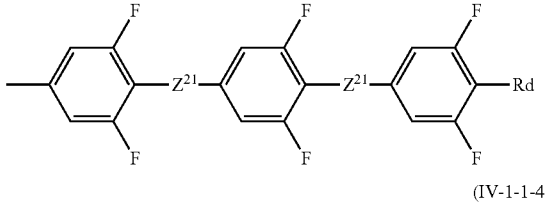
(IV-1-1-46)
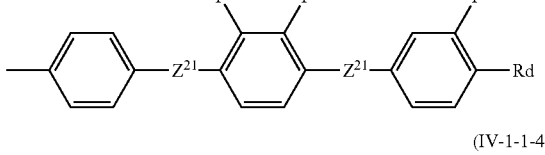
(IV-1-1-47)
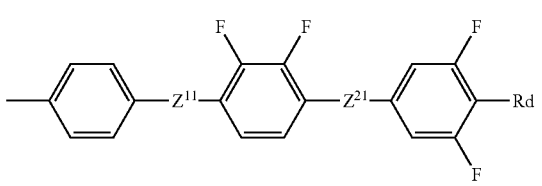

-continued

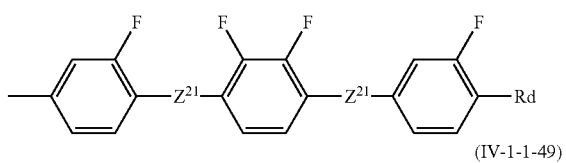
(IV-1-1-48)

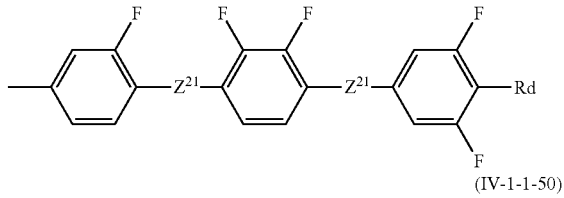
(IV-1-1-49)

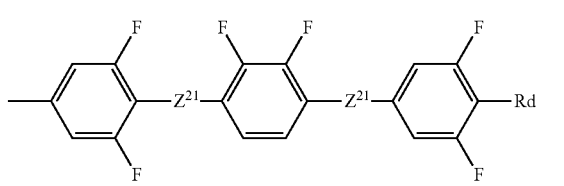
(IV-1-1-50)

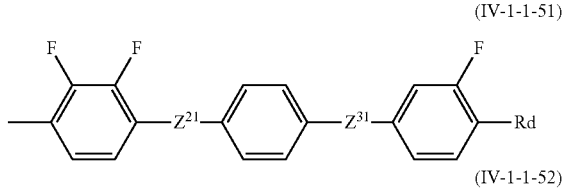
(IV-1-1-51)

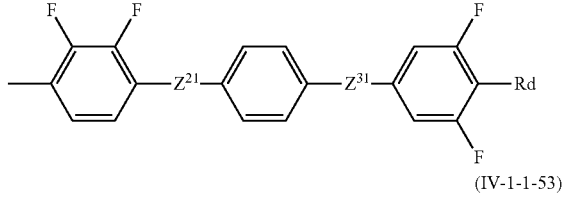
(IV-1-1-52)

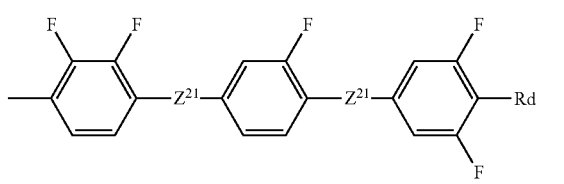
(IV-1-1-53)

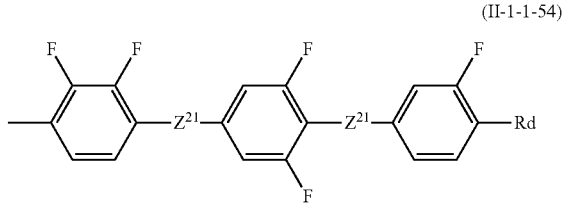
(II-1-1-54)

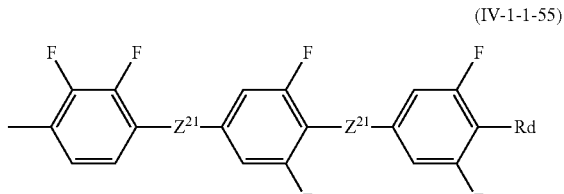
(IV-1-1-55)

wherein, in formula (IV-1-1-1) to formula (IV-1-1-55), Rd is independently —CN, —NCS, —C≡C—CN, —SF$_5$, fluorine, —CF$_3$, —CF$_2$H, —OCF$_3$ or —C$_2$F$_5$; and Z$^{11}$, Z$^{21}$ and Z$^{31}$ are independently a single bond, —(CH$_2$)$_2$—, —CF$_2$O—, —CH=CH—, —CF=CF— or —C≡C—, and a plurality of Z$^{11}$, Z$^{21}$ or Z$^{31}$ may be an identical group or a different group.

8. The compound according to claim 1, wherein, in formula (1), MG$^1$ and MG$^2$ are represented by formulas (IV-1-2-1) to (IV-1-2-30):

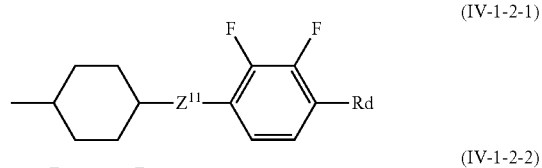
(IV-1-2-1)

(IV-1-2-2)

(IV-1-2-3)

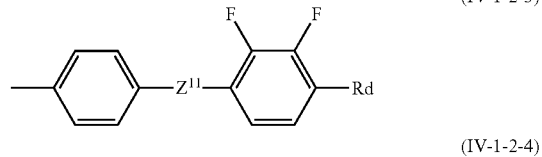
(IV-1-2-4)

(IV-1-2-5)

(IV-1-2-6)

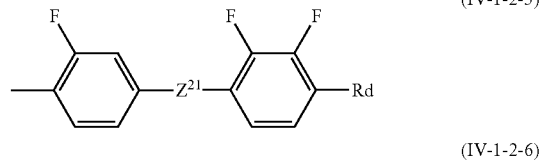
(IV-1-2-7)

(IV-1-2-8)

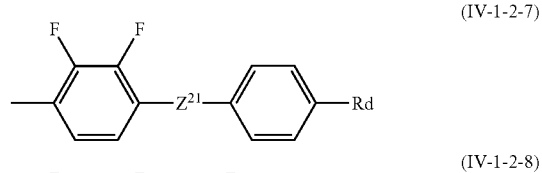
(IV-1-2-9)

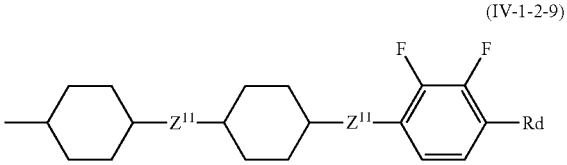
(IV-1-2-10)

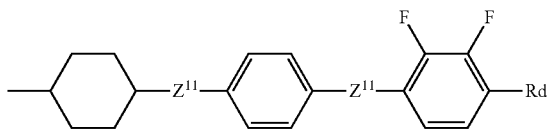

(IV-1-2-11)
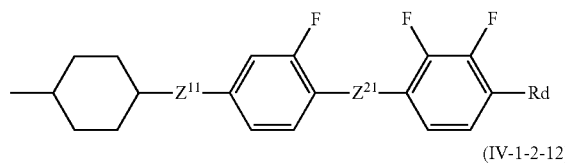
(IV-1-2-12)
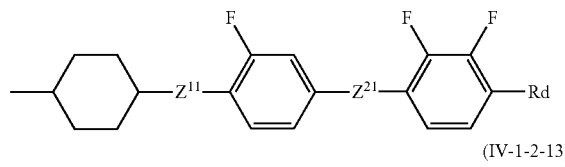
(IV-1-2-13)
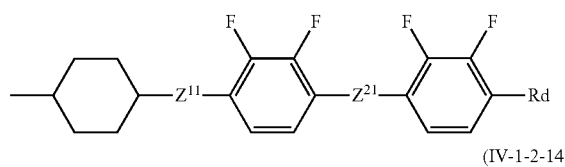
(IV-1-2-14)
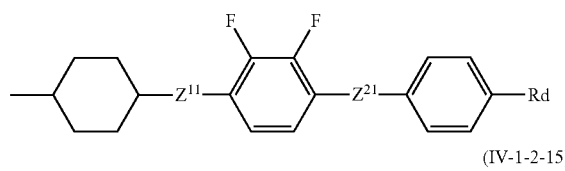
(IV-1-2-15)
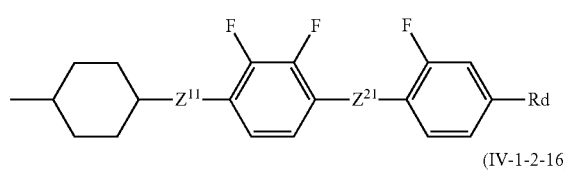
(IV-1-2-16)
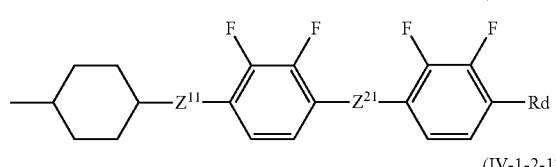
(IV-1-2-17)
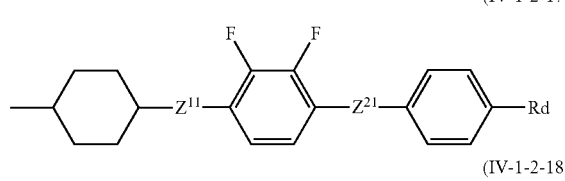
(IV-1-2-18)
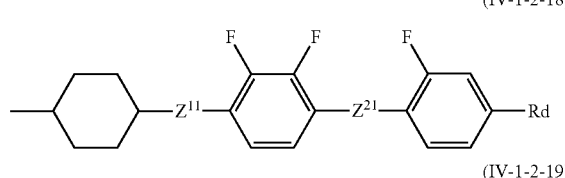
(IV-1-2-19)
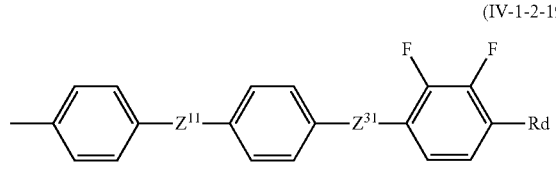
(IV-1-2-20)
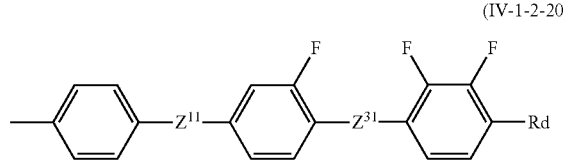
(IV-1-2-21)
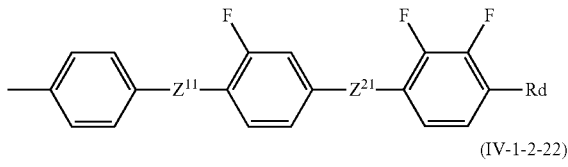
(IV-1-2-22)
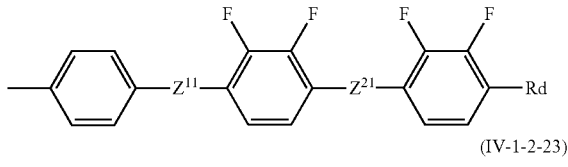
(IV-1-2-23)
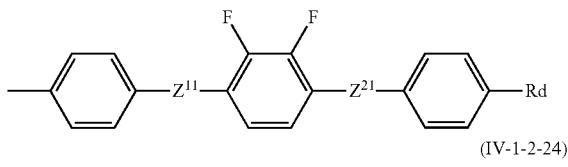
(IV-1-2-24)
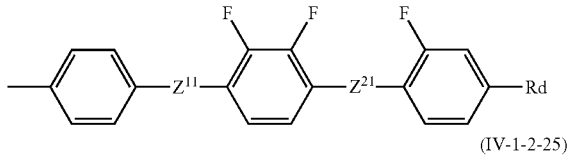
(IV-1-2-25)
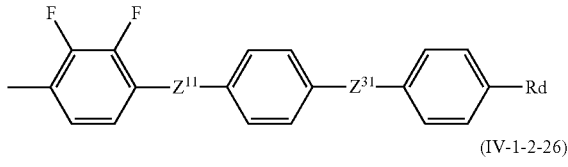
(IV-1-2-26)
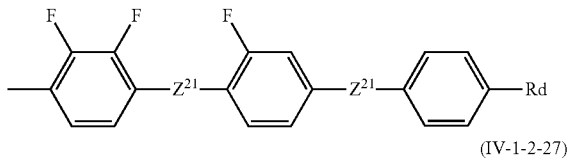
(IV-1-2-27)
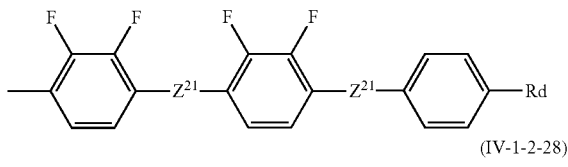
(IV-1-2-28)
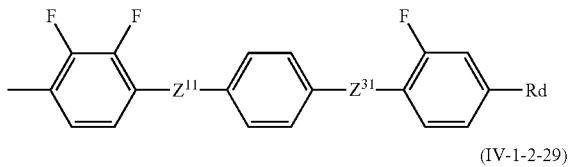
(IV-1-2-29)
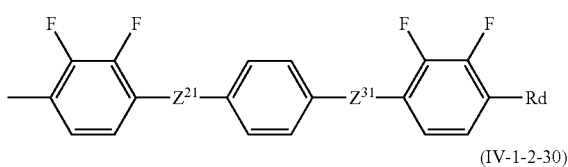
(IV-1-2-30)
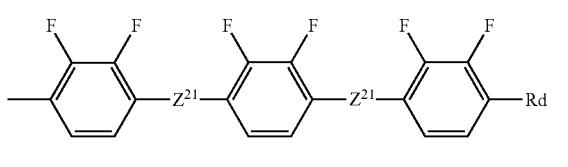

wherein, in formulas (IV-1-2-1) to (IV-1-2-30), Rd is independently straight-chain alkyl having 1 to 6 carbons, straight-chain alkenyl having 2 to 6 carbons or straight-chain alkoxy having 1 to 6 carbons; and $Z^{11}$, $Z^{21}$ and $Z^{31}$ are independently a single bond, —$(CH_2)_2$—, —$CH_2O$—, —$OCH_2$—, —$CF_2O$—, —$OCF_2$—, —CH=CH—, —CF=CF— or —C≡C—, and a plurality of $Z^{11}$, $Z^{21}$ and $Z^{31}$ may be an identical group or a different group.

9. A liquid crystal composition, containing the compound according to claim 1.

10. The liquid crystal composition, containing at least two kinds of the compounds according to claim 1.

11. The liquid crystal composition according to claim 10, further containing a compound represented by formula (cp-1):

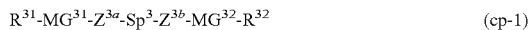

$$R^{31}\text{-}MG^{31}\text{-}Z^{3a}\text{-}Sp^3\text{-}Z^{3b}\text{-}MG^{32}\text{-}R^{32} \quad \text{(cp-1)}$$

wherein, $R^{31}$ and $R^{32}$ are each independently fluorine, chlorine, —CN, —NCS, —$SF_5$ or alkyl having 1 to 20 carbons, and in the $R^{31}$ and $R^{32}$, at least one piece of —$CH_2$— may be replaced by —O—, —S—, —CO— or —$SiH_2$—, and at least one piece of —$(CH_2)_2$— may be replaced by —CH=CH— or —C≡C—; $MG^{31}$ and $MG^{32}$ are each independently a mesogenic group; $Z^{3a}$ and $Z^{3b}$ are each independently —O—, —S—, —CO—, —COO—, —OCO—, —O—CO—O—, —CO—NH—, —NH—CO—, —$CH_2CH_2$—, —$OCH_2$—, —$CH_2O$—, —$SCH_2$—, —$CH_2S$—, —CH=CH—, —CH=CHCOO—, —OCO—CH=CH—, —C≡C— or a single bond; and $Sp^3$ is a straight-chain spacer group containing 4 to 40 carbons, and at least one piece of a —$CH_2$ group may be replaced by —O—, —S—, —NH—, —N($CH_3$)—, —OCO—, —S—CO—, —O—COO—, —CO—S—, —CO—O—, —CH=CH— or —C≡C—.

12. The liquid crystal composition according to claim 9, further containing at least one selected from an optically active compound and a polymerizable compound.

13. The liquid crystal composition according to claim 9, further containing at least one selected from an antioxidant and an ultraviolet light absorber.

14. Sheath-core conjugate fibers with an encapsulated liquid crystal, wherein the liquid crystal composition according to claim 9 is applied as a core component.

15. A fiber aggregate containing a liquid crystal, formed by uniaxially arranging the conjugate fibers with the encapsulated liquid crystal according to claim 14.

16. A fiber composite containing a liquid crystal, composed of the fiber aggregate containing the liquid crystal according to claim 15, and a binder.

17. A liquid crystal display device, including the liquid crystal composition according to claim 9.

18. The liquid crystal display device according to claim 17, wherein the device is a flexo-electric apparatus.

19. A liquid crystal display device, including the fiber composite containing the liquid crystal according to claim 16.

20. The liquid crystal display device according to claim 19, wherein the device is a flexo-electric apparatus.

* * * * *